United States Patent
Wang

(10) Patent No.: US 6,696,247 B2
(45) Date of Patent: Feb. 24, 2004

(54) COMPOUNDS AND METHODS FOR THERAPY AND DIAGNOSIS OF LUNG CANCER

(75) Inventor: Tongtong Wang, Medina, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/466,396

(22) Filed: Dec. 17, 1999

(65) Prior Publication Data

US 2003/0119763 A1 Jun. 26, 2003

Related U.S. Application Data

(63) Continuation-in-part of application No. 09/285,479, filed on Apr. 2, 1999, and a continuation of application No. PCT/US99/05798, filed on Mar. 17, 1999, and a continuation-in-part of application No. 09/221,107, filed on Dec. 22, 1998, which is a continuation-in-part of application No. 09/123,912, filed on Jul. 27, 1998, now Pat. No. 6,312,695, which is a continuation-in-part of application No. 09/040,802, filed on Mar. 18, 1998, now abandoned.

(51) Int. Cl.$^7$ ............... C12Q 1/68; C12Q 1/00; C07H 21/02; C07H 21/04
(52) U.S. Cl. ............... 435/6; 435/4; 536/23.1; 536/24.3; 536/24.31; 536/24.33
(58) Field of Search .......... 435/6, 870; 536/23.1, 536/24.3, 24.31, 24.33

(56) References Cited

U.S. PATENT DOCUMENTS

| | | | |
|---|---|---|---|
| 5,589,579 A | * 12/1996 | Torczynski et al. | 536/23.1 |
| 5,705,159 A | 1/1998 | Irie et al. | 424/185.1 |
| 5,783,422 A | 7/1998 | Suminami et al. | 435/69.3 |
| 6,297,364 B1 | 10/2001 | Chen et al. | 536/23.1 |

FOREIGN PATENT DOCUMENTS

| | | |
|---|---|---|
| EP | 679716 A1 | 11/1994 |
| EP | 0695760 A1 | 2/1996 |
| EP | 1033401 A2 | 9/2000 |
| WO | WO 91/18926 | 12/1991 |
| WO | WO 94/06929 | 3/1994 |
| WO | WO 95/21862 | 8/1995 |
| WO | WO96/02552 | 2/1996 |
| WO | WO 96/28473 | 9/1996 |
| WO | WO96/30389 | 10/1996 |
| WO | WO 97/07244 | 2/1997 |
| WO | WO 98/35985 | 8/1998 |
| WO | WO 98/46788 | 10/1998 |
| WO | WO 99/38973 | 8/1999 |
| WO | WO 99/46594 | 9/1999 |
| WO | WO 99/47674 | 9/1999 |
| WO | WO 99/54738 | 10/1999 |
| WO | WO 00/61612 | 10/2000 |
| WO | WO 01/47944 | 7/2001 |
| WO | WO 01/57272 | 8/2001 |
| WO | WO 01/57275 | 8/2001 |
| WO | WO 01/57276 | 8/2001 |
| WO | WO 01/57277 | 8/2001 |
| WO | WO 01/75067 | 10/2001 |

OTHER PUBLICATIONS

Mueller–Pillasch et al., Sep. 11, 1998, ACC No: U97188.*
Chen, Shen–Lin et al., "Isolation and characterization of a novel gene expressed in multiple cancers," *Oncogene* 12:741–751, 1996.
Güre, A.O. et al., "Human Lung Cancer Antigens Recognized by Autologous Antibodies: Definition of a Novel cDNA Derived from the Tumor Suppressor," *Cancer Research* 58: 1034–1041, Mar. 1, 1998.
Geneseq Accession No. AAC66035, Feb. 21, 2001.
Geneseq Accession No. AAZ36150, Dec. 7, 1999.
Jolly, D., "Viral vector systems for gene therapy," *Cancer Gene Therapy* 1(1):51–64, 1994.
GenBank Accession No. AF043977, Jun. 23, 1999.
GenBank Accession No. U85946, Jul. 30, 1999.
Geneseq Accession No. AAZ24653, Dec. 7, 1999.
Gruber et al., "Molecular cloning and transmembrane structure of hCLCA2 from human lung, trachea, and mammary gland," *Am. J. Physiol.* 276(Cell Physiol 45):C1261–C1270, 1999.
Guo et al., "Identification and characterization of homologues of the Exocyst component Sec 10p," *FEBS Letters* 404(2–3):135–139, 1997.
Brass et al., "Translation initiation factor eIF–4gamma is encoded by an amplified gene and induces an immune response in squamous cell lung carcinoma," *Human Molecular Genetics*, 6(1):33–39, 1997.
Database EMBLest17 Accession No. AA340797:EST46165 Fetal kidney II Homo sapiens cDNA 3' end, Apr. 18, 1997.
Database EMBLest17 Accession No. W22264:Human retina cDNATsp–509I–cleaved sublibrary Homo spaiens cDNA not directional, May 9, 1996.
Finch et al., "Identification of a cloned sequence activated during multi–stage carcinogenesis in mouse skin," *Carcinogenesis*, 12(8):1519–1522, Aug. 1991.
Gerhold and Caskey, "It's the genes! EST access to human genome content," *BioEssays* 18(12):973–981, 1996.
Russell and Barton, "Structural features can be unconserved in proteins with similar folds," *J. Mol. Biol.* 244:332–350, 1994.

(List continued on next page.)

Primary Examiner—Shin-Lin Chen
(74) *Attorney, Agent, or Firm*—SEED IP Law Group PLLC

(57) ABSTRACT

Compounds and methods for the treatment and diagnosis of lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

6 Claims, No Drawings

OTHER PUBLICATIONS

Wells and Peitsch, "The chemokine information source: identification and characterization of novel chemokines using the WorldWideWeb and expressed sequence tag databases," *Journal of Leukocyte Biology* 61:545–550, May 1997.

Baldi et al., "Differential expression of Rb2/p130 and p107 in normal human tissues and in primary lung cancer," *Clinical Cancer Research* 3(10):1691–1697, Oct. 1997.

Database EMBL Nucleotide and Protein Sequence, Accession No. AI468638, Mar. 17, 1999.

Davidson et al., "Lung tumours immunoreactive for parathyroid hormone related peptide: analysis of serum calcium levels and tumour type," *Journal of Pathology* 178:398–401, Jan. 1996.

Hara et al., "Characterization of cell phenotype by a novel cDNA library subtraction system: expression of CD8α in a mast cell–derived interleukin–4–dependent cell line," *Blood* 84(1):189–199, Jul. 1, 1994.

Henderson et al., "Identification of lung tumor antigens for cancer immunotherapy: immunological and molecular approaches," *Immunological Investigation* 29(2):87–91, May 2000.

Hogan et al., "The peptide recognized by HLA–A68.2–restricted, squamous cell carcinoma of the lung–specific cytotoxic T lymphocytes is derived from a mutated elongation factor 2 gene," *Cancer Research* 58(22):5144–5150, Nov. 15, 1998.

Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.

Marshall and Hodgson, "DNA chips: an array of possibilities," *Nature Biotechnology* 16:27 31, Jan 1998.

Pastor et al., "Diagnostic value of SCC, CEA and CYFRA 21.1 in lung cancer: a Bayesian analysis," *Eur. Respir J.* 10(3):603–609, Mar. 1997.

Ramsay, G., "DNA chips: state–of–the art," *Nature Biotechnology* 16:40–44, Jan. 1998.

Visseren et al., "Identification of HLA–A *0201–restricted CTL epitopes encoded by the tumor–specific MAGE–2 gene product," *International Journal of Cancer* 73(1):125–130, 1997.

Wang et al., "Identification of genes differentially over–expressed in lung squamous cell carcinoma using combination of cDNA subtraction and microarray analysis," *Oncogene* 19(12):1519–1528, Mar. 16, 2000.

GenBank Database, Accession No. AAB82295, Oct. 30, 1997.

GenBank Database, Accession No. AAB97457, Jan. 22, 1998.

GenBank Database, Accession No. AAC18597, Jun. 3, 1998.

GenBank Database, Accession No. AAC18598, Jun. 3, 1998.

GenBank Database, Accession No. AAC35208, May 13, 1997.

GenBank Database, Accession No. AAC41285, May 13, 1998.

GenBank Database, Accession No. AAD09223, Jan. 26, 1999.

GenBank Database, Accession No. AAD09827, Jan. 26, 1999.

GenBank Database, Accession No. AAD09828, Jan. 26, 1999.

GenBank Database, Accession No. AAF37203, Mar. 2, 2000.

Genbank Database, Accession No. AC005082, Sep. 8, 1999.

Genbank Database, Accession No. AC021876, Jan. 21, 2000.

GenBank Database, Accession No. AC079780, Feb. 21, 2002.

GenBank Database, Accession No. AC092447, Jul. 4, 2001.

GenBank Database, Accession No. AF117108, Jan. 26, 1999.

GenBank Database, Accession No. AF198254, Mar. 2, 2000.

GenBank Database, Accession No. AL023775, Nov. 23, 1999.

GenBank Database, Accession No. BAB19755, Dec. 20, 2000.

GenBank Database, Accession No. BAB27779, Feb. 8, 2001.

GenBank Database, Accession No. BAB27848, Feb. 8, 2001.

GenBank Database, Accession No. BC019258, Dec. 19, 2001.

GenBank Database, Accession No. NM_006547, Nov. 1, 2000.

GenBank Database, Accession No. NP_034081, Jan. 25, 2000.

GenBank Database, Accession No. NP_006537, Aug. 10, 1999.

GenBank Database, Accession No. NP_006538, Nov. 1, 2000.

GenBank Database, Accession No. NP_006539, Aug. 10, 1999.

GenBank Database, Accession No. NP_571566, Feb. 20, 2002.

GenBank Database, Accession No. NP_076159, Feb. 19, 2001.

GenBank Database, Accession No. U76705, Jan. 26, 1999.

Genbank Database, Accession No. U97188, May 20, 1997.

Geneseq Database (Thomson Derwent), Accession AAL28189, Jan. 24, 2002.

Geneseq Database (Thomson Derwent), Accession AAM93826, Nov. 6, 2001.

Geneseq Database (Thomson Derwent), Accession AAT26750, Oct. 23, 1996.

Geneseq Database (Thomson Derwent), Accession AAU16161 Nov. 7, 2001.

Geneseq Database (Thomson Derwent), Accession AAU16163, Nov. 7, 2001.

Geneseq Database (Thomson Derwent), Accession AAU16164, Nov. 7, 2001.

Geneseq Database (Thomson Derwent), Accession AAU16166, Nov. 7, 2001.

Geneseq Database (Thomson Derwent), Accession AAU16579, Nov. 7, 2001.

Geneseq Database (Thomson Derwent), Accession AAU16583, Nov. 7, 2001.

* cited by examiner

COMPOUNDS AND METHODS FOR THERAPY AND DIAGNOSIS OF LUNG CANCER

REFERENCE TO RELATED APPLICATIONS

This application is a continuation-inpart of U.S. patent application Ser. No. 09/285,479, filed Apr. 2, 1999, which claims priority from and is a continuation of PCT supplication No. PCT/US99/05798, filed Mar. 17, 1999, which claims priority from and is a continuation-in-part of U.S. patent application Ser. No. 09/221,107, filed Dec. 22, 1998, which is a continuation-in-part of U.S. patent application Ser. No. 09/123,912, filed Jul. 27, 1998, now U.S. Pat. No. 6,312,695, which is a continuation-in-part of U.S. patent application Ser. No. 09/040,802, filed Mar. 18, 1998 abandoned.

TECHNICAL FIELD

The present invention relates generally to therapy and diagnosis of cancer, such as lung cancer. The invention is more specifically related to polypeptides comprising at least a portion of a lung tumor protein, and to polynucleotides encoding such polypeptides. Such polypeptides and polynucleotides may be used in vaccines and pharmaceutical compositions for prevention and treatment of lung cancer, and for the diagnosis and monitoring of such cancers.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compositions and methods for the diagnosis and therapy of cancer, such as lung cancer. In one aspect, the present invention provides polypeptides comprising at least a portion of a lung, tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217 and 220–224, (b) variants of a sequence recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217 and 220–224; and (c) complements of a sequence of (a) or (b). In specific embodiments, the polypeptides of the present invention comprise at least a portion of a tumor protein that includes an amino acid sequence selected from the group consisting of sequences recited in any one of SEQ ID NO: 152, 155, 156, 165, 166, 169, 170, 172, 174 and 176 and variants thereof.

The present invention further provides polynucleotides that encode a polypeptide as described above, or a portion thereof (such as a portiornencoding at least 15 amino acid residues of a lung tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines for prophylactic or therapeutic use are provided. Such vaccines comprise a polypeptide or polynucleotide as described above and an immunostimulant.

The present invention further provides pharmaceutical compositions that comprise: (a) an antibody or antigen-binding fragment thereof that specifically binds to a lung tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above, and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a lung tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a lung tumor protein, comprising contacting T cells with one or more of: (i) a polypeptide as described above; (ii) a polynucleotide encoding such a polypeptide; and/or (ii) an antigen presenting cell that expresses such a polypeptide; under conditions and for a time sufficient to permit the stimulation and/or expansion of T cells. Determined T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells determined from a patient with one or more of: (i) a polypeptide comprising at least an immunogenic portion of a lung tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be lung cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent, (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a lung tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mtiNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a lung tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

SEQUENCE IDENTIFIERS

SEQ ID NO: 1 is the determined cDNA sequence for LST-S1-2

SEQ ID NO: 2 is the determined cDNA sequence for LST-S1-28

SEQ ID NO: 3 is the determined cDNA sequence for LST-S1-90

SEQ ID NO: 4 is the determined cDNA sequence for LST-S1-144

SEQ ID NO: 5 is the determined cDNA sequence for LST-S1-133

SEQ ID NO: 6 is the determined cDNA sequence for LST-S1-169

SEQ ID NO: 7 is the determined cDNA sequence for LST-S2-6

SEQ ID NO: 8 is the determined cDNA sequence for LST-S2-11

SEQ ID NO: 9 is the determined cDNA sequence for LST-S2-17

SEQ ID NO: 10 is the determined cDNA sequence for LST-S2-25

SEQ ID NO: 11 is the determined cDNA sequence for LST-S2-39

SEQ ID NO: 12 is a first determined cDNA sequence for LST-S2-43

SEQ ID NO: 13 is a second determined cDNA sequence for LST-S2-43

SEQ ID NO: 14 is the determined cDNA sequence for LST-S2-65

SEQ ID NO: 15 is the determined cDNA sequence for LST-S2-68

SEQ ID NO: 16 is the determined cDNA sequence for LST-S2-72

SEQ ID NO: 17 is the determined cDNA sequence for LST-S2-74

SEQ ID NO: 18 is the determined cDNA sequence for LST-S2-103

SEQ ID NO: 19 is the determined cDNA sequence for LST-S2-N1-1F

SEQ ID NO: 20 is the determined cDNA sequence for LST-S2-N1-2A

SEQ ID NO: 21 is the determined cDNA sequence for LST-S2-N1-4H

SEQ ID NO: 22 is the determined cDNA sequence for LST-S2-N1-5A

SEQ ID NO: 23 is the determined cDNA sequence for LST-S2-N1-6B

SEQ ID NO: 24 is the determined cDNA sequence for LST-S2-N1-7B

SEQ ID NO: 25 is the determined cDNA sequence for LST-S2-N1-7H

SEQ ID NO: 26 is the determined cDNA sequence for LST-S2-N1-8A

SEQ ID NO: 27 is the determined cDNA sequence for LST-S2-N1-8D

SEQ ID NO: 28 is the determined cDNA sequence for LST-S2-N1-9A

SEQ ID NO: 29 is the determined cDNA sequence for LST-S2-N1-9E

SEQ ID NO: 30 is the determined cDNA sequence for LST-S2-N1-10A

SEQ ID NO: 31 is the determined cDNA sequence for LST-S2-N1-10G

SEQ ID NO: 32 is the determined cDNA sequence for LST-S2-N1-11A

SEQ ID NO: 33 is the determined cDNA sequence for LST-S2-N1-12C

SEQ ID NO: 34 is the determined cDNA sequence for LST-S2-N1-12E

SEQ ID NO: 35 is the determined cDNA sequence for LST-S2-B1-3D

SEQ ID NO: 36 is the determined cDNA sequence for LST-S2-B1-6C

SEQ ID NO: 37 is the determined cDNA sequence for LST-S2-B1-5D

SEQ ID NO: 38 is the determined cDNA sequence for LST-S2-B1-5F

SEQ ID NO: 39 is the determined cDNA sequence for LST-S2-B1-6G

SEQ ID NO: 40 is the determined cDNA sequence for LST-S2-B1-8A

SEQ ID NO: 41 is the determined cDNA sequence for LST-S2-B1-8D

SEQ ID NO: 42 is the determined cDNA sequence for LST-S2-B1-10A

SEQ ID NO: 43 is the determined cDNA sequence for LST-S2-B1-9B

SEQ ID NO: 44 is the determined cDNA sequence for LST-S2-B1-9F

SEQ ID NO: 45 is the determined cDNA sequence for LST-S2-B1-12D

SEQ ID NO: 46 is the determined cDNA sequence for LST-S2-I2-2B

SEQ ID NO: 47 is the determined cDNA sequence for LST-S2-I2-5F

SEQ ID NO: 48 is the determined cDNA sequence for LST-S2-I2-6B

SEQ ID NO: 49 is the determined cDNA sequence for LST-S2-I2-7F

SEQ ID NO: 50 is the determined cDNA sequence for LST-S2-I2-8G

SEQ ID NO: 51 is the determined cDNA sequence for LST-S2-I2-9E

SEQ ID NO: 52 is the determined cDNA sequence for LST-S2-I2-12B

SEQ ID NO: 53 is the determined cDNA sequence for LST-S2-H2-2C

SEQ ID NO: 54 is the determined cDNA sequence for LST-S2-H2-1G

SEQ ID NO: 55 is the determined cDNA sequence for LST-S2-H2-4G

SEQ ID NO: 56 is the determined cDNA sequence for LST-S2-H2-3H

SEQ ID NO: 57 is the determined cDNA sequence for LST-S2-H2-5G

SEQ ID NO: 58 is the determined cDNA sequence for LST-S2-H2-9B

SEQ ID NO: 59 is the determined cDNA sequence for LST-S2-H2-10H

SEQ ID NO: 60 is the determined cDNA sequence for LST-S2-H2-12D

SEQ ID NO: 61 is the determined cDNA sequence for LST-S3-2

SEQ ID NO: 62 is the determined cDNA sequence for LST-S3-4

SEQ ID NO: 63 is the determined cDNA sequence for LST-S3-7

SEQ ID NO: 64 is the determined cDNA sequence for LST-S3-8

SEQ ID NO: 65 is the determined cDNA sequence for LST-S3-12

SEQ ID NO: 66 is the determined cDNA sequence for LST-S3-13

SEQ ID NO: 67 is the determined cDNA sequence for LST-S3-14

SEQ ID NO: 68 is the determined cDNA sequence for LST-S3-16

SEQ ID NO: 69 is the determined cDNA sequence for LST-S3-21

SEQ ID NO: 70 is the determined cDNA sequence for LST-S3-22

SEQ ID NO: 71 is the determined cDNA sequence for LST-S1-7

SEQ ID NO: 72 is the determined cDNA sequence for LST-S1-A-1E

SEQ ID NO: 73 is the determined cDNA sequence for LST-S1-A-1G

SEQ ID NO: 74 is the determined cDNA sequence for LST-S1-A-3E

SEQ ID NO: 75 is the determined cDNA sequence for LST-S1-A-4E

SEQ ID NO: 76 is the determined cDNA sequence for LST-S1-A-6D

SEQ ID NO: 77 is the determined cDNA sequence for LST-S1-A-8D

SEQ ID NO: 78 is the determined cDNA sequence for LST-S1-A-10A

SEQ ID NO: 79 is the determined cDNA sequence for LST-S1-A-10C

SEQ ID NO: 80 is the determined cDNA sequence for LST-S1-A-9D

SEQ ID NO: 81 is the determined cDNA sequence for LST-S1-A-10D

SEQ ID NO: 82 is the determined cDNA sequence for LST-S1-A-9H

SEQ ID NO: 83 is the determined cDNA sequence for LST-S1-A-11D

SEQ ID NO: 84 is the determined cDNA sequence for LST-S1-A-12D

SEQ ID NO: 85 is the determined cDNA sequence for LST-S1-A-11E

SEQ ID NO: 86 is the determined cDNA sequence for LST-S1-A-12E

SEQ ID NO: 87 is the determined cDNA sequence for L513S (T3).

SEQ ID NO: 88 is the determined cDNA sequence for L513S contig 1.

SEQ ID NO: 89 is a first determined cDNA sequence for L514S.

SEQ ID NO: 90 is a second determined cDNA sequence for L514S.

SEQ ID NO: 91 is a first determined cDNA sequence for L516S.

SEQ ID NO: 92 is a second determined cDNA sequence for L516S.

SEQ ID NO: 93 is the determined cDNA sequence for L517S.

SEQ ID NO: 94 is the extended cDNA sequence for LST-S1-169 (also known as L519S).

SEQ ID NO: 95 is a first determined cDNA sequence for L520S.

SEQ ID NO: 96 is a second determined cDNA sequence for L520S.

SEQ ID NO: 97 is a first determined cDNA sequence for L521S.

SEQ ID NO: 98 is a second determined cDNA sequence for L521S.

SEQ ID NO: 99 is the determined cDNA sequence for L522S.

SEQ ID NO: 100 is the determined cDNA sequence for L523S.

SEQ ID NO: 101 is the determined cDNA sequence for L524S.

SEQ ID NO: 102 is the determined cDNA sequence for L525S.

SEQ ID NO: 103 is the determined cDNA sequence for L526S.

SEQ ID NO: 104 is the determined cDNA sequence for L527S.

SEQ ID NO: 105 is the determined cDNA sequence for L528S.

SEQ ID NO: 106 is the determined cDNA sequence for L529S.

SEQ ID NO: 107 is a first determined cDNA sequence for L530S.

SEQ ID NO: 108 is a second determined cDNA sequence for L530S.

SEQ ID NO: 109 is the determined full-length cDNA sequence for L531S short form

SEQ ID NO: 110 is the predicted amino acid sequence encoded by SEQ ID NO: 109.

SEQ ID NO: 111 is the determined full-length cDNA sequence for L531S long form

SEQ ID NO: 112 is the predicted amino acid sequence encoded by SEQ ID NO: 111.

SEQ ID NO: 113 is the determined full-length cDNA sequence for L520S.

SEQ ID NO: 114 is the predicted amino acid sequence encoded by SEQ ID NO: 113.

SEQ ID NO: 115 is the determined cDNA sequence for contig 1.

SEQ ID NO: 116 is the determined cDNA sequence for contig 3.

SEQ ID NO: 117 is the determined cDNA sequence for contig 4.

SEQ ID NO: 118 is the determined cDNA sequence for contig 5.

SEQ ID NO: 119 is the determined cDNA sequence for contig 7.

SEQ ID NO: 120 is the determined cDNA sequence for contig 8.

SEQ ID NO: 121 is the determined cDNA sequence for contig 9.

SEQ ID NO: 122 is the determined cDNA sequence for contig 10.

SEQ ID NO: 123 is the determined cDNA sequence for contig 12.

SEQ ID NO: 124 is the determined cDNA sequence for contig 11.

SEQ ID NO: 125 is the determined cDNA sequence for contig 13.

SEQ ID NO: 126 is the determined cDNA sequence for contig 15.

SEQ ID NO: 127 is the determined cDNA sequence for contig 16.

SEQ ID NO: 128 is the determined cDNA sequence for contig 17.

SEQ ID NO: 129 is the determined cDNA sequence for contig 19.

SEQ ID NO: 130 is the determined cDNA sequence for contig 21.

SEQ ID NO: 131 is the determined cDNA sequence for contig 22.

SEQ ID NO: 132 is the determined cDNA sequence for contig 24.

SEQ ID NO: 133 is the determined cDNA sequence for contig 29.

SEQ ID NO: 134 is the determined cDNA sequence for contig 31.

SEQ ID NO: 135 is the determined cDNA sequence for contig 31.

SEQ ID NO: 136 is the determined cDNA sequence for contig 38.

SEQ ID NO: 137 is the determined cDNA sequence for contig 39.

SEQ ID NO: 138 is the determined cDNA sequence for contig 41.

SEQ ID NO: 139 is the determined cDNA sequence for contig 41.

SEQ ID NO: 140 is the determined cDNA sequence for contig 44.

SEQ ID NO: 140 is the determined cDNA sequence for contig 44.
SEQ ID NO: 141 is the determined cDNA sequence for contig 45.
SEQ ID NO: 142 is the determined cDNA sequence for contig 47.
SEQ ID NO: 143 is the determined cDNA sequence for contig 48.
SEQ ID NO: 145 is the determined cDNA sequence for contig 49.
SEQ ID NO: 146 is the determined cDNA sequence for contig 54.
SEQ ID NO: 147 is the determined cDNA sequence for contig 54.
SEQ ID NO: 148 is the determined cDNA sequence for contig 56.
SEQ ID NO: 149 is the determined cDNA sequence for contig 57.
SEQ ID NO: 149 is the determined cDNA sequence for contig 57.
SEQ ID NO: 147 is the determined cDNA sequence for contig 58.
SEQ ID NO: 151 is the full-leneth cDNA sequence for L530S.
SEQ ID NO: 152 is the amino acid sequence en coded by SEQ ID NO: 151
SEQ ID NO: 153 is the full-leneth cDNA sequence of a first variant of L514S
SEQ ID NO: 154 is the full-length cDNA sequence ofa second variant of L514S
SEQ ID NO: 155 is the amino acid sequence encoded by SEQ ID NO: 153.
SEQ ID NO: 156 is the amino acid sequence encoded by SEQ ID NO: 154.
SEQ ID NO: 157 is the determined cDNA sequence for contig 59.
SEQ ID NO: 158 is the full-length cDNA sequence for L763P (also referred to as contig 22).
SEQ ID NO: 159 is the amino acid sequence encoded by SEQ-ID NO: 158.
SEQ ID NO: 160 is the full-length cDNA sequence for L762P (also referred to as contig 17).
SEQ ID NO: 161 is the amino acid sequence encoded by SEQ ID NO: 160.
SEQ ID NO: 162 is the determined cDNA sequence for L515S.
SEQ ID NO: 163 is the full-length cDNA sequence of a first variant of L524S.
SEQ ID NO: 164 is the full-length cDNA sequence of a second variant of L524S.
SEQ ID NO: 165 is the amino acid sequence encoded by SEQ ID NO: 163.
SEQ ID NO: 166 is the amino acid sequence encoded by SEQ ID NO: 164.
SEQ ID NO: 167 is the full-length cDNA sequence of a first variant of L762P.
SEQ ID NO: 168 is the full-length cDNA sequence of a second variant of L762P.
SEQ ID NO: 169 is the amino acid sequence encoded by SEQ ID NO: 167.
SEQ ID NO: 170 is the amino acid sequence encoded by SEQ ID NO: 168.
SEQ ID NO: 171 is the full-length cDNA sequence for L773P (also referred to as contig 56).
SEQ ID NO: 172 is the amino acid sequence encoded by SEQ ID NO: 171.
SEQ ID NO: 173 is an extended cDNA sequence for L519S.
SEQ ID NO: 174 is the predicted amino acid sequence encoded by SEQ ID NO: 174.
SEQ ID NO: 175 is the full-length cDNA sequence for L523S.
SEQ ID NO: 176 is the predicted amino acid sequence encoded by SEQ ID NO: 175.
SEQ ID NO: 177 is the determined cDNA sequence for LST-sub5-7A.
SEQ ID NO: 178 is the determined cDNA sequence for LST-sub5-8G.
SEQ ID NO: 179 is the determined cDNA sequence for LST-sub5-8H.
SEQ ID NO: 180 is the determined cDNA sequence for LST-sub5-10B.
SEQ ID NO: 181 is the determined cDNA sequence for LST-sub5-10H.
SEQ ID NO: 182 is the determined cDNA sequence for LST-sub5-12B.
SEQ ID NO: 183 is the determined cDNA sequence for LST-sub5-11C.
SEQ ID NO: 184 is the determined cDNA sequence for LST-sub6-1c.
SEQ ID NO: 185 is the determined cDNA sequence for LST-sub6-2f
SEQ ID NO: 186 is the determined cDNA sequence for LST-sub6-2G.
SEQ ID NO: 187 is the determined cDNA sequence for LST-sub6-4d.
SEQ ID NO: 188 is the determined cDNA sequence for LST-sub6-4e.
SEQ ID NO: 189 is the determined cDNA sequence for LST-sub6-4f
SEQ ID NO: 190 is the determined cDNA sequence for LST-sub6-3h.
SEQ ID NO: 191 is the determined cDNA sequence for LST-sub6-5d.
SEQ ID NO: 192 is the determined cDNA sequence for LST-sub6-5h.
SEQ ID NO: 193 is the determined cDNA sequence for LST-sub6-6h.
SEQ ID NO: 194 is the determined cDNA sequence for LST-sub6-7a.
SEQ ID NO: 195 is the determined cDNA sequence for LST-sub6-8a.
SEQ ID NO: 196 is the determined cDNA sequence for LST-sub6-7d.
SEQ ID NO: 197 is the determined cDNA sequence for LST-sub6-7e.
SEQ ID NO: 198 is the determined cDNA sequence for LST-sub6-8e.
SEQ ID NO: 199 is the determined cDNA sequence for LST-sub6-7.
SEQ ID NO: 200 is the determined cDNA sequence for LST-sub6-9f.
SEQ ID NO: 201 is the determined cDNA sequence for LST-sub6-9h.

SEQ ID NO: 202 is the determined cDNA sequence for LST-sub6-11b.

SEQ ID NO: 203 is the determined cDNA sequence for LST-sub6-11c.

SEQ ID NO: 204 is the determined cDNA sequence for LST-sub6-12c.

SEQ ID NO: 205 is the determined cDNA sequence for LST-sub6-12e.

SEQ ID NO: 206 is the determined cDNA sequence for LST-sub6-12f.

SEQ ID NO: 207 is the determined cDNA sequence for LST-sub6-11g.

SEQ ID NO: 208 is the determined cDNA sequence for LST-sub6-12g.

SEQ ID NO: 209 is the determined cDNA sequence for LST-sub6-12h.

SEQ ID NO: 210 is the determined cDNA sequence for LST-sub6-II-1a.

SEQ ID NO: 211 is the determined cDNA sequence for LST-sub6-II-2b.

SEQ ID NO: 212 is the determined cDNA sequence for LST-sub6-II-2g.

SEQ ID NO: 213 is the determined cDNA sequence for LST-sub6-II-1h.

SEQ ID NO: 214 is the determined cDNA sequence for LST-sub6-II-4a.

SEQ ID NO: 215 is the determined cDNA sequence for LST-sub6-II-4b.

SEQ ID NO: 216 is the determined cDNA sequence for LST-sub6-II-3e.

SEQ ID NO: 217 is the determined cDNA sequence for LST-sub6-II-4f.

SEQ ID NO: 218 is the determined cDNA sequence for LST-sub6-II-4g.

SEQ ID NO: 219 is the determined cDNA sequence for LST-sub6-II-4h.

SEQ ID NO: 220 is the determined cDNA sequence for LST-sub6-II-5c.

SEQ ID NO: 221 is the determined cDNA sequence for LST-sub6-II-5e.

SEQ ID NO: 222 is the determined cDNA sequence for LST-sub6-II-6f.

SEQ ID NO: 223 is the determined cDNA sequence for LST-sub6-II-5g.

SEQ ID NO: 224 is the determined cDNA sequence for LST-sub6-II-6g.

DETAILED DESCRIPTION OF THE INVENTION

As noted above, the present invention is generally directed to compositions and methods for the therapy and diagnosis of cancer, such as lung cancer. The compositions described herein may include lung tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a lung tumor protein or a variant thereof A "lungr tumor protein" is a protein that is expressed in lung tumor cells at a level that is at least two fold, and preferably at least five fold, greater than the level of expression in a normal tissue, as determined using a representative assay provided herein. Certain lung tumor proteins are tumor proteins that react detectably (within an immunoassay, such as an ELISA or Western blot) with antisera of a patient afflicted with lung cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery human lung tumor proteins. Sequences of polynucleotides encoding specific tumor proteihs are provided in SEQ ID NO: 1–109, 111, 113, 115–151, 153, 154, 157, 158, 160, 162–164, 167, 168, 171, 173, 175 and 177–224.

Lung Tumor Protein Polynucleotides

Any polynucleotide that encodes a lung tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a lung tumor protein. More preferably, a polynucleotide encodes an immunogenic portion of a lung tumor protein. Polynucleotides complementary to any such sequences are also encompassed by the present invention. Polynucleotides may be sing,le-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a lung tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native lung tumor protein or a portion thereof. The term "variants" also encompasses homologous genes of xenogenic origin.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary chance in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358, Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153, Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native lung tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least two fold greater in a lung tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as lung tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a lung tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region.

The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Certain nucleic acid sequences of cDNA molecules encoding portions of lung tumor proteins are provided in SEQ ID NO: 1–109, 111, 113, 115–151, 153, 154, 157, 158, 160, 162–164, 167, 168, 171, 173, 175 and 177–224.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a lung tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to-a patient such that the encoded polypeptide is generated in vivo (e.g., by transfecting antigen-presenting cells, such as dendritic cells, with a cDNA construct encoding a lung tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability inl vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g. avian pox virus). ). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle isi vitro and iii vivo is a liposome (i.e., an artificial membrane vesicle). The preparation and use of such systems is well known in the art.

Lung Tumor Polypeptides

Within the context of the present invention, polypeptides may comprise at least an immunogenic portion of a lung tumor protein or a variant thereof, as described herein. As noted above, a "lung tumor protein" is a protein that is expressed by lung tumor cells. Proteins that are lung tumor proteins also react detectably within an immunoassay (such as an ELISA) with antisera from a patient with lung cancer.

Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a lung tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native lung tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native lung tumor protein. A polypeptide "variant," as used herein, is a polypeptide that differs from a native lung tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (erg., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine, and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences usintg any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, higher eukaryotic and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcis pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a lung tumor protein. As used herein, an antibody, or antigen-binding fragment thereof, is said to "specifically bind" to a lung tumor protein if it reacts at a detectable level (within, for example, an ELISA) with a lung tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Bindingy agents may be further capable of differentiating between patients with and without a cancer, such as lung cancer, using the representative assays provided herein. In other words, antibodies or other binding agents that bind to a lung tumor protein will generate a signal indicating the presence of a cancer in at least about 20% of patients with the disease, and will generate a negYative signal indicating the absence of the disease in at least about 90% of individuals without the cancer. To determine whether a binding agent satisfies this requirement, biological samples (e.g., blood, sera, sputum urine andior tumor biopsies ) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria, however, those of ordinary skill in the art will recognize that binding agyents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding, fragment thereof Antibodies may be prepared by any of a variety of techniques known to those of ordinary skill in the art. See, e.g., Harlow and Lane, *Antibodies: A Laboratory Manual*, Cold Spring Harbor Laboratory. 1988. In general, antibodies can be produced by cell culture techniques, including the Generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogren without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Nionoclonal antibodies mav then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antihodies: A Lahoratory Mamual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkvl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agsents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638.045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjuvates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g. U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a lung tumor protein. Such cells may generally be prepared inl vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc.

Irvine, Calif. (see also U.S. Pat. No. 5,240,856, U.S. Pat. No. 5,215,926, WO 89/06280; WO 91/16116 and WO 92/07243). Alternatively, T cells may be derived from related or unrelated humans, non-human mammals, cell lines or cultures.

T cells may be stimulated with a lung tumor polypeptide, polynucleotide encoding a lung tumor polypeptide and/or an antigen presenting cell (APC) that expresses such a polypeptide. Such stimulation is performed under conditions and for a time sufficient to permit the generation of T cells that are specific for the polypeptide. Preferably, a lung tumor polypeptide or polynucleotide is present within a delivery vehicle, such as a microsphere, to facilitate the generation of specific T cells.

T cells are considered to be specific for a lun, tumor polypeptide if the T cells specifically proliferate, secrete cytokines or kill taret cells coated with the polypeptide or expressing, a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a lung tumor polypeptide (100 ng/ml–100 $\mu$g/ml, preferably 200 ng/ml–25 $\mu$g/ml) for 3–7 days should result in at least a two fold increase in proliferation of the T cells. Contact as described above for 2–3-hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998)). T cells that have been activated in response to a lung tumor polypeptide, polynucleotide or polypeptide-expressing APC may be $CD4^+$ and/or $CD8^+$. Lung tumor protein-specific T cells may be expanded using standard techniques. Within preferred embodiments, the T cells are derived from either a patient or a related, or unrelated, donor and are administered to the patient followino stimulation and expansion.

For therapeutic purposes, $CD4^+$ or $CD8^+$ T cells that proliferate in response to a lung tumor polypeptide, polynucleotide or APC can be expanded in number either inl vitro or in vivo. Proliferation of such T cells iii vitro may be accomplished in a variety of ways. For example, the T cells can be re-exposed to a lung tumor polypeptide, or a short peptide corresponding to an immunogenic portion of such a polypeptide, with or without the addition of T cell growvth factors, such as interleukin-2, and/or stimulator cells that synthesize a lung tumor polypeptide. Alternatively, one or more T cells that proliferate in the presence of a lung tumor protein can be expanded in number by cloning. Methods for cloning cells are well known in the art, and include limiting dilution.

Pharmaceutical Compositions and Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated, see e.g., Fullerton, U.S. Pat. No. 4,235,877). Vaccine preparation is Generally described in for example. M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated itt Ysitit. As noted above, the DNA may be present within anv of a variety of delivery systems known to those of ordinary skill in the art, including nucleic acid expression systems, bacteria and viral expression systems. Numerous gene delivery techniques are well known in the art, such as those described by Rolland, *Crit. Ret. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-patholenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993, and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione adjuvants (e.g., aluminum hydroxide) and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-$\gamma$, TNF$\alpha$, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immuol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, MT) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situt, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells i)? vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing. which correlates with the hitgh expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a lung tumor protein (or portion or other variant thereof) such that the lung tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs iii vivo. In vivo and ex vivo transfection of dendritic cells, for example, may generally be performed using any methods known in the art, such as those described in WO 97/24447, or the gene gun approach described by Mahvi et al., Immunology and cell Biology 75:456–460, 1997. Antigen loading of dendritic cells may be achieved by incubating dendritic cells or progenitor cells with the lung tumor polypeptide, DNA (naked or within a plasmid vector) or RNA; or with antigen-expressing, recombinant bacterium or viruses (e.g. vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as lung cancer. Within such methods, pharmaceutical compositions and vaccines are typically administered to a patient. As used herein, a "patient" refers to anv warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting, cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand anti(,en-specific T cell cultures in order to generate a sufficient number of cells for immunotherapy. In particular, antigen-presentino cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells iii vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a lung tumor protein generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more lung tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as lung cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a lung tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, Antibodies: *A Laboratory Manual*, Cold Spring Harbor Laboratory, 1988. In General, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length lung tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as lass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter groupris added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as lung cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science, for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond. to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about Ipy, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use lung tumor polypeptides to detect antibodies that bind to such polypeptides in a biological sample. The detection of such lung tumor protein specific antibodies may correlate with the presence of a cancer.

A cancer may also, or alternatively, be detected based on the presence of T cells that specifically react with a lung tumor protein in a biological sample. Within certain methods, a biological sample comprising $CD4^+$ and/or $CD8^+$ T cells isolated from a patient is incubated with a lung tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated iti vitro for 2–9 days (typically 4 days) at 37° C. with polypeptide (e.g., 5–25 $\mu$g/ml). It may be desirable to incubate another aliquot of a T cell sample in the absence of lun, tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a lung tumor protein in a biological sample. For example, at least two oligonucleotide primers may be employed in a polymerase chain reaction (PCR) based assay to amplify a portion of a lung tumor cDNA derived from a biological sample, wherein at least one of the oligonucleotide primers is specific for (i.e., hybridizes to) a polynucleotide encoding the lung tumor protein. The amplified cDNA is then separated and detected using techniques well known in the art, such as gel electrophoresis. Similarly, oligonucleotide probes that specifically hybridize to a polynucleotide encoding a lung tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a lung tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–109, 111, 113, 115–151, 153, 154, 157, 158, 160, 162–164, 167, 168, 171, 173, 175 and 177–224. Techniques for both PCR based assays and hybridization assays are well known in the art (see, for example, Mullis et al., *Cold Spring Harbor Symp. Qluant. Biol.*, 51:263, 1987, Erlich ed., *PCR Technology*, Stockton Press, N.Y., 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not, progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple lung tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a lung tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mPNA encoding a lung tumor protein in a biological sample. Such kits generally comprise at least one oligonucleotide probe or primer, as described above, that hybridizes to a polynucleotide encoding a lung tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a lung tumor protein.

The following Examples are offered by way of illustration and not by way of limitation.

EXAMPLE 1

ISOLATION AND CHARACTERIZATION OF cDNA SEQUENCES ENCODING LUNG TUMOR POLYPEPTIDES

This example illustrates the isolation of cDNA molecules encoding lung tumor-specific polypeptides from lung tumor cDNA libraries.

A. Isolation of cDNA Sequences From a Lung Squamous Cell Carcinoma Library

A human lung squamous cell carcinoma cDNA expression library was constructed from poly A+ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent(BRL Life Technologies) as directed by the manufacturer. The poly A+ RNA was then purified using an oligo dT cellulose column as described in Sambrook et al., *Moleclular Cloning: A Laboratory Manual*, Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies, with 100% of clones having, an insert and the average insert size being 2100 base pairs. The normal lung cDNA library contained $1.4 \times 10^6$ independent colonies, with 90% of clones having inserts and the average insert size being 1800 base pairs. For both libraries, sequence analysis showed that the majority of clones had a full length cDNA sequence and were synthesized from mRNA cDNA library subtraction was performed using the above lung squamous cell carcinoma and normal lung cDNA libraries, as described by Hara et al. (*Blood*, 84:189–199, 1994) with some modifications. Specifically, a lung squamous cell carcinoma-specific subtracted cDNA library was generated as follows. Normal tissue cDNA library (80 µg) was digested with BamHI and Xhol, followed by a filling-in reaction with DNA polymerase Klenow fragment. After phenol-chloroform extraction and ethanol precipitation, the DNA was dissolved in 133 µl of $H_2O$, heat-denatured and mixed with 133 µl (133 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 µl) was added and the biotinylation reaction was repeated. After extraction with butanol five times, the DNA was ethanol-precipitated and dissolved in 23 µl $H_2O$ to form the driver DNA.

To form the tracer DNA, 10 µg lung squamous cell carcinoma cDNA library was digested with NotI and SpeI, phenol chloroform extracted and passed through Chroma spin-400 columns (Clontech, Palo Alto, Calif.). Typically, 5 µg of cDNA was recovered after the sizing column. Following ethanol precipitation, the tracer DNA was dissolved in 5 µl $H_2O$. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl $H_2O$, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK⁺ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained 1.76×10⁶ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

In further studies, the subtraction procedure described above was repeated using the above lung squamous cell carcinoma cDNA library as the tracer DNA, and a cDNA library from a pool of normal lung, kidney, colon, pancreas, brain, resting PBMC, heart, skin and esophagus as the driver DNA, with esophagus cDNAs making up one third of the driver material. Since esophagus is enriched in normal epithelial cells, including differentiated squamous cells, this procedure is likely to enrich genes that are tumor specific rather than tissues specific. The cDNA sequences of 48 clones determined in this subtraction are provided in SEQ ID NO: 177–224. The sequences of SEQ ID NO: 177, 178, 180, 181, 183, 187, 192, 195–197, 208, 211, 212, 215, 216, 218 and 219 showed some homology to previously identified genes. The sequences of SEQ ID NO: 179, 182, 184–186, 188–191, 193, 194, 198–207, 209 210, 213, 214, 217, 220 and 224 showed some homology to previously determined ESTs. The sequence of SEQ ID NO: 221–223 showed no homology to any previously determined sequence.

B. Isolation of cDNA Sequences From a Lung Adenocarcinoma Library

A human lung adenocarcinoma cDNA expression library was constructed as described above. The library contained 3.2×10⁶ independent colonies, with 100% of clones having an insert and the average insert size being 1500 base pairs. Library subtraction was performed as described above usin, the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

EXAMPLE 2

DETERMINATION OF TISSUE SPECIFICITY OF LUNG TUMOR POLYPEPTIDES

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 µg of total RINA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 µl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2–12-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCP was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lun, tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung, subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lun, squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99; that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Additionally, the full-length cDNA sequences for L503S and L514S (variants 1 and 2), are provided in SEQ ID NO: 151, 153 and 154, respectively, with the corresponding predicted amino acid sequence being provided in SEQ ID NO: 152, 155 and 156. Due to polymorphisms, the clone L531S appears to have two forms. A first determined full-length cDNA sequence for L531S is provided in SEQ ID NO: 109, with the corresponding predicted amino acid sequence being provided in SEQ ID NO: 110. A second determined full-length cDNA sequence for L531S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion. Similarly, L514S also has two alternatively spliced forms; the first variant cDNA is listed as SEQ ID NO: 153, with the corresponding amino acid sequence being provided in SEQ ID NO: 155. The second variant form of L514S full-length cDNA is provided in SEQ ID NO: 154, with its corresponding amino acid sequence being provided in SEQ ID NO: 156.

Full length cloning for L524S (SEQ ID NO: 101) yielded two variants (SEQ ID NO: 163 and 164) with the corresponding predicted amino acid sequences of SEQ ID NO: 165 and 166, respectively. Both variants have been shown to encode parathyroid hormone-related peptide.

Attempts to isolate the full-length cDNA for L519S, resulted in the isolation of the extended cDNA sequence provided in SEQ ID NO: 173, which contains a potential open reading frame. The predicted amino acid sequence encoded by the sequence of SEQ ID NO: 173 is provided in SEQ ID NO: 174. Additionally, the full-length cDNA sequence for L523S, a known gene, is provided in SEQ ID NO: 175, with the corresponding predicted amino acid sequence provided in SEQ ID NO: 176.

Comparison of the sequences of L514S and L531S (SEQ ID NO: 87 and 88, 89 and 90, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114. Subsequent microarray analysis has shown L520S to be overexpressed in breast tumors in addition to lun, squamous tumors.

Further analysis has demonstrated that L529S (SEQ ID NO: 106 and 115), L525S (SEQ ID NO: 102 and 120) and L527S (SEQ ID NO: 104) are cytoskeletal components and potentially squamous cell specific proteins. L529S is connexin 26, a gap junction protein. It is highly expressed in lung squamous tumor 9688T, and moderately over-expressed in two others. However, lower level expression of connexin 26 is also detectable in normal skin, colon, liver and stomach. The over-expression of connexin 26 in some breast tumors has been reported and a mutated form of L529S may result in over-expression in lung tumors. L525S is plakophilin 1, a desmosomal protein found in plaque-bearing adhering junctions of the skin. Expression levels for L525S mRNA is highly elevated in three out of four lung squamous tumors tested, and in normal skin. L527S has been identified as keratin 6 isoform, type II 58 Kd keratin, and cytokeratin 13 and shows over-expression in squamous tumors and low expression in normal skin, breast and colon tissues. Notably, keratin and keratin-related oenes have been extensively documented as potential markers for lung cancer including CYFRA2.1 (Pastor, A., et al, *Eur. Respir. J.*, 10:603–609, 1997). L513 S (SEQ ID NO: 87 and 88) shows moderate over-expression in several tumor tissues tested, and encodes a protein that was first isolated as a pemphigus vulgaris antigen.

L520S (SEQ ID NO: 95 and 96) and L521S (SEQ ID NO: 97 and 98) are highly expressed in lung squamous tumors, and L520S is up-regulated in normal salivary gland and L521 S is over-expressed in normal skin. Both belong to a family of small proline rich proteins and represent markers for fully differentiated squamous cells. L521S has been described as a specific marker for lung squamous tumor (Hu, R., et al, *Lung Cancer*, 20:25–30, 1998). L515S (SEQ ID NO: 162) encodes IGF-β2 and L516S is an aldose reductase homologue and both are moderately expressed in lung squamous tumors and in normal colon. Notably, L516S (SEQ ID NO: 91 and 92) is up-regulated in metastatic tumors but not primary lung adenocarcinoma, an indication of its potential role in metatasis and a potential prognostic marker. L522S (SEQ ID NO: 99) is moderately over-expressed in lung squamous tumors with minimum expression in normal tissues. L522S has been shown to belong to a class IV alcohol dehydrogenase, ADH7, and its expression profile suggests it is a squamous cell specific antigen. L523S (SEQ ID NO: 100) is moderately over-expressed in lung squamous tumor, human pancreatic cancer cell lines and pancreatic cancer tissues, suggesting this gene may be a shared anti,en between pancreatic and lung squamous cell cancer.

L524S (SEQ ID NO: 101) is over-expressed in the majority of squamous tumors tested and is homologous with parathyroid hormone-related peptide (PTHrP), which is best known to cause humoral hypercalcaemia associated with malignant tumors such as leukemia, prostate and breast cancer. It is also believed that PTHrP is most commonly associated with squamous carcinoma of lung and rarely with lung adenocarcinoma (Davidson, L. A., et al, *J Pathol.*, 178: 398–401, 1996). L528S (SEQ ID NO: 105) is highly over-expressed in two lung squamous tumors with moderate expression in two other squamous tumors, one lung adenocarcinoma and some normal tissues, including skin, lymph nodes, heart, stomach and lung. It encodes the NMB gene that is similar to the precursor of melanocyte specific gene Pmel17, wfhich is reported to be preferentially expressed in low-metastatic potential melanoma cell lines. This suggests that L528S may be a shared antigen in both melanoma and lung squamous cell carcinoma. L526S (SEQ ID NO: 103) is overexpressed in all lung squamous cell tumor tissues tested and has been shown to share homology with a gene (ATM) in which a mutation causes ataxia telangiectasia, a genetic disorder in humans causing a predisposition to cancer, among other symptoms. ATM encodes a protein that activates p53 mediated cell-cycle checkpoint through direct binding and phosphorylation of the p53 molecule. Approximately 40% of lung cancer is associated with p53 mutations, and it is speculated that over-expression of ATM is a result of compensation for loss of p53 function, but it is unknown whether over-expression is the cause of result of lung squamous cell carcinoma. Additionally, expression of L526S (ATM) is also detected in a metastatic but not lung adenocarcinoma, suggesting a role in metastasis.

Expression of L523S (SEQ ID NO: 175), was also examined by real time RT-PCR as described above. In a first study using a panel of lung squamous tumors, L523S was found to be expressed in 4/7 lung squamous tumors, 2/3 head and neck squamous tumors and 2/2 lung adenocarcinomas, with low level expression being observed in skeletal muscle, soft palate and tonsil. In a second study using a lung adenocarcinoma panel, expression of L523S was observed in 4/9 primary adenocarcinomas, 2/2 lung pleural effusions, 1/1 metastatic lung adenocarcinomas and 2/2 lung squamous tumors, with little expression being observed in normal tissues.

Expression of L523S in lung tumors and various normal tissues was also examined by Northern blot analysis, using, standard techniques. In a first study, L523S was found to be expressed in a number of lung adenocarcinomas and squamous cell carcinomas, as well as normal tonsil. No expression was observed in normal lung. In a second study usingy a normal tissue blot (HB-12) from Clontech, no expression was observed in brain, skeletal muscle, colon, thymus, spleen, kidney, liver, small intestine, lung or PBMC, although there was strong expression in placenta.

EXANPLE 3

ISOLATION AND CHARACTERIZATION OF LUNG TUMOR POLYPEPTIDES BY PCR-BASED SUBTRACTION

Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcdoned into the vector P7- Adv vector (Clontech, Palo Alto, Calif.) and transformed into DH5α *E. coli* (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the the EMBL and GenBank databases, as described above, revealed no significant homologies to 13 of these clones, hereinafter referred to as Configs 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in U.S. patent application Ser. No. 09/123,912, filed Jul. 27, 1998. To the best of the inventors' knowledge, none of these sequences have been previously shown to be differentially over-expressed in lung tumors.

mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin, (all derived from human) were determined by RT-PCR as described above. Expression levels using microarray technology, as described above, were examined in one sample of each tissue type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed moderate expression in skin and soft palate, and lowered expression levels in resting PBMC, large intestine, salivary gland, tonsil, pancreas, esophagus, and colon. Contig 11 (SEQ ID NO: 124) was found to be expressed in all head and neck squamous cell tumors tested (17/17): highly expressed in 14/17, and moderately expressed in 3/17. Additionally, expression in lung squamous tumors showed high expression in 3/12 and moderate in 4/12. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17): highly expressed in 12/17, and moderately expressed in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 did show low to moderate reactivity to resting PBMC, salivary gland, bladder, pancreas, tonsil, skin, esophagus, and large intestine, as well as high expression in soft palate. Contig 16 (SEQ ID NO: 127) was found to be moderately expressed in some head and neck squamous cell tumors (6/17) and one lung squamous tumor; while showing no expression in any normal lung samples tested. Contig 16 did show low reactivity to resting PBMC, large intestine, skin, salivary gland, and soft palate. Contig 17 (SEQ ID NO: 128) was shown to be expressed in all head and neck squamous cell tumors tested (17/17): highly expressed in 5/17, and moderately expressed in 12/17. Expression levels in lung squamous tumors showed one tumor sample with high expression and 3/12 with moderate levels. Contig 17 was negative for 2/4 normal lung samples, with the remaining samples having only low expression. Additionally, low level expression was found in esophagus and soft palate. Contig 19 (SEQ ID NO: 129) was found to be expressed in most head and neck squamous cell tumors tested (11/17); with two samples having high levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 showed low expression levels in esophagus, resting PBMIC, salivary gland, bladder, soft palate and pancreas.

Contig 22 (SEQ ID NO: 131), was shown to be expressed in most head and neck squamous cell tumors tested (13/17) with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 showed low expression in skin, salivary gland and soft palate. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 showed low expression in skin, salivary gland and soft palate. Contig 29 (SEQ ID NO: 133) was expressed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed low to moderate expression in large intestine, skin, salivary gland, pancreas, tonsil, heart and soft palate. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=13). Contig 47 was negative for 2/4 normal lung samples, with the remaining two samples having moderate expression. Also, Contig 47 showed moderate expression in large intestine, and pancreas, and low expression in skin, salivary gland, soft palate, stomach, bladder, resting PBMC, and tonsil.

Contig 48 (SEQ ID NO: 143) was expressed in all head and neck squamous cell tumors tested (17/17): higihly expressed in 8/17 and moderately expressed in 7/17, with low expression in two samples. Expression levels in lung squamous tumors were high to moderate in three samples (n=13). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart. Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil. Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary gland, soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung squamous tumors showed low to moderate levels in three out of thirteen samples. Contig 58 was negative for 3/4 normal lung samples, with one sample having low expression. Moderate expression levels in skin, large intestine, and resting PBMC were demonstrated, as well as low expression in salivary gland, soft palate, pancreas, and bladder. Contig 59 (SEQ ID NO: 157) was expressed in some head, neck, and lung, squamous tumors. Low level expression of Contig 59 was also detected in salivary gland and large intestine.

The full-length cDNA sequence for Contig 22, also referred to as L763P, is provided in SEQ ID NO: 158, with the corresponding predicted amino acid sequence being provided in SEQ ID NO: 159. Real-time RT-PCR analysis of L763P revealed that is it highly expressed in 3/4 lung squamous tumors as well as 4/4 head and neck squamous tumors, with low level expression being observed in normal brain, skin, soft pallet and trachea.

The full-length cDNA sequence incorporating Contigs 17, 19, and 24, referred to as L762P, is provided in SEQ ID NO: 160, with the corresponding predicted amino acid sequence being provided in SEQ ID NO: 161. Further analysis of L762P has determined it to be a type I membrane protein and two additional variants have been sequenced. Variant 1

(SEQ ID NO: 167, with the corresponding amino acid sequence in SEQ ID NO: 169) is an alternatively spliced form of SEQ ID NO: 160 resulting in deletion of 503 nucleotides, as well as deletion of a short segment of the expressed protein. Variant 2 (SEQ ID NO: 168, with the corresponding amino acid sequence in SEQ ID NO: 170) has a two nucleotide deletion at the 3' coding region in comparison to SEQ ID NO: 160, resulting in a secreted form of the expressed protein. Real-time RT-PCR analysis of L762P revealed that is over-expressed in 3/4 lung squamous tumors and 4/4 head & neck tumors, with low level expression being observed in normal skin, soft pallet and trachea.

The full-length cDNA sequence for contig 56 (SEQ ID NO: 148), also referred to as L773P, is provided in SEQ ID NO: 171, with the predicted amino acid sequence in SEQ ID NO: 172. L773P was found to be identical to dihydroxyl dehydrogenase at the 3' portion of the gene, with divergent 5' sequence. As a result, the 69 N-terminal amino acids are unique. Real-time PCR revealed that L773P is highly expressed in lung squamous tumor and lung adenocarcinoma, with no detectable expression in normal tissues. Subsequent Northern blot analysis of L773P demonstrated that this transcript is differentially over-expressed in squamous tumors and detected at approximately 1.6 Kb in primary lung tumor tissue and approximately 1.3 Kb in primary head and neck tumor tissue.

Subsequent microarray analysis has shown Contig 58, also referred to as L769S (SEQ ID NO: 150), to be over-expressed in breast tumors in addition to lung squamous tumors.

EXAMPLE 4

SYNTHESIS OF POLYPEPTIDES

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for determining the presence of a lung cancer in a patient, comprising the steps of:

(a) contacting a biological sample obtained from a patient with at least two oligonucleotides under conditions wherein said oligonucleotides are effective for amplifying a polynucleotide sequence of SEQ ID NO: 175 in a reverse transcription polymerase chain reaction;

(b) detecting in the sample an amount of polynucleotide amplified in step (a); and (c) comparing the amount of the polynucleotide amplified in step (a) to a predetermined cut-off value, and therefrom determining the presence of a cancer in the patient.

2. A method for monitoring the progression of a lung cancer in a patient, comprising the steps of:

(a) contacting a biological sample obtained from a patient with at least two oligonucleotides under conditions wherein said oligonucleotides are effective for amplifying a polynucleotide sequence of SEQ ID NO: 175 in a reverse transcription polymerase chain reaction;

(b) detecting in the sample an amount of polynucleotide amplified in step (a);

(c) repeating steps (a) and (b) using a biological sample obtained from the patient at a subsequent point in time; and (d) comparing the amount of polynucleotide detected in step (c) to the amount detected in step (b) and therefrom monitoring the progression of the cancer in the patient.

3. The method of any one of claims 1 and 2, wherein said oligonucleotides consist of 10 to 40 consecutive residues of SEQ ID NO: 175 or 10 to 40 consecutive residues of the complement of SEQ ID NO: 175.

4. The method of any one of claims 1 and 2, wherein the biological sample is derived from a human lung tissue sample.

5. The method of any one of claims 1 and 2, wherein the biological sample is derived from a human lung tissue sample suspected of being cancerous.

6. The method of any one of claims 1 and 2, wherein the cut-off value is determined using a normal human lung tissue sample.

* * * * *

SEQUENCE LISTING

```
<160> NUMBER OF SEQ ID NOS:   224

<210> SEQ ID NO 1
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 1
gcagagacag actggtggtt gaacctggag gtgccaaaaa agccagctgc gggcccagga      60
cagctgccgt gagactcccg atgtcacagg cagtctgtgt ggttacagcg cccctcagtg     120
ttcatctcca gcagagacaa cggaggaggc tcccaccagg acggttctca ttatttatat     180
gttaatatgt ttgtaaactc atgtacagtt tttttttgggg gggaagcaat gggaanggta    240
naaattacaa atagaatcat ttgctgtaat ccttaaatgg caaacggtca ggccacgtga     300
aaaaaaaaaa aaaaa                                                     315

<210> SEQ ID NO 2
<211> LENGTH: 380
<212> TYPE: DNA
<213> ORGANISM: Homo sapien

<400> SEQUENCE: 2
atttaggctt aagattttgt ttacccttgt tactaaggag caaattagta ttaaagtata      60
atatatataa acaaatacaa aaagtttga gtggttcagc tttttttattt tttttaatgg    120
```

-continued

```
cataactttt aacaacactg ctctgtaatg ggttgaactg tggtactcag actgagataa    180
ctgaaatgag tggatgtata gtgttattgc ataattatcc cactatgaag caaagggact    240
ggataaattc ccagtctaga ttattagcct ttgttaacca tcaagcacct agaagaagaa    300
ttattggaaa ttttgtcctc tgtaactggc actttggggt gtgacttatc ttttgccttt    360
gtaaaaaaaa aaaaaaaaaa                                                380

<210> SEQ ID NO 3
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 3
ttgtaagtat acaattttag aaaggattaa atgttattga tcattttact gaatactgca     60
catcctcacc atacaccatc cactttccaa taacatttaa tcctttctaa aattgtaagt    120
atacaattgt actttctttg gattttcata acaaatatac catagactgt taattttatt    180
gaagtttcct taatggaatg agtcattttt gtcttgtgct tttgaggtta cctttgcttt    240
gacttccaac aatttgatca tatagtgttg agctgtggaa atctttaagt ttattctata    300
gcaataattt ctattnnnag anccnggnn naaaannann annaaa                    346

<210> SEQ ID NO 4
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 4
actagtctca ttactccaga attatgctct tgtacctgtg tggctgggtt tcttagtcgt     60
tggtttggtt tggttttttg aactggtatg tagggtggtt cacagttcta atgtaagcac    120
tctcttctcc aagttgtgct tgtggggac aatcattctt tgaacattag agaggaaggc    180
agttcaagct gttgaaaaga ctattgctta tttttgtttt taaagaccta cttgacgtca    240
tgtggacagt gcacgtgcct tacgctacat cttgttttct aggaagaagg ggatgcnggg    300
aaggantggg tgctttgtga tggataaaac gnctaaataa cacacccttta cattttgaaa    360 aaaacaaaac aa                                                        372

<210> SEQ ID NO 5
<211> LENGTH: 698
<212> TYPE: DNA
<213> ORGANISM: Homo sapien
<220> FEATURE:
<221> NAME/KEY: misc_feature
<222> LOCATION: (1)...(698)
<223> OTHER INFORMATION: n = A,T,C or G

<400> SEQUENCE: 5
actagtanga tagaaacact gtgtcccgag agtaaggaga gaagctacta ttgattagag     60
cctaacccag gttaactgca agaagaggcg ggatactttc agctttccat gtaactgtat    120
gcataaagcc aatgtagtcc agtttctaag atcatgttcc aagctaactg aatcccactt    180
caatacacac tcatgaactc ctgatggaac aataacaggc ccaagcctgt ggtatgatgt    240
```

-continued

```
gcacacttgc tagactcaga aaaaatacta ctctcataaa tgggtgggag tattttgggt      300
gacaacctac tttgcttggc tgagtgaagg aatgatattc atatnttcat ttattccatg      360
gacatttagt tagtgctttt tatataccag gcatgatgct gagtgacact cttgtgtata      420
tntccaaatn ttngtncngt cgctgcacat atctgaaatc ctatattaag antttcccaa      480
natgangtcc ctggtttttc cacgccactt gatcngtcaa ngatctcacc tctgtntgtc      540
ctaaaaccnt ctnctnnang gttagacngg acctctcttc tcccttcccg aanaataag       600 tgtgngaaga nanccncncn cccccctncn tncnncctng ccngctnnnc cncntgtngg      660
gggngccgcc cccgcggggg gaccccccn ttttcccc                              698
```

<210> SEQ ID NO 6
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 6

```
actagtcaaa aatgctaaaa taatttggga gaaaatattt tttaagtagt gttatagttt       60
catgtttatc ttttattatg tnttgtgaag ttgtgtcttt tcactaatta cctatactat      120
gccaatattt cctatatatct atccataaca tttatactac atttgtaaga gaatatgcac     180
gtgaaactta acactttata aggtaaaaat gaggtttcca agatttaata atctgatcaa     240
gttcttgtta ttttccaaata gaatggactt ggtctgttaa ggggctaagg gagaagaaga    300
agataaggtt aaaagttgtt aatgaccaaa cattctaaaa gaaatgcaaa aaaaaattta     360
ttttcaagcc ttcgaactat ttaaggaaag caaaatcatt tcctanatgc atatcatttg    420 tgaganttc tcantaatat cctgaatcat tcatttcagc tnaggcttca tgttgactcg    480
atatgtcatc tagggaaagt ctatttcatg gtccaaacct gttgccatag ttggtnaggc    540
tttcctttaa ntgtgaanta ttnacangaa attttctctt tnanagttct tnatagggtt    600 agggggtgtgg gaaaagcttc taacaatctg tagtgttncg tgttatctgt ncagaaccan   660
aatnacggat cgnangaagg actgggtcta tttacangaa cgaatnatct ngttnnntgt   720
gtnnncaact ccngggagcc                                                740
```

<210> SEQ ID NO 7
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 7

```
gctggggagc tcggcatggc ggtccccgct gcagccatgg ggccctcggc gttgggccag       60
agcggccccg gctcgatggc cccgtggtgc tcagtgagca gcggcccgtc gcgctacgtg     120
cttgggatgc aggagctgtt ccggggccac agcaagaccg cgagttcctg cgcacagcg     180 ccaaggtgca ctcggtggcc tggagttgcg acgggcgtcg cctacctcgg ggtcttcgac    240
aagacgccac gtcttcttgc tgganaanga ccgttggtca aagaaaacaa ttatcgggga   300
catggggata gtgtggacca ctttgttggc atccaagtaa tcctgaccta tttgttacgg    360
```

```
cgtctggaga taaaaccatt cgcatctggg atgtgaggac tacaaaatgc attgccactg    420
tgaacactaa aggggagaac attaatatct gctggantcc tgatgggcan accattgctg    480
tagcnacaag gatgatgtgg tgactttatt gatgccaaga acccccgttc caaagcaaaa    540
aaacanttcc aanttcgaag tcaccnaaat ctcctggaac aatgaacatn aatatnttct    600
tcctgacaat ggnccttggg tgtntcacat cctcagctnc cccaaaactg aancctgtnc    660 natccacccc                                                           670
```

<210> SEQ ID NO 8
<211> LENGTH: 689
<212> TYPE: DNA
<213> ORGANISM: Homo sapien
<220> FEATURE:
<221> NAME/KEY: misc_feature
<222> LOCATION: (1)...(689)
<223> OTHER INFORMATION: n = A,T,C or G

<400> SEQUENCE: 8

```
actagtatct aggaatgaac agtaaaagag gagcagttgg ctacttgatt acaacagagt     60
aaatgaagta ctggatttgg gaaaacctgg ttttattaga acatatggaa tgaaagccta    120
cacctagcat tgcctactta gcccctgaa ttaacagagc ccaattgaga caaaccctg      180 gcaacaggaa attcaaggga gaaaagtaa gcaacttggg ctaggatgag ctgactccct    240
tagagcaaag ganagacagc ccccattacc aaataccatt tttgcctggg gcttgtgcag    300
ctggcagtgt tcctgcccca gcatggcacc ttatngtttt gatagcaact tcgttgaatt    360 ttaccaact tattacttga aattataata tagcctgtcc gtttgctgtn tccaggctgt    420
gatatatntt cctagtggtt tgactttnaa aataaatnag gtttantttt ctcccccnn    480 cnntnctncc nntcnctcnn cnntccccc cnctcngtcc tccnnnnttn gggggggccn    540
cccccncggn ggacccccct ttggtccctt agtggaggtt natggcccct ggnnttatcc    600
nggccntann tttccccgtn nnaaatgntt cccctccca ntcccnccac ctcaanccgg    660
aagcctaagt ttntaccctg ggggtcccc                                     689
```

<210> SEQ ID NO 9
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 9

```
gtccactctc ctttgagtgt actgtcttac tgtgcactct gtttttcaac tttctagata     60
taaaaaatgc ttgttctata gtggagtaag agctcacaca cccaaggcag caagataact    120 gaaaaagcg aggctttttt gccaccttgg taaaggccag ttcactgcta tagaactgct    180
ataagcctga agggaagtag ctatgagact ttccattttt cttagttctc ccaataggct    240
ccttcatgga aaaaggcttc ctgtaataat tttcacctaa tgaattagca gtgtgattat    300
ttctgaaata agagacaaat tgggccgcag agtcttcctg tgatttaaaa taaacaaccc    360
aaagttttgt ttggtcttca ccaaaggaca tactctaggg ggtatgttgt tgaagacatt    420
caaaaacatt agctgttctg tctttcaatt tcaagttatt ttggagactg cctccatgtg    480
agttaattac tttgctctgg aactagcatt attgtcatta tcatcacatt ctgtcatcat    540
catctgaata atattgtgga tttcccccctc tgcttgcatc ttcttttgac tcctctggga    600
```

```
anaaatgtca aaaaaaaagg tcgatctact cngcaaggnc catctaatca ctgcgctgga    660
aggacccnct gccc                                                     674

<210> SEQ ID NO 10
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 10
actagtctgc tgatagaaag cactatacat cctattgttt ctttctttcc aaaatcagcc     60
ttctgtctgt aacaaaaatg tactttatag agatggagga aaggtctaa tactacatag    120 ccttaagtgt ttctgtcatt gttcaagtgt attttctgta acagaaacat atttggaatg    180
tttttctttt cccttataa attgtaattc ctgaaatact gctgctttaa aaagtcccac     240
tgtcagatta tattatctaa caattgaata ttgtaaatat acttgtctta cctctcaata    300
aaagggtact tttctattan nnagnngnnn gnnnnataaa anaaaa                   346

<210> SEQ ID NO 11
<211> LENGTH: 602
<212> TYPE: DNA
<213> ORGANISM: Homo sapien

<400> SEQUENCE: 11
actagtaaaa agcagcattg ccaaataatc cctaattttc cactaaaaat ataatgaaat     60
gatgttaagc ttttttgaaaa gtttaggtta aacctactgt tgttagatta atgtatttgt   120 tgcttcccttt tatctggaat gtggcattag cttttttatt ttaaccctct ttaattctta   180
ttcaattcca tgacttaagg ttggagagct aaacactggg attttttggat aacagactga   240 cagttttgca taattataat cggcattgta catagaaagg atatggctac cttttgttaa    300
atctgcactt tctaaatatc aaaaaaggga aatgaagtta taaatcaatt tttgtataat    360
ctgtttgaaa catgagttttt atttgcttaa tattagggct ttgccccttt tctgtaagtc   420
tcttgggatc ctgtgtagaa ctgttctcat taaacaccaa acagttaagt ccattctctg    480
gtactagcta caaattcggt ttcatattct acttaacaat ttaaataaac tgaaatattt    540
ctagatggtc tacttctgtt catataaaaa caaaacttga tttccaaaaa aaaaaaaaaa    600
aa                                                                   602

<210> SEQ ID NO 12
<211> LENGTH: 685
<212> TYPE: DNA
<213> ORGANISM: Homo sapien
<220> FEATURE:
<221> NAME/KEY: misc_feature
<222> LOCATION: (1)...(685)
<223> OTHER INFORMATION: n = A,T,C or G

<400> SEQUENCE: 12
actagtcctg tgaaagtaca actgaaggca gaaagtgtta ggattttgca tctaatgttc     60
attatcatgg tattgatgga cctaagaaaa taaaaattag actaagcccc caaataagct    120
gcatgcattt gtaacatgat tagtagattt gaatatatag atgtagtatn ttgggtatct    180
aggtgtttta tcattatgta aaggaattaa agtaaaggac tttgtagttg ttttttattaa   240
```

| | |
|---|---|
| atatgcatat agtagagtgc aaaaatatag caaaaatana aactaaaggt agaaaagcat | 300 |
| tttagatatg ccttaatnta nnaactgtgc caggtggccc tcggaataga tgccaggcag | 360 |
| agaccagtgc ctgggtggtg cctcccctttg tctgcccccc tgaagaactt ccctcacgtg | 420 |
| angtagtgcc ctcgtaggtg tcacgtggan tantgggane aggccgnncn gtnanaagaa | 480 |
| ancanngtga nagtttcncc gtngangcng aactgtccct gngccnnnac gctcccanaa | 540 |
| cntntccaat ngacaatcga gtttccnnnc tccngnaacc tngccgnnnn cnngcccnnc | 600 |
| cantntgnta acccgcgcc cggatcgctc tcnnntcgtt ctcncncnaa ngggntttcn | 660 |
| cnnccgccgt cncnncccg cnncc | 685 |

<210> SEQ ID NO 13
<211> LENGTH: 694
<212> TYPE: DNA
<213> ORGANISM: Homo sapien
<220> FEATURE:
<221> NAME/KEY: misc_feature
<222> LOCATION: (1)...(694)
<223> OTHER INFORMATION: n = A,T,C or G

<400> SEQUENCE: 13

| | |
|---|---|
| cactagtcac tcattagcgt tttcaatagg gctcttaagt ccagtagatt acgggtagtc | 60 |
| agttgacgaa gatctggttt acaagaacta attaaatgtt tcattgcatt tttgtaagaa | 120 |
| cagaataatt ttataaaatg tttgtagttt ataattgccg aaaataattt aaagacactt | 180 |
| tttctctgtg tgtgcaaatg tgtgtttgtg atccattttt tttttttttt taggacacct | 240 |
| gtttactagc tagctttaca atatgccaaa aaaggatttc tccctgaccc catccgtggt | 300 |
| tcaccctctt ttcccccccat gcttttttgcc ctagtttata acaaaggaat gatgatgatt | 360 |
| taaaaagtag ttctgtatct tcagtatctt ggtcttccag aaccctctgg ttgggaaggg | 420 |
| gatcatttttt tactggtcat ttcccttttgg agtgtactac tttaacagat ggaaagaact | 480 |
| cattggccat ggaaacagcc gangtgttgg gagccagcag tgcatggcac cgtccggcat | 540 |
| ctggcntgat tggtctggct gccgtcattg tcagcacagt gccatgggac atggggaana | 600 |
| ctgactgcac ngccaatggt tttcatgaag aatacngcat ncncngtgat cacgtnancc | 660 |
| angacgctat gggggncana gggccanttg cttc | 694 |

<210> SEQ ID NO 14
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 14

| | |
|---|---|
| cagccgcctg catctgtatc cagcgccang tcccgccagt cccagctgcg cgcgccccc | 60 |
| agtcccgnac ccgttcggcc cangctnagt tagncctcac catnccggtc aaaggangca | 120 |
| ccaagtgcat caaatacctg cngtncggat ntaaattcat cttctggctt gccgggattg | 180 |
| ctgtccntgc cattggacta nggctccgat ncgactctca gaccanganc atcttcganc | 240 |
| naganactaa tnatnattnt tccagcttct acacaggagt ctatattctg atcggatccg | 300 |
| gcncccctcnt gatgctggtg ggcttcctga gctgctgcgg ggctgtgcaa gagtcccant | 360 |
| gcatgctggg actgttcttc ggcttctctct tggtgatatn cgccattgaa atacctgcgg | 420 |
| ccatctgggg atattccact ncgatnatgt gattaaggaa ntccacggag ttttacaagg | 480 |

-continued

```
acacgtacaa cnacctgaaa accnnggatg anccccaccg ggaancnctg aangccatcc      540
actatgcgtt gaactgcaat ggtttggctg gggnccttga acaatttaat cncatacatc      600
tggccccann aaaggacntn ctcgaccct tcnccgtgna attcgttct gatnccatca        660 cagaagtctc gaacaatcc                                                   679
```

<210> SEQ ID NO 15
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 15

```
actagtggat aaaggccagg gatgctgctc aacctcctac catgtacagg gacgtctccc       60
cattacaact acccaatccg aagtgtcaac tgtgtcagga ctaanaaacc ctggttttga      120
ttaaaaaagg gcctgaaaaa aggggagcca caaatctgtc tgcttcctca cnttantcnt      180
tggcaaatna gcattctgtc tcnttggctg cngcctcanc ncaaaaaanc ngaactcnat      240
cnggcccagg aatacatctc ncaatnaacn aaattganca aggcnntggg aaatgccnga      300
tgggattatc ntccgcttgt tgancttcta agtttcnttc ccttcattcn accctgccag      360
ccnagttctg ttagaaaaat gccngaattc naacnccggt tttcntactc ngaatttaga      420
tctncanaaa cttcctggcc acnattcnaa ttnanggnca cgnacanatn ccttccatna      480
ancncacccc acntttgana gccangacaa tgactgcntn aantgaaggc ntgaaggaan      540
aactttgaaa ggaaaaaaaa ctttgtttcc ggcccttcc aacncttctg tgttnancac       600
tgccttctng naaccctgga agcccngnga cagtgttaca tgttgttcta nnaaacngac      660
ncttnaatnt cnatcttccc nanaacgatt ncncc                                 695
```

<210> SEQ ID NO 16
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 16

```
cgccgaagca gcagcgcagg ttgtccccgt ttccctccc ccttcccttc tccggttgcc        60
ttcccgggcc ccttacactc cacagtcccg gtcccgccat gtcccagaaa caagaagaag      120
agaaccctgc ggaggagacc ggcgaggaga agcaggacac gcaggagaaa gaaggtattc      180
tgcctgagag agctgaagag gcaaagctaa aggccaaata cccaagccta ggacaaaagc      240
ctggaggctc cgacttcctc atgaagagac tccagaaagg gcaaaagtac tttgactcng      300
gagactacaa catggccaaa gccaacatga agaataagc gctgccaagt gcangaccag      360
acaagaacct ggtgactggt gatcacatcc ccaccccaca ggatctgccc agagaaagtc      420
ctcgctcgtc accagcaagc ttgcgggtgg ccaagttgaa tgatgctgcc ggggctctgc      480
canatctgag acgcttccct ccctgcccca ccgggtcct gtgctggctc ctgccttcc        540 tgcttttgca gccangggtc aggaagtggc ncnggtngtg gctggaaagc aaaacccttt      600
cctgttggtg tcccacccat ggagcccctg gggcgagccc angaacttga nccttttgt      660
```

| | |
|---|---:|
| tntcttncc | 669 |

<210> SEQ ID NO 17
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 17

| | | | | | | |
|---|---|---|---|---|---|---:|
| gcaagatatg | gacaactaag | tgagaaggta | atnctctact | gctctagntn | ctccnggcnn | 60 |
| gacgcgctga | ggagannnac | gctggcccan | ctgccggcca | cacacgggga | tcntggtnat | 120 |
| gcctgcccan | gggancccca | ncnctcggan | cccatntcac | acccgnnccn | tncgcccacn | 180 |
| ncctggctcn | cncngcccng | nccagctcnc | gnccccctcc | gccnnnctcn | ttnncntctc | 240 |
| cncncccctcc | ncnacnacct | cctacccncg | gctccctccc | cagccccccc | ccgcaancct | 300 |
| ccacnacncc | ntcnncncga | ancnccctc | gcnctcngcc | ccngccccct | gcccccccgcc | 360 |
| cncnacnncg | cgntccccg | cgcncgcngc | ctcnccccct | cccacacag | ncncacccgc | 420 |
| agncacgcnc | tccgcccnct | gacgccccnn | cccgccgcgc | tcaccttcat | ggnccnacng | 480 |
| ccccgctcnc | nccnctgcnc | gccgncnngg | cgccccgccc | cnnccgngtn | ccncgcgnng | 540 |
| ccccngcngn | angcngtgcg | cnncangncc | gngccgnncn | ncaccctccg | nccnccgccc | 600 |
| cgcccgctgg | gggctcccgc | cncgcggntc | antcccnccc | cntncgccca | ctntccgntc | 660 |
| cnncnctcnc | gctcngcgcn | cgcccnccnc | ccccccc | | | 697 |

<210> SEQ ID NO 18
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 18

| | | | | | | |
|---|---|---|---|---|---|---:|
| ctcgtgtgaa | gggtgcagta | cctaagccgg | agcggggtag | aggcgggccg | gcaccccctt | 60 |
| ctgacctcca | gtgccgccgg | cctcaagatc | agacatggcc | cagaacttga | acgacttggc | 120 |
| gggacggctg | cccgccgggc | cccggggcat | gggcacggcc | ctgaagctgt | tgctgggggc | 180 |
| cggcgccgtg | gcctacggtg | tgcgcgaatc | tgtgttcacc | gtggaaggcg | ggcncagagc | 240 |
| catcttcttc | aatcggatcg | gtggagtgca | caggacacta | tcctgggccg | anggccttca | 300 |
| cttcaggatc | cttggttcca | gtaccccanc | atctatgaca | ttcgggccag | acctcgaaaa | 360 |
| aatctcctcc | ctacaggctc | caaagaccta | cagatggtga | atatctccct | gcgagtgttg | 420 |
| tctcgaccaa | tgctcangaa | cttcctaaca | tgttccancg | cctaagggct | ggactacnaa | 480 |
| gaacgantgt | tgccgtccat | tgtcacgaag | tgctcaagaa | tttnggtggc | caagttcaat | 540 |
| gncctcacnn | ctgatcnccc | agcggggcca | agttanccct | ggttgatccc | cggggganctg | 600 |
| acnnaaaagg | gccaaggact | tcccctcatc | ctggataatg | tggccntcac | aaagctcaac | 660 |
| tttanccacc | | | | | | 670 |

<210> SEQ ID NO 19
<211> LENGTH: 606
<212> TYPE: DNA
<213> ORGANISM: Homo sapien

```
<220> FEATURE:
<221> NAME/KEY: misc_feature
<222> LOCATION: (1)...(606)
<223> OTHER INFORMATION: n = A,T,C or G

<400> SEQUENCE: 19
actagtgcca acctcagctc ccaggccagt tctctgaatg tcgaggagtt ccaggatctc      60
tggcctcagt tgtccttggt tattgatggg ggacaaattg gggatggcca gagccccgag     120
tgtcgccttg gctcaactgt ggttgatttg tctgtgcccg gaaagtttgg catcattcgt     180
ccaggctgtg ccctggaaag tactacagcc atcctccaac agaagtacgg actgctcccc     240
tcacatgcgt cctacctgtg aaactctggg aagcaggaag cccaagacc tggtgctgga      300
tactatgtgt ctgtccactg acgactgtca aggcctcatt tgcagaggcc accggagcta     360
gggcactagc ctgactttta aggcagtgtg tctttctgag cactgtagac caagcccttg     420
gagctgctgt tttagccttg cacctgggga aaggatgtat ttatttgtat tttcatatat     480
cagccaaaag ctgaatggaa aagttnagaa cattcctagg tggccttatt ctaataagtt     540
tcttctgtct gttttgtttt tcaattgaaa agttattaaa taacagattt agaatctagt     600
gagacc                                                                606

<210> SEQ ID NO 20
<211> LENGTH: 449
<212> TYPE: DNA
<213> ORGANISM: Homo sapien

<400> SEQUENCE: 20
actagtaaac aacagcagca gaaacatcag tatcagcagc gtcgccagca ggagaatatg      60
cagcgccaga gccgaggaga acccccgctc cctgaggagg acctgtccaa actcttcaaa     120
ccaccacagc cgcctgccag gatggactcg ctgctcattg caggccagat aaacacttac     180
tgccagaaca tcaaggagtt cactgcccaa aacttaggca agctcttcat ggcccaggct     240
cttcaagaat acaacaacta agaaaaggaa gtttccagaa aagaagttaa catgaactct     300
tgaagtcaca ccagggcaac tcttggaaga aatatatttg catattgaaa agcacagagg     360
atttctttag tgtcattgcc gattttggct ataacagtgt cttctagcc ataataaaat      420
aaaacaaaat cttgactgct tgctcaaaa                                       449

<210> SEQ ID NO 21
<211> LENGTH: 409
<212> TYPE: DNA
<213> ORGANISM: Homo sapien

<400> SEQUENCE: 21
tatcaatcaa ctggtgaata attaaacaat gtgtggtgtg atcatacaaa gggtaccact       60
caatgataaa aggaacaagc tgcctatatg tggaacaaca tggatgcatt tcagaaactt     120
tatgttgagt gaaagaacaa acacggagaa catactatgt ggttctcttt atgtaacatt     180
acagaaataa aaacagaggc aaccacctt gaggcagtat ggagtgagat agactggaaa     240
aaggaaggaa ggaaactcta cgctgatgga aatgtctgtg tcttcattgg gtggtagtta     300
tgtggggata tacatttgtc aaaatttatt gaactatata ctaaagaact ctgcatttta     360
ttgggatgta aataatacct caattaaaaa gacaaaaaaa aaaaaaaaa                 409

<210> SEQ ID NO 22
<211> LENGTH: 649
<212> TYPE: DNA
```

<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 22

| | | | | | |
|---|---|---|---|---|---|
| acaattttca | ttatcttaag | cacattgtac | atttctacag | aacctgtgat | tattctcgca | 60 |
| tgataaggat | ggtacttgca | tatggtgaat | tactactgtt | gacagtttcc | gcagaaatcc | 120 |
| tatttcagtg | gaccaacatt | gtggcatggc | agcaaatgcc | aacattttgt | ggaatagcag | 180 |
| caaatctaca | agagaccctg | gttggttttt | cgttttgttt | tctttgtttt | ttccccttc | 240 |
| tcctgaatca | gcagggatgg | aagagggta | ggaagttat | gaattactcc | ttccagtagt | 300 |
| agctctgaag | tgtcacattt | aatatcagtt | ttttttaaac | atgattctag | ttnaatgtag | 360 |
| aagagagaaa | aaagaggaag | tgttcacttt | tttaatacac | tgatttagaa | atttgatgtc | 420 |
| ttatatcagt | agttctgagg | tattgatagc | ttgctttatt | tctgccttta | cgttgacagt | 480 |
| gttgaagcag | ggtgaataac | tagggcata | tatatttttt | tttttgtaa | gctgtttcat | 540 |
| gatgttttct | ttggaatttc | cggataagtt | caggaaaaca | tctgcatgtt | gttatctagt | 600 |
| ctgaagttcn | tatccatctc | attacaacaa | aaacncccag | aacggnttg | | 649 |

<210> SEQ ID NO 23
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 23

| | | | | | |
|---|---|---|---|---|---|
| actagtgccg | tactggctga | aatccctgca | ggaccaggaa | gagaaccagt | tcagactttg | 60 |
| tactctcagt | caccagctct | ggaattagat | aaattccttg | aagatgtcag | gaatgggatc | 120 |
| tatcctctga | cagcctttgg | gctgcctcgg | ccccagcagc | cacagcagga | ggaggtgaca | 180 |
| tcacctgtcg | tgccccctc | tgtcaagact | ccgacacctg | aaccagctga | ggtggagact | 240 |
| cgcaaggtgg | tgctgatgca | gtgcaacatt | gagtcggtgg | aggagggagt | caaacaccac | 300 |
| ctgacacttc | tgctgaagtt | ggaggacaaa | ctgaaccggc | acctgagctg | tgacctgatg | 360 |
| ccaaatgaga | atatccccga | gttggcggct | gagctggtgc | agctgggctt | cattagtgag | 420 |
| gctgaccaga | gccggttgac | ttctctgcta | gaagagactt | gaacaagttc | aattttgcca | 480 |
| ggaacagtac | cctcaactca | gccgctgtca | ccgtctcctc | ttagagctca | ctcgggccag | 540 |
| gccctgatct | gcgctgtggc | tgtcctggac | gtgctgcacc | ctctgtcctt | cccccagtc | 600 |
| agtattacct | gtgaagccct | tccctccttt | attattcagg | anggctgggg | gggctccttg | 660 |
| nttctaacc | | | | | | 669 |

<210> SEQ ID NO 24
<211> LENGTH: 442
<212> TYPE: DNA
<213> ORGANISM: Homo sapien

<400> SEQUENCE: 24

| | | | | | |
|---|---|---|---|---|---|
| actagtacca | tcttgacaga | ggatacatgc | tcccaaaacg | tttgttacca | cacttaaaaa | 60 |
| tcactgccat | cattaagcat | cagtttcaaa | attatagcca | ttcatgattt | acttttttcca | 120 |
| gatgactatc | attattctag | tcctttgaat | ttgtaagggg | aaaaaaaaca | aaaacaaaaa | 180 |

```
cttacgatgc acttttctcc agcacatcag atttcaaatt gaaaattaaa gacatgctat      240
ggtaatgcac ttgctagtac tacacacttt ggtacaacaa aaaacagagg caagaaacaa      300
cggaaagaga aaagccttcc tttgttggcc cttaaactga gtcaagatct gaaatgtaga      360
gatgatctct gacgatacct gtatgttctt attgtgtaaa taaaattgct ggtatgaaat      420
gacctaaaaa aaaaaaaaga aa                                               442
```

<210> SEQ ID NO 25
<211> LENGTH: 656
<212> TYPE: DNA
<213> ORGANISM: Homo sapien
<220> FEATURE:
<221> NAME/KEY: misc_feature
<222> LOCATION: (1)...(656)
<223> OTHER INFORMATION: n = A,T,C or G

<400> SEQUENCE: 25

```
tgcaagtacc acacactgtt tgaattttgc acaaaaagtg actgtaggat caggtgatag      60
ccccggaatg tacagtgtct tggtgcacca agatgccttc taaaggctga catacctggg     120 aaccctaatgg ggcagagagt atagccctag cccagtggtg acatgaccac tccctttggg    180
aggcctgagg tagaggggag tggtatgtgt tttctcagtg gaagcagcac atgagtgggt    240
gacaggatgt tagataaagg ctctagttag ggtgtcattg tcatttgaga gactgacaca    300
ctcctagcag ctggtaaagg ggtgctggan gccatggagg anctctagaa acattagcat    360
gggctgatct gattacttcc tggcatcccg ctcactttta tgggaagtct tattagangg    420
atgggacagt tttccatatc cttgctgtgg agctctggaa cactctctaa atttccctct    480
attaaaaatc actgccctaa ctacacttcc tccttgaagg aatagaaatg gaactttctc    540
tgacatantt cttggcatgg ggagccagcc acaaatgana atctgaacgt gtccaggttt    600
ctcctganac tcatctacat agaattggtt aaaccctccc ttggaataag gaaaaa       656
```

<210> SEQ ID NO 26
<211> LENGTH: 434
<212> TYPE: DNA
<213> ORGANISM: Homo sapien
<220> FEATURE:
<221> NAME/KEY: misc_feature
<222> LOCATION: (1)...(434)
<223> OTHER INFORMATION: n = A,T,C or G

<400> SEQUENCE: 26

```
actagttcag actgccacgc caaccccaga aatacccca catgccagaa aagtgaagtc       60
ctaggtgttt ccatctatgt ttcaatctgt ccatctacca ggcctcgcga taaaacaaa     120 acaaaaaaac gctgccaggt tttagaagca gttctggtct caaaaccatc aggatcctgc    180
caccagggtt cttttgaaat agtaccacat gtaaagggga atttggcttt cacttcatct    240
aataactgaa ttgtcaggct ttgattgata attgtagaaa taagtagcct tctgttgtgg    300
gaataagtta taatcagtat tcatctcttt gttttttgtc actctttct ctctaattgt    360 gtcatttgta ctgtttgaaa atatttctt ctatnaaatt aaactaacct gccttaaaaa    420
aaaaaaaaaa aaaa                                                     434
```

<210> SEQ ID NO 27
<211> LENGTH: 654
<212> TYPE: DNA
<213> ORGANISM: Homo sapien
<220> FEATURE:

<221> NAME/KEY: misc_feature
<222> LOCATION: (1)...(654)
<223> OTHER INFORMATION: n = A,T,C or G

<400> SEQUENCE: 27

| | | |
|---|---|---|
| actagtccaa cacagtcaga aacattgttt tgaatcctct gtaaaccaag gcattaatct | 60 |
| taataaacca ggatccattt aggtaccact tgatataaaa aggatatcca taatgaatat | 120 |
| tttatactgc atcctttaca ttagccacta aatacgttat tgcttgatga agacctttca | 180 |
| cagaatccta tggattgcag catttcactt ggctacttca tacccatgcc ttaaagaggg | 240 |
| gcagtttctc aaaagcagaa acatgccgcc agttctcaag ttttcctcct aactccattt | 300 |
| gaatgtaagg gcagctggcc cccaatgtgg ggaggtccga acattttctg aattcccatt | 360 |
| ttcttgttcg cggctaaatg acagtttctg tcattactta gattccgatc tttcccaaag | 420 |
| gtgttgattt acaaagaggc cagctaatag cagaaatcat gaccctgaaa gagagatgaa | 480 |
| attcaagctg tgagccaggc agganctcag tatggcaaag gtcttgagaa tcngccattt | 540 |
| ggtacaaaaa aaatttttaaa gcntttatgt tataccatgg aaccatagaa anggcaaggg | 600 |
| aattgttaag aanaatttta agtgtccaga cccanaanga aaaaaaaaaa aaaa | 654 |

<210> SEQ ID NO 28
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 28

| | | |
|---|---|---|
| cgtgtgcaca tactgggagg atttccacag ctgcacggtc acagccctta cggattgcca | 60 |
| ggaaggggcg aaagatatgt gggataaact gagaaaagaa nccaaaaacc tcaacatcca | 120 |
| aggcagctta ttcgaactct gcggcagcgg caacggggcg gcgggtccc tgctcccggc | 180 |
| gttcccggtg ctcctggtgt ctctctcggc agctttagcg acctgncttt ccttctgagc | 240 |
| gtggggccag ctcccccccgc ggcgcccacc cacnctcact ccatgctccc ggaaatcgag | 300 |
| aggaagatca ttagttcttt ggggacgttn gtgattctct gtgatgctga aaacactca | 360 |
| tatagggaat gtgggaaatc ctganctctt tnttatntcg tntgatttct tgtgttttat | 420 |
| ttgccaaaat gttaccaatc agtgaccaac cnagcacagc caaaaatcgg acntcngctt | 480 |
| tagtccgtct tcacacacag aataagaaaa cggcaaaccc accccacttt tnantttnat | 540 |
| tattactaan ttttttctgt tgggcaaaag aatctcagga acngccctgg ggccnccgta | 600 |
| ctanagttaa ccnagctagt tncatgaaaa atgatgggct ccnccctcaat gggaaagcca | 660 |
| agaaaaagnc | 670 |

<210> SEQ ID NO 29
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 29

| | | |
|---|---|---|
| actagtcctc cacagcctgt gaatcccct agacctttca agcatagtga gcggagaaga | 60 |
| agatctcagc gtttagccac cttacccatg cctgatgatt ctgtagaaaa ggtttcttct | 120 |

```
ccctctccag ccactgatgg gaaagtattc tccatcagtt ctcaaaatca gcaagaatct      180
tcagtaccag aggtgcctga tgttgcacat ttgccacttg agaagctggg accctgtctc      240
cctcttgact taagtcgtgg ttcagaagtt acagcaccgg tagcctcaga ttcctcttac      300
cgtaatgaat gtcccagggc agaaaaagag gatacncaga tgcttccaaa tccttcttcc      360
aaagcaatag ctgatgggaa gaggagctcc agcagcagca ggaatatcga aaacagaaaa      420
aaaagtgaaa ttgggaagac aaaagctcaa cagcatttgg taaggagaaa aganaagatg      480
aggaaggaag agagaagaga gacnaagatc nctacggacc gnnncggaag aagaagaagn      540
aaaaaanaaa a                                                           551

<210> SEQ ID NO 30
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 30
actagttcta tctggaaaaa gcccggggttg gaagaagctg tggagagtgc gtgtgcaatg      60
cgagactcat ttcttggaag catccctggc aaaaatgcag ctgagtacaa ggttatcact     120
gtgatagaac ctggactgct ttttgagata atagagatgc tgcagtctga agagacttcc     180
agcacctctc agttgaatga attaatgatg gcttctgagt caactttact ggctcaggaa     240
ccacgagaga tgactgcaga tgtaatcgag cttaaaggga aattcctcat caacttagaa     300
ggtggtgata ttcgtgaaga gtcttcctat aaagtaattg tcatgccgac tacgaaagaa     360
aaatgccccc gttgttggaa gtatacagcg ggagtcttca gatacactgt gtcctcgatg     420
tgcagaagtt gtcagtggga aaatagtatt aacagctcac tcgagcaaga accctcctga     480
cagtactggg ctagaagttt ggatggatta tttacaatat aggaaagaaa gccaagaatt     540
aggtnatgag tggatgagta aatggtggan gatggggaat tcaaatcaga attatggaag     600
aagttnttcc tgttactata gaaggaatt atgtttattt acatgcagaa aatatanatg     660
tgtggtgtgt accgtggatg gaan                                             684

<210> SEQ ID NO 31
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 31
gcgcagaaaa ggaaccaata tttcagaaac aagcttaata ggaacagctg cctgtacatc      60
aacatcttct cagaatgacc cagaagttat catcgtggga gctggcgtgc ttggctctgc     120
tttggcagct gtgctttcca gagatggaag aaaggtgaca gtcattgaga gagacttaaa     180
agagcctgac agaatagttg gagaattcct gcagccgggt ggttatcatg ttctcaaaga     240
ccttggtctt ggagatacag tggaaggtct tgatgcccag gttgtaaatg gttacatgat     300
tcatgatcag ggaaagcaaa tcagangttc agattcctta ccctctgtca gaaacaatc      360 aagtgcagag tggaagagct ttccatcacg gaagattcat catgagtctc cggaaagcag     420
```

-continued

```
ctatggcaga gcccaatgca aagtttattg aaggtgttgt gttacagtta ttagaggaag     480
atgatgttgt gatgggagtt cagtacaagg ataaagagac tgggagatat caaggaactc     540
catgctccac tgactgttgt tgcagatggg cttttctcca anttcaggaa aagcctggtc     600
tcaataaagt ttctgtatca ctcatttggt tggcttctta tgaagaatgc nccc           654
```

<210> SEQ ID NO 32
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 32

```
actagtgaag aaaagaaat tctgatacgg gacaaaaatg ctcttcaaaa catcattctt      60
tatcacctga caccaggagt tttcattgga aaaggatttg aacctggtgt tactaacatt    120
ttaaagacca cacaaggaag caaaatcttt ctgaaagaag taaatgatac acttctggtg    180
aatgaattga atcaaaaga atctgacatc atgcaacaa atggtgtaat tcatgttgta     240
gataaactcc tctatccagc agacacacct gttggaaatg atcaactgct ggaaatactt    300
aataaattaa tcaaatacat ccaaattaag tttgttcgtg gtagcacctt caaagaaatc    360
cccgtgactg tctatnagcc aattattaaa aaatacacca aaatcattga tgggagtgcc    420
tgtgggaaat aactgaaaaa gagaccgaga gaacgaatc attacaggtc ctgaaataaa     480
atacctagga tttctactgg aggtggagaa acagaagaac tctgaagaaa ttgttacaag    540
aagangtccc aaggtcacca aattcattga aggtggtgat ggtctttatt tgaagatgaa    600
gaaattaaaa gacgcttcag ggagacnccc catgaaggaa ttgccagcca caaaaaatt    660 cagggattag aaa                                                      673
```

<210> SEQ ID NO 33
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 33

```
actagttatt tactttcctc cgcttcagaa ggtttttcag actgagagcc taagcatact      60
ggatctgttg tttcttttgg gtctcacctc atcagtgtgc atagtggcag aaattataaa    120
gaaggttgaa aggagcaggg aaaagatcca gaagcatgtt agttcgacat catcatcttt    180
tcttgaagta tgatgcatat tgcattattt tatttgcaaa ctaggaattg cagtctgagg    240
atcatttaga agggcaagtt caagaggata tgaagatttg agaactttt aactattcat     300 tgactaaaaa tgaacattaa tgttnaagac ttaagacttt aacctgctgg cagtcccaaa    360
tgaaattatg caactttgat atcatattcc ttgatttaaa ttgggctttt gtgattgant    420
gaaactttat aaagcatatg gtcagttatt tnattaaaaa ggcaaaacct gaaccacctt    480
ctgcacttaa agaagtctaa cagtacaaat acctatctat cttagatgga tntatttntt    540 tntatttta aatattgtac tatttatggt nggtggggct ttcttactaa tacacaaatn    600
aatttatcat ttcaanggca ttctatttgg gtttagaagt tgattccaag nantgcatat    660
ttcgctactg tnt                                                      673
```

<210> SEQ ID NO 34
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 34

```
actagtttat tcaagaaaag aacttactga ttcctctgtt cctaaagcaa gagtggcagg      60
tgatcagggc tggtgtagca tccggttcct ttagtgcagc taactgcatt tgtcactgat     120
gaccaaggag gaaatcacta agacatttga gaagcagtgg tatgaacgtt cttggacaag     180
ccacagttct gagccttaac cctgtagttt gcacacaaga acgagctcca cctcccttc      240
ttcaggagga atctgtgcgg atagattggc tggacttttc aatggttctg ggttgcaagt     300
gggcactgtt atggctgggt atggagcgga cagccccagg aatcagagcc tcagcccggc     360
tgcctggttg gaaggtacag gtgttcagca ccttcggaaa aagggcataa agtngtgggg     420
gacaattctc agtccaagaa gaatgcattg accattgctg gctatttgct tncctagtan     480
gaattggatn cattttttgac cangatnntt ctnctatgct ttnttgcaat gaaatcaaat     540
cccgcattat ctacaagtgg tatgaagtcc tgcnncccc agagaggctg ttcaggcnat      600
gtcttccaag ggcagggtgg gttacaccat tttacctccc ctctccccc agattatgna      660
cncagaagga atttntttcc tccc                                             684
```

<210> SEQ ID NO 35
<211> LENGTH: 614
<212> TYPE: DNA
<213> ORGANISM: Homo sapien
<220> FEATURE:
<221> NAME/KEY: misc_feature
<222> LOCATION: (1)...(614)
<223> OTHER INFORMATION: n = A,T,C or G

<400> SEQUENCE: 35

```
actagtccaa cgcgttngcn aatattcccc tggtagccta cttccttacc cccgaatatt      60
ggtaagatcg agcaatggct tcaggacatg ggttctcttc tcctgtgatc attcaagtgc     120
tcactgcatg aagactggct tgtctcagtg tntcaacctc accagggctg tctcttggtc     180
cacacctcgc tccctgttag tgccgtatga cagcccccat canatgacct tggccaagtc     240
acggtttctc tgtggtcaat gttggtnggc tgattggtgg aaagtanggt ggaccaaagg     300
aagncncgtg agcagncanc nccagttctg caccagcagc gcctccgtcc tactngggtg     360
ttccngtttc tcctggccct gngtgggcta nggcctgatt cgggaanatg cctttgcang     420
gaaggganga taantgggat ctaccaattg attctggcaa aacnatntct aagattnttn     480
tgctttatgt gggnacana tctanctctc atttnntgct gnanatnaca ccctactcgt      540
gntcgancnc gtcttcgatt ttcggganaca cnccantnaa tactggcgtt ctgttgttaa     600
aaaaaaaaaa aaaa                                                       614
```

<210> SEQ ID NO 36
<211> LENGTH: 686
<212> TYPE: DNA
<213> ORGANISM: Homo sapien
<220> FEATURE:
<221> NAME/KEY: misc_feature
<222> LOCATION: (1)...(686)

-continued

<223> OTHER INFORMATION: n = A,T,C or G

<400> SEQUENCE: 36

| gtggctggcc cggttctccg cttctcccca tcccctactt tcctccctcc ctcccttccc | 60 |
| ctccctcgtc gactgttgct tgctggtcgc agactccctg acccctccct caccccctccc | 120 |
| taacctcggt gccaccggat tgccttctt ttcctgttgc ccagcccagc cctagtgtca | 180 |
| gggcggggc ctggagcagc ccgaggcact gcagcagaag ananaaaaga cacgacnaac | 240 |
| ctcagctcgc cagtccggtc gctngcttcc cgccgcatgg caatnagaca gacgccgctc | 300 |
| acctgctctg ggcacacgcg acccgtggtt gatttggcct tcagtggcat cacccttatg | 360 |
| ggtatttctt aatcagcgct tgcaaagatg gttaacctat gctacgccag ggagatacag | 420 |
| gagactggat tggaacattt ttggggtcta aaggtctgtt tggggtgcaa cactgaataa | 480 |
| ggatgccacc aaagcagcta cagcagctgc agatttcaca gcccaagtgt gggatgctgt | 540 |
| ctcagganat naattgataa cctggctcat aacacattgt caagaatgtg gatttcccca | 600 |
| ggatattatt atttgtttac cggggganag gataactgtt tcncntattt taattgaaca | 660 |
| aactnaaaca aaanctaagg aaatcc | 686 |

<210> SEQ ID NO 37
<211> LENGTH: 681
<212> TYPE: DNA
<213> ORGANISM: Homo sapien
<220> FEATURE:
<221> NAME/KEY: misc_feature
<222> LOCATION: (1)...(681)
<223> OTHER INFORMATION: n = A,T,C or G

<400> SEQUENCE: 37

| gagacanacn naacgtcang agaanaaaag angcatggaa cacaanccag gcncgatggc | 60 |
| caccttccca ccagcancca gcgccccca gcngccccca ngccggang accangactc | 120 |
| cancctgnat caatctganc tctattcctg gcccatncct acctcggagg tggangccgn | 180 |
| aaaggtcgca cnnncagaga agctgctgcc ancaccancc gccccnncc tgncgggctn | 240 |
| nataggaaac tggtgaccnn gctgcanaat tcatacagga gcacgcgang ggcacnnnct | 300 |
| cacactgagt tnnngatgan gcctnaccan ggacctnccc cagcnnattg annacnggac | 360 |
| tgcggaggaa ggaagacccc gnacnggatc ctggccggcn tgccacccc ccaccctag | 420 |
| gattatnccc cttgactgag tctctgaggg gctacccgaa cccgcctcca ttccctacca | 480 |
| natnntgctc natcgggact acangctggg ggatnggagg ggctatcccc cancatcccc | 540 |
| tnanaccaac agcnacngan natngggggct cccnggtc ggngcaacnc tcctncaccc | 600 |
| cggcgcnggc cttcggtgnt gtcctccntc aacnaattcc naaanggcgg gccccccngt | 660 |
| ggactcctcn ttgttccctc c | 681 |

<210> SEQ ID NO 38
<211> LENGTH: 687
<212> TYPE: DNA
<213> ORGANISM: Homo sapien
<220> FEATURE:
<221> NAME/KEY: misc_feature
<222> LOCATION: (1)...(687)
<223> OTHER INFORMATION: n = A,T,C or G

<400> SEQUENCE: 38

| canaaaaaaa aaaacatggc cgaaaccagn aagctgcgcg atggcgccac ggcccctctt | 60 |
| ctcccggcct gtgtccggaa ggtttccctc cgaggcgccc cggctcccgc aagcggagga | 120 |

```
gagggcggga cntgccgggg ccggagctca naggccctgg ggccgctctg ctctcccgcc    180
atcgcaaggg cggcgctaac ctnaggcctc cccgcaaagg tccccnangc ggnggcggcg    240
gggggctgtg anaaccgcaa aaanaacgct gggcgcgcng cgaacccgtc cacccccgcg    300
aaggananac ttccacagan gcagcgtttc cacagcccan agccacnttt ctagggtgat    360
gcaccccagt aagttcctgn cggggaagct caccgctgtc aaaaaanctc ttcgctccac    420
cggcgcacna aggggangan ggcangangc tgccgcccgc acaggtcatc tgatcacgtc    480
gcccgcccta ntctgctttt gtgaatctcc actttgttca accccacccg ccgttctctc    540
ctccttgcgc cttcctctna ccttaanaac cagcttcctc tacccnatng tanttnctct    600
gcncnngtng aaattaattc ggtccnccgg aacctcttnc ctgtggcaac tgctnaaaga    660
aactgctgtt ctgnttactg cngtccc                                       687

<210> SEQ ID NO 39
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 39
actagtctgg cctacaatag tgtgattcat gtaggacttc tttcatcaat tcaaaacccc     60
tagaaaaacg tatacagatt atataagtag ggataagatt tctaacattt ctgggctctc    120
tgacccctgc gctagactgt ggaaagggag tattattata gtatacaaca ctgctgttgc    180
cttattagtt ataacatgat aggtgctgaa ttgtgattca caatttaaaa acactgtaat    240
ccaacttttt tttttaact gtagatcatg catgtgaatg ttaatgttaa tttgttcaan    300
gttgttatgg gtagaaaaaa ccacatgcct taaaatttta aaaagcaggg cccaaactta    360
ttagtttaaa attaggggta tgtttccagt ttgttattaa ntggttatag ctctgtttag    420
aanaaatcna ngaacangat ttngaaantt aagntgacat tatttnccag tgacttgtta    480
atttgaaatc anacacggca ccttccgttt tggtnctatt ggnntttgaa tccaancngg    540
ntccaaatct tnttggaaac ngtccnttta actttttac nanatcttat tttttattt    600 tggaatggcc ctatttaang ttaaaagggg ggggnnccac naccattcnt gaataaaact    660
naatatatat ccttggtccc ccaaaattta aggng                              695

<210> SEQ ID NO 40
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 40
actagtagtc agttgggagt ggttgctata ccttgacttc atttatatga atttccactt     60
tattaaataa tagaaaagaa atcccggtg cttgcagtag agttataggu cattctatgc    120
ttacagaaaa tatagccatg attgaaatca aatagtaaag gctgttctgg ctttttatct    180
tcttagctca tcttaaataa gtagtacact tgggatgcag tgcgtctgaa gtgctaatca    240
gttgtaacaa tagcacaaat cgaacttagg atgtgtttct tctcttctgt gtttcgattt    300
```

```
tgatcaattc tttaattttg ggaacctata atacagtttt cctattcttg gagataaaaa      360
ttaaatggat cactgatatt taagtcattc tgcttctcat ctnaatattc catattctgt      420
attagganaa antacctccc agcacagccc cctctcaaac cccacccaaa accaagcatt      480
tggaatgagt ctcctttatt tccgaantgt ggatggtata acccatatcn ctccaatttc      540
tgnttgggtt gggtattaat ttgaactgtg catgaaaagn ggaatctttt nctttgggtc      600
aaantttncc ggttaatttg nctngncaaa tccaatttnc tttaagggtg tctttataaa      660
atttgctatt cngg                                                       674

<210> SEQ ID NO 41
<211> LENGTH: 657
<212> TYPE: DNA
<213> ORGANISM: Homo sapien
<220> FEATURE:
<221> NAME/KEY: misc_feature
<222> LOCATION: (1)...(657)
<223> OTHER INFORMATION: n = A,T,C or G

<400> SEQUENCE: 41
gaaacatgca agtaccacac actgtttgaa ttttgcacaa aaagtgactg tagggatcag       60
gtgatagccc cggaatgtac agtgtcttgg tgcaccaaga tgccttctaa aggctgacat      120
accttgggac cctaatgggg cagagagtat agccctagcc cagtggtgac atgaccactc      180
cctttgggag gctgaagtta aagggaatgg tatgtgtttt ctcatggaag cagcacatga      240
atnggtnaca ngatgttaaa ntaaggntct antttgggtg tcttgtcatt tgaaaaantg      300
acacactcct ancanctggt aaaggggtgc tggaagccat ggaagaactc taaaaacatt      360
agcatgggct gatctgatta cttcctggca tcccgctcac ttttatggga agtcttatta      420
naaggatggg ananttttcc atatccttgc tgttggaact ctggaacact ctctaaattt      480
ccctctatta aaaatcactg nccttactac acttcctcct tganggaata gaaatggacc      540
tttctctgac ttagttcttg gcatgggane cagcccaaat taaaatctga cttntccggt      600
ttctccngaa ctcacctact tgaattggta aaacctcctt tggaattagn aaaaacc         657

<210> SEQ ID NO 42
<211> LENGTH: 389
<212> TYPE: DNA
<213> ORGANISM: Homo sapien
<220> FEATURE:
<221> NAME/KEY: misc_feature
<222> LOCATION: (1)...(389)
<223> OTHER INFORMATION: n = A,T,C or G

<400> SEQUENCE: 42
actagtgctg aggaatgtaa acaagtttgc tgggccttgc gagacttcac caggttgttt       60
cgatagctca cactcctgca ctgtgcctgt cacccaggaa tgtctttttt aattagaaga      120
caggaagaaa acaaaaacca gactgtgtcc cacaatcaga aacctccgtt gtggcagang      180
ggccttcacc gccaccaggg tgtcccgcca gacaggagaa gactccagcc ttctgaggcc      240
atcctgaaga attcctgttt ggggttgtg aaggaaaatc acccggattt aaaaagatgc      300
tgttgcctgc ccgcgtngtn gggaagggac tggtttcctg gtgaatttct taaagaaaa       360 atattttaag ttaagaaaaa aaaaaaaaa                                        389

<210> SEQ ID NO 43
<211> LENGTH: 279
<212> TYPE: DNA
<213> ORGANISM: Homo sapien
```

<400> SEQUENCE: 43

```
actagtgaca agctcctggt cttgagatgt cttctcgtta aggagatggg cctttggag      60
gtaaaggata aaatgaatga gttctgtcat gattcactat tctagaactt gcatgacctt    120
tactgtgtta gctctttgaa tgttcttgaa attttagact ttctttgtaa acaaataata    180
tgtccttatc attgtataaa agctgttatg tgcaacagtg tggagatcct tgtctgattt    240
aataaaatac ttaaacactg aaaaaaaaaa aaaaaaaa                            279
```

<210> SEQ ID NO 44
<211> LENGTH: 449
<212> TYPE: DNA
<213> ORGANISM: Homo sapien
<220> FEATURE:
<221> NAME/KEY: misc_feature
<222> LOCATION: (1)...(449)
<223> OTHER INFORMATION: n = A,T,C or G

<400> SEQUENCE: 44

```
actagtagca tcttttctac aacgttaaaa ttgcagaagt agcttatcat taaaaaacaa     60
caacaacaac aataacaata aatcctaagt gtaaatcagt tattctaccc cctaccaagg    120
atatcagcct gttttttccc ttttttctcc tgggaataat tgtgggcttc ttcccaaatt    180
tctacagcct ctttcctctt ctcatgcttg agcttccctg tttgcacgca tgcgttgtgc    240
aagantgggc tgtttngctt ggantncggt ccnagtggaa ncatgctttc ccttgttact    300
gttggaagaa actcaaacct tcnacccta ggtgttncca ttttgtcaag tcatcactgt     360
attttttgtac tggcattaac aaaaaaagaa atnaaatatt gttccattaa actttaataa    420
aactttaaaa gggaaaaaaa aaaaaaaa                                       449
```

<210> SEQ ID NO 45
<211> LENGTH: 559
<212> TYPE: DNA
<213> ORGANISM: Homo sapien
<220> FEATURE:
<221> NAME/KEY: misc_feature
<222> LOCATION: (1)...(559)
<223> OTHER INFORMATION: n = A,T,C or G

<400> SEQUENCE: 45

```
actagtgtgg gggaatcacg gacacttaaa gtcaatctgc gaaataattc ttttattaca     60
cactcactga agtttttgag tcccagagag ccattctatg tcaaacattc caagtactct    120
ttgagagccc agcattacat caacatgccc gtgcagttca aaccgaagtc cgcaggcaaa    180
tttgaagctt tgcttgtcat tcaaacagat gaaggcaaga gtattgctat tcgactaatt    240
ggtgaagctc ttggaaaaaa ttnactagaa tacttttttgt gttaagttaa ttacataagt    300
tgtattttgt taactttatc tttctacact acaattatgc ttttgtatat atattttgta    360
tgatggatat ctataattgt agattttgtt tttacaagct aatactgaag actcgactga    420
aatattatgt atctagccca tagtattgta cttaactttt acagggtgaa aaaaaaattc    480
tgtgtttgca ttgattatga tattctgaat aaatatggga atatattta atgtgggtaa    540
aaaaaaaaaa aaaaggaa                                                   559
```

<210> SEQ ID NO 46
<211> LENGTH: 731
<212> TYPE: DNA
<213> ORGANISM: Homo sapien
<220> FEATURE:

```
<221> NAME/KEY: misc_feature
<222> LOCATION: (1)...(731)
<223> OTHER INFORMATION: n = A,T,C or G

<400> SEQUENCE: 46
actagttcta gtaccatggc tgtcatagat gcaaccatta tattccattt agtttcttcc      60
tcaggttccc taacaattgt ttgaaactga atatatatgt ttatgtatgt gtgtgtgttc    120
actgtcatgt atatggtgta tatgggatgt gtgcagtttt cagttatata tatattcata    180
tatacatatg catatatatg tataatatac atatatacat gcatacactt gtataatata    240
catatatata cacatatatg cacacatatn atcactgagt tccaaagtga gtctttattt    300
ggggcaattg tattctctcc ctctgtctgc tcactgggcc tttgcaagac atagcaattg    360
cttgatttcc tttggataag agtcttatct tcggcactct tgactctagc cttaacttta    420
gatttctatt ccagaatacc tctcatatct atcttaaaac ctaaganggg taaagangtc    480
ataagattgt agtatgaaag antttgctta gttaaattat atctcaggaa actcattcat    540
ctacaaatta aattgtaaaa tgatggtttg ttgtatctga aaaaatgttt agaacaagaa    600
atgtaactgg gtacctgtta tatcaaagaa cctcnattta ttaagtctcc tcatagccan    660
atccttatat ngccctctct gacctgantt aatananact tgaataatga atagttaatt    720
taggnttggg c                                                        731

<210> SEQ ID NO 47
<211> LENGTH: 640
<212> TYPE: DNA
<213> ORGANISM: Homo sapien
<220> FEATURE:
<221> NAME/KEY: misc_feature
<222> LOCATION: (1)...(640)
<223> OTHER INFORMATION: n = A,T,C or G

<400> SEQUENCE: 47
tgcgngccgg tttggcccctt ctttgtanga cactttcatc cgccctgaaa tcttcccgat      60
cgttaataac tcctcaggtc cctgcctgca cagggttttt tcttantttg ttgcctaaca    120
gtacaccaaa tgtgacatcc tttcaccaat atngattnct tcataccaca tcntcnatgg    180
anacgactnc aacaattttt tgatnacccn aaanactggg ggctnnaana agtacantct    240
ggagcagcat ggacctgtcn gcnactaang gaacaanagt nntgaacatt tacacaacct    300
ttggtatgtc ttactgaaag anagaaacat gcttctnncc ctagaccacg aggncaaccg    360
caganattgc caatgccaag tccgagcggt tagatcaggt aatacattcc atggatgcat    420
tacatacntt gtccccgaaa nanaagatgc cctaanggct tcttcanact ggtccngaaa    480
acanctacac ctggtgcttg ganaacanac tctttggaag atcatctggc acaagttccc    540
cccagtgggt tttnccttgg cacctancctt accanatcna ttcggaancc attctttgcc    600
ntggcnttnt nttgggacca ntcttctcac aactgnaccc                         640

<210> SEQ ID NO 48
<211> LENGTH: 257
<212> TYPE: DNA
<213> ORGANISM: Homo sapien

<400> SEQUENCE: 48
actagtatat gaaaatgtaa atatcacttg tgtactcaaa caaaagttgg tcttaagctt      60
ccaccttgag cagccttgga aacctaacct gcctcttttta gcataatcac attttctaaa    120
tgattttctt tgttcctgaa aaagtgattt gtattagttt tacatttgtt ttttggaaga    180
```
ttatatttgt atatgtatca tcataaaata tttaaataaa aagtatcttt agagtgaaaa     240
aaaaaaaaaa aaaaaaa                                                   257

<210> SEQ ID NO 49
<211> LENGTH: 652
<212> TYPE: DNA
<213> ORGANISM: Homo sapien
<220> FEATURE:
<221> NAME/KEY: misc_feature
<222> LOCATION: (1)...(652)
<223> OTHER INFORMATION: n = A,T,C or G

<400> SEQUENCE: 49
actagttcag atgagtggct gctgaagggg ccccctttgtc attttcatta taacccaatt     60
tccacttatt tgaactctta agtcataaat gtataatgac ttatgaatta gcacagttaa    120
gttgacacta gaaactgccc atttctgtat tacactatca aataggaaac attggaaaga    180
tggggaaaaa aatcttattt taaaatggct tagaaagttt tcagattact ttgaaaattc    240
taaacttctt tctgtttcca aaacttgaaa atatgtagat ggactcatgc attaagactg    300
ttttcaaagc tttcctcaca tttttaaagt gtgattttcc ttttaatata catatttatt    360
ttctttaaag cagctatatc ccaacccatg actttggaga tatacctatn aaaccaatat    420
aacagcangg ttattgaagc agctttctca aatgttgctt cagatgtgca agttgcaaat    480
tttattgtat ttgtanaata cattttttgt tttaaactgt atttcaatct atttctccaa    540
gatgcttttc atatagagtg aaatatccca ngataactgc ttctgtgtcg tcgcatttga    600
cgcataactg cacaaatgaa cagtgtatac ctcttggttg tgcattnacc cc            652

<210> SEQ ID NO 50
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 50
ttgcgctttg attttttttag ggcttgtgcc ctgtttcact tatagggtct agaatgcttg     60
tgttgagtaa aaaggagatg cccaatattc aaagctgcta aatgttctct ttgccataaa    120
gactccgtgt aactgtgtga acacttggga ttttttctcct ctgtcccgag gtcgtcgtct    180
gctttctttt ttgggttctt tctagaagat tgagaaatgc atatgacagg ctgagancac    240
ctccccaaac acacaagctc tcagccacan gcagcttctc cacagcccca gcttcgcaca    300
ggctcctgga nggctgcctg ggggaggcag acatgggagt gccaaggtgg ccagatggtt    360
ccaggactac aatgtctttta ttttttaactg tttgccactg ctgccctcac ccctgcccgg    420
ctctggagta ccgtctgccc canacaagtg ggantgaaat gggggtgggg gggaacactg    480
attcccantt aggggtgcc taactgaaca gtagggatan aaggtgtgaa cctgngaant    540
gcttttataa attatnttcc ttgttanatt tatttttttaa tttaatctct gttnaactgc    600
ccngggaaaa ggggaaaaaa aaaaaaaaat tctntttaaa cacatgaaca               650

<210> SEQ ID NO 51
<211> LENGTH: 545
<212> TYPE: DNA
<213> ORGANISM: Homo sapien
<220> FEATURE:

<221> NAME/KEY: misc_feature
<222> LOCATION: (1)...(545)
<223> OTHER INFORMATION: n = A,T,C or G

<400> SEQUENCE: 51

| | | | | | |
|---|---|---|---|---|---|
| tggcgtgcaa | ccagggtagc | tgaagtttgg | gtctgggact | ggagattggc | cattaggcct | 60 |
| cctganattc | cagctccctt | ccaccaagcc | cagtcttgct | acgtggcaca | gggcaaacct | 120 |
| gactcccttt | gggcctcagt | ttcccctccc | cttcatgana | tgaaaagaat | actactttt | 180 |
| cttgttggtc | taacnttgct | ggacncaaag | tgtngtcatt | attgttgtat | tgggtgatgt | 240 |
| gtncaaaact | gcagaagctc | actgcctatg | agaggaanta | agagagatag | tggatganag | 300 |
| ggacanaagg | agtcattatt | tggtatagat | ccacccntcc | caacctttct | ctcctcagtc | 360 |
| cctgcnctc | atgtntctgg | tntggtgagt | cctttgtgcc | accanccatc | atgctttgca | 420 |
| ttgctgccat | cctgggaagg | gggtgnatcc | tctcacaact | tgttgtcatc | gtttganatg | 480 |
| catgctttct | tnatnaaaca | aanaaannaa | tgtttgacag | ngtttaaaat | aaaaaanaaa | 540 |
| caaaa | | | | | | 545 |

<210> SEQ ID NO 52
<211> LENGTH: 678
<212> TYPE: DNA
<213> ORGANISM: Homo sapien
<220> FEATURE:
<221> NAME/KEY: misc_feature
<222> LOCATION: (1)...(678)
<223> OTHER INFORMATION: n = A,T,C or G

<400> SEQUENCE: 52

| | | | | | |
|---|---|---|---|---|---|
| actagtagaa | gaactttgcc | gcttttgtgc | ctctcacagg | cgcctaaagt | cattgccatg | 60 |
| ggaggaagac | gatttggggg | gggagggggg | ggggcangg | tccgtgggc | tttccctant | 120 |
| ntatctccat | ntccantgnn | cnntgtcgcc | tcttccctcg | tcncattnga | anttantccc | 180 |
| tggnccccnn | nccctctcc | ncctncncct | cccccctccg | ncncctccnn | cttttntan | 240 |
| ncttcccat | ctccntcccc | cctnanngtc | ccaacnccgn | cagcaatnnc | ncacttnctc | 300 |
| nctccncncc | tccnnccgtt | cttctntttct | cnacntntnc | ncnnntnccn | tgccnntnaa | 360 |
| annctctccc | cnctgcaanc | gattctctcc | ctccncnnan | ctntccactc | cntncttctc | 420 |
| ncncgctcct | nttcntcnnc | ccacctctcn | ccttcgnccc | cantacnctc | nccncccttn | 480 |
| cgnntcnttn | nnntcctcnn | accnccccncc | tcccttcncc | cctcttctcc | ccggtntntc | 540 |
| tctctcccnc | nncncnnct | cnnccntcc | nngcgnccnt | ttccgccccn | cnccncnctt | 600 |
| ccttcntcnc | cantccatcn | cntntnccat | nctncctncc | nctcacnccc | gctncccccn | 660 |
| ntctctttca | cacngtcc | | | | | 678 |

<210> SEQ ID NO 53
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 53

| | | | | | |
|---|---|---|---|---|---|
| tgaagatcct | ggtgtcgcca | tgggccgccg | ccccgcccgt | tgttaccggt | attgtaagaa | 60 |
| caagccgtac | ccaaagtctc | gcttctgccg | aggtgtccct | gatgccaaaa | ttcgcatttt | 120 |
| tgacctgggg | cggaaaaaang | caaaantgga | tgagtctccg | ctttgtggcc | acatggtgtc | 180 |

```
agatcaatat gagcagctgt cctctgaagc cctgnangct gcccgaattt gtgccaataa    240
gtacatggta aaaagtngtg gcnaagatgc ttccatatcc gggtgcggnt ccacccttc    300 cacgtcatcc gcatcaacaa gatgttgtcc tgtgctgggg ctgacaggct cccaacaggc    360
atgcgaagtg cctttggaaa acccanggca ctgtggccag ggttcacatt gggccaattn    420
atcatgttca tccgcaccaa ctgcagaaca angaacntgt naattnaagc cctgcccagg    480
gncaanttca aatttcccgg cc                                            502

<210> SEQ ID NO 54
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 54
actagtccaa gaaaaatatg cttaatgtat attacaaagg ctttgtatat gttaacctgt     60
tttaatgcca aaagtttgct ttgtccacaa tttccttaag acctcttcag aaagggattt    120
gtttgcctta atgaatactg ttgggaaaaa acacagtata atgagtgaaa agggcagaag    180
caagaaattt ctacatctta gcgactccaa gaagaatgag tatccacatt tagatggcac    240
attatgagga ctttaatctt tccttaaaca caataatgtt ttctttttc ttttattcac    300 atgatttcta agtatatttt tcatgcagga cagttttca accttgatgt acagtgactg    360
tgttaaattt ttctttcagt ggcaacctct ataatcttta aaatatggtg agcatcttgt    420
ctgttttgaa ngggatatga cnatnaatct atcagatggg aaatcctgtt tccaagttag    480
aaaaaaaaaa aaaa                                                     494

<210> SEQ ID NO 55
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 55
actagtaaaa agcagcattg ccaaataatc cctaattttc cactaaaaat ataatgaaat     60
gatgttaagc tttttgaaaa gtttaggtta aacctactgt tgttagatta atgtatttgt    120 tgcttcccttt tatctggaat gtggcattag cttttttatt ttaaccctct ttaattctta    180
ttcaattcca tgacttaagg ttggagagct aaacactggg attttttggat aacagactga    240 cagttttgca taattataat cggcattgta catagaaagg atatggctac cttttgttaa    300
atctgcactt tctaaatatc aaaaagggga aatgaagtat aaatcaattt ttgtataatc    360
tgtttgaaac atganttta tttgcttaat attanggctt tgccctttc tgttagtctc    420 ttgggatcct gtgtaaaact gttctcatta aacaccaaac agttaagtcc attctctggt    480
actagctaca aattccgttt catattctac ntaacaattt aaattaactg aaatatttct    540
anatggtcta cttctgtcnt ataaaacna aacttgantt nccaaaaaaa aaaaaaaaa    600 aaaaaa                                                              606

<210> SEQ ID NO 56
```

```
<211> LENGTH: 183
<212> TYPE: DNA
<213> ORGANISM: Homo sapien

<400> SEQUENCE: 56
actagtatat ttaaacttac aggcttattt gtaatgtaaa ccaccatttt aatgtactgt      60
aattaacatg gttataatac gtacaatcct tccctcatcc catcacacaa cttttttgt     120 gtgtgataaa ctgattttgg tttgcaataa aaccttgaaa aataaaaaaa aaaaaaaaaa     180
aaa                                                                 183

<210> SEQ ID NO 57
<211> LENGTH: 622
<212> TYPE: DNA
<213> ORGANISM: Homo sapien
<220> FEATURE:
<221> NAME/KEY: misc_feature
<222> LOCATION: (1)...(622)
<223> OTHER INFORMATION: n = A,T,C or G

<400> SEQUENCE: 57
actagtcact actgtcttct ccttgtagct aatcaatcaa tattcttccc ttgcctgtgg      60
gcagtggaga gtgctgctgg gtgtacgctg caccctgccca ctgagttggg gaaagaggat    120
aatcagtgag cactgttctg ctcagagctc ctgatctacc ccacccccta ggatccagga    180
ctgggtcaaa gctgcatgaa accaggcct ggcagcaacc tgggaatggc tggaggtggg    240
agagaacctg acttctcttt ccctctccct cctccaacat tactggaact ctatcctgtt    300
agggatcttc tgagcttgtt tccctgctgg gtgggacaga agacaaagga gaagggangg    360
tctacaanaa gcagcccttc tttgtcctct ggggttaatg agcttgacct ananttcatg    420
gaganaccan aagcctctga tttttaattt ccntnaaatg tttgaagtnt atatntacat    480
atatatattt ctttnaatnt ttgagtcttt gatatgtctt aaaatccant ccctctgccn    540
gaaacctgaa ttaaaaccat gaanaaaaat gtttncctta aagatgttan taattaattg    600
aaacttgaaa aaaaaaaaaa aa                                             622

<210> SEQ ID NO 58
<211> LENGTH: 433
<212> TYPE: DNA
<213> ORGANISM: Homo sapien

<400> SEQUENCE: 58
gaacaaattc tgattggtta tgtaccgtca aaagacttga agaaatttca tgattttgca      60
gtgtggaagc gttgaaaatt gaaagttact gcttttccac ttgctcatat agtaaaggga    120
tcctttcagc tgccagtgtt gaataatgta tcatccagag tgatgttatc tgtgacagtc    180
accagcttta agctgaacca ttttatgaat accaaataaa tagacctctt gtactgaaaa    240
catatttgtg actttaatcg tgctgcttgg atagaaatat ttttactggt tcttctgaat    300
tgacagtaaa cctgtccatt atgaatggcc tactgttcta ttatttgttt tgacttgaat    360
ttatccacca aagacttcat ttgtgtatca tcaataaagt tgtatgtttc aactgaaaaa    420
aaaaaaaaaa aaa                                                      433

<210> SEQ ID NO 59
<211> LENGTH: 649
<212> TYPE: DNA
<213> ORGANISM: Homo sapien
<220> FEATURE:
<221> NAME/KEY: misc_feature
```

<222> LOCATION: (1)...(649)
<223> OTHER INFORMATION: n = A,T,C or G

<400> SEQUENCE: 59

```
actagttatt atctgacttt cnggttataa tcattctaat gagtgtgaag tagcctctgg      60
tgtcatttgg atttgcattt ctctgatgag tgatgctatc aagcacctt gctggtgctg     120
ttggccatat gtgtatgttc cctggagaag tgtctgtgct gagccttggc ccactttta     180
attaggcgtn tgtcttttta ttactgagtt gtaaganttc tttatatatt ctggattcta     240
gacccttatc agatacatgg tttgcaaata ttttctccca ttctgtgggt tgtgttttca     300
ctttatcgat aatgtcctta gacatataat aaatttgtat tttaaaagtg acttgatttg     360
ggctgtgcaa ggtgggctca cgcttgtaat cccagcactt tgggagactg aggtgggtgg     420
atcatatgan gangctagga gttcgaggtc agcctggcca gcatagcgaa aacttgtctc     480
tacnaaaaat acaaaaatta gtcaggcatg gtggtgcacg tctgtaatac cagcttctca     540
ggangctgan gcacaaggat cacttgaacc ccagaangaa gangttgcag tganctgaag     600
atcatgccag gcaacaaaa atgagaactt gtttaaaaaa aaaaaaaaa                  649
```

<210> SEQ ID NO 60
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 60

```
actagttcag gccttccagt tcactgacaa acatgggaa gtgtgcccag ctggctggaa       60
acctggcagt gataccatca agcctgatgt ccaaaagagc aaagaatatt tctccaagca     120
gaagtgagcg ctgggctgtt ttagtgccag gctgcggtgg gcagccatga gaacaaaacc     180
tcttctgtat ttttttttc cattagtana acacaagact cngattcagc cgaattgtgg      240
tgtcttacaa ggcagggctt tcctacaggg ggtgganaaa acagcctttc ttcctttggt     300
aggaatggcc tgagttggcg ttgtgggcag gctactggtt tgtatgatgt attagtagag     360
caacccatta atcttttgta gtttgtatna aacttganct gagaccttaa acaaaaaaaa     420
aaa                                                                   423
```

<210> SEQ ID NO 61
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 61

```
cgggactgga atgtaaagtg aagttcggag ctctgagcac gggctcttcc cgccgggtcc      60
tccctcccca gacccagag ggagaggccc acccgccca gccccgcccc agcccctgct      120
cagtctgag tatggctggg agtcggggc cacaggcctc tagctgtgct gctcaagaag       180
actggatcag ggtanctaca agtggccggg ccttgccttt gggattctac cctgttccta     240
atttggtgtt ggggtgcggg gtccctggcc cccttttcca cactncctcc ctccngacag     300
caacctccct tggggcaatt gggcctggnt ctccncccgn tgttgcnacc ctttgttggt     360
```

```
ttaaggncttt taaaaatgtt annttttccc ntgccngggt taaaaaagga aaaaactnaa      420
aaa                                                                     423

<210> SEQ ID NO 62
<211> LENGTH: 683
<212> TYPE: DNA
<213> ORGANISM: Homo sapien
<220> FEATURE:
<221> NAME/KEY: misc_feature
<222> LOCATION: (1)...(683)
<223> OTHER INFORMATION: n = A,T,C or G

<400> SEQUENCE: 62
gctggagagg ggtacggact ttcttggagt tgtcccaggt tggaatgaga ctgaactcaa       60
gaagagaccc taagagactg gggaatggtt cctgccttca ggaaagtgaa agacgcttag      120
gctgtcaaca cttaaaggaa gtccccttga agcccagagt ggacagacta gacccattga      180
tggggccact ggccatggtc cgtggacaag acattccngt gggccatggc acaccggggg      240
ggatcaaaat gtgtacttgt ggggtctcgc cccttgccaa aaccaaacca ntcccactcc      300
tgtcnttgga ctttcttccc attccctcct ccccaaatgc acttccccctc ctccctctgc     360 ccctcctgtg tttttggaat tctgttttccc tcaaaattgt taattttta nttttngacc      420 atgaacttat gtttggggtc nangttcccc ttnccaatgc atactaatat attaatggtt      480
atttattttt gaatatttt ttaatgaact tggaaaaaat tnntgaatt tccttncttc        540 cnttttnttt gggggggggtg gggggntggg ttaaaatttt tttggaancc cnatnggaaa     600
ttnttacttg ggccccccct naaaaaantn anttccaatt cttnnatngc ccctnttccn     660
ctaaaaaaaa anananaaa aan                                              683

<210> SEQ ID NO 63
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 63
actagtcata aagggtgtgc gcgtcttcga cgtggcggtc ttggcgccac tgctgcgaga       60
cccggccctg gacctcaagg tcatccactt ggtgcgtgat ccccgcgcgg tggcgagttc     120
acggatccgc tcgcgccacg gcctcatccg tgagagccta caggtggtgc gcagccgaga     180
ccgcgagctc accgcatgcc cttcttggag gccgcgggcc acaagcttgg cgcccanaaa     240
gaaggcgtng ggggcccgca aantaccacg ctctgggcgc tatggaangt cctcttgcaa     300
taatattggt tnaaaanctg canaanagcc cctgcanccc cctgaactgg gntgcagggc     360 cncttaccctn gtttggntgc ggttacaaag aacctgtttn ggaaaaccct nccnaaaacc    420
ttccgggaaa attntncaaa tttttnttgg ggaattnttg ggtaaaccc ccnaaaatgg      480 gaaacntttt tgccctnnaa antaaaccat tnggttccgg ggggcccccc ncaaaaccct    540 ttttntttt tttntgcccc cantnnccc ccggggcccc tttttttgg ggaaaancccc      600 cccccctncc nanantttta aaagggnggg anaattttt nttnccccc gggncccccn      660 ggngntaaaa nggtttcncc cccccgaggg gngggnnnc ctcnnaaacc cntntcnnna     720
ccncnttttt n                                                         731
```

<210> SEQ ID NO 64
<211> LENGTH: 313
<212> TYPE: DNA
<213> ORGANISM: Homo sapien
<220> FEATURE:
<221> NAME/KEY: misc_feature
<222> LOCATION: (1)...(313)
<223> OTHER INFORMATION: n = A,T,C or G

<400> SEQUENCE: 64

```
actagttgtg caaaccacga ctgaagaaag acgaaaagtg ggaaataact tgcaacgtct    60
gttagagatg gttgctacac atgttgggtc tgtagagaaa catcttgagg agcagattgc   120
taaagttgat agagaatatg aagaatgcat gtcagaagat ctctcggaaa atattaaaga   180
gattagagat aagtatgaga agaaagctac tctaattaag tcttctgaag aatgaagatn   240
aaatgttgat catgtatata tatccatagt gaataaaatt gtctcagtaa agttgtaaaa   300
aaaaaaaaaa aaa                                                      313
```

<210> SEQ ID NO 65
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 65

```
actagttccc tggcaggcaa gggcttccaa ctgaggcagt gcatgtgtgg cagagagagg    60
caggaagctg gcagtggcag cttctgtgtc tagggagggg tgtggctccc tccttccctg   120
tctgggaggt tggagggaag aatctaggcc ttagcttgcc ctcctgccac ccttcccctt   180
gtagatactg cctaacact ccctcctctc tcagctgtgg ctgccaccca agccaggttt    240
ctccgtgctc actaatttat ttccaggaaa ggtgtgtgga agacatgagc cgtgtataat   300
atttgtttta acattttcat tgcaagtatt gaccatcatc cttggttgtg tatcgttgta   360
acacaaatta atgatattaa aaagcatcca aacaaagccn annnnnaana nnannngaaa   420
```

<210> SEQ ID NO 66
<211> LENGTH: 676
<212> TYPE: DNA
<213> ORGANISM: Homo sapien
<220> FEATURE:
<221> NAME/KEY: misc_feature
<222> LOCATION: (1)...(676)
<223> OTHER INFORMATION: n = A,T,C or G

<400> SEQUENCE: 66

```
actagtttcc tatgatcatt aaactcattc tcagggttaa gaaaggaatg taaatttctg    60
cctcaatttg tacttcatca ataagttttt gaagagtgca gatttttagt caggtcttaa   120
aaataaactc acaaatctgg atgcatttct aaattctgca aatgtttcct ggggtgactt   180
aacaaggaat aatcccacaa tatacctagc tacctaatac atggagctgg ggctcaaccc   240
actgttttta aggatttgcg cttacttgtg gctgagggaa aataagtagt tccgagggaa   300
gtagttttta aatgtgagct tatagatngg aaacagaata tcaacttaat tatggaaatt   360
gttagaaacc tgttctcttg ttatctgaat cttgattgca attactattg tactggatag   420
actccagccc attgcaaagt ctcagatatc ttanctgtgt agttgaattc cttggaaatt   480
cttttttaaga aaaattgga gtttnaaaga aataaacccc tttgttaaat gaagcttggc   540
```

```
tttttggtga aaaanaatca tcccgcaggg cttattgttt aaaaanggaa ttttaagcct      600
ccctggaaaa anttgttaat taaatgggga aaatgntggg naaaaattat ccgttagggt      660
ttaaagggaa aactta                                                     676
```

<210> SEQ ID NO 67
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 67

```
caccattaaa gctgcttacc aagaacttcc ccagcatttt gacttccttg tttgatagct       60
gaattgtgag caggtgatag aagagccttt ctagttgaac atacagataa tttgctgaat      120
acattccatt taatgaaggg gttacatctg ttacgaagct actaagaagg agcaagagca      180 tagggggaaaa aaatctgatc agaacgcatc aaactcacat gtgccccctc tactacaaac      240
agattgtagt gctgtggtgg tttattccgt tgtgcagaac ttgcaagctg agtcactaaa      300
cccaaagaga ggaaattata ggttagttaa acattgtaat cccaggaact aagtttaatt      360
cacttttgaa gtgttttgtt ttttatttttt ggtttgtctg atttactttg ggggaaaang      420
ctaaaaaaaa agggatatca atctctaatt cagtgcccac taaagttgt ccctaaaaag       480 tctttactgg aanttatggg acttttttaag ctccaggtnt tttggtcctc caaattaacc      540
ttgcatgggc cccttaaaat tgttgaaggg cattcctgcc tctaagtttg gggaaaattc      600
ccccnttttn aaaatttgga                                                 620
```

<210> SEQ ID NO 68
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 68

```
actagtagct ggtacataat cactgaggag ctatttctta acatgctttt atagaccatg       60
ctaatgctag accagtattt aagggctaat ctcacacctc cttagctgta agagtctggc      120
ttagaacaga cctctctgtg caataacttg tggccactgg aaatccctgg gccggcattt      180
gtattggggt tgcaatgact cccaagggcc aaaagagtta aaggcacgac tgggatttct      240
tctgagactg tggtgaaact ccttccaagg ctgaggggt cagtangtgc tctgggaggg       300
actcggcacc actttgatat tcaacaagcc acttgaagcc caattataaa attgttattt      360
tacagctgat ggaactcaat ttgaaccttc aaaactttgt tagtttatcc tattatattg      420
ttaaacctaa ttcatttgt ctagcattgg atttggttcc tgtngcatat gttttttttcn      480 cctatgtgct ccctccccc nnatcttaat ttaaaccnca attttgcnat tcnccnnnnn      540
nannnannna a                                                         551
```

<210> SEQ ID NO 69
<211> LENGTH: 396
<212> TYPE: DNA
<213> ORGANISM: Homo sapien
<220> FEATURE:

```
<221> NAME/KEY: misc_feature
<222> LOCATION: (1)...(396)
<223> OTHER INFORMATION: n = A,T,C or G

<400> SEQUENCE: 69
cagaaatgga aagcagagtt ttcatttctg tttataaacg tctccaaaca aaaatggaaa        60
gcagagtttt cattaaatcc ttttacctttt ttttttttctt ggtaatcccc tcaaataaca    120
gtatgtggga tattgaatgt taaagggata ttttttttcta ttatttttat aattgtacaa    180
aattaagcaa atgttaaaag ttttatatgc tttattaatg ttttcaaaag gtatnataca    240
tgtgatacat tttttaagct tcagttgctt gtcttctggt actttctgtt atgggctttt    300
ggggagccan aaaccaatct acnatctctt tttgtttgcc aggacatgca ataaaattta    360
aaaaataaat aaaaactatt nagaaattga aaaaaa                               396

<210> SEQ ID NO 70
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 70
actagtgcaa aagcaaatat aaacatcgaa aaggcgttcc tcacgttagc tgaagatatc        60
cttcgaaaga cccctgtaaa agagcccaac agtgaaaatg tagatatcag cagtggagga    120
ggcgtgacag gctggaagag caaatgctgc tgagcattct cctgttccat cagttgccat    180
ccactacccc gttttctctt cttgctgcaa ataaaaccac tctgtccatt tttaactcta    240
aacagatatt tttgtttctc atcttaacta tccaagccac ctatttttatt tgttctttca    300 tctgtgactg cttgctgact ttatcataat tttcttcaaa caaaaaaatg tatagaaaaa    360
tcatgtctgt gacttcattt ttaaatgnta cttgctcagc tcaactgcat ttcagttgtt    420
ttatagtcca gttcttatca acattnaaac ctatngcaat catttcaaat ctattctgca    480
aattgtataa gaataaaagt tagaatttaa caattaaaaa aaaaaaaaa aaaaaa         536

<210> SEQ ID NO 71
<211> LENGTH: 865
<212> TYPE: DNA
<213> ORGANISM: Homo sapien
<220> FEATURE:
<221> NAME/KEY: misc_feature
<222> LOCATION: (1)...(865)
<223> OTHER INFORMATION: n = A,T,C or G

<400> SEQUENCE: 71
gacaaagcgt taggagaaga anagaggcag ggaanactnc ccaggcacga tggccnccttt     60 cccaccagca accagcgccc cccaccagcc cccaggcccg gacgacgaag actccatcct    120
ggattaatct nacctctntc gcctgnccca ttcctacctc ggaggtggag gccggaaagg    180
tcncaccaag aganaanctg ctgccaacac caaccgcccc agccctggcg ggcacganag    240
gaaactggtg accaatctgc agaattctna gaggaanaag cnaggggccc cgcgctnaga    300
cagagctgga tatgangcca gaccatggac nctacnccccn ncaatncana cgggactgcg    360
gaagatggan gacccncgac nngatcaggc ngctnnccaa nccccccacc cctatgaatt    420
attcccgctg aangaatctc tganngggctt ccannaaagc gcctccccnc cnaacgnaan    480
tncaacatng ggattanang ctgggaactg naagggggcaa anccttnnaat atccccagaa    540
```

```
acaanctctc ccnaanaaac tggggcncct catnggtggn accaactatt aactaaaccg      600
cacgccaagn aantataaaa gggggcccc  tccncggnng accccctttt gtcccttaat      660
ganggttatc cnccttgcgt accatggtnc ccnnttctgt ntgnatgttt ccnctcccct      720
ccncctatnt cnagccgaac tcnnatttnc ccggggtgc  natcnantng tncnccttttn    780 ttngttgncc cngcccttc  cgncggaacn cgtttccccg ttantaacgg cacccggggn     840
aagggtgntt ggccccctcc ctccc                                            865

<210> SEQ ID NO 72
<211> LENGTH: 560
<212> TYPE: DNA
<213> ORGANISM: Homo sapien
<220> FEATURE:
<221> NAME/KEY: misc_feature
<222> LOCATION: (1)...(560)
<223> OTHER INFORMATION: n = A,T,C or G

<400> SEQUENCE: 72
cctggacttg tcttggttcc agaacctgac gacccggcga cggcgacgtc tcttttgact      60
aaaagacagt gtccagtgct ccngcctagg agtctacggg gaccgcctcc cgcgccgcca     120
ccatgcccaa cttctctggc aactggaaaa tcatccgatc ggaaaacttc gangaattgc     180
tcnaantgct gggggtgaat gtgatgctna ngaanattgc tgtggctgca gcgtccaagc     240
cagcagtgga gatcnaacag gagggagaca ctttctacat caaaacctcc accaccgtgc     300
gcaccacaaa gattaacttc nnngttgggg aggantttga ggancaaact gtggatngga     360
ngcctgtnaa aacctggtga aatgggagaa tganaataaa atggtctgtg ancanaaact     420
cctgaaagga gaaggccccc anaactcctg gaccngaaaa actgacccnc cnatnggga     480 actgatnctt gaaccctgaa cgggcgggat ganccttttt tnttgccncc naangggttc     540
tttccntttc cccaaaaaaa                                                 560

<210> SEQ ID NO 73
<211> LENGTH: 379
<212> TYPE: DNA
<213> ORGANISM: Homo sapien
<220> FEATURE:
<221> NAME/KEY: misc_feature
<222> LOCATION: (1)...(379)
<223> OTHER INFORMATION: n = A,T,C or G

<400> SEQUENCE: 73
ctggggancc ggcggtnngc nccatntcnn gncgcgaagg tggcaataaa aanccnctga      60
aaccgcncaa naaacatgcc naagatatgg acgaggaaga tngngctttc nngnacaanc     120
gnanngagga acanaacaaa ctcnangagc tctcaagcta atgccgcggg gaaggggccc     180
ttggccacnn gtgaattaa  gaaatctggc aaanngtann tgttccttgt gcctnangag     240
ataagngacc ctttatttca tctgtattta aacctctctn ttccctgnca taacttcttt     300
tnccacgtan agntggaant anttgttgtc ttggactgtt gtncatttta gannaaactt     360
ttgttcaaaa aaaaaataa                                                  379

<210> SEQ ID NO 74
<211> LENGTH: 437
<212> TYPE: DNA
<213> ORGANISM: Homo sapien
<220> FEATURE:
<221> NAME/KEY: misc_feature
<222> LOCATION: (1)...(437)
```

-continued

<223> OTHER INFORMATION: n = A,T,C or G

<400> SEQUENCE: 74

| actagttcag actgccacgc caaccccaga aaatacccca catgccagaa aagtgaagtc | 60 |
| ctaggtgttt ccatctatgt ttcaatctgt ccatctacca ggcctcgcga taaaaacaaa | 120 |
| acaaaaaaac gctgccaggt tttanaagca gttctggtct caaaaccatc aggatcctgc | 180 |
| caccagggtt cttttgaaat agtaccacat gtaaaaggga atttggcttt cacttcatct | 240 |
| aatcactgaa ttgtcaggct ttgattgata attgtagaaa taagtagcct tctgttgtgg | 300 |
| gaataagtta taatcagtat tcatctcttt gttttttgtc actcttttct ctctnattgt | 360 |
| gtcatttgta ctgtttgaaa aatatttctt ctataaaatt aaactaacct gccttaaaaa | 420 |
| aaaaaaaaaa aaaaaaa | 437 |

<210> SEQ ID NO 75
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 75

| ctccgtcgcc gccaagatga tgtgcggggc gccctccgcc acgcagccgg ccaccgccga | 60 |
| gacccagcac atcgccgacc aggtgaggtc ccagcttgaa gagaaagaaa caagaagtt | 120 |
| ccctgtgttt aaggccgtgt cattcaagag ccaggtggtc gcggggacaa actacttcat | 180 |
| caaggtgcac gtcggcgacg aggacttcgt cacctgcga gtgttccaat ctctccctca | 240 |
| tgaaaacaag cccttgacct tatctaacta ccagaccaac aaagccaagc atgatgagct | 300 |
| gacctatttc tgatcctgac tttggacaag gcccttcagc cagaagactg acaaagtcat | 360 |
| cctccgtcta ccagagcgtg cacttgtgat cctaaaataa gcttcatctc cgggctgtgc | 420 |
| ccttggggtg gaaggggcan gatctgcact gcttttgcat ttctcttcct aaatttcatt | 480 |
| gtgttgattc tttccttcca ataggtgatc ttnattactt tcagaatatt ttccaaatna | 540 |
| gatatatttt naaaatcctt aaaaaaaaaa aaaaaaaa | 579 |

<210> SEQ ID NO 76
<211> LENGTH: 666
<212> TYPE: DNA
<213> ORGANISM: Homo sapien
<220> FEATURE:
<221> NAME/KEY: misc_feature
<222> LOCATION: (1)...(666)
<223> OTHER INFORMATION: n = A,T,C or G

<400> SEQUENCE: 76

| gtttatccta tctctccaac cagattgtca gctccttgag ggcaagagcc acagtatatt | 60 |
| tccctgtttc ttccacagtg cctaataata ctgtggaact aggttttaat aattttttaa | 120 |
| ttgatgttgt tatgggcagg atggcaacca gaccattgtc tcagagcagg tgctggctct | 180 |
| ttcctggcta ctccatgttg gctagcctct ggtaacctct tacttattat cttcaggaca | 240 |
| ctcactacag ggaccaggga tgatgcaaca tccttgtctt tttatgacag gatgtttgct | 300 |
| cagcttctcc aacaataaaa agcacgtggt aaaacacttg cggatattct ggactgtttt | 360 |
| taaaaatat acagtttacc gaaaatcata ttatcttaca atgaaaagga ntttatagat | 420 |
| cagccagtga acaaccttt cccaccatac aaaaattcct tttcccgaan gaaaanggct | 480 |

```
ttctcaataa ncctcactttt cttaanatct tacaagatag ccccganatc ttatcgaaac    540
tcattttagg caaatatgan ttttattgtn cgttacttgt ttcaaaattt ggtattgtga    600
atatcaatta ccacccccat ctcccatgaa anaaanggga aanggtgaan ttcntaancg    660
cttaaa                                                                666
```

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77

```
ctgcagcccg ggggatccac taatctacca nggttatttg gcagctaatt ctanatttgg     60
atcattgccc aaagttgcac ttgctggtct cttgggattt ggccttggaa aggtatcata    120
catanganta tgccanaata aattccattt ttttgaaaat canctccntg gggctggttt    180
tggtccacag cataacangc actgcctcct tacctgtgag gaatgcaaaa taaagcatgg    240
attaagtgag aagggagact ctcagccttc agcttcctaa attctgtgtc tgtgactttc    300
gaagtttttt aaacctctga atttgtacac atttaaaatt tcaagtgtac tttaaaataa    360
aatacttcta atgggaacaa aaaaaaaaaa aaaaaa                              396
```

<210> SEQ ID NO 78
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 78

```
gcatcctagc cgccgactca cacaaggcag gtgggtgagg aaatccagag ttgccatgga     60
gaaaattcca gtgtcagcat tcttgctcct tgtggccctc tcctacactc tggccagaga    120
taccacagtc aaacctggag ccaaaaagga cacaaaggac tctcgaccca aactgcccca    180
gaccctctcc agaggttggg gtgaccaact catctggact cagacatatg aagaagctct    240
atataaatcc aagacaagca acaaaccctt gatgattatt catcacttgg atgagtgccc    300
acacagtcna gctttaaaga aagtgtttgc tgaaaataaa gaaatccaga attggcaga    360 gcagtttgtc ctcctcaatc tggtttatga aacaactgac aaacaccttt ctcctgatgg    420
ccagtatgtc ccaggattat gtttgttgac ccatctctga cagttgaagc cgatatcctg    480
ggaagatatt cnaaccgtct ctatgcttac aaactgcaga tacgctctgt tgcttgacac    540
atgaaaaagc tctcaagttg ctnaaaatga attgtaagaa aaaaaatctc cagccttctg    600
tctgtcggct tgaaaattga aaccagaaaa atgtgaaaaa tggctattgt ggaacanatn    660
gacacctgat taggttttgg ttatgttcac cactattttt aanaaaanan nttttaaaat    720
ttggttcaat tntctttttn aaacaatntg tttctacntt gnganctgat ttctaaaaaa    780
aataatnttt ggc                                                       793
```

<210> SEQ ID NO 79
<211> LENGTH: 456
<212> TYPE: DNA

<213> ORGANISM: Homo sapien
<220> FEATURE:
<221> NAME/KEY: misc_feature
<222> LOCATION: (1)...(456)
<223> OTHER INFORMATION: n = A,T,C or G

<400> SEQUENCE: 79

| | | | | | |
|---|---|---|---|---|---|
| actagtatgg | ggtgggaggc | cccacccttc | tccctaggc | gctgttcttg | ctccaaaggg | 60 |
| ctccgtggag | agggactggc | agagctgang | ccacctgggg | ctggggatcc | cactcttctt | 120 |
| gcagctgttg | agcgcaccta | accactggtc | atgcccccac | ccctgctctc | cgcacccgct | 180 |
| tcctcccgac | cccangacca | ggctacttct | cccctcctct | tgcctccctc | ctgcccctgc | 240 |
| tgcctctgat | cgtangaatt | gangantgtc | ccgccttgtg | gctganaatg | gacagtggca | 300 |
| ggggctggaa | atgggtgtgt | gtgtgtgtgt | gtgtgtgtgt | gtgtgtgtgt | gcnccccccc | 360 |
| tgcaagaccg | agattgaggg | aaancatgtc | tgctgggtgt | gaccatgttt | cctctccata | 420 |
| aantncccct | gtgacnctca | naaaaaaaaa | aaaaaa | | | 456 |

<210> SEQ ID NO 80
<211> LENGTH: 284
<212> TYPE: DNA
<213> ORGANISM: Homo sapien
<220> FEATURE:
<221> NAME/KEY: misc_feature
<222> LOCATION: (1)...(284)
<223> OTHER INFORMATION: n = A,T,C or G

<400> SEQUENCE: 80

| | | | | | |
|---|---|---|---|---|---|
| ctttgtacct | ctagaaaaga | taggtattgt | gtcatgaaac | ttgagtttaa | attttatata | 60 |
| taaaactaaa | agtaatgctc | actttagcaa | cacatactaa | aattggaacc | atactgagaa | 120 |
| gaatagcatg | acctccgtgc | aaacaggaca | agcaaatttg | tgatgtgttg | attaaaaaga | 180 |
| aataaataaa | tgtgtatatg | tgtaacttgt | atgtttatgt | ggaatacaga | ttgggaaata | 240 |
| aaatgtattt | cttactgtga | aaaaaaaaa | aaaaaaaaaa | aana | | 284 |

<210> SEQ ID NO 81
<211> LENGTH: 671
<212> TYPE: DNA
<213> ORGANISM: Homo sapien
<220> FEATURE:
<221> NAME/KEY: misc_feature
<222> LOCATION: (1)...(671)
<223> OTHER INFORMATION: n = A,T,C or G

<400> SEQUENCE: 81

| | | | | | |
|---|---|---|---|---|---|
| gccaccaaca | ttccaagcta | ccctgggtac | ctttgtgcag | tagaagctag | tgagcatgtg | 60 |
| agcaagcggt | gtgcacacgg | agactcatcg | ttataattta | ctatctgcca | agagtagaaa | 120 |
| gaaaggctgg | ggatatttgg | gttggcttgg | ttttgatttt | ttgcttgttt | gtttgttttg | 180 |
| tactaaaaca | gtattatctt | ttgaatatcg | taggacata | agtatataca | tgttatccaa | 240 |
| tcaagatggc | tagaatggtg | cctttctgag | tgtctaaaac | ttgacacccc | tggtaaatct | 300 |
| ttcaacacac | ttccactgcc | tgcgtaatga | agttttgatt | cattttaac | cactggaatt | 360 |
| tttcaatgcc | gtcattttca | gttagatnat | tttgcactttt | gagattaaaa | tgccatgtct | 420 |
| atttgattag | tcttatttttt | ttattttttac | aggcttatca | gtctcactgt | tggctgtcat | 480 |
| tgtgacaaag | tcaaataaac | ccccnaggac | aacacacagt | atgggatcac | atattgtttg | 540 |
| acattaagct | ttggccaaaa | aatgttgcat | gtgttttacc | tcgacttgct | aaatcaatan | 600 |
| canaaaggct | ggctnataat | gttggtggtg | aaataattaa | tnantaacca | aaaaaaaaan | 660 | aaaaaaaaaa a                                                          671

<210> SEQ ID NO 82
<211> LENGTH: 217
<212> TYPE: DNA
<213> ORGANISM: Homo sapien
<220> FEATURE:
<221> NAME/KEY: misc_feature
<222> LOCATION: (1)...(217)
<223> OTHER INFORMATION: n = A,T,C or G

<400> SEQUENCE: 82
ctgcagatgt tcttgaatg ctttgtcaaa ttaanaaagt taaagtgcaa taatgtttga      60
agacaataag tggtggtgta tcttgtttct aataagataa acttttttgt ctttgcttta    120
tcttattagg gagttgtatg tcagtgtata aaacatactg tgtggtataa caggcttaat    180
aaattcttta aaggaaaaa aaaaaaaaaa aaaaaaa                              217

<210> SEQ ID NO 83
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 83
cgcgagtggg agcaccagga tctcgggctc ggaacgagac tgcacggatt gttttaagaa     60
aatggcagac aaaccagaca tgggggaaat cgccagcttc gatnaggcca agctgaanaa   120
aacggagacg caggagaaga acaccctgcc gaccaaagag accattgagc angagaagcg   180
gagtgaaatt tcctaagatc ctggaggatt tcctaccccc gtcctcttcg agaccccagt   240
cgtgatgtgg aggaagagcc acctgcaaga tggacacgag ccacaagctg cactgtgaac   300
ctgggcactc cgcgccgatg ccaccggcct gtgggtctct gaaggaccc cccccaatcg    360 gactgccaaa ttctccggtt tgccccggga tattatacaa nattatttgt atgaataatg   420
annataaaac acacctcgtg gcancaaana aaaaaaaaa                           460

<210> SEQ ID NO 84
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 84
tggtggatct tggctctgtg gagctgctgg gacgggatct aaaagactat tctggaagct     60
gtggtccaan gcattttgct ggcttaacgg gtcccggaac aaaggacacc agctctctaa   120
aattgaagtt tacccganat aacaatcttt tgggcagaga tgcctattt aacaaacncc    180 gtccctgcgc aacaacnaac aatctctggg aaataccggc catgaacntg ctgtctcaat   240
cnancatctc tctagctgac cgatcatatc gtcccagatt actacanatc ataataattg   300
atttcctgta naaaaaaaaa aaa                                            323

<210> SEQ ID NO 85
<211> LENGTH: 771
<212> TYPE: DNA

<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 85

| | | | | | |
|---|---|---|---|---|---|
| aaactgggta | ctcaacactg | agcagatctg | ttctttgagc | taaaaaccat | gtgctgtacc | 60 |
| aanagtttgc | tcctggctgc | tttgatgtca | gtgctgctac | tccacctctg | cggcgaatca | 120 |
| gaagcaagca | actttgactg | ctgtcttgga | tacacagacc | gtattcttca | tcctaaattt | 180 |
| attgtgggct | tcacacggca | gctggccaat | gaaggctgtg | acatcaatgc | tatcatcttt | 240 |
| cacacaaaga | aaaagttgtc | tgtgtgcgca | atccaaaac | agacttgggt | gaaatatatt | 300 |
| gtgcgtctcc | tcagtaaaaa | agtcaagaac | atgtaaaaac | tgtggctttt | ctggaatgga | 360 |
| attggacata | gcccaagaac | agaaagaact | tgctggggtt | ggaggtttca | cttgcacatc | 420 |
| atgganggtt | tagtgcttat | cttatttgtg | cctcctggac | ttgtccaatt | natgaagtta | 480 |
| atcatattgc | atcatanttt | gctttgttta | acatcacatt | naaattaaac | tgtatttat | 540 |
| gttatttata | gctntaggtt | ttctgtgttt | aacttttat | acnaantttc | ctaaactatt | 600 |
| ttggtntant | gcaanttaaa | aattatattt | gggggggaa | taaatattgg | antttctgca | 660 |
| gccacaagct | ttttaaaa | aaccantaca | nccnngttaa | atggtnggtc | ccnaatggtt | 720 |
| tttgcttttn | antagaaaat | ttnttagaac | natttgaaaa | aaaaaaaaa | a | 771 |

<210> SEQ ID NO 86
<211> LENGTH: 628
<212> TYPE: DNA
<213> ORGANISM: Homo sapien
<220> FEATURE:
<221> NAME/KEY: misc_feature
<222> LOCATION: (1)...(628)
<223> OTHER INFORMATION: n = A,T,C or G

<400> SEQUENCE: 86

| | | | | | |
|---|---|---|---|---|---|
| actagtttgc | tttacatttt | tgaaaagtat | tatttttgtc | caagtgctta | tcaactaaac | 60 |
| cttgtgttag | gtaagaatgg | aatttattaa | gtgaatcagt | gtgacccttc | ttgtcataag | 120 |
| attatcttaa | agctgaagcc | aaaatatgct | tcaaaagaaa | angactttat | tgttcattgt | 180 |
| agttcataca | ttcaaagcat | ctgaactgta | gtttctatag | caagccaatt | acatccataa | 240 |
| gtggagaang | aaatagatta | atgtcnaagt | atgattggtg | gagggagcaa | ggttgaagat | 300 |
| aatctggggt | tgaaattttc | tagttttcat | tctgtacatt | tttagttnga | catcagattt | 360 |
| gaaatattaa | tgtttaccttt | tcaatgtgtg | gtatcagctg | gactcantaa | caccccttc | 420 |
| ttccctnggg | gatggggaat | ggattattgg | aaaatggaaa | gaaaaaagta | cttaaagcct | 480 |
| tcctttcnca | gtttctggct | cctaccctac | tgatttancc | agaataagaa | acatttat | 540 |
| catcntctgc | tttattccca | ttaatnaant | tttgatgaat | aaatctgctt | ttatgcnnac | 600 |
| ccaaggaatt | nagtggnttc | ntcnttgt | | | | 628 |

<210> SEQ ID NO 87
<211> LENGTH: 518
<212> TYPE: DNA
<213> ORGANISM: Homo sapien
<220> FEATURE:
<221> NAME/KEY: misc_feature
<222> LOCATION: (1)...(518)
<223> OTHER INFORMATION: n = A,T,C or G

<400> SEQUENCE: 87

```
tttttttattt tttttagaga gtagttcagc ttttatttat aaatttattg cctgttttat        60
tataacaaca ttatactgtt tatggtttaa tacatatggt tcaaaatgta taatacatca       120
agtagtacag ttttaaaatt ttatgcttaa aacaagtttt gtgtaaaaaa tgcagataca       180
ttttacatgg caaatcaatt tttaagtcat cctaaaaatt gatttttttt tgaaatttaa       240
aaacacattt aatttcaatt tctctcttat ataaccttta ttactatagc atggtttcca       300
ctacagttta acaatgcagc aaaattccca tttcacggta aattgggttt taagcggcaa       360
ggttaaaatg ctttgaggat cctnaatacc ctttgaactt caaatgaagg ttatggttgt       420
naatttaacc ctcatgccat aagcagaagc acaagtttag ctgcattttg ctctaaactg       480
taaaancgag cccccgttg aaaaagcaaa agggaccc                                518

<210> SEQ ID NO 88
<211> LENGTH: 1844
<212> TYPE: DNA
<213> ORGANISM: Homo sapien

<400> SEQUENCE: 88
gagacagtga atcctagtat caaaggattt ttggcctcag aaaaagttgt tgattatttt        60
tattttattt tattttttcga gactccgtct caaaaaaaaa aaaaaaaaaa agaatcacaa       120
ggtatttgct aaagcatttt gagctgcttg gaaaagggga agtagttgca gtagagtttc       180
ttccatcttc ttggtgctgg gaagccatat atgtgtcttt tactcaagct aaggggtata       240
agcttatgtg ttgaatttgc tacatctata tttcacatat tctcacaata agagaatttt       300
gaaatagaaa tatcatagaa catttaagaa agtttagtat aaataatatt ttgtgtgttt       360
taatcccttt gaagggatct atccaaagaa aatattttac actgagctcc ttcctacacg       420
tctcagtaac agatcctgtg ttagtctttg aaaatagctc atttttttaaa tgtcagtgag       480 tagatgtagc atacatatga tgtataatga cgtgtattat gttaacaatg tctgcagatt       540
ttgtaggaat acaaaacatg gccttttta taagcaaaac gggccaatga ctagaataac       600
acatagggca atctgtgaat atgtattata agcagcattc cagaaaagta gttggtgaaa       660
taattttcaa gtcaaaaagg gatatggaaa gggaattatg agtaacctct atttttttaag      720 ccttgctttt aaattaaacg ctacagccat ttaagccttg aggataataa agcttgagag       780
taataatgtt aggttagcaa aggtttagat gtatcacttc atgcatgcta ccatgatagt       840
aatgcagctc ttcgagtcat ttctggtcat tcaagatatt cacccttttg cccatagaaa       900
gcaccctacc tcacctgctt actgacattg tcttagctga tcacaagatc attatcagcc       960
tccattattc cttactgtat ataaaataca gagttttata ttttcctttc ttcgttttc       1020 accatattca aaacctaaat ttgttttttgc agatggaatg caaagtaatc aagtgttcgt      1080
gctttcacct agaagggtgt ggtcctgaag gaaagaggtc cctaaatatc ccccaccctg      1140
ggtgctcctc cttccctggt accctgacta ccagaagtca ggtgctagag cagctggaga      1200
agtgcagcag cctgtgcttc cacagatggg ggtgctgctg caacaaggct ttcaatgtgc      1260
ccatcttagg gggagaagct agatcctgtg cagcagcctg gtaagtcctg aggaggttcc      1320
attgctcttc ctgctgctgt cctttgcttc tcaacggggc tcgctctaca gtctagagca      1380
catgcagcta acttgtgcct ctgcttatgc atgagggtta aattaacaac cataaccttc      1440
atttgaagtt caaaggtgta ttcaggatcc tcaaagcatt ttaaccttgc cgcttaaaac      1500
ccaatttacc gtgaaatggg aattttgctg cattgttaaa ctgtagtgga aaccatgcta      1560
```

-continued

| | |
|---|---|
| tagtaataaa ggttatataa gagagaaatt gaaattaaat gtgttttaa atttcaaaaa | 1620 |
| aaaatcaatc tttaggatga cttaaaaatt gatttgccat gtaaaatgta tctgcatttt | 1680 |
| ttacacaaaa cttgttttaa gcataaaatt ttaaaactgt actacttgat gtattataca | 1740 |
| ttttgaacca tatgtattaa accataaaca gtaaatgtt gttataataa aacaggcaat | 1800 |
| aaatttataa ataaaagctg aaaaaaaaaa aaaaaaaaa aaaa | 1844 |

<210> SEQ ID NO 89
<211> LENGTH: 523
<212> TYPE: DNA
<213> ORGANISM: Homo sapien
<220> FEATURE:
<221> NAME/KEY: misc_feature
<222> LOCATION: (1)...(523)
<223> OTHER INFORMATION: n = A,T,C or G

<400> SEQUENCE: 89

| | |
|---|---|
| tttttttttt tttttttagt caatccacat ttattgatca cttattatgt accaggcact | 60 |
| gggataaaga tgactgttag tcactcacag taaggaagaa aactagcaaa taagacgatt | 120 |
| acaatatgat gtagaaaatg ctaagccaga gatatagaaa ggtcctattg ggtccttctg | 180 |
| tcaccttgtc tttccacatc cctacccttc acaggccttc cctccagctt cctgcccccg | 240 |
| ctccccactg cagatcccct gggattttgc ctagagctaa acgagganat gggcccctg | 300 |
| gccctggcat gacttgaacc caaccacaga ctgggaaagg gagcctttcg anagtggatc | 360 |
| actttgatna gaaaacacat agggaattga agagaaantc cccaaatggc cacccgtgct | 420 |
| ggtgctcaag aaaagtttgc agaatggata aatgaaggat caagggaatt aatanatgaa | 480 |
| taattgaatg gtggctcaat aagaatgact ncnttgaatg acc | 523 |

<210> SEQ ID NO 90
<211> LENGTH: 604
<212> TYPE: DNA
<213> ORGANISM: Homo sapien
<220> FEATURE:
<221> NAME/KEY: misc_feature
<222> LOCATION: (1)...(604)
<223> OTHER INFORMATION: n = A,T,C or G

<400> SEQUENCE: 90

| | |
|---|---|
| ccagtgtggt ggaatgcaaa gattaccccg gaagctttcg agaagctggg attccctgca | 60 |
| gcaaaggaaa tagccaatat gtgtcgtttc tatgaaatga agccagaccg agatgtcaat | 120 |
| ctcacccacc aactaaatcc caaagtcaaa agcttcagcc agtttatctc agagaaccag | 180 |
| gggagccttc aagggcatgt agaaaatcag ctgttcagat aggcctctgc accacacagc | 240 |
| ctctttcctc tctgatcctt ttcctcttta cggcacaaca ttcatgtttg acagaacatg | 300 |
| ctggaatgca attgtttgca acaccgaagg atttcctgcg gtcgcctctt cagtaggaag | 360 |
| cactgcattg gtgataggac acggtaattt gattcacatt taacttgcta gttagtgata | 420 |
| aggggtggta cacctgtttg gtaaaatgag aagcctcgga aacttgggag cttctctcct | 480 |
| accactaatg gggagggcag attattactg ggatttctcc tggggtgaat taatttcaag | 540 |
| ccctaattgc tgaaattccc ctnggcaggc tccagttttc tcaactgcat tgcaaaattc | 600 |
| cccc | 604 |

<210> SEQ ID NO 91
<211> LENGTH: 858
<212> TYPE: DNA
<213> ORGANISM: Homo sapien
<220> FEATURE:
<221> NAME/KEY: misc_feature
<222> LOCATION: (1)...(858)
<223> OTHER INFORMATION: n = A,T,C or G

<400> SEQUENCE: 91

| | | | | | |
|---|---|---|---|---|---|
| tttttttttt | tttttttta | tgattattat | ttttttttatt | gatctttaca | tcctcagtgt | 60 |
| tggcagagtt | tctgatgctt | aataaacatt | tgttctgatc | agataagtgg | aaaaaattgt | 120 |
| catttcctta | ttcaagccat | gcttttctgt | gatattctga | tcctagttga | acatacagaa | 180 |
| ataaatgtct | aaaacagcac | ctcgattctc | gtctataaca | ggactaagtt | cactgtgatc | 240 |
| ttaaataagc | ttggctaaaa | tgggacatga | gtggaggtag | tcacacttca | gcgaagaaag | 300 |
| agaatctcct | gtataatctc | accaggagat | tcaacgaatt | ccaccacact | ggactagtgg | 360 |
| atcccccggg | ctgcaggaat | tcgatatcaa | gcttatcgat | accgtcgacc | tcgagggggg | 420 |
| gcccggtacc | caattcgccc | tatagtgagt | cgtattacgc | gcgctcactg | gccgtcgttt | 480 |
| tacaacgtcg | tgactgggaa | aaccctggcg | ttacccaact | taatcgcctt | gcagcacatc | 540 |
| cccctttcgc | cagctggcgt | aatagcgaan | agcccgcacc | gatcgccctt | ncaacagttg | 600 |
| cgcagcctga | atggcgaatg | ggacgcgccc | tgtagcggcg | cattaaagcg | cggcngggtg | 660 |
| tggnggntcc | cccacgtgac | cgntacactt | ggcagcgcct | tacgccggtc | nttcgctttc | 720 |
| ttcccttcct | ttctcgcacc | gttcgccggg | tttccccgnn | agctnttaat | cggggggnctc | 780 |
| cctttanggg | tncnaattaa | nggnttacng | gaccttngan | cccaaaaact | ttgattaggg | 840 |
| ggaaggtccc | cgaagggg | | | | | 858 |

<210> SEQ ID NO 92
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 92

| | | | | | |
|---|---|---|---|---|---|
| gttgaatctc | ctggtgagat | tatacaggag | attctctttc | ttcgctgaag | tgtgactacc | 60 |
| tccactcatg | tcccatttta | gccaagctta | tttaagatca | cagtgaactt | agtcctgtta | 120 |
| tagacgagaa | tcgaggtgct | gttttagaca | tttatttctg | tatgttcaac | taggatcaga | 180 |
| atatcacaga | aaagcatggc | ttgaataagg | aaatgacaat | ttttccact | tatctgatca | 240 |
| gaacaaatgt | ttattaagca | tcagaaactc | tgccaacact | gaggatgtaa | agatcaataa | 300 |
| aaaaaataat | aatcatnann | naananannan | nngaagggcg | gccgccaccg | cggtggagct | 360 |
| ccagcttttg | ttccctttag | tgagggttaa | ttgcgcgctt | ggcgttaatc | atggtcatag | 420 |
| ctgtttcctg | tgtgaaattg | ttatccggct | cacaattccn | cncaacatac | gagccgggaa | 480 |
| gcntnangtg | taaaagcctg | ggggtgccta | attgagtgag | ctnactcaca | ttaattgngt | 540 |
| tgcgctccac | ttgcccgctt | ttccantccg | ggaaacctgt | tcgnc | | 585 |

<210> SEQ ID NO 93
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 93

```
cggcagtgtt gctgtctgcg tgtccacctt ggaatctggc tgaactggct gggaggacca      60
agactgcggc tggggtgggc anggaaggga accgggggct gctgtgaagg atcttggaac     120
ttccctgtac ccaccttccc cttgcttcat gtttgtanag gaaccttgtg ccggccaagc     180
ccagtttcct tgtgtgatac actaatgtat ttgctttttt tgggaaatan anaaaaatca     240
attaaattgc tantgtttct ttgaannnnn nnnnnnnnnn nnnnnnnggg ggggncgccc     300
ccncggngga aacnccccct tttgttccct taattgaaa ggttaattng cncncntggc      360
gttaanccnt gggccaaanc tngttncccg tgntgaaatt gttatcccc tcccaaattc      420
cccccnncc ttccaaaccc ggaaancctn annntgttna ncccggggg gttgcctaan       480
ngnaattnaa ccnaacccc ntttaaatng nntttgcncn ccacnngccc cnctttccca     540
nttcggggaa aaccctntcc gtgccca                                         567
```

<210> SEQ ID NO 94
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 94

```
actagtcaaa aatgctaaaa taatttggga gaaaatattt ttaagtagt gttatagttt       60
catgtttatc ttttattatg ttttgtgaag ttgtgtcttt tcactaatta cctatactat     120
gccaatattt cctatatcct atccataaca tttatactac atttgtaana naatatgcac     180
gtgaaactta cactttata aggtaaaaat gaggtttcca anatttaata atctgatcaa     240
gttcttgtta tttccaaata gaatggactt ggtctgttaa gggctaagga gaagaggaag    300
ataaggttaa aagttgttaa tgaccaaaca ttctaaaaga aatgcaaaaa aaaagtttat    360
tttcaagcct tcgaactatt taaggaaagc aaaatcattt cctaaatgca tatcatttgt    420
gagaatttct cattaatatc ctgaatcatt catttcacta aggctcatgt tnactccgat    480
atgtctctaa gaaagtacta tttcatggtc caaacctggt tgccatantt gggtaaaggc    540
tttcccttaa gtgtgaaant atttaaaatg aaatttttcct ctttttaaaa attctttana    600
agggttaagg gtgttgggga                                                  620
```

<210> SEQ ID NO 95
<211> LENGTH: 470
<212> TYPE: DNA
<213> ORGANISM: Homo sapien
<220> FEATURE:
<221> NAME/KEY: misc_feature
<222> LOCATION: (1)...(470)
<223> OTHER INFORMATION: n = A,T,C or G

<400> SEQUENCE: 95

```
ctcgaccttc tctgcacagc ggatgaaccc tgagcagctg aagaccagaa aagccactat      60
nactttntgc ttaattcang agcttacang attcttcaaa gagtgngtcc agcatccttt     120
gaaacatgag ttcttaccag cagaagcaga cctttacccc accacctcag cttcaacagc    180
agcaggtgaa acaacccatc cagcctccac ctnaggaaat atttgttccc acaaccaagg    240
agccatgcca ctcaaaggtt ccacaacctg naaacacaaa nattccagag ccaggctgta    300
ccaaggtccc tgagccaggg ctgtaccaan gtccctgagc caggttgtac caangtccct    360
```

| | |
|---|---|
| gagccaggat gtaccaaggt ccctgancca ggttgtccaa ggtccctgag ccaggctaca | 420 |
| ccaagggcct gngccaggca gcatcaangt ccctgaccaa ggcttatcaa | 470 |

<210> SEQ ID NO 96
<211> LENGTH: 660
<212> TYPE: DNA
<213> ORGANISM: Homo sapien
<220> FEATURE:
<221> NAME/KEY: misc_feature
<222> LOCATION: (1)...(660)
<223> OTHER INFORMATION: n = A,T,C or G

<400> SEQUENCE: 96

| | |
|---|---|
| tttttttttt tttttttttt ggaattaaaa gcaatttaat gagggcagag caggaaacat | 60 |
| gcatttcttt tcattcgaat cttcagatga accctgagca gccgaagacc agaaaagcca | 120 |
| tgaagacttt ctgcttaatt caggggctta caggattctt cagagtgtgt gtgaacaaaa | 180 |
| gctttatagt acgtattttt aggatacaaa taagagagag actatggctt ggggtgagaa | 240 |
| tgtactgatt acaaggtcta cagacaatta agacacagaa acagatggga agaggtgnc | 300 |
| cagcatctgg nggttggctt ctcaagggct tgtctgtgca ccaaattact tctgcttggn | 360 |
| cttctgctga gctgggcctg gagtgaccgt tgaaggacat ggctctggta cctttgtgta | 420 |
| gcctgncaca ggaactttgg tgtatccttg ctcaggaact ttgatggcac ctggctcagg | 480 |
| aaacttgatg aagccttggt caagggacct tgatgcttgc tggctcaggg accttggngn | 540 |
| anccctgggct canggacctt tgncncaacc ttggcttcaa gggacccttg gnacatcctg | 600 |
| gcnnagggac ccttgggncc aaccctgggc ttnagggacc ctttggntnc nanccttggc | 660 |

<210> SEQ ID NO 97
<211> LENGTH: 441
<212> TYPE: DNA
<213> ORGANISM: Homo sapien
<220> FEATURE:
<221> NAME/KEY: misc_feature
<222> LOCATION: (1)...(441)
<223> OTHER INFORMATION: n = A,T,C or G

<400> SEQUENCE: 97

| | |
|---|---|
| gggaccatac anagtattcc tctcttcaca ccaggaccag ccactgttgc agcatgagtt | 60 |
| cccagcagca gaagcagccc tgcatcccac cccctcagct tcagcagcag caggtgaaac | 120 |
| agccttgcca gcctccacct caggaaccat gcatcccaa aaccaaggag ccctgccacc | 180 |
| ccaaggtgcc tgagccctgc caccccaaag tgcctgagcc ctgccagccc aaggttccag | 240 |
| agccatgcca ccccaaggtg cctgagccct gcccttcaat agtcactcca gcaccagccc | 300 |
| agcagaanac caagcagaag taatgtggtc cacagccatg cccttgagga gccggccacc | 360 |
| agatgctgaa tcccctatcc cattctgtgt atgagtccca tttgccttgc aattagcatt | 420 |
| ctgtctcccc caaaaaaaaa a | 441 |

<210> SEQ ID NO 98
<211> LENGTH: 600
<212> TYPE: DNA
<213> ORGANISM: Homo sapien
<220> FEATURE:
<221> NAME/KEY: misc_feature
<222> LOCATION: (1)...(600)
<223> OTHER INFORMATION: n = A,T,C or G

<400> SEQUENCE: 98

-continued

```
gtattcctct cttcacacca ggaccagcca ctgttgcagc atgagttccc agcagcagaa    60
gcagccctgc atcccacccc ctcagcttca gcagcagcag gtgaaacagc cttgccagcc   120
tccacctcag gaaccatgca tccccaaaac caaggagccc tgccacccca aggtgcctga   180
gccctgccac cccaaagtgc ctgagccctg ccagcccaag gttccagagc atgccaccc    240
caaggtgcct gagccctgcc cttcaatagt cactccagca ccagcccagc agaanaccaa   300
gcagaagtaa tgtggtccac agccatgccc ttgaggagcc ggccaccana tgctgaatcc   360
cctatcccat tctgtgtatg agtcccattt gccttgcaat tagcattctg tctcccccaa   420
aaaagaatgt gctatgaagc tttctttcct acacactctg agtctctgaa tgaagctgaa   480
ggtcttaant acaganctag ttttcagctg ctcagaattc tctgaagaaa agatttaaga   540
tgaaaggcaa atgattcagc tccttattac cccattaaat tcnctttcaa ttccaaaaaa   600
```

<210> SEQ ID NO 99
<211> LENGTH: 667
<212> TYPE: DNA
<213> ORGANISM: Homo sapien
<220> FEATURE:
<221> NAME/KEY: misc_feature
<222> LOCATION: (1)...(667)
<223> OTHER INFORMATION: n = A,T,C or G

<400> SEQUENCE: 99

```
actagtgact gagttcctgg caaagaaatt tgacctggac cagttgataa ctcatgtttt    60
accatttaaa aaaatcagtg aaggatttga gctgctcaat tcaggacaaa gcattcgaac   120
ggtcctgacg ttttgagatc caaagtggca ggaggtctgt gttgtcatgg tgaactggag   180
tttctcttgt gagagttccc tcatctgaaa tcatgtatct gtctcacaaa tacaagcata   240
agtagaagat ttgttgaaga catagaaccc ttataaagaa ttattaacct ttataaacat   300
ttaaagtctt gtgagcacct gggaattagt ataataacaa tgtttnatatt tttgatttac   360
attttgtaag gctataattg tatcttttaa gaaaacatac cttggatttc tatgttgaaa   420
tggagatttt taagagtttt aaccagctgc tgcagatata ttactcaaaa cagatatagc   480
gtataaagat atagtaaatg catctcctag agtaatattc acttaacaca ttggaaacta   540
ttattttta gatttgaata tnaatgttat tttttaaaca cttgttatga gttacttggg   600
attacatttt gaaatcagtt cattccatga tgcanattac tgggattaga ttaagaaga    660
cggaaaa                                                            667
```

<210> SEQ ID NO 100
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 100

```
gttttgtttg taagatgatc acagtcatgt tacactgatc taaaggacat atatataacc    60
ctttaaaaaa aaaatcactg cctcattctt atttcaagat gaatttctat acagactaga   120
tgttttctg aagatcaatt agacattttg aaaatgattt aaagtgtttt ccttaatgtt    180
ctctgaaaac aagtttcttt tgtagtttta accaaaaaag tgcccttttt gtcactggat   240
tctcctagca ttcatgattt ttttttcata caatgaaatt aaaattgcta aaatcatgga   300
ctggctttct ggttggattt caggtaagat gtgtttaagg ccagagcttt tctcagtatt   360
```

```
tgatttttt   ccccaatatt  tgatttttta  aaaatataca  catnggtgct  gcatttatat    420
ctgctggttt  aaaattctgt  catatttcac  ttctagcctt  ttagttatgg  caaatcatat    480
tttactttta  cttaaagcat  ttggtnattt  ggantatctg  gttctannct  aaaaaaanta    540
attctatnaa  ttgaantttt  ggtactcnnc  catatttgga  tcc                       583
```

<210> SEQ ID NO 101
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 101

```
gtggagacgt  acaaagagca  gccgctcaag  acacctggga  agaaaaagaa  aggcaagccc     60
gggaaacgca  aggagcagga  aaagaaaaaa  cggcgaactc  gctctgcctg  gttagactct    120
ggagtgactg  ggagtgggct  agaaggggac  cacctgtctg  acacctccac  aacgtcgctg    180
gagctcgatt  cacggaggca  ttgaaatttt  cagcaganac  cttccaagga  catattgcag    240
gattctgtaa  tagtgaacat  atggaaagta  ttagaaatat  ttattgtctg  taaatactgt    300
aaatgcattg  gaataaaact  gtctccccca  ttgctctatg  aaactgcaca  ttggtcattg    360
tgaatatttt  tttttttgcc  aaggctaatc  caattattat  tatcacattt  accataattt    420
attttgtcca  ttgatgtatt  tattttgtaa  atgtatcttg  gtgctgctga  atttctatat    480
tttttgtaca  taatgcnttt  anatataacct atcaagtttg  ttgataaatg  acncaatgaa    540
gtgncncnan  ttggnggttg  aatttaatga  atgcctaatt  ttattatccc  aa            592
```

<210> SEQ ID NO 102
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 102

```
cgtcctaagc  acttagacta  catcagggaa  gaacacagac  cacatccctg  tcctcatgcg     60
gcttatgttt  tctggaagaa  agtggagacc  nagtccttgg  ctttagggct  ccccggctgg    120
gggctgtgca  ntccggtcag  ggcgggaagg  gaaatgcacc  gctgcatgtg  aacttacagc    180
ccaggcggat  gccccttccc  ttagcactac  ctggcctcct  gcatcccctc  gctcatgtt    240 cctcccacct  tcaaanaatg  aanaacccca  tgggcccagc  cccttgccct  ggggaaccaa    300
ggcagccttc  caaaactcag  gggctgaagc  anactattag  ggcaggggct  gactttgggt    360
gacactgccc  attccctctc  agggcagctc  angtcaccon  ggnctcttga  acccagcctg    420
ttcctttgaa  aaagggcaaa  actgaaaagg  gcttttccta  naaaagaaa   aaccagggaa    480 ctttgccagg  gcttcnntnt  taccaaaacn  ncttctcnng  gattttaat   tcccccattng   540 gcctccactt  accnggggcn  atgccccaaa  attaanaatt  tcccatc                   587
```

<210> SEQ ID NO 103
<211> LENGTH: 496
<212> TYPE: DNA
<213> ORGANISM: Homo sapien
<220> FEATURE:

<221> NAME/KEY: misc_feature
<222> LOCATION: (1)...(496)
<223> OTHER INFORMATION: n = A,T,C or G

<400> SEQUENCE: 103

| | | | | | |
|---|---|---|---|---|---|
| anaggactgg | ccctacntgc | tctctctcgt | cctacctatc | aatgcccaac | atggcagaac | 60 |
| ctgcanccct | tggncactgc | anatggaaac | ctctcagtgt | cttgacatca | ccctacccnt | 120 |
| gcggtgggtc | tccaccacaa | ccactttgac | tctgtggtcc | ctgnanggtg | gnttctcctg | 180 |
| actggcagga | tggaccttan | ccacatatc | cctctgttcc | ctctgctnag | anaaagaatt | 240 |
| cccttaacat | gatataatcc | acccatgcaa | ntngctactg | gcccagctac | catttaccat | 300 |
| ttgcctacag | aatttcattc | agtctacact | ttggcattct | ctctggcgat | agagtgtggc | 360 |
| tgggctgacc | gcaaaaggtg | ccttacacac | tggcccccac | cctcaaccgt | tgacncatca | 420 |
| gangcttgcc | tcctccttct | gattnncccc | catgttggat | atcagggtgc | tcnagggatt | 480 |
| ggaaaagaaa | caaaac | | | | | 496 |

<210> SEQ ID NO 104
<211> LENGTH: 575
<212> TYPE: DNA
<213> ORGANISM: Homo sapien
<220> FEATURE:
<221> NAME/KEY: misc_feature
<222> LOCATION: (1)...(575)
<223> OTHER INFORMATION: n = A,T,C or G

<400> SEQUENCE: 104

| | | | | | |
|---|---|---|---|---|---|
| gcacctgctc | tcaatccnnc | tctcaccatg | atcctccgcc | tgcanaaact | cctctgccaa | 60 |
| ctatggangt | ggtttcnggg | gtggctcttg | ccaactggga | agaagccgtg | gtgtctctac | 120 |
| ctgttcaact | cngtttgtgt | ctgggggatc | aactngggc | tatggaagcg | gctnaactgt | 180 |
| tgttttggtg | gaagggctgg | taattggctt | tgggaagtng | cttatngaag | ttggcctngg | 240 |
| gaagttgcta | ttgaaagtng | ccntggaagt | ngntttggtg | ggggttttg | ctggtggcct | 300 |
| ttgttnaatt | tgggtgcttt | gtnaatggcg | gcccctcnc | ctgggcaatg | aaaaaaatca | 360 |
| ccnatgcngn | aaacctcnac | nnaacagcct | gggcttccct | cacctcgaaa | aagttgctc | 420 |
| cccccccaaa | aaaggncaan | ccctcaann | tggaangttg | aaaaaatcct | cgaatgggga | 480 |
| ncccnaaaac | aaaaanccc | ccntttcccn | gnaanggggg | aaataccncc | ccccactta | 540 |
| cnaaaaccct | tntaaaaac | ccccgggaa | aaaaa | | | 575 |

<210> SEQ ID NO 105
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 105

| | | | | | |
|---|---|---|---|---|---|
| cactagtagg | atagaaacac | tgtgtcccga | gagtaaggag | agaagctact | attgattaga | 60 |
| gcctaaccca | ggttaactgc | aagaagaggc | gggatacttt | cagctttcca | tgtaactgta | 120 |
| tgcataaagc | caatgtagtc | cagtttctaa | gatcatgttc | caagctaact | gaatcccact | 180 |
| tcaatacaca | ctcatgaact | cctgatggaa | caataacagg | cccaagcctg | tggtatgatg | 240 |
| tgcacacttg | ctagactcan | aaaaaatact | actctcataa | atgggtggga | gtattttggt | 300 |
| gacaacctac | tttgcttggc | tgagtgaagg | aatgatattc | atatattcat | ttattccatg | 360 |

```
gacatttagt tagtgctttt tatataccag gcatgatgct gagtgacact cttgtgtata      420
tttccaaatt tttgtacagt cgctgcacat atttgaaatc atatattaag acttccaaaa      480
aatgaagtcc ctggtttttc atggcaactt gatcagtaaa ggattcncct ctgtttggta      540
cttaaaacat ctactatatn gttnanatga aattccttt ccccnctcc cgaaaaaana       600 aagtggtggg gaaaaaaaa                                                   619
```

<210> SEQ ID NO 106
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 106

```
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgccccngt gtcagaggct catattgtgt      180
tatgtaaatg gtatntcatt cgctactatn antcaattng aaatanggtc tttgggttat     240
gaatantnng cagcncanct nanangctgt ctgtngtatt cattgtggtc atagcacctc     300
acancattgt aacctcnatc nagtgagaca nactagnaan ttcctagtga tggctcanga     360
ttccaaatgg nctcatntcn aatgtttaaa agttanttaa gtgtaagaaa tacagactgg     420
atgttccacc aactagtacc tgtaatgacn ggcctgtccc aacacatctc cctttccat     480 gactgtggta ncccgcatcg gaaaaa                                          506
```

<210> SEQ ID NO 107
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 107

```
gttgagtctg tactaaacag taagatatct caatgaacca taaattcaac tttgtaaaaa     60
tcttttgaag catagataat attgtttggt aaatgtttct tttgtttggt aaatgtttct    120
tttaaagacc ctcctattct ataaaactct gcatgtagag gcttgtttac ctttctctct    180
ctaaggttta caataggagt ggtgatttga aaaatataaa attatgagat tggttttcct    240
gtggcataaa ttgcatcact gtatcatttt cttttttaac cggtaagant ttcagttgt     300 tggaaagtaa ctgtganaac ccagtttccc gtccatctcc cttagggact acccatagaa    360
catgaaaagg tccccacnga agcaagaaga taagtctttc atggctgctg gttgcttaaa    420
ccactttaaa accaaaaaat tccccttgga aa                                   452
```

<210> SEQ ID NO 108
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 108

```
atcttcttcc cttaattagt tnttatttat ntattaaatt ttattgcatg tcctggcaaa      60
caaaaagaga ttgtagattg gcttctggct ccccaaaagc ccataacaga aagtaccaca     120
agaccncaac tgaagcttaa aaaatctatc acatgtataa tacctttnga agaacattaa     180
tanagcatat aaaacttttta acatntgctt aatgttgtnc aattataaaa ntaatngaaa   240
aaaatgtccc tttaacatnc aatatcccac atagtgttat ttnagggat taccnngnaa     300
naaaaaaagg gtagaaggga tttaatgaaa actctgcttn ccatttctgt ttanaaacgt    360
ctccagaaca aaaacttntc aantctttca gctaaccgca tttgagctna ggccactcaa   420
aaactccatt agnccactt tctaanggtc tctanagctt actaanccctt ttgacccctt   480
accctggnta ctcctgccct ca                                            502
```

<210> SEQ ID NO 109
<211> LENGTH: 1308
<212> TYPE: DNA
<213> ORGANISM: Homo sapien

<400> SEQUENCE: 109

```
acccgaggtc tcgctaaaat catcatggat tcacttggcg ccgtcagcac tcgacttggg     60
tttgatcttt tcaaagagct gaagaaaaca aatgatggca acatcttctt ttcccctgtg   120
ggcatcttga ctgcaattgg catggtcctc ctggggaccc gaggagccac cgcttcccag   180
ttggaggagg tgtttcactc tgaaaaagag acgaagagct caagaataaa ggctgaagaa   240
aaagaggtga ttgagaacac agaagcagta catcaacaat tccaaaagtt tttgactgaa   300
ataagcaaac tcactaatga ttatgaactg aacataacca acaggctgtt tggagaaaaa   360
acatacctct tccttcaaaa atacttagat tatgttgaaa aatattatca tgcatctctg   420
gaacctgttg attttgtaaa tgcagccgat gaaagtcgaa agaagattaa ttcctggggtt   480
gaaagcaaaa caaatgaaaa aatcaaggac ttgttcccag atggctctat tagtagctct   540
accaagctgg tgctggtgaa catggtttat tttaaagggc aatgggacag ggagtttaag   600
aaagaaaata ctaaggaaga gaaattttgg atgaataaga gcacaagtaa atctgtacag   660
atgatgacac agagccattc ctttagcttc actttcctgg aggacttgca ggccaaaatt   720
ctagggattc catataaaaa caacgaccta agcatgtttg tgcttctgcc caacgacatc   780
gatggcctgg agaagataat agataaaata agtcctgaga aattggtaga gtggactagt   840
ccagggcata tggaagaaag aaaggtgaat ctgcacttgc cccggtttga ggtggaggac   900
agttacgatc tagaggcggt cctggctgcc atggggatgg gcgatgcctt cagtgagcac   960
aaagccgact actcgggaat gtcgtcaggc tccgggttgt acgcccagaa gttcctgcac  1020
agttcctttg tggcagtaac tgaggaaggc accgaggctg cagctgccac tggcataggc  1080
tttactgtca catccgcccc aggtcatgaa aatgttcact gcaatcatcc cttcctgttc  1140
ttcatcaggc acaatgaatc caacagcatc ctcttcttcg gcagattttc ttctccttaa  1200
gatgatcgtt gccatggcat tgctgctttt agcaaaaaac aactaccagt gttactcata  1260
tgattatgaa aatcgtccat tcttttaaat ggtggctcac ttgcattt                1308
```

<210> SEQ ID NO 110
<211> LENGTH: 391
<212> TYPE: PRT
<213> ORGANISM: Homo sapien

<400> SEQUENCE: 110

```
Met Asp Ser Leu Gly Ala Val Ser Thr Arg Leu Gly Phe Asp Leu Phe
 1               5                  10                  15

Lys Glu Leu Lys Lys Thr Asn Asp Gly Asn Ile Phe Phe Ser Pro Val
                 20                  25                  30

Gly Ile Leu Thr Ala Ile Gly Met Val Leu Leu Gly Thr Arg Gly Ala
             35                  40                  45

Thr Ala Ser Gln Leu Glu Glu Val Phe His Ser Glu Lys Glu Thr Lys
         50                  55                  60

Ser Ser Arg Ile Lys Ala Glu Glu Lys Glu Val Ile Glu Asn Thr Glu
 65                  70                  75                  80

Ala Val His Gln Gln Phe Gln Lys Phe Leu Thr Glu Ile Ser Lys Leu
                 85                  90                  95

Thr Asn Asp Tyr Glu Leu Asn Ile Thr Asn Arg Leu Phe Gly Glu Lys
                100                 105                 110

Thr Tyr Leu Phe Leu Gln Lys Tyr Leu Asp Tyr Val Glu Lys Tyr Tyr
            115                 120                 125

His Ala Ser Leu Glu Pro Val Asp Phe Val Asn Ala Ala Asp Glu Ser
        130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Thr Lys Leu Val
                165                 170                 175

Leu Val Asn Met Val Tyr Phe Lys Gly Gln Trp Asp Arg Glu Phe Lys
                180                 185                 190

Lys Glu Asn Thr Lys Glu Glu Lys Phe Trp Met Asn Lys Ser Thr Ser
                195                 200                 205

Lys Ser Val Gln Met Met Thr Gln Ser His Ser Phe Ser Phe Thr Phe
210                 215                 220

Leu Glu Asp Leu Gln Ala Lys Ile Leu Gly Ile Pro Tyr Lys Asn Asn
225                 230                 235                 240

Asp Leu Ser Met Phe Val Leu Leu Pro Asn Asp Ile Asp Gly Leu Glu
                245                 250                 255

Lys Ile Ile Asp Lys Ile Ser Pro Glu Lys Leu Val Glu Trp Thr Ser
                260                 265                 270

Pro Gly His Met Glu Glu Arg Lys Val Asn Leu His Leu Pro Arg Phe
            275                 280                 285

Glu Val Glu Asp Ser Tyr Asp Leu Glu Ala Val Leu Ala Ala Met Gly
            290                 295                 300

Met Gly Asp Ala Phe Ser Glu His Lys Ala Asp Tyr Ser Gly Met Ser
305                 310                 315                 320

Ser Gly Ser Gly Leu Tyr Ala Gln Lys Phe Leu His Ser Ser Phe Val
                325                 330                 335

Ala Val Thr Glu Glu Gly Thr Glu Ala Ala Ala Thr Gly Ile Gly
            340                 345                 350

Phe Thr Val Thr Ser Ala Pro Gly His Glu Asn Val His Cys Asn His
            355                 360                 365

Pro Phe Leu Phe Phe Ile Arg His Asn Glu Ser Asn Ser Ile Leu Phe
            370                 375                 380

Phe Gly Arg Phe Ser Ser Pro
385                 390

<210> SEQ ID NO 111
<211> LENGTH: 1419
```

<212> TYPE: DNA
<213> ORGANISM: Homo sapien

<400> SEQUENCE: 111

```
ggagaactat aaattaagga tcccagctac ttaattgact tatgcttcct agttcgttgc      60
ccagccacca ccgtctctcc aaaaacccga ggtctcgcta aaatcatcat ggattcactt     120
ggcgccgtca gcactcgact tgggtttgat cttttcaaag agctgaagaa aacaaatgat     180
ggcaacatct tcttttcccc tgtgggcatc ttgactgcaa ttggcatggt cctcctgggg     240
acccgaggag ccaccgcttc ccagttggag gaggtgtttc actctgaaaa agagacgaag     300
agctcaagaa taaaggctga gaaaaagag gtggtaagaa taaaggctga aggaaaagag      360
attgagaaca cagaagcagt acatcaacaa ttccaaaagt ttttgactga ataagcaaa      420
ctcactaatg attatgaact gaacataacc aacaggctgt ttggagaaaa acatacctc      480
ttccttcaaa atacttaga ttatgttgaa aaatattatc atgcatctct ggaacctgtt      540
gattttgtaa atgcagccga tgaaagtcga agaagatta attcctgggt tgaaagcaaa      600
acaaatgaaa aaatcaagga cttgttccca gatggctcta ttagtagctc taccaagctg     660
gtgctggtga acatggttta ttttaaaggg caatgggaca gggagtttaa gaaagaaaat     720
actaaggaag agaaattttg gatgaataag agcacaagta atctgtaca gatgatgaca      780
cagagccatt cctttagctt cactttcctg gaggacttgc aggccaaaat tctagggatt     840
ccatataaaa caacgacct aagcatgttt gtgcttctgc ccaacgacat cgatggcctg      900
gagaagataa tagataaaat aagtcctgag aaattggtag agtggactag tccagggcat     960
atggaagaaa gaaggtgaa tctgcacttg ccccggtttg aggtggagga cagttacgat    1020
ctagaggcgg tcctggctgc catggggatg ggcgatgcct tcagtgagca caaagccgac    1080
tactcgggaa tgtcgtcagg ctccggggttg tacgcccaga agttcctgca cagttccttt    1140
gtggcagtaa ctgaggaagg caccgaggct gcagctgcca ctggcatagg ctttactgtc    1200
acatccgccc caggtcatga aaatgttcac tgcaatcatc ccttcctgtt cttcatcagg    1260
cacaatgaat ccaacagcat cctcttcttc ggcagatttt cttctcctta agatgatcgt    1320
tgccatggca ttgctgcttt tagcaaaaaa caactaccag tgttactcat atgattatga    1380
aaatcgtcca ttcttttaaa tggtggctca cttgcattt                           1419
```

<210> SEQ ID NO 112
<211> LENGTH: 400
<212> TYPE: PRT
<213> ORGANISM: Homo sapien

<400> SEQUENCE: 112

```
Met Asp Ser Leu Gly Ala Val Ser Thr Arg Leu Gly Phe Asp Leu Phe
  1               5                  10                  15

Lys Glu Leu Lys Lys Thr Asn Asp Gly Asn Ile Phe Phe Ser Pro Val
             20                  25                  30

Gly Ile Leu Thr Ala Ile Gly Met Val Leu Leu Gly Thr Arg Gly Ala
         35                  40                  45

Thr Ala Ser Gln Leu Glu Glu Val Phe His Ser Glu Lys Glu Thr Lys
     50                  55                  60

Ser Ser Arg Ile Lys Ala Glu Glu Lys Glu Val Val Arg Ile Lys Ala
 65                  70                  75                  80

Glu Gly Lys Glu Ile Glu Asn Thr Glu Ala Val His Gln Gln Phe Gln
                 85                  90                  95
```

-continued

```
Lys Phe Leu Thr Glu Ile Ser Lys Leu Thr Asn Asp Tyr Glu Leu Asn
                100                 105                 110
Ile Thr Asn Arg Leu Phe Gly Glu Lys Thr Tyr Leu Phe Leu Gln Lys
            115                 120                 125
Tyr Leu Asp Tyr Val Glu Lys Tyr Tyr His Ala Ser Leu Glu Pro Val
        130                 135                 140
Asp Phe Val Asn Ala Ala Asp Glu Ser Arg Lys Lys Ile Asn Ser Trp
145                 150                 155                 160
Val Glu Ser Lys Thr Asn Glu Lys Ile Lys Asp Leu Phe Pro Asp Gly
                165                 170                 175
Ser Ile Ser Ser Ser Thr Lys Leu Val Leu Val Asn Met Val Tyr Phe
            180                 185                 190
Lys Gly Gln Trp Asp Arg Glu Phe Lys Lys Glu Asn Thr Lys Glu Glu
        195                 200                 205
Lys Phe Trp Met Asn Lys Ser Thr Ser Lys Ser Val Gln Met Met Thr
210                 215                 220
Gln Ser His Ser Phe Ser Phe Thr Phe Leu Glu Asp Leu Gln Ala Lys
225                 230                 235                 240
Ile Leu Gly Ile Pro Tyr Lys Asn Asn Asp Leu Ser Met Phe Val Leu
                245                 250                 255
Leu Pro Asn Asp Ile Asp Gly Leu Glu Lys Ile Ile Asp Lys Ile Ser
            260                 265                 270
Pro Glu Lys Leu Val Glu Trp Thr Ser Pro Gly His Met Glu Glu Arg
        275                 280                 285
Lys Val Asn Leu His Leu Pro Arg Phe Glu Val Glu Asp Ser Tyr Asp
290                 295                 300
Leu Glu Ala Val Leu Ala Ala Met Gly Met Gly Asp Ala Phe Ser Glu
305                 310                 315                 320
His Lys Ala Asp Tyr Ser Gly Met Ser Ser Gly Ser Gly Leu Tyr Ala
                325                 330                 335
Gln Lys Phe Leu His Ser Ser Phe Val Ala Val Thr Glu Glu Gly Thr
            340                 345                 350
Glu Ala Ala Ala Ala Thr Gly Ile Gly Phe Thr Val Thr Ser Ala Pro
        355                 360                 365
Gly His Glu Asn Val His Cys Asn His Pro Phe Leu Phe Phe Ile Arg
370                 375                 380
His Asn Glu Ser Asn Ser Ile Leu Phe Phe Gly Arg Phe Ser Ser Pro
385                 390                 395                 400
```

<210> SEQ ID NO 113
<211> LENGTH: 957
<212> TYPE: DNA
<213> ORGANISM: Homo sapien

<400> SEQUENCE: 113

```
ctcgaccttc tctgcacagc ggatgaaccc tgagcagctg aagaccagaa aagccactat     60
gactttctgc ttaattcagg agcttacagg attcttcaaa gagtgtgtcc agcatccttt    120
gaaacatgag ttcttaccag cagaagcaga cctttacccc accacctcag cttcaacagc    180
agcaggtgaa acaacccagc cagcctccac ctcaggaaat atttgttccc acaaccaagg    240
agccatgcca ctcaaaggtt ccacaacctg aaacacaaa gattccagag ccaggctgta     300
ccaaggtccc tgagccaggc tgtaccaagg tccctgagcc aggttgtacc aaggtccctg    360
agccaggatg taccaaggtc cctgagccag gttgtaccaa ggtccctgag ccaggctaca    420
```

-continued

```
ccaaggtccc tgagccaggc agcatcaagg tccctgacca aggcttcatc aagtttcctg    480
agccaggtgc catcaaagtt cctgagcaag gatacaccaa agttcctgtg ccaggctaca    540
caaaggtacc agagccatgt ccttcaacgg tcactccagg cccagctcag cagaagacca    600
agcagaagta atttggtgca cagacaagcc cttgagaagc caaccaccag atgctggaca    660
ccctcttccc atctgtttct gtgtcttaat tgtctgtaga ccttgtaatc agtacattct    720
caccccaagc catagtctct ctcttatttg tatcctaaaa atacggtact ataaagcttt    780
tgttcacaca cactctgaag aatcctgtaa gcccctgaat taagcagaaa gtcttcatgg    840
cttttctggt cttcggctgc tcagggttca tctgaagatt cgaatgaaaa gaaatgcatg    900
tttcctgctc tgccctcatt aaattgcttt taattccaaa aaaaaaaaaa aaaaaaa      957
```

<210> SEQ ID NO 114
<211> LENGTH: 161
<212> TYPE: PRT
<213> ORGANISM: Homo sapien

<400> SEQUENCE: 114

```
Met Ser Ser Tyr Gln Gln Lys Gln Thr Phe Thr Pro Pro Gln Leu
 1               5                  10                  15

Gln Gln Gln Gln Val Lys Gln Pro Ser Gln Pro Pro Gln Glu Ile
            20                  25                  30

Phe Val Pro Thr Thr Lys Glu Pro Cys His Ser Lys Val Pro Gln Pro
        35                  40                  45

Gly Asn Thr Lys Ile Pro Glu Pro Gly Cys Thr Lys Val Pro Glu Pro
    50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Tyr Thr Lys Val Pro Glu Pro Gly Ser Ile Lys Val Pro Asp Gln
            100                 105                 110

Gly Phe Ile Lys Phe Pro Glu Pro Gly Ala Ile Lys Val Pro Glu Gln
        115                 120                 125

Gly Tyr Thr Lys Val Pro Val Pro Gly Tyr Thr Lys Val Pro Glu Pro
    130                 135                 140

Cys Pro Ser Thr Val Thr Pro Gly Pro Ala Gln Gln Lys Thr Lys Gln
145                 150                 155                 160

Lys
```

<210> SEQ ID NO 115
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 115

```
cattggtnct ttcatttgct ntggaagtgt nnatctctaa cagtggacaa agttcccngt     60
gccttaaact ctgtnacact tttgggaant gaaaanttng tantatgata ggttattctg    120
angtanagat gttctggata ccattanatn tgccccngt gtcagaggct catattgtgt     180
tatgtaaatg gtatntcatt cgctactatn antcaattg aaatanggtc tttgggttat    240
gaatantnng cagcncanct nanangctgt ctgtngtatt cattgtggtc atagcacctc    300
```

```
acancattgt aacctcnatc nagtgagaca nactagnaan ttcctagtga tggctcanga    360
ttccaaatgg nctcatntcn aatgtttaaa agttanttaa gtgtaagaaa tacagactgg    420
atgttccacc aactagtacc tgtaatgacn ggcctgtccc aacacatctc ccttttccat    480
gactgtggta ncccgcatcg gaaaaa                                        506
```

<210> SEQ ID NO 116
<211> LENGTH: 3079
<212> TYPE: DNA
<213> ORGANISM: Homo sapien

<400> SEQUENCE: 116

```
ggatccccgg gtttcctaaa ccccccacag agtcctgccc aggccaaaga gcaaggaaaa     60
ggtcaaaggg cagaaaaaat gctgagttag gaggagctat ggaaggataa acctggcctt    120
aaagaggtca aagtggttta taggggggcgc tgagggcttc ccacattctc tggcctaaac    180
cttgcaggca gatctgccca gtgggctctg ggatagctgt gccttcccta acaaaaaaat    240
tgtgcacaaa aggatgaaac tctatttttcc ctctagcaca taaccaagaa tataaggcta    300
cagattgcct ttcccagagg gaaaaccctg cagcaacctg ctgcctggaa aagtgtaaga    360
gcagatcact ggggaatcgt ttgccccccg ctgatgaca gcttcccaa gctccaaggg     420 caggtgctca gcatgtaccg tactgggatg gttgtcaata ctcctggtcc tgtaagagtc    480
ccaggacact gccatgccaa tgcccctca gttcctggca tccttttgg gctgctcaca     540 gccccagcct ctatggtgaa gacatacttg ctagcagcgt caccaacttg ttgccaagag    600
atcagtgctc gaaggcaagg ttatttctaa ctgagcagag cctgccagga agaaagcgtt    660
tgcaccccac accactgtgc aggtgtgacc ggtgagctca cagctgcccc ccaggcatgc    720
ccagcccact taatcatcac agctcgacag ctctctcgcc cagcccagtt ctggaaggga    780
taaaaggggg catcaccgtt cctgggtaac agagccacct tctgcgtcct gctgagctct    840
gttctctcca gcacctccca acccactagt gcctggttct cttgctccac caggaacaag    900
ccaccatgtc tcgccagtca agtgtgtctt ccggagcggg gggcagtcgt agcttcagca    960
ccgcctctgc catcaccccg tctgtctccc gcaccagctt cacctccgtg tcccggtccg   1020
ggggtggcgg tggtggtggc ttcggcaggg tcagccttgc gggtgcttgt ggagtgggtg   1080
gctatggcag ccggagcctc tacaacctgg ggggctccaa gaggtatatcc atcagcacta   1140 gtggtggcag cttcaggaac cggtttggtg ctggtgctgg aggcggctat ggctttggag   1200
gtggtgccgg tagtggattt ggtttcggcg gtgagctgg tggtggcttt gggctcggtg   1260
gcggagctgg ctttggaggt ggcttcgtg gccctggctt cctgtctgc cctcctggag    1320 gtatccaaga ggtcactgtc aaccagagtc tcctgactcc cctcaacctg caaatcgacc   1380
ccagcatcca gagggtgagg accgaggagc gcgagcagat caagaccctc aacaataagt   1440
ttgcctcctt catcgacaag gtgcggttcc tggagcagca gaacaaggtt ctggaaacaa   1500 agtggacct gctgcaggag cagggcacca agactgtgag gcagaacctg gagccgttgt   1560
tcgagcagta catcaacaac ctcaggaggc agctggacag catcgtgggg gaacggggcc   1620
gcctggactc agagctgaga aacatgcagg acctggtgga agacttcaag aacaagtatg   1680
aggatgaaat caacaagcgt accactgctg agaatgagtt tgtgatgctg aagaaggatg   1740
tagatgctgc ctacatgaac aaggtggagc tggaggccaa ggttgatgca ctgatggatg   1800
agattaactt catgaagatg ttctttgatg cggagctgtc ccagatgcag acgcatgtct   1860
```

-continued

```
ctgacacctc agtggtcctc tccatggaca acaaccgcaa cctggacctg gatagcatca    1920
tcgctgaggt caaggcccag tatgaggaga ttgccaaccg cagccggaca gaagccgagt    1980
cctggtatca gaccaagtat gaggagctgc agcagacagc tggccggcat ggcgatgacc    2040
tccgcaacac caagcatgag atctctgaga tgaaccggat gatccagagg ctgagagccg    2100
agattgacaa tgtcaagaaa cagtgcgcca atctgcagaa cgccattgcg gatgccgagc    2160
agcgtgggga gctggccctc aaggatgcca ggaacaagct ggccgagctg aggaggccc    2220 tgcagaaggc caagcaggac atggcccggc tgctgcgtga gtaccaggag ctcatgaaca    2280
ccaagctggc cctggacgtg gagatcgcca cttaccgcaa gctgctggag ggcgaggaat    2340
gcagactcag tggagaagga gttggaccag tcaacatctc tgttgtcaca agcagtgttt    2400
cctctggata tggcagtggc agtggctatg gcggtggcct cggtggaggt cttggcggcg    2460
gcctcggtgg aggtcttgcc ggaggtagca gtggaagcta ctactccagc agcagtgggg    2520
gtgtcggcct agtggtggg ctcagtgtgg ggggctctgg cttcagtgca agcagtagcc    2580
gagggctggg ggtgggcttt ggcagtggcg ggggtagcag ctccagcgtc aaatttgtct    2640
ccaccacctc ctcctcccgg aagagcttca agagctaaga acctgctgca agtcactgcc    2700
ttccaagtgc agcaacccag cccatggaga ttgcctcttc taggcagttg ctcaagccat    2760
gttttatcct tttctggaga gtagtctaga ccaagccaat gcagaaccca cattctttgg    2820
ttcccaggag agccccattc ccagcccctg gtctcccgtg ccgcagttct atattctgct    2880
tcaaatcagc cttcaggttt cccacagcat ggccctgct gacacgagaa cccaaagttt    2940
tcccaaatct aaatcatcaa aacagaatcc caccccaat cccaattttt gttttggttc    3000
taactacctc cagaatgtgt tcaataaaat gttttataat ataagctggt gtgcagaatt    3060 gtttttttt tctacccaa                                                  3079
```

<210> SEQ ID NO 117
<211> LENGTH: 6921
<212> TYPE: DNA
<213> ORGANISM: Homo sapien

<400> SEQUENCE: 117

```
gaattctgac tgtccactca aaacttctat tccgatcaaa gctatctgtg actacagaca     60
aattgagata accatttaca aagacgatga atgtgttttg gcgaataact ctcatcgtgc    120
taaatggaag gtcattagtc ctactgggaa tgaggctatg gtcccatctg tgtgcttcac    180
cgttcctcca ccaaacaaag aagcggtgga ccttgccaac agaattgagc aacagtatca    240
gaatgtcctg actctttggc atgagtctca cataaacatg aagagtgtag tatcctggca    300
ttatctcatc aatgaaattg atagaattcg agctagcaat gtggcttcaa taaagacaat    360
gctacctggt gaacatcagc aagttctaag taatctacaa tctcgttttg aagattttct    420
ggaagatagc caggaatccc aagtcttttc aggctcagat ataacacaac tggaaaagga    480
ggttaatgta tgtaagcagt attatcaaga acttcttaaa tctgcagaaa gagaggagca    540
agaggaatca gtttataatc tctacatctc tgaagttcga acattagac ttcggttaga    600 gaactgtgaa gatcggctga ttagacagat tcgaactccc ctggaaagag atgatttgca    660
tgaaagtgtg ttcagaatca cagaacagga gaaactaaag aaagagctgg aacgacttaa    720
agatgatttg ggaacaatca caaataagtg tgaggagttt ttcagtcaag cagcagcctc    780
ttcatcagtc cctaccctac gatcagagct taatgtggtc cttcagaaca tgaaccaagt    840
ctattctatg tcttccactt acatagataa gttgaaaact gttaacttgg tgttaaaaaa    900
```

```
cactcaagct gcagaagccc tcgtaaaact ctatgaaact aaactgtgtg aagaagaagc      960
agttatagct gacaagaata atattgagaa tctaataagt actttaaagc aatggagatc     1020
tgaagtagat gaaaagagac aggtattcca tgccttagag gatgagttgc agaaagctaa     1080
agccatcagt gatgaaatgt ttaaaacgta taaagaacgg gaccttgatt ttgactggca     1140
caaagaaaaa gcagatcaat tagttgaaag gtggcaaaat gttcatgtgc agattgacaa     1200
caggttacgg gacttagagg gcattggcaa atcactgaag tactacagag acacttacca     1260
tcctttagat gattggatcc agcaggttga aactactcag agaaagattc aggaaaatca     1320
gcctgaaaat agtaaaaccc tagccacaca gttgaatcaa cagaagatgc tggtgtccga     1380
aatagaaatg aaacagagca aaatggacga gtgtcaaaaa tatgcagaac agtactcagc     1440
tacagtgaag gactatgaat tacaaacaat gacctaccgg gccatggtag attcacaaca     1500
aaaatctcca gtgaaacgcc gaagaatgca gagttcagca gatctcatta ttcaagagtt     1560
catggaccta aggactcgat atactgccct ggtcactctc atgacacaat atattaaatt     1620
tgctggtgat tcattgaaga ggctggaaga ggaggagatt aaaaggtgta aggagacttc     1680
tgaacatggg gcatattcag atctgcttca gcgtcagaag gcaacagtgc ttgagaatag     1740
caaacttaca ggaaagataa gtgagttgga agaatggta gctgaactaa agaaacaaaa     1800
gtcccgagta gaggaagaac ttccgaaggt cagggaggct gcagaaaatg aattgagaaa     1860
gcagcagaga aatgtagaag atatctctct gcagaagata agggctgaaa gtgaagccaa     1920
gcagtaccgc agggaacttg aaaccattgt gagagagaag gaagccgctg aaagagaact     1980
ggagcgggtg aggcagctca ccatagaggc cgaggctaaa agagctgccg tggaagagaa     2040
cctcctgaat tttcgcaatc agttggagga aaacaccttt accagacgaa cactggaaga     2100
tcatcttaaa agaaaagatt taagtctcaa tgatttggag caacaaaaaa ataaattaat     2160
ggaagaatta agaagaaaga gagacaatga ggaagaactc ttgaagctga taaagcagat     2220
ggaaaaagac cttgcatttc agaaacaggt agcagagaaa cagttgaaag aaaagcagaa     2280
aattgaattg gaagcaagaa gaaaaataac tgaaattcag tatacatgta gagaaaatgc     2340
attgccagtg tgtccgatca cacaggctac atcatgcagg gcagtaacgg gtctccagca     2400
agaacatgac aagcagaaag cagaagaact caaacagcag gtagatgaac taacagctgc     2460
caatagaaag gctgaacaag acatgagaga gctgacatat gaacttaatg ccctccagct     2520
tgaaaaaacg tcatctgagg aaaaggctcg tttgctaaaa gataaactag atgaaacaaa     2580
taatacactc agatgcctta agttggagct ggaaaggaag gatcaggcgg agaaagggta     2640
ttctcaacaa ctcagagagc ttggtaggca attgaatcaa accacaggta agctgaaga     2700 agccatgcaa gaagctagtg atctcaagaa aataaagcgc aattatcagt tagaattaga     2760
atctcttaat catgaaaaag ggaaactaca agagaagta gacagaatca aagggcaca     2820 tgctgtagct gagaagaata ttcagcattt aaattcacaa attcattctt ttcgagatga     2880 gaagaatta gaaagactac aaatctgcca gagaaaatca gatcatctaa agaacaatt     2940 tgagaaaagc catgagcagt tgcttcaaaa tatcaaagct gaaaagaaa ataatgataa     3000 aatccaaagg ctcaatgaag aattggagaa aagtaatgag tgtgcagaga tgctaaaaca     3060
aaaagtagag gagcttacta ggcagaataa tgaaaccaaa ttaatgatgc agagaattca     3120
ggcagaatca gagaatatag ttttagaaa acaaactatc cagcaaagat gtgaagcact     3180
gaaaattcag gcagatggtt ttaaagatca gctacgcagc acaaatgaac acttgcataa     3240
```

```
acagacaaaa acagagcagg attttcaaag aaaaattaaa tgcctagaag aagacctggc  3300
gaaaagtcaa aatttggtaa gtgaatttaa gcaaaagtgt gaccaacaga acattatcat  3360
ccagaatacc aagaaagaag ttagaaatct gaatgcggaa ctgaatgctt ccaaagaaga  3420
gaagcgacgc ggggagcaga aagttcagct acaacaagct caggtgcaag agttaaataa  3480
caggttgaaa aaagtacaag acgaattaca cttaaagacc atagaggagc agatgaccca  3540
cagaaagatg gttctgtttc aggaagaatc tggtaaattc aaacaatcag cagaggagtt  3600
tcggaagaag atggaaaaat taatggagtc caaagtcatc actgaaaatg atatttcagg  3660
cattaggctt gactttgtgt ctcttcaaca agaaaactct agagcccaag aaaatgctaa  3720
gctttgtgaa acaaacatta aagaacttga agacagctt caacagtatc gtgaacaaat  3780
gcagcaaggg cagcacatgg aagcaaatca ttaccaaaaa tgtcagaaac ttgaggatga  3840
gctgatagcc cagaagcgtg aggttgaaaa cctgaagcaa aaaatggacc aacagatcaa  3900
agagcatgaa catcaattag ttttgctcca gtgtgaaatt caaaaaaaga gcacagccaa  3960
agactgtacc ttcaaaccag attttgagat gacagtgaag gagtgccagc actctggaga  4020
gctgtcctct agaaacactg gacaccttca cccaacaccc agatcccctc tgttgagatg  4080
gactcaagaa ccacagccat ggaagagaa gtggcagcat cgggttgttg aacagatacc  4140
caaagaagtc caattccagc caccagggc tccactcgag aaagagaaaa gccagcagtg  4200
ttactctgag tactttctc agacaagcac cgagttacag ataacttttg atgagacaaa  4260
ccccattaca agactgtctg aaattgagaa gataagagac caagccctga caattctag  4320 accacctgtt aggtatcaag ataacgcatg tgaaatggaa ctggtgaagg ttttgacacc  4380
cttagagata gctaagaaca gcagtatga tatgcataca gaagtcacaa cattaaaaca  4440
agaaaagaac ccagttccca gtgctgaaga atggatgctt gaagggtgca gagcatctgg  4500
tggactcaag aaaggggatt tccttaagaa gggcttagaa ccagagacct tccagaactt  4560
tgatggtgat catgcatgtt cagtcaggga tgatgaattt aaattccaag ggcttaggca  4620
cactgtgact gccaggcagt tggtggaagc taagcttctg acatgagaa caattgagca  4680 gctgcgactc ggtcttaaga ctgttgaaga agttcagaaa actcttaaca agtttctgac  4740
gaaagccacc tcaattgcag ggcttttacct agaatctaca aaagaaaaga tttcatttgc  4800
ctcagcggcc gagagaatca taatagacaa aatggtggct ttggcatttt tagaagctca  4860
ggctgcaaca ggtttttataa ttgatcccat ttcaggtcag acatattctg ttgaagatgc  4920
agttcttaaa ggagttgttg accccgaatt cagaattagg cttcttgagg cagagaaggc  4980
agctgtggga tattcttatt cttctaagac attgtcagtg tttcaagcta tggaaaatag  5040
aatgcttgac agacaaaaag gtaaacatat cttggaagcc cagattgcca gtgggggtgt  5100
cattgaccct gtgagaggca ttcgtgttcc tccagaaatt gctctgcagc aggggttgtt  5160
gaataatgcc atcttacagt ttttacatga gccatccagc aacacaagag ttttccctaa  5220
tcccaataac aagcaagctc tgtattactc agaattactg cgaatgtgtg tatttgatgt  5280
agagtcccaa tgctttctgt ttccatttgg ggagaggaac atttccaatc tcaatgtcaa  5340
gaaaacacat agaatttctg tagtagatac taaaacagga tcagaattga ccgtgtatga  5400
ggctttccag agaaacctga ttgagaaaag tatatatctt gaactttcag gcagcaata  5460 tcagtggaag gaagctatgt ttttttgaatc ctatgggcat tcttctcata tgctgactga  5520
tactaaaaca ggattacact tcaatattaa tgaggctata gagcagggaa caattgacaa  5580
agccttggtc aaaaagtatc aggaaggcct catcacactt acagaacttg ctgattcttt  5640
```

```
gctgagccgg ttagtcccca agaaagattt gcacagtcct gttgcagggt attggctgac    5700
tgctagtggg gaaaggatct ctgtactaaa agcctcccgt agaaatttgg ttgatcggat    5760
tactgccctc cgatgccttg aagcccaagt cagtacaggg ggcataattg atcctcttac    5820
tggcaaaaag taccgggtgg ccgaagcttt gcatagaggc ctggttgatg aggggtttgc    5880
ccagcagctg cgacagtgtg aattagtaat cacagggatt ggccatccca tcactaacaa    5940
aatgatgtca gtggtggaag ctgtgaatgc aaatattata ataaggaaa tgggaatccg     6000
atgtttggaa tttcagtact tgacaggagg gttgatagag ccacaggttc actctcggtt    6060
atcaatagaa gaggctctcc aagtaggtat tatagatgtc ctcattgcca caaaactcaa    6120
agatcaaaag tcatatgtca gaaatataat atgccctcag acaaaaagaa agttgacata    6180
taaagaagcc ttagaaaaag ctgattttga tttccacaca ggacttaaac tgttagaagt    6240
atctgagccc ctgatgacag gaatttctag cctctactat tcttcctaat gggacatgtt    6300
taaataactg tgcaaggggt gatgcaggct ggttcatgcc acttttcag agtatgatga     6360
tatcggctac atatgcagtc tgtgaattat gtaacatact ctatttcttg agggctgcaa    6420
attgctaagt gctcaaaata gagtaagttt taaattgaaa attacataag atttaatgcc    6480
cttcaaatgg tttcatttag ccttgagaat ggttttttga aacttggcca cactaaaatg    6540
tttttttttt tttacgtaga atgtgggata aacttgatga actccaagtt cacagtgtca    6600
tttcttcaga actccccttc attgaatagt gatcatttat taaatgataa attgcactcg    6660
ctgaaagagc acgtcatgaa gcaccatgga atcaaagaga agatataaa ttcgttccca     6720
cagccttcaa gctgcagtgt tttagattgc ttcaaaaaat gaaaaagttt tgccttttc     6780
gatatagtga ccttctttgc atattaaaat gtttaccaca atgtcccatt tctagttaag    6840
tcttcgcact tgaaagctaa cattatgaat attatgtgtt ggaggagggg aaggattttc    6900
ttcattctgt gtattttccg g                                              6921

<210> SEQ ID NO 118
<211> LENGTH: 946
<212> TYPE: DNA
<213> ORGANISM: Homo sapien

<400> SEQUENCE: 118
cttctgactg ggctcaggct gacaggtaga gctcaccatg gcttcttgtg tccttgtccc     60
ctccccatca cagctgtggt gcagtccacc gtctccagtg gctatggcgg tgccagtggt    120
gtcggcagtg gcttaggcct gggtggagga agcagctact cctatggcag tggtcttggc    180
gttggaggtg gcttcagttc cagcagtggc agagccattg ggggtggcct cagctctgtt    240
ggaggcggca gttccaccat caagtacacc accacctcct cctccagcag gaagagctat    300
aagcactaaa gtgcgtctgc tagctctcgg tcccacagtc tcaggcccc tctctggctg     360
cagagccctc tcctcaggtt gcctgtcctc tcctggcctc cagtctcccc tgctgtccca    420
ggtagagctg gggatgaatg cttagtgccc tcacttcttc tctctctctc tataccatct    480
gagcacccat tgctcaccat cagatcaacc tctgatttta catcatgatg taatcaccac    540
tggagcttca ctgttactaa attattaatt tcttgcctcc agtgttctat ctctgaggct    600
gagcattata agaaaatgac ctctgctcct tttcattgca gaaaattgcc agggcttat     660
ttcagaacaa cttccactta ctttccactg gctctcaaac tctctaactt ataagtgttg    720
tgaaccccca cccaggcagt atccatgaaa gcacaagtga ctagtcctat gatgtacaaa    780
```

```
gcctgtatct ctgtgatgat ttctgtgctc ttcactgttt gcaattgcta aataaagcag      840
atttataata catatattct tttactttgc cttgctttgg ggccaaagtt ttgggcttaa      900
acttttttat ctgataagtg aatagttgtt tttaaaagat aatcta                    946

<210> SEQ ID NO 119
<211> LENGTH: 8948
<212> TYPE: DNA
<213> ORGANISM: Homo sapien

<400> SEQUENCE: 119
tcaacagccc ctgctccttg ggcccctcca tgccatgccg taatctctcc cacccgacca       60
acaccaacac ccagctccga cgcagctcct ctgcgccctt gccgccctcc gagccacagc      120
tttcctcccg ctcctgcccc cggcccgtcg ccgtctccgc gctcgcagcg gcctcgggag      180
ggcccaggta gcgagcagcg acctcgcgag ccttccgcac tccgcccggg ttccccggcc      240
gtccgcctat ccttggcccc ctccgctttc tccgcgccgg cccgcctcgc ttatgcctcg      300
gcgctgagcc gctctcccga ttgcccgccg acatgagctg caacgaggc tcccacccgc       360 ggatcaacac tctgggccgc atgatccgcg ccgagtctgg cccggacctg cgctacgagg      420
tgaccagcgg cggcggggc accagcagga tgtactattc tcggcgcggc gtgatcaccg       480
accagaactc ggacggctac tgtcaaaccg gcacgatgtc caggcaccag aaccagaaca      540
ccatccagga gctgctgcag aactgctccg actgcttgat gcgagcagag ctcatcgtgc      600
agcctgaatt gaagtatgga gatggaatac aactgactcg gagtcgagaa ttggatgagt      660
gttttgccca ggccaatgac caaatggaaa tcctcgacag cttgatcaga gagatgcggc      720
agatgggcca gccctgtgat gcttaccaga aaaggcttct tcagctccaa gagcaaatgc      780 gagccctta taaagccatc agtgtccctc gagtccgcag ggccagctcc aagggtggtg       840
gaggctacac ttgtcagagt ggctctggct gggatgagtt caccaaacat gtcaccagtg      900
aatgtttggg gtggatgagg cagcaaaggg cggagatgga catggtggcc tggggtgtgg      960
acctggcctc agtggagcag cacattaaca gccaccgggg catccacaac tccatcggcg     1020
actatcgctg gcagctggac aaaatcaaag ccgacctgcg cgagaaatct gcgatctacc     1080
agttggagga ggagtatgaa aacctgctga aagcgtcctt tgagaggatg gatcacctgc     1140
gacagctgca gaacatcatt caggccacgt ccagggagat catgtggatc aatgactgcg     1200
aggaggagga gctgctgtac gactggagcg acaagaacac caacatcgct cagaaacagg     1260
aggccttctc catacgcatg agtcaactgg aagttaaaga aaaagagctc aataagctga     1320
aacaagaaag tgaccaactt gtcctcaatc agcatccagc ttcagacaaa attgaggcct     1380
atatggacac tctgcagacg cagtggagtt ggattcttca gatcaccaag tgcattgatg     1440
ttcatctgaa agaaaatgct gcctactttc agtttttga agaggcgcag tctactgaag      1500
catacctgaa ggggctccag gactccatca ggaagaagta cccctgcgac aagaacatgc     1560
ccctgcagca cctgctggaa cagatcaagg agctggagaa agaacgagag aaaatccttg     1620
aatacaagcg tcaggtgcag aacttggtaa acaagtctaa gaagattgta cagctgaagc     1680
ctcgtaaccc agactacaga agcaataaac ccattattct cagagctctc tgtgactaca    1740
aacaagatca gaaaatcgtg cataaggggg atgagtgtat cctgaaggac aacaacgagc     1800
gcagcaagtg gtacgtgacg ggcccgggag gcgttgacat gcttgttccc tctgtggggc     1860
tgatcatccc tcctccgaac ccactggccg tggacctctc ttgcaagatt gagcagtact     1920
acgaagccat cttggctctg tggaaccagc tctacatcaa catgaagagc ctggtgtcct     1980
```

-continued

```
ggcactactg catgattgac atagagaaga tcagggccat gacaatcgcc aagctgaaaa    2040
caatgcggca ggaagattac atgaagacga tagccgacct tgagttacat taccaagagt    2100
tcatcagaaa tagccaaggc tcagagatgt ttggagatga tgacaagcgg aaaatacagt    2160
ctcagttcac cgatgcccag aagcattacc agaccctggt cattcagctc cctggctatc    2220
cccagcacca gacagtgacc acaactgaaa tcactcatca tggaacctgc caagatgtca    2280
accataataa agtaattgaa accaacagag aaaatgacaa gcaagaaaca tggatgctga    2340
tggagctgca gaagattcgc aggcagatag agcactgcga gggcaggatg actctcaaaa    2400
acctccctct agcagaccag ggtcttctc accacatcac agtgaaaatt aacgagctta    2460
agagtgtgca gaatgattca caagcaattg ctgaggttct caaccagctt aaagatatgc    2520
ttgccaactt cagaggttct gaaaagtact gctatttaca gaatgaagta tttggactat    2580
ttcagaaact ggaaaatatc aatggtgtta cagatggcta cttaaatagc ttatgcacag    2640
taagggcact gctccaggct attctccaaa cagaagacat gttaaaggtt tatgaagcca    2700
ggctcactga ggaggaaact gtctgcctgg acctggataa agtggaagct taccgctgtg    2760
gactgaagaa aataaaaaat gacttgaact tgaagaagtc gttgttggcc actatgaaga    2820
cagaactaca gaaagcccag cagatccact ctcagacttc acagcagtat ccactttatg    2880
atctggactt gggcaagttc ggtgaaaaag tcacacagct gacagaccgc tggcaaagga    2940
tagataaaca gatcgacttt agattatggg acctggagaa acaaatcaag caattgagga    3000
attatcgtga taactatcag gctttctgca gtggctcta tgatcgtaaa cgccgccagg    3060
attccttaga atccatgaaa tttggagatt ccaacacagt catgcggttt ttgaatgagc    3120
agaagaactt gcacagtgaa atatctggca aacgagacaa atcagaggaa gtacaaaaaa    3180
ttgctgaact ttgcgccaat tcaattaagg attatgagct ccagctggcc tcatacacct    3240
caggactgga aactctgctg aacataccta tcaagaggac catgattcag tccccttctg    3300
gggtgattct gcaagaggct gcagatgttc atgctcggta cattgaacta cttacaagat    3360
ctggagacta ttacaggttc ttaagtgaga tgctgaagag tttggaagat ctgaagctga    3420
aaaataccaa gatcgaagtt ttggaagagg agctcagact ggcccgagat gccaactcgg    3480
aaaactgtaa taagaacaaa ttcctggatc agaacctgca gaaataccag gcagagtgtt    3540
cccagttcaa agcgaagctt gcgagcctgg aggagctgaa gagacaggct gagctggatg    3600
ggaagtcggc taagcaaaat ctagacaagt gctacggcca aataaaagaa ctcaatgaga    3660
agatcacccg actgacttat gagattgaag atgaaaagag aagaagaaaa tctgtggaag    3720
acagatttga ccaacagaag aatgactatg accaactgca gaaagcaagg caatgtgaaa    3780
aggagaacct tggttggcag aaattagagt ctgagaaagc catcaaggag aaggagtacg    3840
agattgaaag gttgagggtt ctactgcagg aagaaggcac ccggaagaga gaatatgaaa    3900
atgagctggc aaaggtaaga aaccactata tgaggagat gagtaattta aggaacaagt    3960
atgaaacaga gattaacatt acgaagacca ccatcaagga gatatccatg caaaagagg    4020 atgattccaa aaatcttaga aaccagcttg atagactttc aagggaaaat cgagatctga    4080
aggatgaaat tgtcaggctc aatgacagca tcttgcaggc cactgagcag cgaaggcgag    4140
ctgaagaaaa cgcccttcag caaaaggcct gtggctctga gataatgcag aagaagcagc    4200
atctggagat agaactgaag caggtcatgc agcagcgctc tgaggacaat gcccggcaca    4260
agcagtccct ggaggaggct gccaagacca ttcaggacaa aaataaggag atcgagagac    4320
```

-continued

| | | | | |
|---|---|---|---|---|
| tcaaagctga | gtttcaggag | gaggccaagc | gccgctggga | atatgaaaat gaactgagta | 4380 |
| aggtaagaaa | caattatgat | gaggagatca | ttagcttaaa | aaatcagttt gagaccgaga | 4440 |
| tcaacatcac | caagaccacc | atccaccagc | tcaccatgca | gaaggaagag ataccagtg | 4500 |
| gctaccgggc | tcagatagac | aatctcaccc | gagaaaacag | gagcttatct gaagaaataa | 4560 |
| agaggctgaa | gaacactcta | acccagacca | cagagaatct | caggagggtg gaagaagaca | 4620 |
| tccaacagca | aaaggccact | ggctctgagg | tgtctcagag | gaaacagcag ctggaggttg | 4680 |
| agctgagaca | agtcactcag | atgcgaacag | aggagagcgt | aagatataag caatctcttg | 4740 |
| atgatgctgc | caaaaccatc | caggataaaa | acaaggagat | agaaaggtta aaacaactga | 4800 |
| tcgacaaaga | aacaaatgac | cggaaatgcc | tggaagatga | aaacgcgaga ttacaaaggg | 4860 |
| tccagtatga | cctgcagaaa | gcaaacagta | gtgcgacgga | gacaataaac aaactgaagg | 4920 |
| ttcaggagca | agaactgaca | cgcctgagga | tcgactatga | aagggtttcc caggagagga | 4980 |
| ctgtgaagga | ccaggatatc | acgcggttcc | agaactctct | gaaagagctg cagctgcaga | 5040 |
| agcagaaggt | ggaagaggag | ctgaatcggc | tgaagaggac | cgcgtcagaa gactcctgca | 5100 |
| agaggaagaa | gctggaggaa | gagctggaag | gcatgaggag | gtcgctgaag gagcaagcca | 5160 |
| tcaaaatcac | caacctgacc | cagcagctgg | agcaggcatc | cattgttaag aagaggagtg | 5220 |
| aggatgacct | ccggcagcag | agggacgtgc | tggatggcca | cctgagggaa aagcagagga | 5280 |
| cccaggaaga | gctgaggagg | ctctcttctg | aggtcgaggc | cctgaggcgg cagttactcc | 5340 |
| aggaacagga | aagtgtcaaa | caagctcact | tgaggaatga | gcatttccag aaggcgatag | 5400 |
| aagataaaag | cagaagctta | aatgaaagca | aaatagaaat | tgagaggctg cagtctctca | 5460 |
| cagagaacct | gaccaaggag | cacttgatgt | tagaagaaga | actgcggaac ctgaggctgg | 5520 |
| agtacgatga | cctgaggaga | ggacgaagcg | aagcggacag | tgataaaaat gcaaccatct | 5580 |
| tggaactaag | gagccagctg | cagatcagca | acaaccggac | cctggaactg cagggctga | 5640 |
| ttaatgattt | acagagagag | agggaaaatt | tgagacagga | aattgagaaa ttccaaaagc | 5700 |
| aggctttaga | ggcatctaat | aggattcagg | aatcaaagaa | tcagtgtact caggtggtac | 5760 |
| aggaaagaga | gagccttctg | gtgaaaatca | aagtcctgga | gcaagacaag gcaaggctgc | 5820 |
| agaggctgga | ggatgagctg | aatcgtgcaa | aatcaactct | agaggcagaa accagggtga | 5880 |
| aacagcgcct | ggagtgtgag | aaacagcaaa | ttcagaatga | cctgaatcag tggaagactc | 5940 |
| aatattcccg | caaggaggag | gctattagga | agatagaatc | ggaaagagaa aagagtgaga | 6000 |
| gagagaagaa | cagtcttagg | agtgagatcg | aaagactcca | agcagagatc aagagaattg | 6060 |
| aagagaggtg | caggcgtaag | ctggaggatt | ctaccaggga | gacacagtca cagttagaaa | 6120 |
| cagaacgctc | ccgatatcag | agggagattg | ataaactcag | acagcgccca tatgggtccc | 6180 |
| atcgagagac | ccagactgag | tgtgagtgga | ccgttgacac | ctccaagctg gtgtttgatg | 6240 |
| ggctgaggaa | gaaggtgaca | gcaatgcagc | tctatgagtg | tcagctgatc gacaaaacaa | 6300 |
| ccttggacaa | actattgaag | gggaagaagt | cagtggaaga | agttgcttct gaaatccagc | 6360 |
| cattccttcg | gggtgcagga | tctatcgctg | gagcatctgc | ttctcctaag gaaaaatact | 6420 |
| ctttggtaga | ggccaagaga | aagaaattaa | tcagcccaga | atccacagtc atgcttctgg | 6480 |
| aggcccaggc | agctacaggt | ggtataattg | atccccatcg | gaatgagaag ctgactgtcg | 6540 |
| acagtgccat | agctcgggac | ctcattgact | tcgatgaccg | tcagcagata tatgcagcag | 6600 |
| aaaaagctat | cactggtttt | gatgatccat | tttcaggcaa | gacagtatct gtttcagaag | 6660 |
| ccatcaagaa | aaatttgatt | gatagagaaa | ccggaatgcg | cctgctggaa gcccagattg | 6720 |

-continued

```
cttcaggggg tgtagtagac cctgtgaaca gtgtcttttt gccaaaagat gtcgccttgg      6780
cccgggggct gattgataga gatttgtatc gatccctgaa tgatccccga gatagtcaga      6840
aaaactttgt ggatccagtc accaaaaaga aggtcagtta cgtgcagctg aaggaacggt      6900
gcagaatcga accacatact ggtctgctct tgctttcagt acagaagaga agcatgtcct      6960
tccaaggaat cagacaacct gtgaccgtca ctgagctagt agattctggt atattgagac      7020
cgtccactgt caatgaactg aatctggtc agatttctta tgacgaggtt ggtgagagaa       7080
ttaaggactt cctccaggg t tcaagctgca tagcaggcat atacaatgag accacaaaac     7140
agaagcttgg catttatgag gccatgaaaa ttggcttagt ccgacctggt actgctctgg      7200
agttgctgga agcccaagca gctactggct ttatagtgga tcctgttagc aacttgaggt      7260
taccagtgga ggaagcctac aagagaggtc tggtgggcat tgagttcaaa gagaagctcc      7320
tgtctgcaga acgagctgtc actgggtata atgatcctga acaggaaac atcatctctt       7380 tgttccaagc catgaataag gaactcatcg aaaagggcca cggtattcgc ttattagaag      7440
cacagatcgc aaccgggggg atcattgacc caaggagag ccatcgttta ccagttgaca       7500
tagcatataa gagggctat ttcaatgagg aactcagtga gattctctca gatccaagtg       7560
atgataccaa aggatttttt gaccccaaca ctgaagaaaa tcttacctat ctgcaactaa      7620
aagaaagatg cattaaggat gaggaaacag gctctgtct tctgcctctg aaagaaaga       7680 agaaacaggt gcagacatca caaaagaata ccctcaggaa gcgtagagtg gtcatagttg      7740
acccagaaac caataaagaa atgtctgttc aggaggccta caagaagggc taattgatt       7800 atgaaacctt caagaactg tgtgagcagg aatgtgaatg ggaagaaata accatcacgg       7860
gatcagatgg ctccaccagg gtggtcctgg tagatagaaa gacaggcagt cagtatgata      7920
ttcaagatgc tattgacaag ggccttgttg acaggaagtt ctttgatcag taccgatccg      7980
gcagcctcag cctcactcaa tttgctgaca tgatctcctt gaaaaatggt gtcggcacca      8040
gcagcagcat gggcagtggt gtcagcgatg atgtttttag cagctcccga catgaatcag      8100
taagtaagat ttccaccata tccagcgtca ggaatttaac cataaggagc agctctttt       8160 cagacaccct ggaagaatcg agccccattg cagccatctt tgacacagaa aacctggaga      8220
aaatctccat tacagaaggt atagagcggg gcatcgttga cagcatcacg ggtcagaggc      8280
ttctggaggc tcaggcctgc acaggtggca tcatccaccc aaccacgggc cagaagctgt      8340
cacttcagga cgcagtctcc cagggtgtga ttgaccaaga catggccacc agcgtgaagc      8400
ctgctcagaa agccttcata ggcttcgagg gtgtgaaggg aaagaagaag atgtcagcag      8460
cagaggcagt gaaagaaaaa tggctcccgt atgaggctgg ccagcgcttc ctggagttcc      8520
agtacctcac gggaggtctt gttgacccgg aagtgcatgg gaggataagc accgaagaag      8580
ccatccggaa ggggttcata gatggccgcg ccgcacagag gctgcaagac accagcagct      8640
atgccaaaat cctgacctgc cccaaaacca aattaaaaat atcctataag gatgccataa      8700
atcgctccat ggtagaagat atcactgggc tgcgccttct ggaagccgcc tccgtgtcgt      8760
ccaagggctt acccagccct tacaacatgt cttcggctcc ggggtcccgc tccggctccc      8820
gctcgggatc tcgctccgga tctcgctccg ggtcccgcag tgggtcccgg agaggaagct      8880
ttgacgccac agggaattct tcctactctt attcctactc atttagcagt agttctattg      8940
ggcactag                                                               8948
```

<210> SEQ ID NO 120

<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 120

| | | | | | |
|---|---|---|---|---|---|
| cgtcctaagc | acttagacta | catcagggaa | gaacacagac | cacatccctg | tcctcatgcg | 60 |
| gcttatgttt | tctggaagaa | agtggagacc | nagtccttgg | ctttagggct | ccccggctgg | 120 |
| gggctgtgca | ntccggtcag | ggcgggaagg | gaaatgcacc | gctgcatgtg | aacttacagc | 180 |
| ccaggcggat | gccccttccc | ttagcactac | ctggcctcct | gcatccctc | gcctcatgtt | 240 |
| cctcccacct | tcaaanaatg | aanaacccca | tgggcccagc | cccttgccct | ggggaaccaa | 300 |
| ggcagccttc | caaaactcag | gggctgaagc | anactattag | ggcaggggct | gactttgggt | 360 |
| gacactgccc | attccctctc | agggcagctc | angtcacccn | ggnctcttga | acccagcctg | 420 |
| ttcctttgaa | aagggcaaa | actgaaaagg | gcttttccta | naaaaagaaa | aaccagggaa | 480 |
| ctttgccagg | gcttcnntnt | taccaaaacn | ncttctcnng | gattttaat | tccccattng | 540 |
| gcctccactt | accngggcn | atgccccaaa | attaanaatt | tcccatc | | 587 |

<210> SEQ ID NO 121
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 121

| | | | | | |
|---|---|---|---|---|---|
| cactagtagg | atagaaacac | tgtgtcccga | gagtaaggag | agaagctact | attgattaga | 60 |
| gcctaaccca | ggttaactgc | aagaagaggc | gggatacttt | cagctttcca | tgtaactgta | 120 |
| tgcataaagc | caatgtagtc | cagtttctaa | gatcatgttc | caagctaact | gaatcccact | 180 |
| tcaatacaca | ctcatgaact | cctgatggaa | caataacagg | cccaagcctg | tggtatgatg | 240 |
| tgcacacttg | ctagactcan | aaaaaatact | actctcataa | atgggtggga | gtattttggt | 300 |
| gacaacctac | tttgcttggc | tgagtgaagg | aatgatattc | atatattcat | ttattccatg | 360 |
| gacatttagt | tagtgctttt | tatataccag | gcatgatgct | gagtgacact | cttgtgtata | 420 |
| tttccaaatt | tttgtacagt | cgctgcacat | atttgaaatc | atatattaag | acttccaaaa | 480 |
| aatgaagtcc | ctggtttttc | atggcaactt | gatcagtaaa | ggattcncct | ctgtttggta | 540 |
| cttaaaacat | ctactatatn | gttnanatga | aattccttt | cccncctcc | cgaaaaaana | 600 |
| aagtggtggg | gaaaaaaaa | | | | | 619 |

<210> SEQ ID NO 122
<211> LENGTH: 1475
<212> TYPE: DNA
<213> ORGANISM: Homo sapien

<400> SEQUENCE: 122

| | | | | | |
|---|---|---|---|---|---|
| tccacctgtc | cccgcagcgc | cggctcgcgc | cctcctgccg | cagccaccga | gccgccgtct | 60 |
| agcgccccga | cctcgccacc | atgagagccc | tgctggcgcg | cctgcttctc | tgcgtcctgg | 120 |
| tcgtgagcga | ctccaaaggc | agcaatgaac | ttcatcaagt | tccatcgaac | tgtgactgtc | 180 |
| taaatggagg | aacatgtgtg | tccaacaagt | acttctccaa | cattcactgg | tgcaactgcc | 240 |

-continued

```
caaagaaatt cggagggcag cactgtgaaa tagataagtc aaaaacctgc tatgagggga      300
atggtcactt ttaccgagga aaggccagca ctgacaccat gggccggccc tgcctgccct      360
ggaactctgc cactgtcctt cagcaaacgt accatgccca cagatctgat gctcttcagc      420
tgggcctggg gaaacataat tactgcagga acccagacaa ccggaggcga ccctggtgct      480
atgtgcaggt gggcctaaag ccgcttgtcc aagagtgcat ggtgcatgac tgcgcagatg      540
gaaaaaagcc ctcctctcct ccagaagaat taaaatttca gtgtggccaa agactctga       600 ggccccgctt taagattatt gggggagaat tcaccaccat cgagaaccag ccctggtttg      660
cggccatcta caggaggcac cggggggggct ctgtcaccta cgtgtgtgga ggcagcctca     720
tcagcccttg ctgggtgatc agcgccacac actgcttcat tgattaccca agaaggagg      780 actacatcgt ctacctgggt cgctcaaggc ttaactccaa cacgcaaggg agatgaagt      840 ttgaggtgga aaacctcatc ctacacaagg actacagcgc tgacacgctt gctcaccaca     900
acgacattgc cttgctgaag atccgttcca aggagggcag gtgtgcgcag ccatcccgga     960
ctatacagac catctgcctg ccctcgatgt ataacgatcc ccagtttggc acaagctgtg    1020
agatcactgg ctttggaaaa gagaattcta ccgactatct ctatccggag cagctgaaga    1080
tgactgttgt gaagctgatt tccaccggga gtgtcagca gccccactac tacggctctg     1140
aagtcaccac caaaatgctg tgtgctgctg acccacagtg aaaacagat tcctgccagg     1200 gagactcagg ggacccctc gtctgttccc tccaaggccg catgactttg actggaattg     1260
tgagctgggg ccgtggatgt gccctgaagg acaagccagg cgtctacacg agagtctcac    1320
acttcttacc ctggatccgc agtcacacca aggaagagaa tggcctggcc ctctgagggt    1380
ccccagggag gaaacgggca ccacccgctt tcttgctggt tgtcattttt gcagtagagt    1440
catctccatc agctgtaaga agagactggg aagat                                1475
```

<210> SEQ ID NO 123
<211> LENGTH: 2294
<212> TYPE: DNA
<213> ORGANISM: Homo sapien

<400> SEQUENCE: 123

```
cagcgccggc tcgcgccctc ctgccgcagc caccgagccg ccgtctagcg ccccgacctc      60
gccaccatga gagccctgct ggcgcgcctg cttctctgcg tcctggtcgt gagcgactcc     120
aaaggcagca atgaacttca tcaagttcca tcgaactgtg actgtctaaa tggaggaaca     180
tgtgtgtcca acaagtactt ctccaacatt cactggtgca actgcccaaa gaaattcgga     240
gggcagcact gtgaaataga taagtcaaaa acctgctatg aggggaatgg tcacttttac     300
cgaggaaagg ccagcactga caccatgggc cggccctgcc tgcctggaa ctctgccact     360 gtccttcagc aaacgtacca tgcccacaga tctgatgctc ttcagctggg cctggggaaa    420
cataattact gcaggaaccc agacaaccgg aggcgaccct ggtgctatgt gcaggtgggc    480
ctaaagccgc ttgtccaaga gtgcatggtg catgactgcg cagatggaaa aaagccctcc    540
tctcctccag aagaattaaa atttcagtgt ggccaaaaga ctctgaggcc ccgctttaag    600
attattgggg gagaattcac caccatcgag aaccagccct ggtttgcggc catctacagg    660
aggcaccggg ggggctctgt cacctacgtg tgtggaggca gcctcatcag cccttgctgg    720
gtgatcagcg ccacacactg cttcattgat tacccaaaga aggaggacta catcgtctac    780
ctgggtcgct caaggcttaa ctccaacacg caaggggaga tgaagtttga ggtggaaaac    840
```

-continued

```
ctaatcctac acaaggacta cagcgctgac acgcttgctc accacaacga cattgccttg      900
ctgaagatcc gttccaagga gggcaggtgt gcgcagccat cccggactat acagaccatc      960
tgcctgccct cgatgtataa cgatccccag tttggcacaa gctgtgagat cactggcttt     1020
ggaaaagaga attctaccga ctatctctat ccggagcagc tgaaaatgac tgttgtgaag     1080
ctgatttccc accgggagtg tcagcagccc cactactacg gctctgaagt caccaccaaa     1140
atgctgtgtg ctgctgaccc acagtggaaa acagattcct gccagggaga ctcaggggga     1200
cccctcgtct gttccctcca aggccgcatg actttgactg gaattgtgag ctggggccgt     1260
ggatgtgccc tgaaggacaa gccaggcgtc tacacgagag tctcacactt cttaccctgg     1320
atccgcagtc acaccaagga agagaatggc ctggccctct gagggtcccc agggaggaaa     1380
cgggcaccac ccgctttctt gctggttgct attttgcagt agagtcatct ccatcagctg     1440
taagaagagc tgggaatata ggctctgcac agatggattt gcctgtgcca ccaccagggc     1500
gaacgacaat agctttaccc tcaggcatag gcctgggtgc tggctgccca gacccctctg     1560
gccaggatgg aggggtggtc ctgactcaac atgttactga ccagcaactt gtcttttttct     1620
ggactgaagc ctgcaggagt taaaaagggc agggcatctc ctgtgcatgg gctcgaaggg     1680
agagccagct cccccgaccg gtgggcattt gtgaggccca tggttgagaa atgaataatt     1740
tcccaattag gaagtgtaag cagctgaggt ctcttgaggg agcttagcca atgtgggagc     1800
agcggtttgg ggagcagaga cactaacgac ttcagggcag ggctctgata ttccatgaat     1860
gtatcaggaa atatatatgt gtgtgtatgt ttgcacactt gtgtgtgggc tgtgagtgta     1920
agtgtgagta agagctggtg tctgattgtt aagtctaaat atttccttaa actgtgtgga     1980
ctgtgatgcc acacagagtg gtctttctgg agaggttata ggtcactcct ggggcctctt     2040
gggtcccca cgtgacagtg cctgggaatg tattattctg cagcatgacc tgtgaccagc     2100
actgtctcag tttcactttc acatagatgt ccctttcttg gccagttatc ccttcctttt     2160
agcctagttc atccaatcct cactgggtgg ggtgaggacc actcctgtac actgaatatt     2220
tatatttcac tatttttatt tatattttg taattttaaa taaagtgat caataaaatg     2280
tgattttttct gatg                                                      2294
```

<210> SEQ ID NO 124
<211> LENGTH: 956
<212> TYPE: DNA
<213> ORGANISM: Homo sapien

<400> SEQUENCE: 124

```
gatgagttcc gcaccaagtt tgagacagac caggccctgc gcctgagtgt ggaggccgac       60
atcaatggcc tgcgcagggt gctggatgag ctgaccctgg ccagagccga cctggagatg      120
cagattgaga acctcaagga ggagctggcc tacctgaaga gaaccacga ggaggagatg      180
aacgccctgc gaggccaggt gggtggtgag atcaatgtgg agatggacgc tgccccaggc      240
gtggacctga gccgcatcct caacgagatg cgtgaccagt atgagaagat ggcagagaag      300
aaccgcaagg atgccgagga ttggttcttc agcaagacag aggaactgaa ccgcgaggtg      360
gccaccaaca gtgagctggt gcagagtggc aagagtgaga tctcggagct ccggcgcacc      420
atgcaggcct tggagataga gctgcagtcc cagctcagca tgaaagcatc cctggaggc      480
aacctggcgg agacagagaa ccgctactgc gtgcagctgt cccagatcca gggctgatt      540
ggcagcgtga aggagcagct ggcccagctt cgctgcgaga tggagcagca gaaccaggaa      600
tacaaaatcc tgctggatgt gaagacgcgg ctggagcagg agattgccac ctaccgccgc      660
```

```
ctgctggagg gagaggatgc ccacctgact cagtacaaga agaaccggt gaccacccgt      720 caggtgcgta ccattgtgga agaggtccag gatggcaagg tcatctcctc ccgcgagcag      780
gtccaccaga ccacccgctg aggactcagc taccccggcc ggccacccag gaggcaggga      840
cgcagccgcc ccatctgccc cacagtctcc ggcctctcca gcctcagccc cctgcttcag      900
tcccttcccc atgcttcctt gcctgatgac aataaaagct tgttgactca gctatg         956
```

<210> SEQ ID NO 125
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 125

```
aaattatata tagtgnttca gctcccattg tggtgttcat agtcttctag gaacagataa       60
acttaagtat tcaattcact cttggcattt tttcttaat ataggcttt tagcctattt       120 ttggaaaact gcttttcttc tgagaacctt attctgaatg tcatcaactt taccaaacct     180
tctaagtcca gagctaactt agtactgttt aagttactat tgactgaatt ttcttcattt     240
tctgtttagc cagtgttacc aaggtaagct ggggaatgaa gtataccaac ttctttcaga     300
gcattttagg acattatggc agctttagaa ggctgtcttg tttctagcca agggagagcc     360
agcgcaggtt ttggatacta gagaaagtca tttgcttgta ctattgccat tttagaaagc     420
tctgatgtga attcaaattt tacctctgtt acttaaagcc aacaatttta aggcagtagt     480
tttact                                                                486
```

<210> SEQ ID NO 126
<211> LENGTH: 3552
<212> TYPE: DNA
<213> ORGANISM: Homo sapien

<400> SEQUENCE: 126

```
cggcaggcag gtctcgtctc ggcaccctcc cggcgcccgc gttctcctgg ccctgcccgg       60
catcccgatg gccgccgctg ggccccggcg ctccgtgcgc ggagccgtct gcctgcatct      120
gctgctgacc ctcgtgatct tcagtcgtgc tggtgaagcc tgcaaaaagg tgatacttaa     180
tgtaccttct aaactagagg cagacaaaat aattggcaga gttaatttgg aagagtgctt     240
caggtctgca gacctcatcc ggtcaagtga tcctgatttc agagttctaa atgatgggtc     300
agtgtacaca gccagggctg ttgcgctgtc tgataagaaa agatcattta ccatatggct     360
ttctgacaaa aggaaacaga cacagaaaga ggttactgtg ctgctagaac atcagaagaa     420
ggtatcgaag acaagacaca ctagagaaac tgttctcagg cgtgccaaga ggagatgggc     480
acctattcct tgctctatgc aagagaattc cttgggccct ttcccattgt ttcttcaaca     540
agttgaatct gatgcagcac agaactatac tgtcttctac tcaataagtg gacgtggagt     600
tgataaagaa ccttaaatt tgttttatat agaaagagac actggaaatc tattttgcac     660
tcggcctgtg gatcgtgaag aatatgatgt ttttgatttg attgcttatg cgtcaactgc     720
agatggatat tcagcagatc tgccctccc actacccatc agggtagagg atgaaaatga     780
caaccaccct gttttcacag aagcaattta atttttgaa gttttggaaa gtagtagacc     840
tggtactaca gtgggggtgg tttgtgccac agacagagat gaaccggaca caatgcatac     900
```

```
gcgcctgaaa tacagcatttt tgcagcagac accaaggtca cctgggctct tttctgtgca    960
tcccagcaca ggcgtaatca ccacagtctc tcattatttg acagagagg ttgtagacaa    1020
gtactcattg ataatgaaag tacaagacat ggatggccag ttttttggat tgataggcac    1080
atcaacttgt atcataacag taacagattc aaatgataat gcacccactt tcagacaaaa    1140
tgcttatgaa gcatttgtag aggaaaatgc attcaatgtg aaatcttac gaatacctat    1200
agaagataag gatttaatta acactgccaa ttggagagtc aattttacca ttttaagggg    1260
aaatgaaaat ggacatttca aaatcagcac agacaaagaa actaatgaag gtgttctttc    1320
tgttgtaaag ccactgaatt atgaagaaaa ccgtcaagtg aacctggaaa ttggagtaaa    1380
caatgaagcg ccatttgcta gagatattcc cagagtgaca gccttgaaca gagccttggt    1440
tacagttcat gtgagggatc tggatgaggg gcctgaatgc actcctgcag cccaatatgt    1500
gcggattaaa gaaaacttag cagtggggtc aaagatcaac ggctataagg catatgaccc    1560
cgaaaataga aatggcaatg gtttaaggta caaaaaattg catgatccta aaggttggat    1620
caccattgat gaaatttcag ggtcaatcat aacttccaaa atcctggata gggaggttga    1680
aactcccaaa atgagttgt ataatattac agtcctggca atagacaaag atgatagatc    1740
atgtactgga acacttgctg tgaacattga agatgtaaat gataatccac cagaaatact    1800
tcaagaatat gtagtcattt gcaaaccaaa atgggggtat accgacattt tagctgttga    1860
tcctgatgaa cctgtccatg gagctccatt ttatttcagt ttgcccaata cttctccaga    1920
aatcagtaga ctgtggagcc tcaccaaagt taatgataca gctgcccgtc tttcatatca    1980
gaaaaatgct ggatttcaag aatataccat tcctattact gtaaaagaca gggccggcca    2040
agctgcaaca aaattattga gagttaatct gtgtgaatgt actcatccaa ctcagtgtcg    2100
tgcgacttca aggagtacag gagtaatact tggaaaatgg caatccttg caatattact    2160
gggtatagca ctgctctttt ctgtattgct aactttagta tgtggagttt ttggtgcaac    2220
taagggaaa cgttttcctg aagatttagc acagcaaaac ttaattatat caaacacaga    2280
agcacctgga gacgatagag tgtgctctgc caatggattt atgacccaaa ctaccaacaa    2340
ctctagccaa ggttttttgtg gtactatggg atcaggaatg aaaaatggag gcaggaaac    2400
cattgaaatg atgaaaggag gaaaccagac cttggaatcc tgccggggg ctgggcatca    2460
tcataccctg gactcctgca ggggaggaca cacggaggtg gacaactgca gatacactta    2520
ctcggagtgg cacagtttta ctcaaccccg tctcggtgaa aaattgcatc gatgtaatca    2580
gaatgaagac cgcatgccat cccaagatta tgtcctcact tataactatg agggaagagg    2640
atctccagct ggttctgtgg gctgctgcag tgaaaagcag gaagaagatg gccttgactt    2700
tttaaataat ttggaaccca aatttattac attagcagaa gcatgcacaa agagataatg    2760
tcacagtgct acaattaggt ctttgtcaga cattctggag gtttccaaaa ataatattgt    2820
aaagttcaat ttcaacatgt atgtatatga tgatttttt ctcaattttg aattatgcta    2880
ctcaccaatt tatattttta agcaagttg ttgcttatct tttccaaaaa gtgaaaaatg    2940
ttaaaacaga caactggtaa atctcaaact ccagcactgg aattaaggtc tctaaagcat    3000
ctgctctttt ttttttttac agatatttta gtaataaata tgctggataa atattagtcc    3060
aacaatagct aagttatgct aatatcacat tattatgtat tcactttaag tgatagttta    3120
aaaaataaac aagaaatatt gagtatcact atgtgaagaa agttttggaa agaaaacaat    3180
gaagactgaa ttaaattaaa aatgttgcag ctcataaaga attggactca cccctactgc    3240
actaccaaat tcatttgact ttggaggcaa aatgtgttga agtgccctat gaagtagcaa    3300
```

-continued

```
ttttctatag gaatatagtt ggaaataaat gtgtgtgtgt atattattat taatcaatgc        3360
aatatttaaa tgaaatgaga acaaagagga aaatggtaaa aacttgaaat gaggctgggg        3420
tatagtttgt cctacaatag aaaaaagaga gagcttccta ggcctgggct cttaaatgct        3480
gcattataac tgagtctatg aggaaatagt tcctgtccaa tttgtgtaat ttgtttaaaa        3540
ttgtaaataa at                                                            3552

<210> SEQ ID NO 127
<211> LENGTH: 754
<212> TYPE: DNA
<213> ORGANISM: Homo sapien

<400> SEQUENCE: 127
tttttttttt ttgtcattgt tcattgattt taatgagaaa gctaagagag gaaataagta          60
gcctttcaaa ggtcacacag aagtaagtga cagatccagg attcatatcc aagcattctg         120
gctctagtgt ccatgcttct caaccattat gacccaatat tcaaccaaat caatactgaa         180
ggacacgtga aatgtatccg gtattttact attacaaaca aaaatccaat gaacattctt         240
gaagacatac acaaaaataa tggttacaat agaagttact ggaattgaaa ttttggttca         300
acctatatta aaatgtaagg cttttgatat agctaataga ttttttgaaat gatcagtctt        360 aacgtttgta ggggagcaca ctcctgcatg gggaaaagat tcactgtgaa gcacagagca         420
cctttatggt tggatcatct tgtcattaaa gttcaggcgt tatctatcct gtaagtggca         480
gaatcaagac tgcaatatcg cctgcttttc ttttttaactc atgttttccc ttgactacac        540
tggtcctcaa agtaaaaccc ctgtgtcagt gtactattca tggaatactc tgcaattata         600
accaccttct aatactttta atacccaatc aaaatttatt atacatatgt atcatagata         660
ctcatctgta aagctgtgct tcaaaatagt gatctcttcc caacattaca atatatatta         720
atgatgtcga acctgcccgg gcggccgctc gaag                                    754

<210> SEQ ID NO 128
<211> LENGTH: 374
<212> TYPE: DNA
<213> ORGANISM: Homo sapien

<400> SEQUENCE: 128
aggttttgat taaaaaggca atgattttta ttgttcgata atcttttaaa aaaataagag          60
gaaggagtaa aattaaagat gaaagatgat ttttatttcc ttgtgacctc tatatccccc        120
ttcccctgcc cttggtaagt aactcttgat ggagaaagga ttaaagactc ttatttaacc         180
aaaaaacaga gccagctaat catttccaaa ggttagtatc tccctgctga cctcttcttt         240
ggtttaattg aataaaacta tatgttcata tatgtattaa acaactcag aataacatct          300 tttcttcctt agttaaggca ttataagggc tatactatca tccataataa ccaaggcaat         360
aacttaaaaa gctg                                                           374

<210> SEQ ID NO 129
<211> LENGTH: 546
<212> TYPE: DNA
<213> ORGANISM: Homo sapien

<400> SEQUENCE: 129
agtgtgatgg atatctgcag aattcgggct aagcgtggtc gcggccgag gtctggaact           60 tcccagcacy tgaaaaggag cctcctgagc tgactcggct aaagccccac tttcgctcct         120
```

-continued

| | |
|---|---|
| cctcatttct gcctactgat ttccttggag cattcatctg aatattaccg tttgctgtgt | 180 |
| aacctggtac atacatagca tgactccctg gaatagagtg ggctggggtg cttatgctgg | 240 |
| gagagtgatt gacatgcact ttcaagctat atctaccatt tgcagcaaag gagaaaaaat | 300 |
| acctcgagta aattccatca ttttttataa catcagcacc tgctccatca tcaaggagtc | 360 |
| tcagcgtaac aggatctcca gtctctggct caactgtggc agtgacagtg cattaagaa | 420 |
| tgggataaaa tccctgtttc acattggcat aaatcatcac aggatgagga aaatggaggc | 480 |
| tgtctctttc cacaaaggct tccacagtgg ctgggggcac agacctgccc gggcggccgc | 540 |
| tcgaaa | 546 |

<210> SEQ ID NO 130
<211> LENGTH: 5156
<212> TYPE: DNA
<213> ORGANISM: Homo sapien

<400> SEQUENCE: 130

| | |
|---|---|
| accaaccgag gcgccgggca gcgacccctg cagcggagac agagactgag cggcccggca | 60 |
| ccgccatgcc tgcgctctgg ctgggctgct gcctctgctt gtcgctcctc ctgcccgcag | 120 |
| cccgggccac ctccaggagg gaagtctgtg attgcaatgg gaagtccagg cagtgtatct | 180 |
| tgatcggga acttcacaga caaactggta atggattccg ctgcctcaac tgcaatgaca | 240 |
| acactgatgg cattcactgc gagaagtgca agaatggctt ttaccggcac agagaaaggg | 300 |
| accgctgttt gccctgcaat tgtaactcca aggttctct tagtgctcga tgtgacaact | 360 |
| ccggacggtg cagctgtaaa ccaggtgtga caggagccag atgcgaccga tgtctgccag | 420 |
| gcttccacat gctcacggat gcggggtgca cccaagacca gagactgcta gactccaagt | 480 |
| gtgactgtga cccagctggc atcgcagggc cctgtgacgc gggccgctgt gtctgcaagc | 540 |
| cagctgtcac tggagaacgc tgtgataggt gtcgatcagg ttactataat ctggatgggg | 600 |
| ggaaccctga gggctgtacc cagtgtttct gctatgggca ttcagccagc tgccgcagct | 660 |
| ctgcagaata cagtgtccat aagatcacct ctacctttca tcaagatgtt gatgctgga | 720 |
| aggctgtcca acgaaatggg tctcctgcaa agctccaatg gtcacagcgc atcaagatg | 780 |
| tgtttagctc agcccaacga ctagaccctg tctattttgt ggctcctgcc aaatttcttg | 840 |
| ggaatcaaca ggtgagctat ggtcaaagcc tgtcctttga ctaccgtgtg gacagaggag | 900 |
| gcagacaccc atctgcccat gatgtgattc tggaaggtgc tggtctacgg atcacagctc | 960 |
| ccttgatgcc acttggcaag acactgcctt gtgggctcac caagacttac acattcaggt | 1020 |
| taaatgagca tccaagcaat aattggagcc cccagctgag ttactttgag tatcgaaggt | 1080 |
| tactgcggaa tctcacagcc ctccgcatcc gagctacata tggagaatac agtactgggt | 1140 |
| acattgacaa tgtgaccctg atttcagccc gccctgtctc tggagcccca gcaccctggg | 1200 |
| ttgaacagtg tatatgtcct gttgggtaca aggggcaatt ctgccaggat tgtgcttctg | 1260 |
| gctacaagag agattcagcg agactggggc cttttggcac ctgtattcct tgtaactgtc | 1320 |
| aagggggagg ggcctgtgat ccagacacag agattgtta tcaggggat gagaatcctg | 1380 |
| acattgagtg tgctgactgc ccaattggtt tctacaacga tccgcacgac ccccgcagct | 1440 |
| gcaagccatg tccctgtcat aacgggttca gctgctcagt gatgccggag acggaggagg | 1500 |
| tggtgtgcaa taactgccct cccgggggtca ccggtgcccg ctgtgagctc tgtgctgatg | 1560 |
| gctactttgg ggacccctt ggtgaacatg gcccagtgag gccttgtcag ccctgtcaat | 1620 |
| gcaacaacaa tgtggacccc agtgcctctg ggaattgtga ccggctgaca ggcaggtgtt | 1680 |

```
tgaagtgtat ccacaacaca gccggcatct actgcgacca gtgcaaagca ggctacttcg    1740
gggacccatt ggctcccaac ccagcagaca agtgtcgagc ttgcaactgt aaccccatgg    1800
gctcagagcc tgtaggatgt cgaagtgatg gcacctgtgt ttgcaagcca ggatttggtg    1860
gccccaactg tgagcatgga gcattcagct gtccagcttg ctataatcaa gtgaagattc    1920
agatggatca gtttatgcag cagcttcaga gaatggaggc cctgatttca aaggctcagg    1980
gtggtgatgg agtagtacct gatacagagc tggaaggcag gatgcagcag gctgagcagg    2040
cccttcagga cattctgaga gatgcccaga tttcagaagg tgctagcaga tcccttggtc    2100
tccagttggc caaggtgagg agccaagaga acagctacca gagccgcctg gatgacctca    2160
agatgactgt ggaaagagtt cgggctctgg gaagtcagta ccagaaccga gttcgggata    2220
ctcacaggct catcactcag atgcagctga gcctggcaga aagtgaagct tccttgggaa    2280
acactaacat tcctgcctca gaccactacg tggggccaaa tggctttaaa agtctggctc    2340
aggaggccac aagattagca gaaagccacg ttgagtcagc cagtaacatg gagcaactga    2400
caagggaaac tgaggactat tccaaacaag ccctctcact ggtgcgcaag gccctgcatg    2460
aaggagtcgg aagcggaagc ggtagcccgg acggtgctgt ggtgcaaggg cttgtggaaa    2520
aattggagaa aaccaagtcc ctggcccagc agttgacaag ggaggccact caagcggaaa    2580
ttgaagcaga taggtcttat cagcacagtc tccgcctcct ggattcagtg tctcggcttc    2640
agggagtcag tgatcagtcc tttcaggtgg aagaagcaaa gaggatcaaa caaaaagcgg    2700
attcactctc aagcctggta accaggcata tggatgagtt caagcgtaca cagaagaatc    2760
tgggaaactg gaaagaagaa gcacagcagc tcttacagaa tggaaaaagt gggagagaga    2820
aatcagatca gctgctttcc cgtgccaatc ttgctaaaag cagagcacaa gaagcactga    2880
gtatgggcaa tgccactttt tatgaagttg agagcatcct taaaaacctc agagagtttg    2940
acctgcaggt ggacaacaga aaagcagaag ctgaagaagc catgaagaga ctctcctaca    3000
tcagccagaa ggtttcagat gccagtgaca agacccagca agcagaaaga gccctgggga    3060
gcgctgctgc tgatgcacag agggcaaaga atggggccgg ggaggccctg gaaatctcca    3120
gtgagattga acaggagatt gggagtctga acttggaagc caatgtgaca gcagatggag    3180
ccttggccat ggaaaaggga ctggcctctc tgaagagtga gatgagggaa gtggaaggag    3240
agctggaaag gaaggagctg gagtttgaca cgaatatgga tgcagtacag atggtgatta    3300
cagaagccca gaaggttgat accagagcca gaacgctggg ggttacaatc caagacacac    3360
tcaacacatt agacggcctc ctgcatctga tggaccagcc tctcagtgta gatgaagagg    3420
ggctggtctt actggagcag aagctttccc gagccaagac ccagatcaac agccaactgc    3480
ggcccatgat gtcagagctg gaagagaggg cacgtcagca gaggggccac ctccatttgc    3540
tggagacaag catagatggg attctggctg atgtgaagaa cttggagaac attagggaca    3600
acctgccccc aggctgctac aatacccagg ctcttgagca acagtgaagc tgccataaat    3660
atttctcaac tgaggttctt gggatacaga tctcagggct cggagccat gtcatgtgag    3720 tgggtgggat ggggacattt gaacatgttt aatgggtatg ctcaggtcaa ctgacctgac    3780
cccattcctg atcccatggc caggtggttg tcttattgca ccatactcct tgcttcctga    3840
tgctgggcaa tgaggcagat agcactgggt gtgagaatga tcaaggatct ggaccccaaa    3900
gaatagactg gatggaaaga caaactgcac aggcagatgt ttgcctcata atagtcgtaa    3960
gtggagtcct ggaatttgga caagtgctgt tgggatatag tcaacttatt ctttgagtaa    4020
```

```
tgtgactaaa ggaaaaaact ttgactttgc ccaggcatga aattcttcct aatgtcagaa    4080
cagagtgcaa cccagtcaca ctgtggccag taaaatacta ttgcctcata ttgtcctctg    4140
caagcttctt gctgatcaga gttcctccta cttacaaccc agggtgtgaa catgttctcc    4200
attttcaagc tggaagaagt gagcagtgtt ggagtgagga cctgtaaggc aggcccattc    4260
agagctatgg tgcttgctgg tgcctgccac cttcaagttc tggacctggg catgacatcc    4320
tttcttttaa tgatgccatg gcaacttaga gattgcattt ttattaaagc atttcctacc    4380
agcaaagcaa atgttgggaa agtatttact ttttcggttt caaagtgata gaaaagtgtg    4440
gcttgggcat tgaaagaggt aaaattctct agatttatta gtcctaattc aatcctactt    4500
ttagaacacc aaaaatgatg cgcatcaatg tattttatct tattttctca atctcctctc    4560
tctttcctcc acccataata agagaatgtt cctactcaca cttcagctgg gtcacatcca    4620
tccctccatt catccttcca tccatctttc catccattac ctccatccat ccttccaaca    4680
tatatttatt gagtacctac tgtgtgccag gggctggtgg gacagtggtg acatagtctc    4740
tgccctcata gagttgattg tctagtgagg aagacaagca ttttttaaaaa ataaatttaa    4800 acttacaaac tttgtttgtc acaagtggtg tttattgcaa taaccgcttg gtttgcaacc    4860
tctttgctca acagaacata tgttgcaaga ccctcccatg ggggcacttg agttttggca    4920
aggctgacag agctctgggt tgtgcacatt tctttgcatt ccagctgtca ctctgtgcct    4980
ttctacaact gattgcaaca gactgttgag ttatgataac accagtggga attgctggag    5040
gaaccagagg cacttccacc ttggctggga agactatggt gctgccttgc ttctgtattt    5100
ccttggattt tcctgaaagt gttttaaat aaagaacaat tgttagaaaa aaaaaa        5156
```

<210> SEQ ID NO 131
<211> LENGTH: 671
<212> TYPE: DNA
<213> ORGANISM: Homo sapien

<400> SEQUENCE: 131

```
aggtctggag ggcccacagc cggatgtggg acaccgggaa aaagtggtca tagcacacat      60
ttttgcatcc cggttgcagt gtgttgcaga cgaagtcctc ttgctcgtca ccccacactt     120
cctgggcagc caycacgagg atcatgactc ggaaaataaa gatgactgtg atccacacct     180
tcccgatgct ggtggagtgt ttgttgacac ccccgatgaa agtgtgcagc gtcccccaat     240
ccattgcgct ggtttatccc tgagtcctgt tccaacgac tgccagtgtt tcagacccaa     300
agaatgaggg caagatccct ctgcgagggt ttcagacctc cttctcctac cccactggag     360
tgcctagaag ccaatgggtg cacagtgatg atacgaatgt caatctttgc tcggtcagtg     420
aggatgtcgc ctggaatatt caaattgaat tacagatgca tgaagagggc gtacaagtta     480 gaattttttct ttcgccatac agaaattgtt tagccagatc ttctgtactt cttttccttc     540
cctgacccct cctgctcccc aggaagggag gtcagccccg tttgcaaaac acaggatgcc     600
cgtgacaccg gagacaggtc ttcttcaccg acaggaagtg ccttctggtg cctgcacgtt     660
ttaactgcta t                                                          671
```

<210> SEQ ID NO 132
<211> LENGTH: 590
<212> TYPE: DNA
<213> ORGANISM: Homo sapien

<400> SEQUENCE: 132

```
ctgaatggaa aagcttatgg ctctgtgatg atattagtga ccagcggaga tgataagctt       60
```

```
cttggcaatt gcttacccac tgtgctcagc agtggttcaa caattcactc cattgccctg      120
ggttcatctg cagccccaaa tctggaggaa ttatcacgtc ttacaggagg tttaaagttc      180
tttgttccag atatatcaaa ctccaatagc atgattgatg ctttcagtag aatttcctct      240
ggaactggag acattttcca gcaacatatt cagcttgaaa gtacaggtga aaatgtcaaa      300
cctcaccatc aattgaaaaa cacagtgact gtggataata ctgtgggcaa cgacactatg      360
tttctagtta cgtggcaggc cagtggtcct cctgagatta tattatttga tcctgatgga      420
cgaaaatact acacaaataa ttttatcacc aatctaactt ttcggacagc tagtctttgg      480
attccaggaa cagctaagcc tgggcactgg acttacaccc tgaacaatac ccatcattct      540
ctgcaagccc tgaaagtgac agtgacctct cgcgcctcca actcagacct                590
```

<210> SEQ ID NO 133
<211> LENGTH: 581
<212> TYPE: DNA
<213> ORGANISM: Homo sapien

<400> SEQUENCE: 133

```
aggtcctgtc cgggggcact gagaactccc tctggaattc ttgggggggtg ttggggagag      60 actgtgggcc tggagataaa acttgtctcc tctaccacca ccctgtaccc tagcctgcac      120
ctgtcctcat ctctgcaaag ttcagcttcc ttccccaggt ctctgtgcac tctgtcttgg      180
atgctctggg gagctcatgg gtggaggagt ctccaccaga gggaggctca ggggactggt      240
tgggccaggg atgaatattt gagggataaa aattgtgtaa gagccaaaga attggtagta      300
gggggagaac agagaggagc tgggctatgg gaaatgattt gaataatgga gctgggaata      360
tggctggata tctggtacta aaaaagggtc tttaagaacc tacttcctaa tctcttcccc      420
aatccaaacc atagctgtct gtccagtgct ctcttcctgc ctccagctct gccccaggct      480
cctcctagac tctgtccctg gctagggca ggggaggagg gagagcaggg ttgggggaga      540
ggctgaggag agtgtgacat gtggggagag gaccagacct c                         581
```

<210> SEQ ID NO 134
<211> LENGTH: 4797
<212> TYPE: DNA
<213> ORGANISM: Homo sapien
<220> FEATURE:
<221> NAME/KEY: misc_feature
<222> LOCATION: (1)...(4797)
<223> OTHER INFORMATION: n = A,T,C or G

<400> SEQUENCE: 134

```
cctgggacca aagtgctgcc cagagctgag ggtcctggag ccacatgaga aggcttctcc      60
ctgtgtacct gtgcagcaca gggtagggtg agtccactca gctgtctagg agaggaccca    120
ggagcagcag agacncgcca agcctttact cataccatat tctgatcctt ttccagcaaa    180
ttgtggctac taatttgccc cctgaagatc aagatggctc tggggatgac tctgacaact    240
tctccggctc aggtgcaggt gaggttgtca tgggggcccc ccacccaa gacgcaaca       300 ggtcatgcct gggggcagtg gtcaggcagt ctcctgtgtt tactgagcat gtactgagtg    360
caccctgcct gccctgtctc cacccagctg gctccaaagg gcaatgctga ggagaggaat    420
ggggtcgtga gctgctgtta aggagagctc atgcttggag gtgaggtgaa ggctgtgagc    480
tccagaaggc cccagggcgc nctgctgcac gcaggctcat attcactagg aatagcttta    540
ctcactaaga aacctctgga accccttca gaaggttatt tgactcctga gcctctattt     600
```

```
tctcatctgc aaaatgggaa taataccttg acctgataag cttgtggagc tgtaaggcag    660
cacagagcca gctggggtgt agctcttcca tccaagctcc cttccttact tcccctttcc    720
tgtggggact gggggagaga agtccctgag ctggaggtgg tcaggaagc ttcacagagg     780
aggtggctct tgagtggacc tcaggaagag gggtgagaga gctaaggaag gaggctgagg    840
tcatccctgg ggaagtgacc tagcggaggc ctgagagctg caaggtagga tatctgttgt    900
tggaagtgtc tgttgttgga agtggggggcc ttttttttcag ggagggtggg gccagagaag  960
tgtgtgccct gggataagta ggataaccac agtagttatg cccctaaggg atgcccaccc   1020
caccccctgtg gtcacagaaa agctttccca ggtggcctag gcacctgtct cgtggctcca  1080
gagacaggct gcacctgaca cacacaatgg aaggacagct ctccttgtcc attttccaag   1140
gagcttagcc tcagctgcct tgtccaggta ctagcctccc tcatagcctg agcttggcca   1200
gcccaggtgc tctggagcct cccccgaccc acccaacaca ctctgcttct ggtcctcccc   1260
acccccacc tccccaacac actctgcttc tggtcctgca ggtgctttgc aagatatcac    1320
cttgtcacag cagacccccct ccacttggaa ggacacgcag ctcctgacgg ctattcccac  1380
gtctccagaa cccaccggcc tggaggctac agctgcctcc acctccaccc tgccggctgg   1440
agagggccc aaggagggag aggctgtagt cctgccagaa gtggagcctg gcctcaccgc    1500
ccgggagcag gaggccaccc cccgacccag ggagaccaca cagctcccga ccactcatca   1560
ggcctcaacg accacagcca ccacggccca ggagcccgcc acctccaccc ccacaggga   1620
catgcagcct ggccaccatg agacctcaac ccctgcagga cccagccaag ctgaccttca   1680
cactccccac acagaggatg gaggtccttc tgccaccgag agggctgctg aggatggagc   1740
ctccagtcag ctcccagcag cagagggctc tggggagcag gtgagtggcc tctgcattcc   1800
ttgggaaatt gagtgggttg gtcctaatgc ctggcacttg gcaggcccta cacctgtgcc   1860
ctgcgcgatc tcgtattcct caccaggaag acagggcaca gggccgcct tcccctaccc    1920
ccagggcctc gcagagcagg acagactaac tatgagatca gagcagaagc ccctttaaag   1980
atcacccaag agagggctcc caaactcaca atccaaactt gcagccctcg tcgaagagtg   2040
aacgttatac cagtcatttt atttatagct tcgtggattt acgcttacac taaatagtct   2100
gctattcata caaaatgtgt gctttgtatc acttttttgtg atatccatgc catggtccag   2160
ccagggtccg gagttgatgt ggcaagaagg cctggctttc gggccctgtg cgatcctggt   2220
ttgggtgcat ctgagtgggt ggtggcaaag atcaggagg caggagctgc ttctgggtct    2280
gtagtggagc tggttgctgc tgctggcggt gacctggcca acccaatctg cccctgccct   2340
cccacaggac ttcaccttg aaacctcggg ggagaatacg gctgtagtgg ccgtggagcc    2400
tgaccgccgg aaccagtccc cagtggatca gggggccacg ggggcctcac agggcctcct   2460
ggacaggaaa gaggtgctgg gaggtgagtt ttctttcagg ggggtagttt ggggtgaatt   2520
gctgctgtgg ggtcagggtg gggctgacca cagccaaggc cactgctttg ggagggtctg   2580
cacgagagcc caaggagccg ctgagctgag ctggccccgt ctacctgccc tagggtcat    2640
tgccggaggc ctcgtgggc tcatctttgc tgtgtgcctg gtgggtttca tgctgtaccg    2700
catgaagaag aaggacgaag gcagctactc cttggaggag ccgaaacaag ccaacgcgg    2760
ggcctaccag aagcccacca aacaggagga attctatgcc tgacgcggga gccatgcgcc   2820
ccctccgccc tgccactcac taggccccca cttgcctctt ccttgaagaa ctgcaggccc   2880
tggcctccc tgccaccagg ccacctcccc agcattccag cccctctggt cgctcctgcc    2940
cacggagtcg tgggtgtgct gggagctcca ctctgcttct ctgacttctg cctggagact  3000
```

```
taggggcacca gggggtttctc gcataggacc tttccaccac agccagcacc tggcatcgca      3060
ccattctgac tcggtttctc caaactgaag cagcctctcc ccaggtccag ctctggaggg      3120
gagggggatc cgactgcttt ggacctaaat ggcctcatgt ggctggaaga tcctgcgggt      3180
ggggcttggg gctcacacac ctgtagcact tactggtagg accaagcatc ttgggggggt      3240
ggccgctgag tggcagggga caggagtcac tttgtttcgt ggggaggtct aatctagata      3300
tcgacttgtt tttgcacatg tttcctctag ttctttgttc atagcccagt agaccttgtt      3360
acttctgagg taagttaagt aagttgattc ggtatccccc catcttgctt ccctaatcta      3420
tggtcgggag acagcatcag ggttaagaag actttttttt ttttttttaa actaggagaa      3480
ccaaatctgg aagccaaaat gtaggcttag tttgtgtgtt gtctcttgag tttgtcgctc      3540
atgtgtgcaa cagggtatgg actatctgtc tggtggcccc gttctggtgg tctgttggca      3600
ggctggccag tccaggctgc cgtggggccg ccgcctcttt caagcagtcg tgcctgtgtc      3660
catgcgctca gggccatgct gaggcctggg ccgctgccac gttggagaag cccgtgtgag      3720
aagtgaatgc tgggactcag ccttcagaca gagaggactg tagggagggc ggcagggggcc      3780 tggagatcct cctgcaggct cacgcccgtc ctcctgtggc gccgtctcca ggggctgctt      3840
cctcctggaa attgacgagg ggtgtcttgg gcagagctgg ctctgagcgc ctccatccaa      3900
ggccaggttc tccgttagct cctgtggccc caccctgggc cctgggctgg aatcaggaat      3960
attttccaaa gagtgatagt cttttgcttt tggcaaaact ctacttaatc caatgggttt      4020
ttccctgtac agtagatttt ccaaatgtaa taaactttaa tataaagtag tctgtgaatg      4080
ccactgcctt cgcttcttgc ctctgtgctg tgtgtgacgt gaccggactt ttctgcaaac      4140
accaacatgt tgggaaactt ggctcgaatc tctgtgcctt cgtctttccc atggggaggg      4200
attctggttc cagggtccct ctgtgtattt gcttttttgt tttggctgaa attctcctgg      4260
aggtcggtag gttcagccaa ggttttataa ggctgatgtc aatttctgtg ttgccaagct      4320
ccaagcccat cttctaaatg gcaaaggaag gtggatggcc ccagcacagc ttgacctgag      4380
gctgtggtca cagcggaggt gtggagccga ggcctacccc ncagacacct tggacatcct      4440
cctcccaccc ggctgcagag gccagannnc agcccagggt cctgcactta cttgcttatt      4500
tgacaacgtt tcagcgactc cgttggccac tccgagagtg ggccagtctg tggatcagag      4560
atgcaccacc aagccaaggg aacctgtgtc cggtattcga tactgcgact ttctgcctgg      4620
agtgtatgac tgcacatgac tcgggggtgg ggaaaggggt cggctgacca tgctcatctg      4680
ctggtccgtg ggacggtncc caagccagag gtgggttcat ttgtgtaacg acaataaacg      4740
gtacttgtca tttcgggcaa cggctgctgt ggtggtggtt gagtctcttc ttggcct      4797
```

<210> SEQ ID NO 135
<211> LENGTH: 2856
<212> TYPE: DNA
<213> ORGANISM: Homo sapien

<400> SEQUENCE: 135

```
tagtcgcggg tccccgagtg agcacgccag ggagcaggag accaaacgac gggggtcgga       60
gtcagagtcg cagtgggagt ccccggaccg agcacgagc ctgagcggga gagcgccgct      120
cgcacgcccg tcgccacccg cgtacccggc gcagccagag ccaccagcgc agcgctgcca      180
tggagcccag cagcaagaag ctgacgggtc gcctcatgct ggctgtggga ggagcagtgc      240
ttggctccct gcagtttggc tacaacactg gagtcatcaa tgcccccag aaggtgatcg      300
```

-continued

```
aggagttcta caaccagaca tgggtccacc gctatgggga gagcatcctg cccaccacgc    360
tcaccacgct ctggtccctc tcagtggcca tcttttctgt tggggggcatg attggctcct    420
tctctgtggg ccttttcgtt aaccgctttg gccggcggaa ttcaatgctg atgatgaacc    480
tgctggcctt cgtgtccgcc gtgctcatgg gcttctcgaa actgggcaag tcctttgaga    540
tgctgatcct gggccgcttc atcatcggtg tgtactgcgg cctgaccaca ggcttcgtgc    600
ccatgtatgt gggtgaagtg tcacccacag cctttcgtgg ggccctgggc accctgcacc    660
agctgggcat cgtcgtcggc atcctcatcg cccaggtgtt cggcctggac tccatcatgg    720
gcaacaagga cctgtggccc ctgctgctga gcatcatctt catcccggcc ctgctgcagt    780
gcatcgtgct gcccttctgc cccgagagtc ccgcttcct gctcatcaac cgcaacgagg    840
agaaccgggc caagagtgtg ctaaagaagc tgcgcgggac agctgacgtg acccatgacc    900
tgcaggagat gaaggaagag agtcggcaga tgatgcggga agaaggtc accatcctgg    960
agctgttccg ctcccccgcc taccgccagc ccatcctcat cgctgtggtg ctgcagctgt   1020
cccagcagct gtctggcatc aacgctgtct ctattactc cacgagcatc ttcgagaagg   1080
cgggggtgca gcagcctgtg tatgccacca ttggctccgg tatcgtcaac acggccttca   1140
ctgtcgtgtc gctgtttgtg gtggagcgag caggccggcg gaccctgcac ctcataggcc   1200
tcgctggcat ggcgggttgt gccatactca tgaccatcgc gctagcactg ctggagcagc   1260
taccctggat gtcctatctg agcatcgtgg ccatctttgg ctttgtggcc ttctttgaag   1320
tgggtcctgg ccccatccca tggttcatcg tggctgaact cttcagccag gtccacgtc   1380
cagctgccat tgccgttgca ggcttctcca actggacctc aaatttcatt gtgggcatgt   1440
gcttccagta tgtggagcaa ctgtgtggtc cctacgtctt catcatcttc actgtgctcc   1500
tggttctgtt cttcatcttc acctacttca agttcctga gactaaaggc cggaccttcg   1560
atgagatcgc ttccggcttc cggcagggggg gagccagcca aagtgataag acacccgagg   1620
agctgttcca tcccctgggg gctgattccc aagtgtgagt cgccccagat caccagcccg   1680
gcctgctccc agcagccta aggatctctc aggagcacag gcagctggat gagacttcca   1740
aacctgacag atgtcagccg agccgggcct ggggctcctt tctccagcca gcaatgatgt   1800
ccagaagaat attcaggact taacggctcc aggattttaa caaaagcaag actgttgctc   1860
aaatctattc agacaagcaa caggttttat aattttttta ttactgattt tgttattttt   1920
atatcagcct gagtctcctg tgcccacatc ccaggcttca ccctgaatgg ttccatgcct   1980
gagggtggag actaagccct gtcgagacac ttgccttctt cacccagcta atctgtaggg   2040
ctggacctat gtcctaagga cacactaatc gaactatgaa ctacaaagct tctatcccag   2100
gaggtggcta tggccacccg ttctgctggc ctggatctcc ccactctagg ggtcaggctc   2160
cattaggatt tgccccttcc catctcttcc tacccaacca ctcaaattaa tctttctta   2220
cctgagacca gttgggagca ctggagtgca gggaggagag gggaagggcc agtctgggct   2280
gccgggttct agtctccttt gcactgaggg ccacactatt accatgagaa gagggcctgt   2340
gggagcctgc aaactcactg ctcaagaaga catggagact cctgccctgt tgtgtataga   2400
tgcaagatat ttatatatat ttttggttgt caatattaaa tacagacact aagttatagt   2460
atatctggac aagccaactt gtaaatacac cacctcactc ctgttactta cctaaacaga   2520
tataaatggc tggttttag aaacatggtt ttgaaatgct tgtggattga gggtaggagg   2580
tttggatggg agtgagacag aagtaagtgg ggttgcaacc actgcaacgg cttagacttc   2640
gactcaggat ccagtccctt acacgtacct ctcatcagtg tcctcttgct caaaaatctg   2700
```

```
tttgatccct gttacccaga gaatatatac attctttatc ttgacattca aggcatttct    2760
atcacatatt tgatagttgg tgttcaaaaa aacactagtt ttgtgccagc cgtgatgctc    2820
aggcttgaaa tcgcattatt ttgaatgtga agggaa                              2856
```

<210> SEQ ID NO 136
<211> LENGTH: 356
<212> TYPE: DNA
<213> ORGANISM: Homo sapien

<400> SEQUENCE: 136

```
ggtggagcca aatgaagaaa atgaagatga aagagacaga cacctcagtt tttctggatc     60
aggcattgat gatgatgaag attttatctc cagcaccatt tcaaccacac cacgggcttt    120
tgaccacaca aaacagaacc aggactggac tcagtggaac ccaagccatt caaatccgga    180
agtgctactt cagacaacca caaggatgac tgatgtagac agaaatggca ccactgctta    240
tgaaggaaac tggaacccag aagcacaccc tcccctcatt caccatgagc atcatgagga    300
agaagagacc ccacattcta caagcacaat ccaggcaact cctagtagta caacgg        356
```

<210> SEQ ID NO 137
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 137

```
gcaggtggag aagacatttt attgttcctg gggtctctgg aggcccattg gtggggctgg     60
gtcactggct gccccggaa cagggcgctg ctccatggct ctgcttgtgg tagtctgtgg    120
ctatgtctcc cagcaaggac agaaactcag aaaaatcaat cttcttatcc tcattcttgt    180
cctttttctc aaagacatcg gcgaggtaat ttgtgccctt tttacctcgg cccgcgacca    240
cgctaaggcc aaanttccag acanayggcc gggccggtnc natagggggan cccaacttgg    300 ggacccaaac tctggcgcgg aaacacangg gcataagctt gnttcctgtg gggaaa        356
```

<210> SEQ ID NO 138
<211> LENGTH: 353
<212> TYPE: DNA
<213> ORGANISM: Homo sapien

<400> SEQUENCE: 138

```
aggtccagtc ctccacttgg cctgatgaga gtggggagtg gcaagggacg tttctcctgc     60
aatagacact tagatttctc tcttgtggga agaaaccacc tgtccatcca ctgactcttc    120
tacattgatg tggaaattgc tgctgctacc accacctcct gaagaggctt ccctgatgcc    180
aatgccagcc atcttggcat cctggccctc gagcaggctg cggtaagtag cgatctcctg    240
ctccagccgt gtctttatgt caagcagcat cttgtactcc tggttctgag cctccatctc    300
gcatcggagc tcactcagac ctcgsccgsg mssmcgctam gccgaattcc agc           353
```

<210> SEQ ID NO 139
<211> LENGTH: 371
<212> TYPE: DNA
<213> ORGANISM: Homo sapien

<400> SEQUENCE: 139

-continued

| | |
|---|---|
| agcgtggtcg cggccgaggt ccatccgaag caagattgca gatggcagtg tgaagagaga | 60 |
| agacatattc tacacttcaa agctttggtg caattcccat cgaccagagt tggtccgacc | 120 |
| agccttggaa aggtcactga aaaatcttca attggattat gttgacctct accttattca | 180 |
| ttttccagtg tctgtaaagc caggtgagga agtgatccca aaagatgaaa atggaaaaat | 240 |
| actatttgac acagtggatc tctgtgccac gtgggaggcc gtgagaagt gtaaagatgc | 300 |
| aggattggac ctgcccgggc ggccgctcga agccgaatt ccagcacact ggcggccgtt | 360 |
| actagtggat c | 371 |

<210> SEQ ID NO 140
<211> LENGTH: 370
<212> TYPE: DNA
<213> ORGANISM: Homo sapien

<400> SEQUENCE: 140

| | |
|---|---|
| tagcgtggtc gcggccgagg tccatctccc tttgggaact aggggctgc tggtgggaaa | 60 |
| tgggagccag ggcagatgtt gcattccttt gtgtccctgt aaatgtggga ctacaagaag | 120 |
| aggagctgcc tgagtggtac tttctcttcc tggtaatcct ctggcccagc ctcatggcag | 180 |
| aatagaggta ttttttaggct attttttgtaa tatggcttct ggtcaaaatc cctgtgtagc | 240 |
| tgaattccca agccctgcat tgtacagccc cccactcccc tcaccaccta ataaaggaat | 300 |
| agttaacact caaaaaaaaa aaaaaacctg cccgggcggc cgctcgaaag ccgaattcca | 360 |
| gcacactggc | 370 |

<210> SEQ ID NO 141
<211> LENGTH: 371
<212> TYPE: DNA
<213> ORGANISM: Homo sapien

<400> SEQUENCE: 141

| | |
|---|---|
| tagcgtggtc gcggccgagg tcctctgtgc tgcctgtcac agcccgatgg taccagcgca | 60 |
| gggtgtaggc agtgcaggag ccctcatcca gtggcaggga acaggggtca tcactatccc | 120 |
| aaggagcttc agggtcctgg tactcctcca cagaatactc ggagtattca gagtactcat | 180 |
| catcctcagg gggtacccgc tcttcctcct ctgcatgaga gacgcggagc acaggcacag | 240 |
| catggagctg ggagccggca gtgtctgcag cataactagg gaggggtcgt gatccagatg | 300 |
| cgatgaactg gccctggcag gcacagtgct gactcatctc ttggcgacct gcccgggcgg | 360 |
| ccgctcgaag c | 371 |

<210> SEQ ID NO 142
<211> LENGTH: 343
<212> TYPE: DNA
<213> ORGANISM: Homo sapien

<400> SEQUENCE: 142

| | |
|---|---|
| gcgttttgag gccaatggtg taaaggaaa tatcttcaca taaaaactag atggaagcat | 60 |
| tgtcagaaac ctctttgtga tgtttgcttt caactcacag agttgaacat tccttttcat | 120 |
| agagcagttt tgaaacactc ttttgtagaa tttgcaagcg gatgattgga tcgctatgag | 180 |
| gtcttcattg gaaacgggat acctttacat aaaaactaga cagtagcatt ctcagaaatt | 240 |
| tctttgggat gtgggcattc aacccacaga ggagaacttc atttgataga gcagttttga | 300 |
| aacacccttt ttgtagaatc tacaggtgga catttagagt gct | 343 |

<210> SEQ ID NO 143
<211> LENGTH: 354
<212> TYPE: DNA
<213> ORGANISM: Homo sapien

<400> SEQUENCE: 143

```
aggtctgatg gcagaaaaac tcagactgtc tgcaacttta cagatggtgc attggttcag      60
catcaggagt gggatgggaa ggaaagcaca ataacaagaa aattgaaaga tgggaaatta     120
gtggtggagt gtgtcatgaa caatgtcacc tgtactcgga tctatgaaaa agtagaataa     180
aaattccatc atcactttgg acaggagtta attaagagaa tgaccaagct cagttcaatg     240
agcaaatctc catactgttt ctttcttttt tttttcatta ctgtgttcaa ttatctttat     300
cataaacatt ttacatgcag ctatttcaaa gtgtgttgga ttaattagga tcat           354
```

<210> SEQ ID NO 144
<211> LENGTH: 353
<212> TYPE: DNA
<213> ORGANISM: Homo sapien

<400> SEQUENCE: 144

```
ggtcaaggac ctgggggacc cccaggtcca gcagccacat gattctgcag cagacaggga      60
cctagagcac atctggatct cagccccacc cctggcaacc tgcctgccta gagaactccc     120
aagatgacag actaagtagg attctgccat ttagaataat tctggtatcc tgggcgttgc     180
gttaagttgc ttaactttca ttctgtctta cgatagtctt cagaggtggg aacagatgaa     240
gaaaccatgc cccagagaag gttaagtgac ttcctcttta tggagccagt gttccaacct     300
aggtttgcct gataccagac ctgtggcccc acctcccatg caggtctctg tgg            353
```

<210> SEQ ID NO 145
<211> LENGTH: 371
<212> TYPE: DNA
<213> ORGANISM: Homo sapien

<400> SEQUENCE: 145

```
caggtctgtc ataaactggt ctggagtttc tgacgactcc ttgttcacca aatgcaccat      60
ttcctgagac ttgctggcct ctccgttgag tccacttggc tttctgtcct ccacagctcc     120
attgccactg ttgatcacta gcttttcttt ctgcccacac cttcttcgac tgttgactgc     180
aatgcaaact gcaagaatca aagccaaggc caagagggat gccaagatga tcagccattc     240
tggaatttgg ggtgtcctta taggaccaga ggttgtgttt gctccacctt cttgactccc     300
atgtgagacc tcggccgcga ccacgctaag ccgaattcca gcacactggc ggcccgttac     360
tagtggatcc g                                                          371
```

<210> SEQ ID NO 146
<211> LENGTH: 355
<212> TYPE: DNA
<213> ORGANISM: Homo sapien

<400> SEQUENCE: 146

```
ggtcctccgt cctcttccca gaggtgtcgg ggcttggccc cagcctccat cttcgtctct      60
caggatggcg agtagcagcg gctccaaggc tgaattcatt gtcggaggga aatataaact     120
ggtacggaag atcgggtctg gctccttcgg ggacatctat ttggcgatca acatcaccaa     180
cggcgaggaa gtgcagtgaa gctagaatc tcagaaggcc aggcatcccc agttgctgta     240
cgagagcaag ctctataaga ttcttcaagg tggggttggc atcccccaca tacggtggta     300
```

```
tggtcaggaa aaagactaca atgtactagt catggatctt ctgggaccta gcctc        355
```

<210> SEQ ID NO 147
<211> LENGTH: 355
<212> TYPE: DNA
<213> ORGANISM: Homo sapien

<400> SEQUENCE: 147

```
ggtctgttac aaaatgaaga cagacaacac aacatttact ctgtggagat atcctactca    60
tactatgcac gtgctgtgat tttgaacata actcgtccca aaaacttgtc acgatcatcc   120
tgactttta ggttggctga tccatcaatc ttgcactcaa ctgttacttc tttcccagtg    180
ttgttaggag caaagctgac ctgaacagca accaatggct gtagataccc aacatgcagt   240
tttttcccat aatatgggaa atattttaag tctatcattc cattatgagg ataaactgct   300
acatttggta tatcttcatt ctttgaaaca caatctatcc ttggcactcc ttcag        355
```

<210> SEQ ID NO 148
<211> LENGTH: 369
<212> TYPE: DNA
<213> ORGANISM: Homo sapien

<400> SEQUENCE: 148

```
aggtctctct ccccctctcc ctctcctgcc agccaagtga agacatgctt acttccccctt  60
caccttcctt catgatgtgg gaagagtgct gcaacccagc cctagccaac accgcatgag  120
agggagtgtg ccgagggctt ctgagaaggt ttctctcaca tctagaaaga agcgcttaag  180
atgtggcagc ccctcttctt caagtggctc ttgtcctgtt gccctgggag ttctcaaatt  240
gctgcagcag cctccatcca gcctgaggat gacatcaata cacagaggaa gaagagtcag  300
gaaaagatga gagaagttac agactctcct gggcgacccc gagagcttac cattcctcag  360
acttcttca                                                          369
```

<210> SEQ ID NO 149
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 149

```
actagtcaaa aatgctaaaa taatttggga gaaaatattt tttaagtagt gttatagttt    60
catgtttatc ttttattatg ttttgtgaag ttgtgtctttt tcactaatta cctatactat  120
gccaatattt ccttatatct atccataaca tttatactac atttgtaana naatatgcac   180
gtgaaactta acactttata aggtaaaaat gaggtttcca anatttaata atctgatcaa   240
gttcttgtta tttccaaata gaatggactt ggtctgttaa gggctaagga gaagaggaag   300
ataaggttaa aagttgttaa tgaccaaaca ttctaaaaga aatgcaaaaa aaagtttat   360
tttcaagcct tcgaactatt taaggaaagc aaaatcattt cctaaatgca tatcatttgt   420
gagaatttct cattaatatc ctgaatcatt catttcacta aggctcatgt tnactccgat   480
atgtctctaa gaaagtacta tttcatggtc caaacctggt tgccatantt gggtaaaggc   540
tttcccttaa gtgtgaaant atttaaaatg aaattttcct cttttttaaaa attctttana  600
agggttaagg gtgttgggga                                              620
```

```
<210> SEQ ID NO 150
<211> LENGTH: 371
<212> TYPE: DNA
<213> ORGANISM: Homo sapien

<400> SEQUENCE: 150
ggtccgatca aaacctgcta cctccccaag actttactag tgccgataaa ctttctcaaa      60
gagcaaccag tatcacttcc ctgtttataa aacctctaac catctctttg ttctttgaac     120
atgctgaaaa ccacctggtc tgcatgtatg cccgaatttg yaattctttt ctctcaaatg     180
aaaatttaat tttagggatt catttctata ttttcacata tgtagtatta ttatttcctt     240
atatgtgtaa ggtgaaattt atggtatttg agtgtgcaag aaaatatatt tttaaagctt     300 tcattttttcc cccagtgaat gatttagaat tttttatgta aatatacaga atgttttttc     360
ttacttttat a                                                          371

<210> SEQ ID NO 151
<211> LENGTH: 4655
<212> TYPE: DNA
<213> ORGANISM: Homo sapien

<400> SEQUENCE: 151
gggacttgag ttctgttatc ttcttaagta gattcatatt gtaagggtct cggggtgggg      60
gggttggcaa atcctggag ccagaagaaa ggacagcagc attgatcaat cttacagcta     120
acatgttgta cctggaaaac aatgcccaga ctcaatttag tgagccacag tacacgaacc     180
tggggctcct gaacagcatg gaccagcaga ttcagaacgg ctcctcgtcc accagtccct     240
ataacacaga ccacgcgcag aacagcgtca cggcgccctc gccctacgca cagcccagct     300
ccaccttcga tgctctctct ccatcacccg ccatcccctc caacaccgac tacccaggcc     360
cgcacagttt cgacgtgtcc ttccagcagt cgagcaccgc caagtcggcc acctggacgt     420
attccactga actgaagaaa ctctactgcc aaattgcaaa gacatgcccc atccagatca     480
aggtgatgac cccacctcct cagggagctg ttatccgcgc catgcctgtc tacaaaaaag     540
ctgagcacgt cacggaggtg gtgaagcggt gccccaacca tgagctgagc cgtgaattca     600
acgagggaca gattgcccct yctagtcatt tgattcgagt agaggggaac agccatgccc     660
agtatgtaga agatccatcc acaggaagac agagtgtgct ggtaccttat gagccacccc     720
aggttggcac tgaattcacg acagtcttgt acaatttcat gtgtaacagc agttgtgttg     780
gagggatgaa ccgccgtcca atttttaatca ttgttactct ggaaaccaga gatgggcaag     840
tcctgggccg acgctgcttt gaggcccgga tctgtgcttg cccaggaaga gacaggaagg     900
cggatgaaga tagcatcaga aagcagcaag tttcggacag tacaaagaac ggtgatggta     960
cgaagcgccc gtttcgtcag aacacacatg gtatccagat gacatccatc aagaaacgaa    1020
gatccccaga tgatgaactg gtatacttac cagtgagggg ccgtgagact tatgaaatgc    1080
tggtgaagat caaagagtcc ctggaactca tgcagtacct tcttcagcac acaattgaaa    1140
cgtacaggca acagcaacag cagcagcacc agcacttact tcagaaacag acctcaatac    1200
agtctccatc ttcatatggt aacagctccc cacctctgaa caaaatgaac agcatgaaca    1260
agctgccttc tgtgagccag cttatcaacc ctcagcagcg caacgccctc actcctacaa    1320
ccattcctga tggcatggga gccaacattc ccatgatggg cacccacatg ccaatggctg    1380
gagacatgaa tggactcagc cccacccagg cactccctcc cccactctcc atgccatcca    1440
cctcccactg cacaccccca cctccgtatc ccacagattg cagcattgtc agtttcttag    1500
```

-continued

```
cgaggttggg ctgttcatca tgtctggact atttcacgac ccaggggctg accaccatct   1560
atcagattga gcattactcc atggatgatc tggcaagtct gaaaatccct gagcaatttc   1620
gacatgcgat ctggaagggc atcctggacc accggcagct ccacgaattc tcctccccct   1680
ctcatctcct gcggacccca agcagtgcct ctacagtcag tgtgggctcc agtgagaccc   1740
ggggtgagcg tgttattgat gctgtgcgat tcaccctccg ccagaccatc tctttcccac   1800
cccgagatga gtggaatgac ttcaactttg acatggatgc tcgccgcaat aagcaacagc   1860
gcatcaaaga ggagggggag tgagcctcac catgtgagct cttcctatcc ctctcctaac   1920
tgccagcccc ctaaaagcac tcctgcttaa tcttcaaagc cttctcccta gctcctcccc   1980
ttcctcttgt ctgatttctt aggggaagga gaagtaagag gcttacttct taccctaacc   2040
atctgacctg gcatctaatt ctgattctgg ctttaagcct tcaaaactat agcttgcaga   2100
actgtagctt gccatggcta ggtagaagtg agcaaaaaag agttgggtgt ctccttaagc   2160
tgcagagatt tctcattgac ttttataaag catgttcacc cttatagtct aagactatat   2220
atataaatgt ataaatatac agtatagatt tttgggtggg gggcattgag tattgtttaa   2280
aatgtaattt aaatgaaaga aaattgagtt gcacttattg accattttt aatttacttg   2340 ttttggatgg cttgtctata ctccttccct taagggtat catgtatggt gataggtatc   2400
tagagcttaa tgctacatgt gagtgacgat gatgtacaga ttctttcagt tctttggatt   2460
ctaaatacat gccacatcaa acctttgagt agatccattt ccattgctta ttatgtaggt   2520
aagactgtag atatgtattc ttttctcagt gttggtatat tttatattac tgacatttct   2580
tctagtgatg atggttcacg ttggggtgat ttaatccagt tataagaaga agttcatgtc   2640
caaacgtcct ctttagtttt tggttgggaa tgaggaaaat tcttaaaagg cccatagcag   2700
ccagttcaaa acacccgac gtcatgtatt tgagcatatc agtaaccccc ttaaatttaa   2760
taccagatac cttatcttac aatattgatt gggaaaacat ttgctgccat tacagaggta   2820
ttaaaactaa atttcactac tagattgact aactcaaata cacatttgct actgttgtaa   2880
gaattctgat tgatttgatt gggatgaatg ccatctatct agttctaaca gtgaagtttt   2940
actgtctatt aatattcagg gtaaatagga atcattcaga aatgttgagt ctgtactaaa   3000
cagtaagata tctcaatgaa ccataaattc aactttgtaa aaatcttttg aagcatagat   3060
aatattgttt ggtaaatgtt tcttttgttt ggtaaatgtt tcytttaaag accctcctat   3120
tctataaaac tctgcatgta gaggcttgtt tacctttctc tctctaaggt ttacaatagg   3180
agtggtgatt tgaaaaatat aaaattatga gattggtttt cctgtggcat aaattgcatc   3240
actgtatcat tttctttttt aaccggtaag agtttcagtt tgttggaaag taactgtgag   3300
aacccagttt cccgtccatc tcccttaggg actacccata gacatgaaag gtccccacag   3360
agcaagagat aagtctttca tggctgctgt tgcttaaacc acttaaacga agagttccct   3420
tgaaactttg ggaaaacatg ttaatgacaa tattccagat ctttcagaaa tataacacat   3480
ttttttgcat gcatgcaaat gagctctgaa atcttcccat gcattctggt caagggctgt   3540
cattgcacat aagcttccat tttaattta aagtgcaaaa gggccagcgt ggctctaaaa   3600
ggtaatgtgt ggattgcctc tgaaaagtgt gtatatattt tgtgtgaaat tgcatacttt   3660 gtatttgat tatttttttt tcttcttgg gatagtggga tttccagaac cacacttgaa   3720
accttttttt atcgttttg tattttcatg aaaataccat ttagtaagaa taccacatca   3780
aataagaaat aatgctacaa ttttaagagg ggagggaagg gaaagttttt ttttttatta   3840
tttttttaaa attttgtatg ttaaagagaa tgagtccttg atttcaaagt tttgttgtac   3900
```

```
ttaaatggta ataagcactg taaacttctg caacaagcat gcagctttgc aaacccatta   3960 agggaagaa tgaaagctgt tccttggtcc tagtaagaag acaaactgct tcccttactt    4020
tgctgagggt ttgaataaac ctaggacttc cgagctatgt cagtactatt caggtaacac   4080
tagggccttg gaaatccctg tactgtgtct catggatttg gcactagcca aagcgaggca   4140
ccccttactg gcttacctcc tcatggcagc ctactctcct tgagtgtatg agtagccagg   4200
gtaaggggta aaaggatagt aagcatagaa accactagaa agtgggctta atggagttct   4260
tgtggcctca gctcaatgca gttagctgaa gaattgaaaa gttttttgttt ggagacgttg   4320 ataaacagaa atggaaagca gagttttcat taaatccttt tacctttttt ttttcttggt   4380
aatcccctaa aataacagta tgtgggatat tgaatgttaa agggatattt ttttctatta   4440 ttttttataat tgtacaaaat taagcaaatg ttaaaagttt tatatgcttt attaatgttt   4500
tcaaaaggta ttatacatgt gatacatttt ttaagcttca gttgcttgtc ttctggtact   4560
ttctgttatg ggcttttggg gagccagaag ccaatctaca atctcttttt gtttgccagg   4620
acatgcaata aaatttaaaa aataaataaa aacta                              4655
```

<210> SEQ ID NO 152
<211> LENGTH: 586
<212> TYPE: PRT
<213> ORGANISM: Homo sapien

<400> SEQUENCE: 152

```
Met Leu Tyr Leu Glu Asn Asn Ala Gln Thr Gln Phe Ser Glu Pro Gln
1               5                   10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Ser Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240
```

```
Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
            275                 280                 285

His Gly Ile Gln Met Thr Ser Ile Lys Lys Arg Arg Ser Pro Asp Asp
            290                 295                 300

Glu Leu Val Tyr Leu Pro Val Arg Gly Arg Glu Thr Tyr Glu Met Leu
305                 310                 315                 320

Val Lys Ile Lys Glu Ser Leu Glu Leu Met Gln Tyr Leu Leu Gln His
                325                 330                 335

Thr Ile Glu Thr Tyr Arg Gln Gln Gln Gln Gln His Gln His Leu
                340                 345                 350

Leu Gln Lys Gln Thr Ser Ile Gln Ser Pro Ser Ser Tyr Gly Asn Ser
            355                 360                 365

Ser Pro Pro Leu Asn Lys Met Asn Ser Met Asn Lys Leu Pro Ser Val
            370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
            435                 440                 445

Tyr Pro Thr Asp Cys Ser Ile Val Ser Phe Leu Ala Arg Leu Gly Cys
            450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
            500                 505                 510

Leu His Glu Phe Ser Ser Pro Ser His Leu Leu Arg Thr Pro Ser Ser
            515                 520                 525

Ala Ser Thr Val Ser Val Gly Ser Ser Glu Thr Arg Gly Glu Arg Val
            530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Gly Glu
            580                 585

<210> SEQ ID NO 153
<211> LENGTH: 2007
<212> TYPE: DNA
<213> ORGANISM: Homo sapien

<400> SEQUENCE: 153
gaattcgtcg ctgctccagg gaaagttctg ttactccact gactctctct tttcctgata    60
acatggccag caagaaagta attacagtgt ttggagcaac aggagctcaa ggtggctctg   120
```

```
tggccagggc aatttggag agcaaaaaat ttgcagtgag agcagtgacc agggatgtga      180
cttgaccaaa tgccctggag ctccagcgcc ttggagctga ggtggtcaaa ggtgacctga      240
atgataaagc atcggtggac agtgccttaa aaggtgtcta tggggccttc ttggtgacca      300
acttctggga ccctctcaac caagataagg aagtgtgtcg ggggaagctg gtggcagact      360
ccgccaagca cctgggtctg aagcacgtgg tgtacagcgg cctggagaac gtcaagcgac      420
tgacggatgg caagctggag gtgccgcact ttgacagcaa gggcgaggtg gaggagtact      480
tctggtccat tggcatcccc atgaccagtg tccgcgtggc ggcctacttt gaaaactttc      540
tcgcggcgtg gcggcccgtg aaagcctctg atggagatta ctacaccttg gctgtaccga      600
tgggagatgt accaatggat ggtatctctg ttgctgatat tggagcagcc gtctctagca      660 ttttttaattc tccagaggaa ttttaggca aggccgtggg gctcagtgca gaagcactaa      720
caatacagca atatgctgat gttttgtcca aggctttggg gaaagaagtc cgagatgcaa      780
agattacccc ggaagctttc gagaagctgg gattccctgc agcaaaggaa atagccaata      840
tgtgtcgttt ctatgaaatg aagccagacc gagatgtcaa tctcacccac caactaaatc      900
ccaaagtcaa aagcttcagc cagtttatct cagagaacca gggagccttc aagggcatgt      960
agaaaatcag ctgttcagat aggcctctgc accacacagc ctctttcctc tctgatcctt     1020 ttcctctttta cggcacaaca ttcatgttga cagaacatgc tggaatgcaa ttgtttgcaa     1080
caccgaagga tttcctgcgg tcgcctcttc agtaggaagc actgcattgg tgataggaca     1140
cggtaatttg attcacattt aacttgctag ttagtgataa gggtggtaca actgtttggt     1200
aaaatgagaa gcctcggaac ttggagcttc tctcctacca ctaatgggag ggcagattat     1260
actgggattt ctcctgggtg agtaatttca agccctaatg ctgaaattcc cctaggcagc     1320
tccagttttc tcaactgcat tgcaaaattc ccagtgaact tttaagtact tttaacttaa     1380
aaaaatgaac atctttgtag agaattttct ggggaacatg tgttcaatg aacaagcaca      1440 agcattggaa atgctaaaat tcagttttgc ctcaagattg gaagtttatt ttctgactca     1500
ttcatgaagt catctattga gccaccattc aattattcat ctattaattc cttgatcctt     1560
catttatcca ttctgcaaac ttttcttgag caccagcacg ggtggccatt tgtggacttc     1620
tcttcattcc tatgtgtttt cttatcaaag tgatccactc tcgaaaggct cctttccagt     1680
ctgtggttgg gttcaagtca tgccagggcc aggggggccca tctcctcgtt tagctctagg     1740
caaaatccag gggatctgca gtggggagcg ggggcaggaa gctggaggga aggcctgtga     1800
agggtaggga tgtggaaaga caaggtgaca gaaggaccca ataggaccct tctatatctc     1860
tggcttagca ttttctacat catattgtaa tcgtcttatt tgctagtttt cttccttact     1920
gtgagtgact aacagtcatc tttatcccag tgcctggtac ataataagtg atcaataaat     1980
gttgattgac taaaaaaaaa aaaaaaa                                         2007
```

<210> SEQ ID NO 154
<211> LENGTH: 2148
<212> TYPE: DNA
<213> ORGANISM: Homo sapien

<400> SEQUENCE: 154

```
gaattcgtcg ctgctccagg gaaagttctg ttactccact gactctctct tttcctgata       60
acatggccag caagaaagta attacagtgt ttggagcaac aggagctcaa ggtggctctg      120
tggccagggc aattttggag agcaaaaaat ttgcagtgag agcagtgacc agggatgtga      180
cttgaccaaa tgccctggag ctccagcgcc ttggagctga ggtggtcaaa ggtgacctga      240
```

-continued

```
atgataaagc atcggtggac agtgccttaa aaggggaagc tggtggcaga ctccgccaag    300
cacctgggtc tgaagcacgt ggtgtacagc ggcctggaga acgtcaagcg actgacggat    360
ggcaagctgg aggtgccgca ctttgacagc aagggcgagg tggaggagta cttctggtcc    420
attggcatcc ccatgaccag tgtccgcgtg gcggcctact ttgaaaactt tctcgcggcg    480
tggcggcccg tgaaagcctc tgatggagat tactacacct tggctgtacc gatgggagat    540
gtaccaatgg atggtatctc tgttgctgat attggagcag ccgtctctag cattttttaat    600 tctccagagg aattttagg caaggccgtg gggctcagtg cagaagcact aacaatacag    660
caatatgctg atgttttgtc caaggctttg gggaagaag tccgagatgc aaagactatc    720
tgtgctatag atgaccagaa acagtggaa gaaggtttca tggaagacgt gggcttgagt    780
tggtccttga gggaacatga ccatgtatag acagaggagg catcaagaag gctggcctgg    840
ctaattctgg aataaacacg acaaaccaga ggcagtacgg gaaggaggca aattctggct    900
ctgcctctat ccttgattac cccggaagct ttcgagaagc tgggattccc tgcagcaaag    960
gaaatagcca atatgtgtcg tttctatgaa atgaagccag accgagatgt caatctcacc   1020
caccaactaa atcccaaagt caaaagcttc agccatttta tctcagagaa ccagggagcc   1080
ttcaagggca tgtagaaaat cagctgttca gataggcctc tgcaccacac agcctctttc   1140
ctctctgatc cttttcctct ttacggcaca acattcatgt tgacagaaca tgctggaatg   1200
caattgtttg caacaccgaa ggatttcctg cggtcgcctc ttcagtagga agcactgcat   1260
tggtgatagg acacggtaat tgattcaca tttaacttgc tagttagtga taagggtggt   1320
acaactgttt ggtaaaatga gaagcctcgg aacttggagc ttctctccta ccactaatgg   1380
gagggcagat tatactggga tttctcctgg gtgagtaatt tcaagcccta atgctgaaat   1440 tccctaggc agctccagtt ttctcaactg cattgcaaaa ttcccagtga acttttaagt   1500
acttttaact taaaaaaatg aacatctttg tagagaattt tctggggaac atggtgttca   1560
atgaacaagc acaagcattg gaaatgctaa aattcagttt tgcctcaaga ttggaagttt   1620 atttttctgac tcattcatga agtcatctat tgagccacca ttcaattatt catctattaa   1680
ttccttgatc cttcatttat ccattctgca aactttttctt gagcaccagc acgggtggcc   1740
atttgtggac ttctcttcat tcctatgtgt ttttcttatca aagtgatcca ctctcgaaag   1800
gctcctttcc agtctgtggt tgggttcaag tcatgccagg ccaggggggc ccatctcctc   1860
gtttagctct aggcaaaatc cagggggatct gcagtgggga gcgggggcag gaagctggag   1920
ggaaggcctg tgaagggtag ggatgtggaa agacaaggtg acagaaggac ccaataggac   1980 cttttctatat ctctggctta gcattttcta catcatattg taatcgtctt atttgctagt   2040
tttcttcctt actgtgagtg actaacagtc atctttatcc cagtgcctgg tacataataa   2100
gtgatcaata aatgttgatt gactaaatga aaaaaaaaa aaaaaaaa              2148
```

<210> SEQ ID NO 155
<211> LENGTH: 153
<212> TYPE: PRT
<213> ORGANISM: Homo sapien

<400> SEQUENCE: 155

Met Thr Ser Val Arg Val Ala Ala Tyr Phe Glu Asn Phe Leu Ala Ala
1               5                   10                  15

Trp Arg Pro Val Lys Ala Ser Asp Gly Asp Tyr Tyr Thr Leu Ala Val
            20                  25                  30

-continued

```
Pro Met Gly Asp Val Pro Met Asp Gly Ile Ser Val Ala Asp Ile Gly
         35                  40                  45

Ala Ala Val Ser Ser Ile Phe Asn Ser Pro Glu Glu Phe Leu Gly Lys
 50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                 85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150
```

<210> SEQ ID NO 156
<211> LENGTH: 128
<212> TYPE: PRT
<213> ORGANISM: Homo sapien

<400> SEQUENCE: 156

```
Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
                 20                  25                  30

Pro Met Gly Asp Val Pro Met Asp Gly Ile Ser Val Ala Asp Ile Gly
         35                  40                  45

Ala Ala Val Ser Ser Ile Phe Asn Ser Pro Glu Glu Phe Leu Gly Lys
 50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Thr Ile
                 85                  90                  95

Cys Ala Ile Asp Asp Gln Lys Thr Val Glu Glu Gly Phe Met Glu Asp
            100                 105                 110

Val Gly Leu Ser Trp Ser Leu Arg Glu His Asp His Val Ala Gly Ala
        115                 120                 125
```

<210> SEQ ID NO 157
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 157

| ctgcagcccg ggggatccac tagtccagtg tggtggaatt cattggtctt tacaagactt | 60 |
| ggatacatta cagcagacat ggaaatataa ttttaaaaaa tttctctcca acctccttca | 120 |
| aattcagtca ccactgttat attaccttct ccaggaaccc tccagtgggg aaggctgcga | 180 |
| tattagattt ccttgtatgc aaagttttg ttgaaagctg tgctcagagg aggtgagagg | 240 |
| agaggaagga gaaaactgca tcataacttt acagaattga atctagagtc ttccccgaaa | 300 |
| agcccagaaa cttctctgcn gnatctggct tgtccatctg gtctaaggtg gctgcttctt | 360 |

```
ccccagccat cgagtcagtt tgtgcccatg aataatacac gacctgctat ttcccatgac    420
tgct                                                                 424

<210> SEQ ID NO 158
<211> LENGTH: 2099
<212> TYPE: DNA
<213> ORGANISM: Homo sapien

<400> SEQUENCE: 158
ccgcggttaa aaggcgcagc aggtgggagc cggggccttc acccgaaacc cgacgagagc     60
ccgacagccg gcggcgcccg agcccgacct gcctgcccag ccggagcgaa gggcgccgcc    120
ccgcgcagag cccgcgccag ggccgccggc cgcagagcag ttaaaacgtg caggcaccag    180
aaggcacttc ctgtcggtga agaagacctg tctccggtgt cacgggcatc ctgtgttttg    240
caaacggggc tgacctccct tcctggggag caggaagggt cagggaagga aaagaagtac    300
agaagatctg gctaaacaat ttctgtatgg cgaaagaaaa attctaactt gtacgccctc    360
ttcatgcatc tttaattcaa tttgaatatt ccaggcgaca tcctcactga ccgagcaaag    420
attgacattc gtatcatcac tgtgcaccat ggcttctag gcactccagt ggggtaggag    480
aaggaggtct gaaaccctcg cagagggatc ttgccctcat tctttgggtc tgaaacactg    540
gcagtcgttg gaaacaggac tcaggataaa ccagcgcaa tggattgggg gacgctgcac    600
actttcatcg ggggtgtcaa caaacactcc accagcatcg ggaaggtgtg gatcacagtc    660 atcttatt tccgagtcat gatcctcgtg gtggctgccc aggaagtgtg gggtgacgag    720
caagaggact tcgtctgcaa cacactgcaa ccgggatgca aaaatgtgtg ctatgaccac    780 ttttttcccgg tgtcccacat ccggctgtgg gccctccagc tgatcttcgt ctccacccca    840
gcgctgctgg tggccatgca gtggcctac tacaggcacg aaaccactcg caagttcagg    900
cgaggagaga agaggaatga tttcaaagac atagaggaca ttaaaaagca gaaggttcgg    960
atagaggggt cgctgtggtg gacgtacacc agcagcatct ttttccgaat catctttgaa   1020 gcagcccttta tgtatgtgtt ttacttcctt tacaatgggt accacctgcc ctgggtgttg   1080
aaatgtggga ttgaccccctg ccccaacctt gttgactgct ttatttctag gccaacagag   1140
aagaccgtgt ttaccatttt tatgatttct gcgtctgtga tttgcatgct gcttaacgtg   1200
gcagagttgt gctacctgct gctgaaagtg tgttttagga gatcaaagag agcacagacg   1260
caaaaaaatc accccaatca tgccctaaag gagagtaagc agaatgaaat gaatgagctg   1320
atttcagata gtggtcaaaa tgcaatcaca ggttcccaag ctaaacattt caaggtaaaa   1380
tgtagctgcg tcataaggag acttctgtct tctccagaag gcaataccaa cctgaaagtt   1440
ccttctgtag cctgaagagt ttgtaaatga cttttcataat aaatagacac ttgagttaac   1500
tttttgtagg atacttgctc cattcataca caacgtaatc aaatatgtgg tccatctctg   1560
aaaacaagag actgcttgac aaaggagcat tgcagtcact ttgacaggtt ccttttaagt   1620
ggactctctc acaaagtggg tactttctga aaatttatat aactgttgtt gataaggaac   1680
atttatccag gaattgatac gtttattagg aaaagatatt tttataggct tggatgtttt   1740
tagttctgac tttgaattta tataaagtat ttttataatg actggtcttc cttacctgga   1800
aaaacatgcg atgttagttt tagaattaca ccacaagtat ctaaatttgg aacttacaaa   1860
gggtctatct tgtaaatatt gttttgcatt gtctgttggc aaatttgtga actgtcatga   1920
tacgcttaag gtggaaagtg ttcattgcac aatatatttt tactgctttc tgaatgtaga   1980
```

```
cggaacagtg tggaagcaga aggcttttt  aactcatccg tttgccaatc attgcaaaca    2040
actgaaatgt ggatgtgatt gcctcaataa agctcgtccc cattgcttaa aaaaaaaaa    2099
```

<210> SEQ ID NO 159
<211> LENGTH: 291
<212> TYPE: PRT
<213> ORGANISM: Homo sapien

<400> SEQUENCE: 159

```
Met Asp Trp Gly Thr Leu His Thr Phe Ile Gly Gly Val Asn Lys His
 1               5                  10                  15

Ser Thr Ser Ile Gly Lys Val Trp Ile Thr Val Ile Phe Ile Phe Arg
                20                  25                  30

Val Met Ile Leu Val Val Ala Ala Gln Glu Val Trp Gly Asp Glu Gln
            35                  40                  45

Glu Asp Phe Val Cys Asn Thr Leu Gln Pro Gly Cys Lys Asn Val Cys
 50                  55                  60

Tyr Asp His Phe Phe Pro Val Ser His Ile Arg Leu Trp Ala Leu Gln
 65                  70                  75                  80

Leu Ile Phe Val Ser Thr Pro Ala Leu Leu Val Ala Met His Val Ala
                85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys Gln Lys Val Arg Ile
            115                 120                 125

Glu Gly Ser Leu Trp Trp Thr Tyr Thr Ser Ser Ile Phe Phe Arg Ile
            130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
            195                 200                 205

Glu Leu Cys Tyr Leu Leu Leu Lys Val Cys Phe Arg Arg Ser Lys Arg
            210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Ser Gln Ala Lys His Phe Lys Val Lys Cys Ser Cys Val Ile
            260                 265                 270

Arg Arg Leu Leu Ser Ser Pro Glu Gly Asn Thr Asn Leu Lys Val Pro
            275                 280                 285

Ser Val Ala
    290
```

<210> SEQ ID NO 160
<211> LENGTH: 3951
<212> TYPE: DNA
<213> ORGANISM: Homo sapien

<400> SEQUENCE: 160

```
tctgcatcca tattgaaaac ctgacacaat gtatgcagca ggctcagtgt gagtgaactg    60
```

-continued

| | | | | |
|---|---|---|---|---|
| gaggcttctc | tacaacatga | cccaaaggag | cattgcaggt | cctatttgca | acctgaagtt | 120 |
| tgtgactctc | ctggttgcct | taagttcaga | actcccattc | ctgggagctg | agtacagct | 180 |
| tcaagacaat | gggtataatg | gattgctcat | tgcaattaat | cctcaggtac | ctgagaatca | 240 |
| gaacctcatc | tcaaacatta | aggaaatgat | aactgaagct | tcattttacc | tatttaatgc | 300 |
| taccaagaga | agagtatttt | tcagaaatat | aaagatttta | atacctgcca | catgaaaagc | 360 |
| taataataac | agcaaaataa | aacaagaatc | atatgaaaag | gcaaatgtca | tagtgactga | 420 |
| ctggtatggg | gcacatggag | atgatccata | caccctacaa | tacagagggt | gtggaaaaga | 480 |
| gggaaaatac | attcatttca | cacctaattt | cctactgaat | gataacttaa | cagctggcta | 540 |
| cggatcacga | ggccgagtgt | tgtccatga | atgggcccac | ctccgttggg | gtgtgttcga | 600 |
| tgagtataac | aatgacaaac | ctttctacat | aaatgggcaa | atcaaatta | aagtgacaag | 660 |
| gtgttcatct | gacatcacag | gcattttgt | gtgtgaaaaa | ggtccttgcc | cccaagaaaa | 720 |
| ctgtattatt | agtaagcttt | ttaaagaagg | atgcaccttt | atctacaata | gcacccaaaa | 780 |
| tgcaactgca | tcaataatgt | tcatgcaaag | tttatcttct | gtggttgaat | tttgtaatgc | 840 |
| aagtacccac | aaccaagaag | caccaaacct | acagaaccag | atgtgcagcc | tcagaagtgc | 900 |
| atgggatgta | atcacagact | ctgctgactt | tcaccacagc | tttcccatga | acgggactga | 960 |
| gcttccacct | cctcccacat | tctcgcttgt | agaggctggt | gacaaagtgg | tctgtttagt | 1020 |
| gctggatgtg | tccagcaaga | tggcagaggc | tgacagactc | cttcaactac | aacaagccgc | 1080 |
| agaatttat | ttgatgcaga | ttgttgaaat | tcataccttc | gtgggcattg | ccagtttcga | 1140 |
| cagcaaagga | gagatcagag | cccagctaca | ccaaattaac | agcaatgatg | atcgaaagtt | 1200 |
| gctggtttca | tatctgccca | ccactgtatc | agctaaaaca | gacatcagca | tttgttcagg | 1260 |
| gcttaagaaa | ggatttgagg | tggttgaaaa | actgaatgga | aaagcttatg | ctctgtgat | 1320 |
| gatattagtg | accagcggag | atgataagct | tcttggcaat | tgcttaccca | ctgtgctcag | 1380 |
| cagtggttca | acaattcact | ccattgccct | gggttcatct | gcagccccaa | atctggagga | 1440 |
| attatcacgt | cttacaggag | gtttaaagtt | ctttgttcca | gatatatcaa | actccaatag | 1500 |
| catgattgat | gctttcagta | gaatttcctc | tggaactgga | gacatttttcc | agcaacatat | 1560 |
| tcagcttgaa | agtacaggtg | aaaatgtcaa | acctcaccat | caattgaaaa | acacagtgac | 1620 |
| tgtggataat | actgtgggca | acgacactat | gtttctagtt | acgtggcagg | ccagtggtcc | 1680 |
| tcctgagatt | atattatttg | atcctgatgg | acgaaaatac | tacacaaata | attttatcac | 1740 |
| caatctaact | tttcggacag | ctagtctttg | gattccagga | acagctaagc | ctgggcactg | 1800 |
| gacttacacc | ctgaacaata | cccatcattc | tctgcaagcc | ctgaaagtga | cagtgacctc | 1860 |
| tcgcgcctcc | aactcagctg | tgcccccagc | cactgtggaa | gcctttgtgg | aaagagacag | 1920 |
| cctccatttt | cctcatcctg | tgatgattta | tgccaatgtg | aaacagggat | tttatcccat | 1980 |
| tcttaatgcc | actgtcactg | ccacagttga | gccagagact | ggagatcctg | ttacgctgag | 2040 |
| actccttgat | gatggagcag | gtgctgatgt | tataaaaaat | gatggaaattt | actcgaggta | 2100 |
| ttttttctcc | tttgctgcaa | atggtagata | tagcttgaaa | gtgcatgtca | atcactctcc | 2160 |
| cagcataagc | accccagccc | actctattcc | agggagtcat | gctatgtatg | taccaggtta | 2220 |
| cacagcaaac | ggtaatattc | agatgaatgc | tccaaggaaa | tcagtaggca | gaaatgagga | 2280 |
| ggagcgaaag | tggggcttta | gccgagtcag | ctcaggaggc | tccttttcag | tgctgggagt | 2340 |
| tccagctggc | ccccaccctg | atgtgtttcc | accatgcaaa | attattgacc | tggaagctgt | 2400 |
| aaaagtagaa | gaggaattga | ccctatcttg | gacagcacct | ggagaagact | ttgatcaggg | 2460 |

```
ccaggctaca agctatgaaa taagaatgag taaaagtcta cagaatatcc aagatgactt    2520
taacaatgct attttagtaa atacatcaaa gcgaaatcct cagcaagctg gcatcaggga    2580
gatatttacg ttctcacccc aaatttccac gaatggacct gaacatcagc caaatggaga    2640
aacacatgaa agccacagaa tttatgttgc aatacgagca atggatagga actccttaca    2700
gtctgctgta tctaacattg cccaggcgcc tctgtttatt cccccaatt ctgatcctgt     2760 acctgccaga gattatctta tattgaaagg agttttaaca gcaatgggtt tgataggaat    2820
catttgcctt attatagttg tgacacatca tactttaagc aggaaaaaga gagcagacaa    2880
gaaagagaat ggaacaaaat tattataaat aaatatccaa agtgtcttcc ttcttagata    2940
taagacccat ggccttcgac tacaaaaaca tactaacaaa gtcaaattaa catcaaaact    3000
gtattaaaat gcattgagtt tttgtacaat acagataaga tttttacatg gtagatcaac    3060
aaaattcttt tgggggtaga ttagaaaacc cttacacttt ggctatgaac aaataataaa    3120
aattattctt taaagtaatg tctttaaagg caaagggaag ggtaaagtcg accagtgtc    3180 aaggaaagtt tgttttattg aggtggaaaa atagccccaa gcagagaaaa ggagggtagg    3240
tctgcattat aactgtctgt gtgaagcaat catttagtta ctttgattaa ttttctttt     3300 ctccttatct gtgcagaaca ggttgcttgt ttacaactga agatcatgct atatttcata    3360
tatgaagccc ctaatgcaaa gctctttacc tcttgctatt ttgttatata tattacagat    3420
gaaatctcac tgctaatgct cagagatctt ttttcactgt aagaggtaac ctttaacaat    3480
atgggtatta cctttgtctc ttcataccgg ttttatgaca aaggtctatt gaatttattt    3540
gtttgtaagt ttctactccc atcaaagcag ctttttaagt tattgccttg gttattatgg    3600
atgatagtta tagcccttat aatgccttaa ctaaggaaga aaagatgtta ttctgagttt    3660
gttttaatac atatatgaac atatagtttt attcaattaa accaaagaag aggtcagcag    3720
ggagatacta acctttggaa atgattagct ggctctgttt tttggttaaa taagagtctt    3780
taatcctttc tccatcaaga gttacttacc aagggcaggg gaaggggat atagaggtcc     3840 caaggaaata aaaatcatct ttcatcttta attttactcc ttcctcttat tttttaaaa    3900 gattatcgaa caataaaatc atttgccttt ttaattaaaa acataaaaaa a              3951
```

<210> SEQ ID NO 161
<211> LENGTH: 943
<212> TYPE: PRT
<213> ORGANISM: Homo sapien

<400> SEQUENCE: 161

```
Met Thr Gln Arg Ser Ile Ala Gly Pro Ile Cys Asn Leu Lys Phe Val
  1               5                  10                  15

Thr Leu Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
         35                  40                  45

Pro Gln Val Pro Glu Asn Gln Asn Leu Ile Ser Asn Ile Lys Glu Met
     50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
            100                 105                 110
```

```
Val Thr Asp Trp Tyr Gly Ala His Gly Asp Pro Tyr Thr Leu Gln
    115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
            355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
            435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
                500                 505                 510

Thr Val Thr Val Asp Asn Thr Val Gly Asn Asp Thr Met Phe Leu Val
    515                 520                 525
```

-continued

```
Thr Trp Gln Ala Ser Gly Pro Pro Glu Ile Ile Leu Phe Asp Pro Asp
    530                 535                 540
Gly Arg Lys Tyr Tyr Thr Asn Phe Ile Thr Asn Leu Thr Phe Arg
545                 550                 555                 560
Thr Ala Ser Leu Trp Ile Pro Gly Thr Ala Lys Pro Gly His Trp Thr
                565                 570                 575
Tyr Thr Leu Asn Asn Thr His His Ser Leu Gln Ala Leu Lys Val Thr
            580                 585                 590
Val Thr Ser Arg Ala Ser Asn Ser Ala Val Pro Pro Ala Thr Val Glu
        595                 600                 605
Ala Phe Val Glu Arg Asp Ser Leu His Phe Pro His Pro Val Met Ile
    610                 615                 620
Tyr Ala Asn Val Lys Gln Gly Phe Tyr Pro Ile Leu Asn Ala Thr Val
625                 630                 635                 640
Thr Ala Thr Val Glu Pro Glu Thr Gly Asp Pro Val Thr Leu Arg Leu
                645                 650                 655
Leu Asp Asp Gly Ala Gly Ala Asp Val Ile Lys Asn Asp Gly Ile Tyr
            660                 665                 670
Ser Arg Tyr Phe Phe Ser Phe Ala Ala Asn Gly Arg Tyr Ser Leu Lys
        675                 680                 685
Val His Val Asn His Ser Pro Ser Ile Ser Thr Pro Ala His Ser Ile
    690                 695                 700
Pro Gly Ser His Ala Met Tyr Val Pro Gly Tyr Thr Ala Asn Gly Asn
705                 710                 715                 720
Ile Gln Met Asn Ala Pro Arg Lys Ser Val Gly Arg Asn Glu Glu Glu
                725                 730                 735
Arg Lys Trp Gly Phe Ser Arg Val Ser Ser Gly Gly Ser Phe Ser Val
            740                 745                 750
Leu Gly Val Pro Ala Gly Pro His Pro Asp Val Phe Pro Pro Cys Lys
        755                 760                 765
Ile Ile Asp Leu Glu Ala Val Lys Val Glu Glu Leu Thr Leu Ser
    770                 775                 780
Trp Thr Ala Pro Gly Glu Asp Phe Asp Gln Gly Gln Ala Thr Ser Tyr
785                 790                 795                 800
Glu Ile Arg Met Ser Lys Ser Leu Gln Asn Ile Gln Asp Asp Phe Asn
                805                 810                 815
Asn Ala Ile Leu Val Asn Thr Ser Lys Arg Asn Pro Gln Gln Ala Gly
            820                 825                 830
Ile Arg Glu Ile Phe Thr Phe Ser Pro Gln Ile Ser Thr Asn Gly Pro
        835                 840                 845
Glu His Gln Pro Asn Gly Glu Thr His Glu Ser His Arg Ile Tyr Val
    850                 855                 860
Ala Ile Arg Ala Met Asp Arg Asn Ser Leu Gln Ser Ala Val Ser Asn
865                 870                 875                 880
Ile Ala Gln Ala Pro Leu Phe Ile Pro Pro Asn Ser Asp Pro Val Pro
                885                 890                 895
Ala Arg Asp Tyr Leu Ile Leu Lys Gly Val Leu Thr Ala Met Gly Leu
            900                 905                 910
Ile Gly Ile Ile Cys Leu Ile Ile Val Val Thr His His Thr Leu Ser
        915                 920                 925
Arg Lys Lys Arg Ala Asp Lys Lys Glu Asn Gly Thr Lys Leu Leu
    930                 935                 940
```

```
<210> SEQ ID NO 162
<211> LENGTH: 498
<212> TYPE: DNA
<213> ORGANISM: Homo sapien

<400> SEQUENCE: 162
tggagaacca cgtggacagc accatgaaca tgttgggcgg gggaggcagt gctggccgga      60
agcccctcaa gtcgggtatg aaggagctgg ccgtgttccg ggagaaggtc actgagcagc     120
accggcagat gggcaagggt ggcaagcatc accttggcct ggaggagccc aagaagctgc     180
gaccacccc tgccaggact ccctgccaac aggaactgga ccaggtcctg gagcggatct      240
ccaccatgcg ccttccggat gagcggggcc ctctggagca cctctactcc ctgcacatcc     300
ccaactgtga caagcatggc ctgtacaacc tcaaacagtg gcaagatgtc tctgaacggg     360
cagcgtgggg agtgctggtg tgtgaacccc aacaccggga agctgatcca gggagccccc     420
accatccggg gggaccccga gtgtcatctc ttctacaatg agcagcagga ggctcgcggg     480
gtgcacaccc cagcggat                                                    498

<210> SEQ ID NO 163
<211> LENGTH: 1128
<212> TYPE: DNA
<213> ORGANISM: Homo sapien

<400> SEQUENCE: 163
gccacctggc cctcctgatc gacgacacac gcacttgaaa cttgttctca gggtgtgtgg      60
aatcaacttt ccggaagcaa ccagcccacc agaggaggtc ccgagcgcga gcggagacga     120
tgcagcggag actggttcag cagtggacg tcgcggtgtt cctgctgagc tacgcggtgc      180
cctcctgcgg gcgctcggtg gagggtctca gccgccgcct caaaagagct gtgtctgaac     240
atcagctcct ccatgacaag gggaagtcca tccaagattt acggcgacga ttcttccttc     300
accatctgat cgcagaaatc cacacagctg aaatcagagc tacctcggag gtgtcccta      360
actccaagcc ctctcccaac acaaagaacc accccgtccg atttgggtct gatgatgagg     420
gcagatacct aactcaggaa actaacaagg tggagacgta caaagagcag ccgctcaaga     480
cacctgggaa gaaaaagaaa ggcaagcccg ggaaacgcaa ggagcaggaa aagaaaaaac     540
ggcgaactcg ctctgcctgg ttagactctg gagtgactgg gagtgggcta aagggggacc     600
acctgtctga cacctccaca acgtcgctgg agctcgattc acggaggcat tgaaattttc     660
agcagagacc ttccaaggac atattgcagg attctgtaat agtgaacata tggaaagtat     720
tagaaatatt tattgtctgt aaatactgta aatgcattgg aataaaactg tctcccccat     780
tgctctatga aactgcacat tggtcattgt gaatattttt tttttgcca aggctaatcc     840
aattattatt atcacattta ccataattta ttttgtccat tgatgtattt attttgtaaa     900
tgtatcttgg tgctgctgaa tttctatatt ttttgtaaca taatgcactt tagatataca     960
tatcaagtat gttgataaat gacacaatga agtgtctcta ttttgtggtt gattttaatg    1020
aatgcctaaa tataattatc caaattgatt tccttgtg catgtaaaaa taacagtatt    1080
ttaaatttgt aaagaatgtc taataaaata taatctaatt acatcatg                 1128

<210> SEQ ID NO 164
<211> LENGTH: 1310
<212> TYPE: DNA
<213> ORGANISM: Homo sapien

<400> SEQUENCE: 164
```

-continued

```
gggcctggtt cgcaaagaag ctgacttcag aggggggaaac tttcttcttt taggaggcgg      60
ttagccctgt tccacgaacc caggagaact gctggccaga ttaattagac attgctatgg     120
gagacgtgta acacactac ttatcattga tgcatatata aaaccatttt attttcgcta      180
ttatttcaga ggaagcgcct ctgatttgtt tcttttttcc cttttgctc tttctggctg      240
tgtggtttgg agaaagcaca gttggagtag ccggttgcta aataagtccc gagcgcgagc     300
ggagacgatg cagcggagac tggttcagca gtggagcgtc gcggtgttcc tgctgagcta     360
cgcggtgccc tcctgcgggc gctcggtgga gggtctcagc cgccgcctca aaagagctgt     420
gtctgaacat cagctcctcc atgacaaggg gaagtccatc caagatttac ggcgacgatt     480
cttccttcac catctgatcg cagaaatcca cacagctgaa atcagagcta cctcggaggt     540
gtcccctaac tccaagccct ctcccaacac aaagaaccac cccgtccgat ttgggtctga     600
tgatgagggc agatacctaa ctcaggaaac taacaaggtg gagacgtaca agagcagcc     660
gctcaagaca cctgggaaga aaagaaagg caagcccggg aaacgcaagg agcaggaaaa     720
gaaaaaacgg cgaactcgct ctgcctggtt agactctgga gtgactggga gtgggctaga     780
agggaccac ctgtctgaca cctccacaac gtcgctggag ctcgattcac ggaggcattg      840
aaattttcag cagagacctt ccaaggacat attgcaggat tctgtaatag tgaacatatg     900
gaaagtatta gaaatattta ttgtctgtaa atactgtaaa tgcattggaa taaaactgtc     960
tccccattg ctctatgaaa ctgcacattg gtcattgtga atatttttt ttttgccaag      1020
gctaatccaa ttattattat cacatttacc ataatttatt ttgtccattg atgtatttat    1080
tttgtaaatg tatcttggtg ctgctgaatt tctatatttt ttgtaacata atgcacttta    1140
gatatacata tcaagtatgt tgataaatga cacaatgaag tgtctctatt ttgtggttga    1200
ttttaatgaa tgcctaaata taattatcca aattgattt cctttgtgcc cgtaaaaata     1260
acagtatttt aaatttgtaa agaatgtcta ataaatata atctaattac               1310
```

<210> SEQ ID NO 165
<211> LENGTH: 177
<212> TYPE: PRT
<213> ORGANISM: Homo sapien

<400> SEQUENCE: 165

```
Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Gly
        115                 120                 125

Lys Pro Gly Lys Arg Lys Glu Gln Glu Lys Lys Arg Arg Thr Arg
    130                 135                 140
```

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 166
<211> LENGTH: 177
<212> TYPE: PRT
<213> ORGANISM: Homo sapien

<400> SEQUENCE: 166

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
                20                  25                  30

Arg Leu Lys Arg Ala Val Ser Glu His Gln Leu Leu His Asp Lys Gly
            35                  40                  45

Lys Ser Ile Gln Asp Leu Arg Arg Arg Phe Phe Leu His His Leu Ile
        50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
                100                 105                 110

Thr Tyr Lys Glu Gln Pro Leu Lys Thr Pro Gly Lys Lys Lys Lys Gly
            115                 120                 125

Lys Pro Gly Lys Arg Lys Glu Gln Glu Lys Lys Lys Arg Arg Thr Arg
        130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 167
<211> LENGTH: 3362
<212> TYPE: DNA
<213> ORGANISM: Homo sapien

<400> SEQUENCE: 167
cacaatgtat gcagcaggct cagtgtgagt gaactggagg cttctctaca acatgaccca      60
aaggagcatt gcaggtccta tttgcaacct gaagtttgtg actctcctgg ttgccttaag     120
ttcagaactc ccattcctgg gagctggagt acagcttcaa gacaatgggt ataatggatt     180
gctcattgca attaatcctc aggtacctga gaatcagaac ctcatctcaa acattaagga     240
aatgataact gaagcttcat tttacctatt taatgctacc aagagaagag tattttttcag    300 aaatataaag atttaatac ctgccacatg gaaagctaat aataacagca aaataaaaca     360
agaatcatat gaaaaggcaa atgtcatagt gactgactgg tatggggcac atggagatga     420
tccatacacc ctacaataca gagggtgtgg aaaagaggga aaatacattc atttcacacc     480
taatttccta ctgaatgata acttaacagc tggctacgga tcacgaggcc gagtgtttgt     540
ccatgaatgg gcccacctcc gttggggtgt gttcgatgag tataacaatg acaaaccttt     600

```
ctacataaat gggcaaaatc aaattaaagt gacaaggtgt tcatctgaca tcacaggcat    660
ttttgtgtgt gaaaaaggtc cttgccccca agaaaactgt attattagta agctttttaa    720
agaaggatgc acctttatct acaatagcac ccaaaatgca actgcatcaa taatgttcat    780
gcaaagttta tcttctgtgg ttgaattttg taatgcaagt acccacaacc aagaagcacc    840
aaacctacag aaccagatgt gcagcctcag aagtgcatgg gatgtaatca cagactctgc    900
tgactttcac cacagctttc ccatgaacgg gactgagctt ccacctcctc ccacattctc    960
gcttgtagag gctggtgaca aagtggtctg tttagtgctg gatgtgtcca gcaagatggc   1020
agaggctgac agactccttc aactacaaca agccgcagaa ttttatttga tgcagattgt   1080
tgaaattcat accttcgtgg gcattgccag tttcgacagc aaaggagaga tcagagccca   1140
gctacaccaa attaacagca atgatgatcg aaagttgctg gtttcatatc tgcccaccac   1200
tgtatcagct aaaacagaca tcagcatttg ttcagggctt aagaaggat ttgaggtggt   1260
tgaaaaactg aatggaaaag cttatggctc tgtgatgata ttagtgacca gcggagatga   1320
taagcttctt ggcaattgct tacccactgt gctcagcagt ggttcaacaa ttcactccat   1380
tgccctgggt tcatctgcag ccccaaatct ggaggaatta tcacgtctta caggaggttt   1440
aaagttcttt gttccagata tatcaaactc caatagcatg attgatgctt tcagtagaat   1500
ttcctctgga actggagaca ttttccagca acatattcag cttgaaagta caggtgaaaa   1560
tgtcaaacct caccatcaat tgaaaaacac agtgactgtg gataatactg tgggcaacga   1620
cactatgttt ctagttacgt ggcaggccag tggtcctcct gagattatat tatttgatcc   1680
tgatggacga aaatactaca caaataattt tatcaccaat ctaacttttc ggacagctag   1740
tctttggatt ccaggaacag ctaagcctgg gcactggact tacaccctga tgtgtttcca   1800
ccatgcaaaa ttattgacct ggaagctgta aaagtagaag aggaattgac cctatcttgg   1860
acagcacctg gagaagactt tgatcagggc caggctacaa gctatgaaat aagaatgagt   1920
aaaagtctac agaatatcca agatgacttt aacaatgcta ttttagtaaa tacatcaaag   1980
cgaaatcctc agcaagctgg catcaggag atatttacgt tctcacccca aatttccacg   2040
aatggacctg aacatcagcc aaatggagaa acacatgaaa gccacagaat ttatgttgca   2100
atacgagcaa tggataggaa ctccttacag tctgctgtat ctaacattgc ccaggcgcct   2160
ctgtttattc cccccaattc tgatcctgta cctgccagag attatcttat attgaaagga   2220
gttttaacag caatgggttt gataggaatc atttgcctta ttatagttgt gacacatcat   2280
actttaagca ggaaaaagag agcagacaag aaagagaatg gaacaaaatt attataaata   2340
aatatccaaa gtgtcttcct tcttagatat aagacccatg gccttcgact acaaaaacat   2400
actaacaaag tcaaattaac atcaaaactg tattaaaatg cattgagttt ttgtacaata   2460
cagataagat ttttacatgg tagatcaaca aattcttttt gggggtagat tagaaaaccc   2520
ttacactttg gctatgaaca ataataaaa attattcttt aaagtaatgt ctttaaaggc   2580
aaagggaagg gtaaagtcgg accagtgtca aggaaagttt gttttattga ggtggaaaaa   2640
tagccccaag cagagaaaag gagggtaggt ctgcattata actgtctgtg tgaagcaatc   2700
atttagttac tttgattaat ttttcttttc tccttatctg tgcagaacag gttgcttgtt   2760
tacaactgaa gatcatgcta tatttcatat atgaagcccc taatgcaaag ctctttacct   2820
cttgctattt tgttatatat attacagatg aaatctcact gctaatgctc agatctcttt   2880
tttcactgta agaggtaacc tttaacaata tgggtattac ctttgtctct tcataccggt   2940
tttatgacaa aggtctattg aatttatttg tttgtaagtt tctactccca tcaaagcagc   3000
```

| | | | | |
|---|---|---|---|---|
| tttctaagtt | attgccttgg | ttattatgga | tgatagttat | agcccttata atgccttaac | 3060 |
| taaggaagaa | aagatgttat | tctgagtttg | ttttaataca | tatatgaaca tatagtttta | 3120 |
| ttcaattaaa | ccaaagaaga | ggtcagcagg | gagatactaa | cctttggaaa tgattagctg | 3180 |
| gctctgtttt | ttggttaaat | aagagtcttt | aatcctttct | ccatcaagag ttacttacca | 3240 |
| agggcagggg | aaggggata | tagaggtcac | aaggaaataa | aaatcatctt tcatctttaa | 3300 |
| ttttactcct | tcctcttatt | tttttaaaag | attatcgaac | aataaaatca tttgccttt | 3360 |
| tt | | | | | 3362 |

<210> SEQ ID NO 168
<211> LENGTH: 2784
<212> TYPE: DNA
<213> ORGANISM: Homo sapien

<400> SEQUENCE: 168

| | | | | |
|---|---|---|---|---|
| tctgcatcca | tattgaaaac | ctgacacaat | gtatgcagca | ggctcagtgt gagtgaactg | 60 |
| gaggcttctc | tacaacatga | cccaaaggag | cattgcaggt | cctatttgca acctgaagtt | 120 |
| tgtgactctc | ctggttgcct | aagttcaga | actcccattc | ctgggagctg agtacagct | 180 |
| tcaagacaat | gggtataatg | gattgctcat | tgcaattaat | cctcaggtac ctgagaatca | 240 |
| gaacctcatc | tcaaacatta | aggaaatgat | aactgaagct | tcattttacc tatttaatgc | 300 |
| taccaagaga | agagtatttt | tcagaaatat | aaagatttta | atacctgcca catggaaagc | 360 |
| taataataac | agcaaaataa | aacaagaatc | atatgaaaag | gcaaatgtca tagtgactga | 420 |
| ctggtatggg | gcacatggag | atgatccata | caccctacaa | tacagagggt gtggaaaaga | 480 |
| gggaaaatac | attcatttca | cacctaattt | cctactgaat | gataacttaa cagctggcta | 540 |
| cggatcacga | ggccgagtgt | ttgtccatga | atgggcccac | ctccgttggg gtgtgttcga | 600 |
| tgagtataac | aatgacaaac | ctttctacat | aaatgggcaa | atcaaatta aagtgacaag | 660 |
| gtgttcatct | gacatcacag | gcattttgt | gtgtgaaaaa | ggtccttgcc cccaagaaaa | 720 |
| ctgtattatt | agtaagcttt | ttaaagaagg | atgcaccttt | atctacaata gcacccaaaa | 780 |
| tgcaactgca | tcaataatgt | tcatgcaaag | tttatcttct | gtggttgaat tttgtaatgc | 840 |
| aagtacccac | aaccaagaag | caccaaacct | acagaaccag | atgtgcagcc tcagaagtgc | 900 |
| atgggatgta | atcacagact | ctgctgactt | tcaccacagc | tttcccatga acggactga | 960 |
| gcttccacct | cctcccacat | tctcgcttgt | agaggctggt | gacaaagtgg tctgtttagt | 1020 |
| gctggatgtg | tccagcaaga | tggcagaggc | tgacagactc | cttcaactac aacaagccgc | 1080 |
| agaattttat | ttgatgcaga | ttgttgaaat | tcataccttc | gtgggcattg ccagtttcga | 1140 |
| cagcaaagga | gagatcagag | cccagctaca | ccaaattaac | agcaatgatg atcgaaagtt | 1200 |
| gctggtttca | tatctgccca | ccactgtatc | agctaaaaca | gacatcagca tttgttcagg | 1260 |
| gcttaagaaa | ggatttgagg | tggttgaaaa | actgaatgga | aaagcttatg ctctgtgat | 1320 |
| gatattagtg | accagcggag | atgataagct | tcttggcaat | tgcttaccca ctgtgctcag | 1380 |
| cagtggttca | acaattcact | ccattgccct | gggttcatct | gcagccccaa atctggagga | 1440 |
| attatcacgt | cttacaggag | gtttaaagtt | cttttgttcca | gatatatcaa actccaatag | 1500 |
| catgattgat | gctttcagta | gaatttcctc | tggaactgga | gacatttcc agcaacatat | 1560 |
| tcagcttgaa | agtacaggtg | aaaatgtcaa | acctcaccat | caattgaaaa acacagtgac | 1620 |
| tgtggataat | actgtgggca | acgacactat | gtttctagtt | acgtggcagg ccagtggtcc | 1680 |

-continued

```
tcctgagatt atattatttg atcctgatgg acgaaaatac tacacaaata atttatcac    1740 caatctaact tttcggacag ctagtctttg gattccagga acagctaagc ctgggcactg    1800
gacttacacc ctgaacaata cccatcattc tctgcaagcc ctgaaagtga cagtgacctc    1860
tcgcgcctcc aactcagctg tgcccccagc cactgtggaa gcctttgtgg aaagagacag    1920
cctccatttt cctcatcctg tgatgattta tgccaatgtg aaacagggat tttatcccat    1980
tcttaatgcc actgtcactg ccacagttga gccagagact ggagatcctg ttacgctgag    2040
actccttgat gatggagcag gtgctgatgt tataaaaaat gatggaattt actcgaggta    2100
ttttttctcc tttgctgcaa atggtagata tagcttgaaa gtgcatgtca atcactctcc    2160
cagcataagc accccagccc actctattcc agggagtcat gctatgtatg taccaggtta    2220
cacagcaaac ggtaatattc agatgaatgc tccaaggaaa tcagtaggca gaaatgagga    2280
ggagcgaaag tggggctttα gccgagtcag ctcaggaggc tccttttcag tgctgggagt    2340
tccagctggc ccccaccctg atgtgtttcc accatgcaaa attattgacc tggaagctgt    2400
aaatagaaga ggaattgacc ctatcttgga cagcacctgg agaagacttt gatcagggcc    2460
aggctacaag ctatgaaata gaatgagta aaagtctaca gaatatccaa gatgacttta    2520
acaatgctat tttagtaaat acatcaaagc gaaatcctca gcaagctggc atcagggaga    2580
tatttacgtt ctcaccccaa atttccacga atggacctga acatcagcca aatggagaaa    2640
cacatgaaag ccacagaatt tatgttgcaa tacgagcaat ggataggaac tccttacagt    2700
ctgctgtatc taacattgcc caggcgcctc tgtttattcc ccccaattct gatcctgtac    2760
ctgccagaga ttatcttata ttga                                          2784
```

<210> SEQ ID NO 169
<211> LENGTH: 592
<212> TYPE: PRT
<213> ORGANISM: Homo sapien

<400> SEQUENCE: 169

```
Met Thr Gln Arg Ser Ile Ala Gly Pro Ile Cys Asn Leu Lys Phe Val
  1               5                  10                  15

Thr Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
         35                  40                  45

Pro Gln Val Pro Glu Asn Gln Asn Leu Ile Ser Asn Ile Lys Glu Met
     50                  55                  60

Ile Thr Glu Ala Ser Phe Tyr Leu Phe Asn Ala Thr Lys Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175
```

-continued

```
Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
            245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Ala Glu
            325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
            355                 360                 365

Ser Asn Asp Asp Arg Lys Leu Leu Val Ser Tyr Leu Pro Thr Thr Val
            370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
            405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
            435                 440                 445

Ala Ala Pro Asn Leu Glu Glu Leu Ser Arg Leu Thr Gly Gly Leu Lys
450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
            485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
            515                 520                 525

Thr Trp Gln Ala Ser Gly Pro Pro Glu Ile Ile Leu Phe Asp Pro Asp
            530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
            565                 570                 575

Tyr Thr Leu Met Cys Phe His His Ala Lys Leu Leu Thr Trp Lys Leu
            580                 585                 590
```

```
<210> SEQ ID NO 170
<211> LENGTH: 791
<212> TYPE: PRT
<213> ORGANISM: Homo sapien

<400> SEQUENCE: 170

Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
    370                 375                 380
```

-continued

```
Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
            405                 410                 415

Leu Val Thr Ser Gly Asp Asp Lys Leu Leu Gly Asn Cys Leu Pro Thr
                420                 425                 430

Val Leu Ser Ser Gly Ser Thr Ile His Ser Ile Ala Leu Gly Ser Ser
            435                 440                 445

Ala Ala Pro Asn Leu Glu Glu Leu Ser Arg Leu Thr Gly Gly Leu Lys
        450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
            580                 585                 590

Val Thr Ser Arg Ala Ser Asn Ser Ala Val Pro Pro Ala Thr Val Glu
        595                 600                 605

Ala Phe Val Glu Arg Asp Ser Leu His Phe Pro His Pro Val Met Ile
610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
            660                 665                 670

Ser Arg Tyr Phe Phe Ser Phe Ala Ala Asn Gly Arg Tyr Ser Leu Lys
        675                 680                 685

Val His Val Asn His Ser Pro Ser Ile Ser Thr Pro Ala His Ser Ile
690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser Val
            740                 745                 750

Leu Gly Val Pro Ala Gly Pro His Pro Asp Val Phe Pro Pro Cys Lys
        755                 760                 765

Ile Ile Asp Leu Glu Ala Val Asn Arg Arg Gly Ile Asp Pro Ile Leu
770                 775                 780

Asp Ser Thr Trp Arg Arg Leu
785                 790
```

<210> SEQ ID NO 171
<211> LENGTH: 1491
<212> TYPE: DNA
<213> ORGANISM: Homo sapien

<400> SEQUENCE: 171

```
cctcctgcca gccaagtgaa gacatgctta cttcccttc accttccttc atgatgtggg      60
aagagtgctg caacccagcc ctagccaacg ccgcatgaga gggagtgtgc cgagggcttc    120
tgagaaggtt tctctcacat ctagaaagaa gcgcttaaga tgtggcagcc cctcttcttc    180
aagtggctct tgtcctgttg ccctgggagt tctcaaattg ctgcagcagc tccacccag    240
cctgaggatg acatcaatac acagaggaag aagagtcagg aaaagatgag agaagttaca    300
gactctcctg ggcgacccg agagcttacc attcctcaga cttcttcaca tggtgctaac    360
agatttgttc ctaaaagtaa agctctagag gccgtcaaat tggcaataga gccgggttc    420
caccatattg attctgcaca tgtttacaat aatgaggagc aggttggact ggccatccga    480
agcaagattg cagatggcag tgtgaagaga gaagacatat tctacacttc aaagctttgg    540
agcaattccc atcgaccaga gttggtccga ccagccttgg aaaggtcact gaaaaatctt    600
caattggact atgttgacct ctatcttatt cattttccag tgtctgtaaa gccaggtgag    660
gaagtgatcc caaaagatga aaatggaaaa atactatttg acacagtgga tctctgtgcc    720
acatgggagg ccatggagaa gtgtaaagat gcaggattgg ccaagtccat cggggtgtcc    780
aacttcaacc acaggctgct ggagatgatc ctcaacaagc cagggctcaa gtacaagcct    840
gtctgcaacc aggtggaatg tcatccttac ttcaaccaga gaaaactgct ggatttctgc    900
aagtcaaaag acattgttct ggttgcctat agtgctctgg gatcccatcg agaagaacca    960
tgggtggacc cgaactcccc ggtgctcttg gaggacccag tcctttgtgc cttggcaaaa   1020
aagcacaagc gaaccccagc cctgattgcc ctgcgctacc agctgcagcg tgggggttgtg   1080
gtcctggcca agagctacaa tgagcagcgc atcagacaga acgtgcaggt gtttgaattc   1140
cagttgactt cagaggagat gaaagccata gatggcctaa acagaaatgt gcgatatttg   1200
acccttgata tttttgctgg cccccctaat tatccatttt ctgatgaata ttaacatgga   1260
gggcattgca tgaggtctgc cagaaggccc tgcgtgtgga tggtgacaca gaggatggct   1320
ctatgctggt gactggacac atcgcctctg gttaaatctc tcctgcttgg cgacttcagt   1380
aagctacagc taagcccatc ggccggaaaa gaaagacaat aatttttgttt ttcattttga   1440
aaaaattaaa tgctctctcc taaagattct tcacctaaaa aaaaaaaaa a             1491
```

<210> SEQ ID NO 172
<211> LENGTH: 364
<212> TYPE: PRT
<213> ORGANISM: Homo sapien

<400> SEQUENCE: 172

```
Met Trp Gln Pro Leu Phe Phe Lys Trp Leu Leu Ser Cys Cys Pro Gly
 1               5                  10                  15

Ser Ser Gln Ile Ala Ala Ala Ser Thr Gln Pro Glu Asp Asp Ile
            20                  25                  30

Asn Thr Gln Arg Lys Lys Ser Gln Glu Lys Met Arg Glu Val Thr Asp
        35                  40                  45

Ser Pro Gly Arg Pro Arg Glu Leu Thr Ile Pro Gln Thr Ser Ser His
    50                  55                  60

Gly Ala Asn Arg Phe Val Pro Lys Ser Lys Ala Leu Glu Ala Val Lys
65                  70                  75                  80
```

```
Leu Ala Ile Glu Ala Gly Phe His His Ile Asp Ser Ala His Val Tyr
                85                  90                  95
Asn Asn Glu Glu Gln Val Gly Leu Ala Ile Arg Ser Lys Ile Ala Asp
            100                 105                 110
Gly Ser Val Lys Arg Glu Asp Ile Phe Tyr Thr Ser Lys Leu Trp Ser
        115                 120                 125
Asn Ser His Arg Pro Glu Leu Val Arg Pro Ala Leu Glu Arg Ser Leu
    130                 135                 140
Lys Asn Leu Gln Leu Asp Tyr Val Asp Leu Tyr Leu Ile His Phe Pro
145                 150                 155                 160
Val Ser Val Lys Pro Gly Glu Glu Val Ile Pro Lys Asp Glu Asn Gly
                165                 170                 175
Lys Ile Leu Phe Asp Thr Val Asp Leu Cys Ala Thr Trp Glu Ala Met
            180                 185                 190
Glu Lys Cys Lys Asp Ala Gly Leu Ala Lys Ser Ile Gly Val Ser Asn
        195                 200                 205
Phe Asn His Arg Leu Leu Glu Met Ile Leu Asn Lys Pro Gly Leu Lys
    210                 215                 220
Tyr Lys Pro Val Cys Asn Gln Val Glu Cys His Pro Tyr Phe Asn Gln
225                 230                 235                 240
Arg Lys Leu Leu Asp Phe Cys Lys Ser Lys Asp Ile Val Leu Val Ala
                245                 250                 255
Tyr Ser Ala Leu Gly Ser His Arg Glu Glu Pro Trp Val Asp Pro Asn
            260                 265                 270
Ser Pro Val Leu Leu Glu Asp Pro Val Leu Cys Ala Leu Ala Lys Lys
        275                 280                 285
His Lys Arg Thr Pro Ala Leu Ile Ala Leu Arg Tyr Gln Leu Gln Arg
    290                 295                 300
Gly Val Val Val Leu Ala Lys Ser Tyr Asn Glu Gln Arg Ile Arg Gln
305                 310                 315                 320
Asn Val Gln Val Phe Glu Phe Gln Leu Thr Ser Glu Glu Met Lys Ala
                325                 330                 335
Ile Asp Gly Leu Asn Arg Asn Val Arg Tyr Leu Thr Leu Asp Ile Phe
            340                 345                 350
Ala Gly Pro Pro Asn Tyr Pro Phe Ser Asp Glu Tyr
        355                 360

<210> SEQ ID NO 173
<211> LENGTH: 1988
<212> TYPE: DNA
<213> ORGANISM: Homo sapiens

<400> SEQUENCE: 173
cgggagccgc ctcccgcgg cctcttcgct tttgtggcgg cgcccgcgct cgcaggccac     60
tctctgctgt cgcccgtccc gcgcgctcct ccgacccgct ccgctccgct ccgctcggcc    120
ccgcgccgcc cgtcaacatg atccgctgcg gcctggcctg cgagcgctgc cgctggatcc    180
tgccctgct cctactcagc gccatcgcct tcgacatcat cgcgctggcc ggccgcggct    240
ggttgcagtc tagcgaccac ggccagacgt cctcgctgtg gtggaaatgc tcccaagagg    300
gcggcggcag cgggtcctac gaggagggct gtcagagcct catggagtac gcgtggggta    360
gagcagcggc tgccatgctc ttctgtggct tcatcatctc ggtgatctgt ttcatcctct    420
ccttcttcgc cctctgtgga ccccagatgc ttgtcttcct gagagtgatt ggaggtctcc    480
```

```
ttgccttggc tgctgtgttc cagatcatct ccctggtaat ttaccccgtg aagtacaccc    540
agaccttcac ccttcatgcc aaccctgctg tcacttacat ctataactgg gcctacggct    600
ttgggtgggc agccacgatt atcctgatcg gctgtgcctt cttcttctgc tgcctcccca    660
actacgaaga tgaccttctg ggcaatgcca agcccaggta cttctacaca tctgcctaac    720
ttgggaatga atgtgggaga aaatcgctgc tgctgagatg gactccagaa gaagaaactg    780
tttctccagg cgactttgaa cccattttt ggcagtgttc atattattaa actagtcaaa     840
aatgctaaaa taatttggga gaaaatattt ttaagtagt gttatagttt catgtttatc     900
ttttattatg ttttgtgaag ttgtgtcttt tcactaatta cctatactat gccaatattt    960
ccttatatct atccataaca tttatactac atttgtaaga gaatatgcac gtgaaactta    1020
acactttata aggtaaaaat gaggtttcca agatttaata atctgatcaa gttcttgtta    1080
tttccaaata gaatggactt ggtctgttaa gggctaagga gaagaggaag ataaggttaa    1140
aagttgttaa tgaccaaaca ttctaaaaga aatgcaaaaa aaagtttat tttcaagcct     1200 tcgaactatt taaggaaagc aaaatcattt cctaaatgca tatcatttgt gagaatttct    1260
cattaatatc ctgaatcatt catttcagct aaggcttcat gttgactcga tatgtcatct    1320
aggaaagtac tatttcatgg tccaaacctg ttgccatagt tggtaaggct ttcctttaag    1380
tgtgaaatat ttagatgaaa ttttctcttt taaagttctt tatagggtta gggtgtggga    1440
aaatgctata ttaataaatc tgtagtgttt tgtgtttata tgttcagaac cagagtagac    1500
tggattgaaa gatggactgg gtctaattta tcatgactga tagatctggt taagttgtgt    1560
agtaaagcat taggagggtc attcytgtca caaaagtgcc actaaaacag cctcaggaga    1620
ataaatgact tgcttttcta aatctcaggt ttatctgggc tctatcatat agacaggctt    1680
ctgatagttt gcarctgtaa gcagaaacct acatatagtt aaaatcctgg tctttcttgg    1740
taaacagatt ttaaatgtct gatataaaac atgccacagg agaattcggg gatttgagtt    1800
tctctgaata gcatatatat gatgcatcgg ataggtcatt atgattttt accatttcga     1860 cttacataat gaaaaccaat tcattttaaa tatcagatta ttattttgta agttgtggaa    1920
aaagctaatt gtagttttca ttatgaagtt ttcccaataa accaggtatt ctaaaaaaaa    1980
aaaaaaaa                                                              1988
```

<210> SEQ ID NO 174
<211> LENGTH: 238
<212> TYPE: PRT
<213> ORGANISM: Homo sapiens

<400> SEQUENCE: 174

```
Gly Ala Ala Ser Pro Arg Pro Leu Arg Phe Cys Gly Gly Ala Arg Ala
              5                  10                  15

Arg Arg Pro Leu Ser Ala Val Arg Pro Ala Arg Ser Ser Asp Pro
         20                  25                  30

Leu Arg Ser Ala Pro Leu Gly Pro Ala Pro Val Asn Met Ile Arg
         35                  40                  45

Cys Gly Leu Ala Cys Glu Arg Cys Arg Trp Ile Leu Pro Leu Leu Leu
     50                  55                  60

Leu Ser Ala Ile Ala Phe Asp Ile Ile Ala Leu Ala Gly Arg Gly Trp
 65                  70                  75                  80

Leu Gln Ser Ser Asp His Gly Gln Thr Ser Ser Leu Trp Trp Lys Cys
                 85                  90                  95

Ser Gln Glu Gly Gly Gly Ser Gly Ser Tyr Glu Glu Gly Cys Gln Ser
```

```
                    100                 105                 110
Leu Met Glu Tyr Ala Trp Gly Arg Ala Ala Ala Met Leu Phe Cys
        115                 120                 125

Gly Phe Ile Ile Leu Val Ile Cys Phe Ile Leu Ser Phe Phe Ala Leu
        130                 135                 140

Cys Gly Pro Gln Met Leu Val Phe Leu Arg Val Ile Gly Gly Leu Leu
145                 150                 155                 160

Ala Leu Ala Ala Val Phe Gln Ile Ile Ser Leu Val Ile Tyr Pro Val
                165                 170                 175

Lys Tyr Thr Gln Thr Phe Thr Leu His Ala Asn Pro Ala Val Thr Tyr
                180                 185                 190

Ile Tyr Asn Trp Ala Tyr Gly Phe Gly Trp Ala Thr Ile Ile Leu
        195                 200                 205

Ile Gly Cys Ala Phe Phe Cys Cys Leu Pro Asn Tyr Glu Asp Asp
        210                 215                 220

Leu Leu Gly Asn Ala Lys Pro Arg Tyr Phe Tyr Thr Ser Ala
225                 230                 235
```

<210> SEQ ID NO 175
<211> LENGTH: 4181
<212> TYPE: DNA
<213> ORGANISM: Homo sapiens
<220> FEATURE:
<221> NAME/KEY: unsure
<222> LOCATION: (3347)
<223> OTHER INFORMATION: n=A,T,C or G
<221> NAME/KEY: unsure
<222> LOCATION: (3502)
<223> OTHER INFORMATION: n=A,T,C or G
<221> NAME/KEY: unsure
<222> LOCATION: (3506)
<223> OTHER INFORMATION: n=A,T,C or G
<221> NAME/KEY: unsure
<222> LOCATION: (3520)
<223> OTHER INFORMATION: n=A,T,C or G
<221> NAME/KEY: unsure
<222> LOCATION: (3538)
<223> OTHER INFORMATION: n=A,T,C or G
<221> NAME/KEY: unsure
<222> LOCATION: (3549)
<223> OTHER INFORMATION: n=A,T,C or G
<221> NAME/KEY: unsure
<222> LOCATION: (3646)
<223> OTHER INFORMATION: n=A,T,C or G
<221> NAME/KEY: unsure
<222> LOCATION: (3940)
<223> OTHER INFORMATION: n=A,T,C or G
<221> NAME/KEY: unsure
<222> LOCATION: (3968)
<223> OTHER INFORMATION: n=A,T,C or G
<221> NAME/KEY: unsure
<222> LOCATION: (3974)
<223> OTHER INFORMATION: n=A,T,C or G
<221> NAME/KEY: unsure
<222> LOCATION: (4036)
<223> OTHER INFORMATION: n=A,T,C or G
<221> NAME/KEY: unsure
<222> LOCATION: (4056)
<223> OTHER INFORMATION: n=A,T,C or G
<221> NAME/KEY: unsure
<222> LOCATION: (4062)
<223> OTHER INFORMATION: n=A,T,C or G
<221> NAME/KEY: unsure
<222> LOCATION: (4080)
<223> OTHER INFORMATION: n=A,T,C or G
<221> NAME/KEY: unsure
<222> LOCATION: (4088)
<223> OTHER INFORMATION: n=A,T,C or G
<221> NAME/KEY: unsure
<222> LOCATION: (4115)

<223> OTHER INFORMATION: n=A,T,C or G

<400> SEQUENCE: 175

| | | | | | |
|---|---|---|---|---|---|
| ggtggatgcg | tttgggttgt | agctaggctt | tttcttttct | ttctctttta | aaacacatct | 60 |
| agacaaggaa | aaaacaagcc | tcggatctga | ttttcactc | ctcgttcttg | tgcttggttc | 120 |
| ttactgtgtt | tgtgtatttt | aaaggcgaga | agacgagggg | aacaaaacca | gctggatcca | 180 |
| tccatcaccg | tgggtggttt | taatttttcg | ttttttctcg | ttatttttt | ttaaacaacc | 240 |
| actcttcaca | atgaacaaac | tgtatatcgg | aaacctcagc | gagaacgccg | cccctcgga | 300 |
| cctagaaagt | atcttcaagg | acgccaagat | cccggtgtcg | ggaccctcc | tggtgaagac | 360 |
| tggctacgcg | ttcgtggact | gcccggacga | gagctgggcc | ctcaaggcca | tcgaggcgct | 420 |
| ttcaggtaaa | atagaactgc | acgggaaacc | catagaagtt | gagcactcgg | tcccaaaaag | 480 |
| gcaaaggatt | cggaaacttc | agatacgaaa | tatcccgcct | catttacagt | gggaggtgct | 540 |
| ggatagttta | ctagtccagt | atggagtggt | ggagagctgt | gagcaagtga | acactgactc | 600 |
| ggaaactgca | gttgtaaatg | taacctattc | cagtaaggac | caagctagac | aagcactaga | 660 |
| caaactgaat | ggatttcagt | tagagaattt | caccttgaaa | gtagcctata | tccctgatga | 720 |
| aatggccgcc | cagcaaaacc | ccttgcagca | gccccgaggt | cgccggggc | ttgggcagag | 780 |
| gggctcctca | aggcagggt | ctccaggatc | cgtatccaag | cagaaaccat | gtgatttgcc | 840 |
| tctgcgcctg | ctggttccca | cccaatttgt | tggagccatc | ataggaaaag | aaggtgccac | 900 |
| cattcggaac | atcaccaaac | agacccagtc | taaaatcgat | gtccaccgta | aagaaaatgc | 960 |
| gggggctgct | gagaagtcga | ttactatcct | ctctactcct | gaaggcacct | ctgcggcttg | 1020 |
| taagtctatt | ctggagatta | tgcataagga | agctcaagat | ataaaattca | cagaagagat | 1080 |
| cccccttgaag | attttagctc | ataataactt | tgttggacgt | cttattggta | agaaggaag | 1140 |
| aaatcttaaa | aaaattgagc | aagacacaga | cactaaaatc | acgatatctc | cattgcagga | 1200 |
| attgacgctg | tataatccag | aacgcactat | tacagttaaa | ggcaatgttg | agacatgtgc | 1260 |
| caaagctgag | gaggagatca | tgaagaaaat | cagggagtct | tatgaaaatg | atattgcttc | 1320 |
| tatgaatctt | caagcacatt | taattcctgg | attaaatctg | aacgccttgg | gtctgttccc | 1380 |
| acccacttca | gggatgccac | ctcccacctc | agggccccct | tcagccatga | ctcctcccta | 1440 |
| cccgcagttt | gagcaatcag | aaacggagac | tgttcatcag | tttatcccag | ctctatcagt | 1500 |
| cggtgccatc | atcggcaagc | agggccagca | catcaagcag | cttcctcgct | tgctggagc | 1560 |
| ttcaattaag | attgctccag | cggaagcacc | agatgctaaa | gtgaggatgg | tgattatcac | 1620 |
| tggaccacca | gaggctcagt | tcaaggctca | gggaagaatt | tatggaaaaa | ttaaagaaga | 1680 |
| aaactttgtt | agtcctaaag | aagaggtgaa | acttgaagct | catatcagag | tgccatcctt | 1740 |
| tgctgctggc | agagttattg | gaaaggagg | caaaacggtg | aatgaacttc | agaatttgtc | 1800 |
| aagtgcagaa | gttgttgtcc | ctcgtgacca | gacacctgat | gagaatgacc | aagtggttgt | 1860 |
| caaaataact | ggtcacttct | atgcttgcca | ggttgcccag | agaaaaattc | aggaaattct | 1920 |
| gactcaggta | aagcagcacc | aacaacagaa | ggctctgcaa | agtggaccac | tcagtcaag | 1980 |
| acggaagtaa | aggctcagga | acagcccac | cacagaggca | gatgccaaac | caaagacaga | 2040 |
| ttgcttaacc | aacagatggg | cgctgacccc | ctatccagaa | tcacatgcac | agttttac | 2100 |
| ctagccagtt | gtttctgagg | accagcaac | ttttgaactc | ctgtctctgt | gagaatgtat | 2160 |
| actttatgct | ctctgaaatg | tatgacaccc | agctttaaaa | caaacaaaca | aacaaacaaa | 2220 |
| aaaagggtgg | gggaggggagg | gaaagagaag | agctctgcac | ttcccttgt | tgtagtctca | 2280 |

-continued

```
cagtataaca gatattctaa ttcttcttaa tattcccca taatgccaga aattggctta    2340
atgatgcttt cactaaattc atcaaataga ttgctcctaa atccaattgt taaaattgga   2400
tcagaataat tatcacagga acttaaatgt taagccatta gcatagaaaa actgttctca   2460
gttttatttt tacctaacac taacatgagt aacctaaggg aagtgctgaa tggtgttggc   2520 agggtatta aacgtgcatt tttactcaac tacctcaggt attcagtaat acaatgaaaa    2580
gcaaaattgt tccttttttt tgaaaatttt atatacttta taatgataga agtccaaccg   2640
ttttttaaaa aataaattta aaatttaaca gcaatcagct aacaggcaaa ttaagatttt   2700
tacttctggc tggtgacagt aaagctggaa aattaatttc agggtttttt gaggcttttg   2760
acacagttat tagttaaatc aaatgttcaa aaatacggag cagtgcctag tatctggaga   2820
gcagcactac catttattct ttcatttata gttgggaaag tttttgacgg tactaacaaa   2880
gtggtcgcag gagattttgg aacggctggt ttaaatggct tcaggagact tcagtttttt   2940
gtttagctac atgattgaat gcataataaa tgctttgtgc ttctgactat caatacctaa   3000
agaaagtgca tcagtgaaga gatgcaagac tttcaactga ctggcaaaaa gcaagcttta   3060
gcttgtctta taggatgctt agtttgccac tacacttcag accaatggga cagtcataga   3120
tggtgtgaca gtgtttaaac gcaacaaaag gctacatttc catggggcca gcactgtcat   3180
gagcctcact aagctatttt gaagattttt aagcactgat aaattaaaaa aaaaaaaaaa   3240
aaattagact ccaccttaag tagtaaagta taacaggatt tctgtatact gtgcaatcag   3300
ttctttgaaa aaaagtcaa aagatagaga atacaagaaa agttttnggg atataaatttg    3360 aatgactgtg aaaacatatg acctttgata acgaactcat ttgctcactc cttgacagca   3420
aagcccagta cgtacaattg tgttgggtgt gggtggtctc caaggccacg ctgctctctg   3480
aattgatttt ttgagtttttg gnttgnaaga tgatcacagn catgttacac tgatcttnaa   3540
ggacatatnt tataaccctt taaaaaaaaa atcccctgcc tcattcttat ttcgagatga   3600
atttcgatac agactagatg tctttctgaa gatcaattag acattntgaa aatgatttaa   3660
agtgttttcc ttaatgttct ctgaaaacaa gtttcttttg tagtttaac caaaaaagtg    3720 cccttttttgt cactggtttc tcctagcatt catgattttt ttttcacaca atgaattaaa   3780
attgctaaaa tcatggactg gctttctggt tggatttcag gtaagatgtg tttaaggcca   3840
gagcttttct cagtatttga tttttttccc caatatttga ttttttaaaa atatacacat   3900
aggagctgca tttaaaacct gctggtttaa attctgtcan atttcacttc tagccttta    3960 gtatggcnaa tcanaattta cttttactta agcatttgta atttggagta tctggtacta   4020
gctaagaaat aattcnataa ttgagttttg tactcnccaa anatgggtca ttcctcatgn   4080
ataatgtncc cccaatgcag cttcattttc caganaccctt gacgcaggat aaatttttttc   4140 atcatttagg tccccaaaaa aaaaaaaaaa aaaaaaaaa a                        4181
```

<210> SEQ ID NO 176
<211> LENGTH: 579
<212> TYPE: PRT
<213> ORGANISM: Homo sapiens

<400> SEQUENCE: 176

Met Asn Lys Leu Tyr Ile Gly Asn Leu Ser Glu Asn Ala Ala Pro Ser
                5                  10                  15

Asp Leu Glu Ser Ile Phe Lys Asp Ala Lys Ile Pro Val Ser Gly Pro
            20                  25                  30

```
Phe Leu Val Lys Thr Gly Tyr Ala Phe Val Asp Cys Pro Asp Glu Ser
         35                  40                  45

Trp Ala Leu Lys Ala Ile Glu Ala Leu Ser Gly Lys Ile Glu Leu His
     50                  55                  60

Gly Lys Pro Ile Glu Val Glu His Ser Val Pro Lys Arg Gln Arg Ile
 65                  70                  75                  80

Arg Lys Leu Gln Ile Arg Asn Ile Pro Pro His Leu Gln Trp Glu Val
                 85                  90                  95

Leu Asp Ser Leu Leu Val Gln Tyr Gly Val Val Glu Ser Cys Glu Gln
                100                 105                 110

Val Asn Thr Asp Ser Glu Thr Ala Val Val Asn Val Thr Tyr Ser Ser
            115                 120                 125

Lys Asp Gln Ala Arg Gln Ala Leu Asp Lys Leu Asn Gly Phe Gln Leu
130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
            195                 200                 205

Ala Ile Ile Gly Lys Glu Gly Ala Thr Ile Arg Asn Ile Thr Lys Gln
        210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Gln Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
```

```
                450              455              460
Lys Ala Gln Gly Arg Ile Tyr Gly Lys Ile Lys Glu Glu Asn Phe Val
465                  470              475              480

Ser Pro Lys Glu Glu Val Lys Leu Glu Ala His Ile Arg Val Pro Ser
                485              490              495

Phe Ala Ala Gly Arg Val Ile Gly Lys Gly Gly Lys Thr Val Asn Glu
                500              505              510

Leu Gln Asn Leu Ser Ser Ala Glu Val Val Pro Arg Asp Gln Thr
            515              520              525

Pro Asp Glu Asn Asp Gln Val Val Lys Ile Thr Gly His Phe Tyr
    530              535              540

Ala Cys Gln Val Ala Gln Arg Lys Ile Gln Glu Ile Leu Thr Gln Val
545                  550              555              560

Lys Gln His Gln Gln Gln Lys Ala Leu Gln Ser Gly Pro Pro Gln Ser
                565              570              575

Arg Arg Lys

<210> SEQ ID NO 177
<211> LENGTH: 401
<212> TYPE: DNA
<213> ORGANISM: Homo sapiens

<400> SEQUENCE: 177
atgccccgta aatgtcttca gtgttcttca gggtagttgg gatctcaaaa gatttggttc      60
agatccaaac aaatacacat tctgtgtttt agctcagtgt tttctaaaaa agaaactgc      120 cacacagcaa aaattgtttt actttgttgg acaaaccaaa tcagttctca aaaaatgacc     180
ggtgcttata aaagttataa aatatcgagt agctctaaaa caaaccacct gaccaagagg     240
gaagtgagct tgtgcttagt atttacattg gatgccagtt tgtaatcac tgacttatgt      300 gcaaactggt gcagaaattc tataaactct ttgctgtttt tgatacctgc tttttgtttc     360
attttgtttt gttttgtaaa aatgataaaa cttcagaaaa t                         401

<210> SEQ ID NO 178
<211> LENGTH: 561
<212> TYPE: DNA
<213> ORGANISM: Homo sapiens

<400> SEQUENCE: 178
acgcctttca agggtgtacg caaagcactc attgataccc ttttggatgg ctatgaaaca      60
gcccgctatg ggacaggggt ctttggccag aatgagtacc tacgctatca ggaggccctg     120
agtgagctgg ccactgcggt taaagcacga attgggagct ctcagcgaca tcaccagtca     180
gcagccaaag acctaactca gtcccctgag gtctccccaa caaccatcca ggtgacatac     240
ctcccctcca gtcagaagag taaacgtgcc aagcacttcc ttgaattgaa gagctttaag     300
gataactata cacattggag gagtactctg tgacggagct gaaggactct tgccgtagat     360
taagccagtc agttgcaatg tgcaagacag gctgcttgcc gggccgccct cggaacatct     420
ggcccagcag gcccagactg tatccatcca agttcccgtt gtatccagag ttcttagagc     480
ttgtgtctaa agggtaattc cccaaccctt ccttatgagc atttttagaa cattggctaa     540
gactattttc ccccagtagc g                                               561

<210> SEQ ID NO 179
<211> LENGTH: 521
<212> TYPE: DNA
```

<213> ORGANISM: Homo sapiens

<400> SEQUENCE: 179

| | | | | | |
|---|---|---|---|---|---|
| cccaacgcgt | ttgcaaatat | tcccctggta | gcctacttcc | ttaccccga | 60 |
| gatcgagcaa | tggcttcagg | acatgggttc | tcttctcctg | tgatcattca | agtgctcact | 120 |
| gcatgaagac | tggcttgtct | cagtgtttca | acctcaccag | ggctgtctct | tggtccacac | 180 |
| ctcgctccct | gttagtgccg | tatgacagcc | cccatcaaat | gaccttggcc | aagtcacggt | 240 |
| ttctctgtgg | tcaaggttgg | ttggctgatt | ggtggaaagt | agggtggacc | aaaggaggcc | 300 |
| acgtgagcag | tcagcaccag | ttctgcacca | gcagcgcctc | cgtcctagtg | ggtgttcctg | 360 |
| tttctcctgg | ccctgggtgg | gctagggcct | gattcgggaa | gatgcctttg | cagggagggg | 420 |
| aggataagtg | ggatctacca | attgattctg | gcaaaacaat | ttctaagatt | tttttgcttt | 480 |
| atgtgggaaa | cagatctaaa | tctcattttta | tgctgtattt | t | 521 |

<210> SEQ ID NO 180
<211> LENGTH: 417
<212> TYPE: DNA
<213> ORGANISM: Homo sapiens

<400> SEQUENCE: 180

| | | | | | |
|---|---|---|---|---|---|
| ggtggaattc | gccgaagatg | gcggaggtgc | aggtcctggt | gcttgatggt | cgaggccatc | 60 |
| tcctgggccg | cctggcggcc | atcgtggcta | acaggtact | gctgggccgg | aaggtggtgg | 120 |
| tcgtacgctg | tgaaggcatc | aacatttctg | gcaatttcta | cagaaacaag | ttgaagtacc | 180 |
| tggctttcct | ccgcaagcgg | atgaacacca | acccttcccg | aggcccctac | cacttccggg | 240 |
| cccccagccg | catcttctgg | cggaccgtgc | gaggtatgct | gccccacaaa | accagcgag | 300 |
| gccaggccgc | tctggaccgt | ctcaaggtgt | ttgacggcat | cccaccgccc | tacgacaaga | 360 |
| aaaagcggat | ggtggttcct | gctgccctca | aggtcgtgcg | tctgaagcct | acaagaa | 417 |

<210> SEQ ID NO 181
<211> LENGTH: 283
<212> TYPE: DNA
<213> ORGANISM: Homo sapiens
<220> FEATURE:
<221> NAME/KEY: unsure
<222> LOCATION: (35)
<223> OTHER INFORMATION: n=A,T,C or G

<400> SEQUENCE: 181

| | | | | | |
|---|---|---|---|---|---|
| gatttcttct | aaataggatg | taaaacttct | ttcanattac | tcttcctcag | tcctgcctgc | 60 |
| caagaactca | agtgtaactg | tgataaaata | acctttccca | ggtatattgg | caggtatgtg | 120 |
| tgtaatctca | gaatacacag | gtgacataga | tatgatatga | caactggtaa | tggtggattc | 180 |
| atttacattg | tttacacttc | tatgaccagg | ccttaaggga | aggtcagttt | tttaaaaaac | 240 |
| caagtagtgt | cttcctacct | atctccagat | acatgtcaaa | aaa | | 283 |

<210> SEQ ID NO 182
<211> LENGTH: 401
<212> TYPE: DNA
<213> ORGANISM: Homo sapiens

<400> SEQUENCE: 182

| | | | | | |
|---|---|---|---|---|---|
| atattcttgc | tgcttatgca | gctgacattg | ttgccctccc | taaagcaacc | aagtagcctt | 60 |
| tatttcccac | agtgaaagaa | aacgctggcc | tatcagttac | attacaaaag | gcagatttca | 120 |
| agaggattga | gtaagtagtt | ggatggcttt | cataaaaaca | agaattcaag | aagaggattc | 180 |

```
atgctttaag aaacatttgt tatacattcc tcacaaatta tacctgggat aaaaactatg     240
tagcaggcag tgtgtttcc ttccatgtct ctctgcacta cctgcagtgt gtcctctgag      300
gctgcaagtc tgtcctatct gaattcccag cagaagcact aagaagctcc accctatcac    360
ctagcagata aaactatggg gaaaacttaa atctgtgcat a                         401
```

<210> SEQ ID NO 183
<211> LENGTH: 366
<212> TYPE: DNA
<213> ORGANISM: Homo sapiens
<220> FEATURE:
<221> NAME/KEY: unsure
<222> LOCATION: (325)
<223> OTHER INFORMATION: n=A,T,C or G

<400> SEQUENCE: 183

```
accgtgtcca gtttttaga acccttgtta gccagaccga ggtgtcctgg tcaccgtttc      60
accatcatgc tttgatgttc cctgtctttt ctctcttctg ctctcaagag caaaggttaa    120
tttaaggaca aagatgaagt cactgtaaac taatctgtca ttgttttttac cttcctttc    180 tttttcagtg cagaaattaa agtaagtat aaagcaccgt gattgggagt gttttgcgt      240 gtgtcggaat cactggtaaa tgttggctga aacaatccc tccccttgca cttgtgaaaa    300
cactttgagc gctttaagag attanccctga gaaataatta aatatctttt ctcttcaaaa  360
aaaaaa                                                                366
```

<210> SEQ ID NO 184
<211> LENGTH: 370
<212> TYPE: DNA
<213> ORGANISM: Homo sapiens

<400> SEQUENCE: 184

```
tcttacttca aagaaaaat aaacataaa aataagttgc tggttcctaa caggaaaaat      60
tttaataatt gtactgagag aaactgctta cgtacacatt gcagatcaaa tatttggagt    120
taaaatgtta gtctacatag atgggtgatt gtaactttat tgccattaaa agatttcaaa   180
ttgcattcat gcttctgtgt acacataatg aaaaatgggc aaataatgaa gatctctcct    240
tcagtctgct ctgtttaatt ctgctgtctg ctcttctcta atgctgcgtc cctaattgta    300
cacagtttag tgatatctag gagtataaag ttgtcgccca tcaataaaaa tcacaaagtt    360
ggtttaaaaa                                                           370
```

<210> SEQ ID NO 185
<211> LENGTH: 107
<212> TYPE: DNA
<213> ORGANISM: Homo sapiens

<400> SEQUENCE: 185

```
ctcatattat tttccttttg agaaattgga aactctttct gttgctatta tattaataaa    60
gttggtgttt attttctggt agtcaccttc cccatttaaa aaaaaaa                  107
```

<210> SEQ ID NO 186
<211> LENGTH: 309
<212> TYPE: DNA
<213> ORGANISM: Homo sapiens

<400> SEQUENCE: 186

```
gaaaggatgg ctctggttgc cacagagctg ggacttcatg ttcttctaga gagggccaca    60
```

| | |
|---|---|
| agagggccac agggtggcc gggagttgtc agctgatgcc tgctgagagg caggaattgt | 120 |
| gccagtgagt gacagtcatg agggagtgtc tcttcttggg gaggaaagaa ggtagagcct | 180 |
| ttctgtctga atgaaaggcc aaggctacag tacaggggccc cgcccagcc aggtgttaa | 240 |
| tgcccacgta gtggaggcct ctggcagatc ctgcattcca aggtcactgg actgtacgtt | 300 |
| tttatggtt | 309 |

<210> SEQ ID NO 187
<211> LENGTH: 477
<212> TYPE: DNA
<213> ORGANISM: Homo sapiens

<400> SEQUENCE: 187

| | |
|---|---|
| ttcagtccta gcaagaagcg agaattctga gatcctccag aaagtcgagc agcacccacc | 60 |
| tccaacctcg ggccagtgtc ttcaggcttt actggggacc tgcgagctgg cctaatgtgg | 120 |
| tggcctgcaa gccaggccat ccctgggcgc acagacgag ctccgagcca ggtcaggctt | 180 |
| cggaggccac aagctcagcc tcaggcccag gcactgattg tggcagaggg gccactaccc | 240 |
| aaggtctagc taggcccaag acctagttac ccagacagtg agaagcccct ggaaggcaga | 300 |
| aaagttggga gcatggcaga cagggaaggg aaacattttc agggaaaaga catgtatcac | 360 |
| atgtcttcag aagcaagtca ggtttcatgt aaccgagtgt cctcttgcgt gtccaaaagt | 420 |
| agcccagggc tgtagcacag gcttcacagt gattttgtgt tcagccgtga gtcacac | 477 |

<210> SEQ ID NO 188
<211> LENGTH: 220
<212> TYPE: DNA
<213> ORGANISM: Homo sapiens

<400> SEQUENCE: 188

| | |
|---|---|
| taaatatggt agatattaat attcctctta gatgaccagt gattccaatt gtcccaagtt | 60 |
| ttaaataagt accctgtgag tatgagataa attagtgaca atcagaacaa gtttcagtat | 120 |
| cagatgttca agaggaagtt gctattgcat tgatttaat atttgtacat aaacactgat | 180 |
| ttttttgagc attattttgt atttgttgta ctttaatacc | 220 |

<210> SEQ ID NO 189
<211> LENGTH: 417
<212> TYPE: DNA
<213> ORGANISM: Homo sapiens
<220> FEATURE:
<221> NAME/KEY: unsure
<222> LOCATION: (76)
<223> OTHER INFORMATION: n=A,T,C or G
<221> NAME/KEY: unsure
<222> LOCATION: (77)
<223> OTHER INFORMATION: n=A,T,C or G

<400> SEQUENCE: 189

| | |
|---|---|
| accatcttga cagaggatac atgctcccaa aacgtttgtt accacactta aaaatcactg | 60 |
| ccatcattaa gcatcnnttt caaaattata gccattcatg atttactttt tccagatgac | 120 |
| tatcattatt ctagtccttt gaatttgtaa ggggaaaaaa acaaaaaca aaaacttacg | 180 |
| atgcactttt ctccagcaca tcagatttca aattgaaaat taaagacatg ctatggtaat | 240 |
| gcacttgcta gtactacaca ctttgtacaa caaaaaacag aggcaagaaa caacggaaag | 300 |
| agaaaagcct tcctttgttg gcccttaaac tgagtcaaga tctgaaatgt agagatgatc | 360 |
| tctgacgata cctgtatgtt cttattgtgt aaataaaatt gctggtatga aatgaca | 417 |

<210> SEQ ID NO 190
<211> LENGTH: 497
<212> TYPE: DNA
<213> ORGANISM: Homo sapiens

<400> SEQUENCE: 190

| gcactgcggc | gctctcccgt | cccgcggtgg | ttgctgctgc | tgccgctgct | gctgggcctg | 60 |
| aacgcaggag | ctgtcattga | ctggcccaca | gaggagggca | aggaagtatg | ggattatgtg | 120 |
| acggtccgca | aggatgccta | catgttctgg | tggctctatt | atgccaccaa | ctcctgcaag | 180 |
| aacttctcag | aactgcccct | ggtcatgtgg | cttcagggcg | gtccaggcgg | ttctagcact | 240 |
| ggatttggaa | actttgagga | aattgggccc | cttgacagtg | atctcaaacc | acggaaaacc | 300 |
| acctggctcc | aggctgccag | tctcctattt | gtggataatc | ccgtgggcac | tgggttcagt | 360 |
| tatgtgaatg | gtagtggtgc | ctatgccaag | gacctggcta | tggtggcttc | agacatgatg | 420 |
| gttctcctga | agaccttctt | cagttgccac | aaagaattcc | agacagttcc | attctacatt | 480 |
| ttctcagagt | cctatgg    |            |            |            |            | 497 |

<210> SEQ ID NO 191
<211> LENGTH: 175
<212> TYPE: DNA
<213> ORGANISM: Homo sapiens

<400> SEQUENCE: 191

| atgttgaata | ttttgcttat | taactttgtt | tattgtcttc | tccctcgatt | agaatattag | 60 |
| ctacttgagt | acaaggattt | gagcctgtta | cattcactgc | tgaattttag | gctcctggaa | 120 |
| gatacccagc | attcaataga | gaccacacaa | taaatatatg | tcaaataaaa | aaaaa      | 175 |

<210> SEQ ID NO 192
<211> LENGTH: 526
<212> TYPE: DNA
<213> ORGANISM: Homo sapiens

<400> SEQUENCE: 192

| agtaaacatt | attattttt  | ttatatttgc | aaaggaaaca | tatctaatcc | ttcctataga | 60 |
| aagaacagta | ttgctgtaat | tccttttctt | ttcttcctca | tttcctctgc | cccttaaaag | 120 |
| attgaagaaa | gagaaacttg | tcaactcata | tccacgttat | ctagcaaagt | acataagaat | 180 |
| ctatcactaa | gtaatgtatc | cttcagaatg | tgttggttta | ccagtgacac | cccatattca | 240 |
| tcacaaaatt | aaagcaagaa | gtccatagta | atttatttgc | taatagtgga | ttttaatgc  | 300 |
| tcagagtttc | tgaggtcaaa | ttttatcttt | tcacttacaa | gctctatgat | cttaaataat | 360 |
| ttacttaatg | tattttggtg | tattttcctc | aaattaatat | tggtgttcaa | gactatatct | 420 |
| aattcctctg | atcactttga | gaaacaaact | tttattaaat | gtaaggcact | tttctatgaa | 480 |
| ttttaaatat | aaaaataaat | attgttctga | ttattactga | aaaaaa     |            | 526 |

<210> SEQ ID NO 193
<211> LENGTH: 553
<212> TYPE: DNA
<213> ORGANISM: Homo sapiens
<220> FEATURE:
<221> NAME/KEY: unsure
<222> LOCATION: (290)
<223> OTHER INFORMATION: n=A,T,C or G
<221> NAME/KEY: unsure
<222> LOCATION: (300)
<223> OTHER INFORMATION: n=A,T,C or G
<221> NAME/KEY: unsure

```
<222> LOCATION: (411)
<223> OTHER INFORMATION: n=A,T,C or G
<221> NAME/KEY: unsure
<222> LOCATION: (441)
<223> OTHER INFORMATION: n=A,T,C or G

<400> SEQUENCE: 193
tccattgtgg tggaattcgc tctctggtaa aggcgtgcag gtgttggccg cggcctctga    60
gctgggatga gccgtgctcc cggtggaagc aagggagccc agccggagcc atggccagta   120
cagtggtagc agttggactg accattgctg ctgcaggatt tgcaggccgt tacgttttgc   180
aagccatgaa gcatatggag cctcaagtaa aacaagtttt tcaaagccta ccaaaatctg   240
ccttcagtgg tggctattat agaggtgggt ttgaacccaa aatgacaaan cgggaagcan   300
cattaatact aggtgtaagc cctactgcca ataagggaa aataagagat gctcatcgac    360
gaattatgct tttaaatcat cctgacaaag gaggatctcc ttatatagca nccaaaatca   420
atgaagctaa agatttacta naaggtcaag ctaaaaaatg aagtaaatgt atgatgaatt   480
ttaagttcgt attagtttat gtatatgagt actaagtttt tataataaaa tgcctcagag   540
ctacaatttt aaa                                                      553

<210> SEQ ID NO 194
<211> LENGTH: 320
<212> TYPE: DNA
<213> ORGANISM: Homo sapiens

<400> SEQUENCE: 194
cccttcccaa tccatcagta aagacccat ctgccttgtc catgccgttt cccaacaggg     60
atgtcacttg atatgagaat ctcaaatctc aatgccttat aagcattcct tcctgtgtcc   120
attaagactc tgataattgt ctcccctcca taggaatttc tcccaggaaa gaaatatatc   180
cccatctccg tttcatatca gaactaccgt ccccgatatt cccttcagag agattaaaga   240
ccagaaaaaa gtgagcctct tcatctgcac ctgtaatagt ttcagttcct attttcttcc   300
attgacccat atttataccct                                              320

<210> SEQ ID NO 195
<211> LENGTH: 320
<212> TYPE: DNA
<213> ORGANISM: Homo sapiens
<220> FEATURE:
<221> NAME/KEY: unsure
<222> LOCATION: (203)
<223> OTHER INFORMATION: n=A,T,C or G
<221> NAME/KEY: unsure
<222> LOCATION: (218)
<223> OTHER INFORMATION: n=A,T,C or G

<400> SEQUENCE: 195
aagcatgacc tgggaaatg gtcagacctt gtattgtgtt tttggccttg aaagtagcaa     60
gtgaccagaa tctgccatgg caacaggctt taaaaagac ccttaaaaag acactgtctc    120
aactgtggtg ttagcaccag ccagctctct gtacatttgc tagcttgtag ttttctaaga   180
ctgagtaaac ttcttatttt tanaaggggg aggctggntt gtaactttcc ttgtacttaa   240
ttgggtaaaa gtcttttcca caaaccacca tctattttgt gaactttgtt agtcatcttt   300
tatttggtaa attatgaact                                               320

<210> SEQ ID NO 196
<211> LENGTH: 357
<212> TYPE: DNA
```

```
<213> ORGANISM: Homo sapiens
<220> FEATURE:
<221> NAME/KEY: unsure
<222> LOCATION: (36)
<223> OTHER INFORMATION: n=A,T,C or G

<400> SEQUENCE: 196
atataaaata atacgaaact ttaaaaagca ttggantgtc agtatgttga atcagtagtt      60
tcactttaac tgtaaacaat ttcttaggac accatttggg ctagtttctg tgtaagtgta     120
aatactacaa aaacttattt atactgttct tatgtcattt gttatattca tagatttata     180
tgatgatatg acatctggct aaaaagaaat tattgcaaaa ctaaccacta tgtacttttt     240
tataaatact gtatggacaa aaaatggcat tttttatatt aaattgttta gctctggcaa     300
aaaaaaaaaa ttttaagagc tggtactaat aaaggattat tatgactgtt aaaaaa         357

<210> SEQ ID NO 197
<211> LENGTH: 565
<212> TYPE: DNA
<213> ORGANISM: Homo sapiens
<220> FEATURE:
<221> NAME/KEY: unsure
<222> LOCATION: (27)
<223> OTHER INFORMATION: n=A,T,C or G

<400> SEQUENCE: 197
tcagctgagt accatcagga tatttanccc tttaagtgct gttttgggag tagaaaacta      60
aagcaacaat acttcctctt gacagctttg attggaatgg ggttattaga tcattcacct     120
tggtcctaca cttttagga tgcttggtga acataacacc acttataatg aacatccctg      180
gttcctatat tttgggctat gtgggtagga attgttactt gttactgcag cagcagccct     240
agaaagtaag cccagggctt cagatctaag ttagtccaaa agctaaatga tttaaagtca     300
agttgtaatg ctaggcataa gcactctata atacattaaa ttataggccg agcaattagg     360
gaatgtttct gaaacattaa acttgtattt atgtcactaa aattctaaca caaacttaaa     420
aaatgtgtct catacatatg ctgtactagg cttcatcatg catttctaaa tttgtgtatg     480
atttgaatat atgaaagaat ttatacaaga gtgttattta aaattattaa aaataaatgt     540
atataatttg tacctattgt aaaaa                                           565

<210> SEQ ID NO 198
<211> LENGTH: 484
<212> TYPE: DNA
<213> ORGANISM: Homo sapiens

<400> SEQUENCE: 198
tatgtaagta ttggtgtctg ctttaaaaaa ggagacccag acttcacctg tccttttaa       60
acatttgaga acagtgttac tctgagcagt tgggccacct tcaccttatc cgacagctga     120
ctgttggatg tgtccattgt cgccagtttg gctgttgccc ggacaggaca ggacctccat     180
tgggcgcagc agcaggtggc agggtgtgg cttgaggtgg gtggcagcgt ctggtcctcc      240
tctctggtgc tttctgagag ggtctctaaa gcagagtgtg gttggcctgg gggaaggcag     300
agcacgtatt tctcccctct agtacctctg catttgtgag tgttccctct ggctttctga     360
agggcagcag actcttgagt atactgcaga ggacatgctt tatcagtagg tcctgagggc     420
tccaggggct caactgacca agtaacacag aagttggggt atgtggccta tttgggtcgg     480
aaac                                                                  484
```

```
<210> SEQ ID NO 199
<211> LENGTH: 429
<212> TYPE: DNA
<213> ORGANISM: Homo sapiens
<220> FEATURE:
<221> NAME/KEY: unsure
<222> LOCATION: (77)
<223> OTHER INFORMATION: n=A,T,C or G
<221> NAME/KEY: unsure
<222> LOCATION: (88)
<223> OTHER INFORMATION: n=A,T,C or G
<221> NAME/KEY: unsure
<222> LOCATION: (134)
<223> OTHER INFORMATION: n=A,T,C or G
<221> NAME/KEY: unsure
<222> LOCATION: (151)
<223> OTHER INFORMATION: n=A,T,C or G
<221> NAME/KEY: unsure
<222> LOCATION: (189)
<223> OTHER INFORMATION: n=A,T,C or G
<221> NAME/KEY: unsure
<222> LOCATION: (227)
<223> OTHER INFORMATION: n=A,T,C or G
<221> NAME/KEY: unsure
<222> LOCATION: (274)
<223> OTHER INFORMATION: n=A,T,C or G
<221> NAME/KEY: unsure
<222> LOCATION: (319)
<223> OTHER INFORMATION: n=A,T,C or G

<400> SEQUENCE: 199
gcttatgttt tttgttttaa cttttgtttt ttaacattta gaatattaca ttttgtatta      60
tacagtacct ttctcanaca ttttgtanaa ttcatttcgg cagctcacta ggattttgct     120
gaacattaaa aagngtgata gcgatattag ngccaatcaa atggaaaaaa ggtagtctta     180
ataaacaana cacaacgttt ttatacaaca tactttaaaa tattaanaaa actccttaat     240
attgtttcct attaagtatt attctttggg caanattttc tgatgctttt gattttctct     300
caatttagca tttgctttng gttttttct ctatttagca ttctgttaag gcacaaaaac      360
tatgtactgt atgggaaatg ttgtaaatat taccttttcc acattttaaa cagacaactt     420
tgaatccaa                                                             429

<210> SEQ ID NO 200
<211> LENGTH: 279
<212> TYPE: DNA
<213> ORGANISM: Homo sapiens

<400> SEQUENCE: 200 gctttttga ggaattacag ggaagctcct ggaattgtac atggatatct ttatccctag       60
ggggaaatca aggagctggg caccctaat tctttatgga agtgtttaaa actattttaa      120
ttttattaca agtattacta gagtagtggt tctactctaa gatttcaaaa gtgcatttaa     180
aatcatacat gttcccgcct gcaaatatat tgttattttg gtggagaaaa aaatagtata     240
ttctacataa aaaattaaag atattaacta agaaaaaaa                            279

<210> SEQ ID NO 201
<211> LENGTH: 569
<212> TYPE: DNA
<213> ORGANISM: Homo sapiens

<400> SEQUENCE: 201
taggtcagta tttttagaaa ctcttaatag ctcatactct tgataccaaa agcagccctg      60
attgttaaag cacacacctg cacaagaagc agtgatggtt gcatttacat ttcctgggtg     120
cacaaaaaaa aattctcaaa aagcaaggac ttacgctttt tgcaaagcct tgagaagtt     180
```

```
actggatcat aggaagctta taacaagaat ggaagattct taaataactc actttctttg     240
gtatccagta acagtagatg ttcaaaatat gtagctgatt aataccagca ttgtgaacgc     300
tgtacaacct tgtggttatt actaagcaag ttactactag cttctgaaaa gtagcttcat     360
aattaatgtt atttatacac tgccttccat gactttact ttgccctaag ctaatctcca      420
aaatctgaaa tgctactcca atcagaaa aaaggggga ggtggaatta tatttcctgt        480
gattttaaga gtacagagaa tcatgcacat ctctgattag ttcatatatg tctagtgtgt     540
aataaaagtc aaagatgaac tctcaaaaa                                        569

<210> SEQ ID NO 202
<211> LENGTH: 501
<212> TYPE: DNA
<213> ORGANISM: Homo sapiens

<400> SEQUENCE: 202
attaataggc ttaataattg ttggcaagga tcctttgct ttctttggca tgcaagctcc       60
tagcatctgg cagtggggcc aagaaaataa ggtttatgca tgtatgatgg ttttcttctt     120
gagcaacatg attgagaacc agtgtatgtc aacaggtgca tttgagataa ctttaaatga    180
tgtacctgtg tggtctaagc tggaatctgg tcaccttcca tccatgcaac aacttgttca    240
aattcttgac aatgaaatga agctcaatgt gcatatggat tcaatcccac accatcgatc    300
atagcaccac ctatcagcac tgaaaactct tttgcattaa gggatcattg caagagcagc    360
gtgactgaca ttatgaaggc ctgtactgaa gacagcaagc tgttagtaca gaccagatgc    420
tttcttggca ggctcgttgt acctcttgga aaacctcaat gcaagatagt gtttcagtgc    480
tggcatattt tggaattctg c                                               501

<210> SEQ ID NO 203
<211> LENGTH: 261
<212> TYPE: DNA
<213> ORGANISM: Homo sapiens
<220> FEATURE:
<221> NAME/KEY: unsure
<222> LOCATION: (36)
<223> OTHER INFORMATION: n=A,T,C or G
<221> NAME/KEY: unsure
<222> LOCATION: (96)
<223> OTHER INFORMATION: n=A,T,C or G

<400> SEQUENCE: 203
gacaagctcc tggtcttgag atgtcttctc gttaangaga tgggcctttt ggaggtaaag      60
gataaaatga atgagttctg tcatgattca ctattntata acttgcatga cctttactgt    120
gttagctctt tgaatgttct tgaaatttta gactttcttt gtaaacaaat gatatgtcct    180
tatcattgta taaaagctgt tatgtgcaac agtgtggaga ttccttgtct gatttaataa    240
aatacttaaa cactgaaaaa a                                               261

<210> SEQ ID NO 204
<211> LENGTH: 421
<212> TYPE: DNA
<213> ORGANISM: Homo sapiens

<400> SEQUENCE: 204
agcatctttt ctacaacgtt aaaattgcag aagtagctta tcattaaaaa acaacaacaa      60
caacaataac aataaatcct aagtgtaaat cagttattca accccctacc aaggatatca    120
gcctgttttt tccctttttt ctcctgggaa taattgtggg cttcttccca aatttctaca    180
```

```
gcctctttcc tcttctcatg cttgagcttc cctgtttgca cgcatgcgtg tgcaggactg    240
gcttgtgtgc ttggactcgg ctccaggtgg aagcatgctt tcccttgtta ctgttggaga    300
aactcaaacc ttcaagccct aggtgtagcc attttgtcaa gtcatcaact gtattttgt     360 actggcatta acaaaaaaag aagataaaat attgtaccat taaactttaa taaaacttta    420
a                                                                     421

<210> SEQ ID NO 205
<211> LENGTH: 460
<212> TYPE: DNA
<213> ORGANISM: Homo sapiens

<400> SEQUENCE: 205
tactctcaca atgaaggacc tggaatgaaa atctgtgtc taaacaagtc ctctttagat      60
tttagtgcaa atccagagcc agcgtcggtt gcctcgagta attctttcat gggtaccttt    120
ggaaaagctc tcaggagacc tcacctagat gcctattcaa gctttggaca gccatcagat    180
tgtcagccaa gagccttta tttgaaagct cattcttccc cagacttgga ctctgggtca    240
gaggaagatg ggaaagaaag gacagatttt caggaagaaa atcacatttg tacctttaaa    300
cagactttag aaaactacag gactccaaat tttcagtctt atgacttgga cacatagact    360
gaatgagacc aaaggaaaag cttaacatac tacctcaagg tgaactttta tttaaaagag    420
agagaatctt atgttttta aatggagtta tgaattttaa                            460

<210> SEQ ID NO 206
<211> LENGTH: 481
<212> TYPE: DNA
<213> ORGANISM: Homo sapiens

<400> SEQUENCE: 206
tgtggtggaa ttcgggacgc ccccagaccc tgactttttc ctgcgtgggc cgtctcctcc     60
tgcggaagca gtgacctctg acccctggtg accttcgctt tgagtgcctt ttgaacgctg    120
gtcccgcggg acttggtttt tcaagctct gtctgtccaa agacgctccg gtcgaggtcc     180
cgcctgccct gggtggatac ttgaacccca gacgccctc tgtgctgctg tgtccggagg    240
cggccttccc atctgcctgc ccacccggag ctctttccgc cggcgcaggg tcccaagccc    300
acctcccgcc ctcagtcctg cggtgtgcgt ctgggcacgt cctgcacaca caatgcaagt    360
cctggcctcc gcgcccgccc gcccacgcga gccgtacccg ccgccaactc tgttatttat    420
ggtgtgaccc cctggaggtg ccctcggccc accggggcta tttattgttt aatttatttg    480
t                                                                     481

<210> SEQ ID NO 207
<211> LENGTH: 605
<212> TYPE: DNA
<213> ORGANISM: Homo sapiens

<400> SEQUENCE: 207 acccttttg gattcagggc tcctcacaat taaaatgagt gtaatgaaac aagtgaaaa       60 tatagaagca tcccttttgta tactgttttg ctacttacag tgtacttggc attgctttat    120
ctcactggat tctcacggta ggatttctga gatcttaatc taagctccaa agttgtctac    180 tttttttgatc ctagggtgct ccttttgttt tacagagcag ggtcacttga tttgctagct    240
ggtggcagaa ttggcaccat tacccaggtc tgactgacca ccagtcagag gcactttatt    300
```

```
tgtatcatga aatgatttga aatcattgta aagcagcgaa gtctgataat gaatgccagc    360
tttccttgtg ctttgataac aaagactcca aatattctgg agaacctgga taaaagtttg    420
aagggctaga ttgggatttg aagacaaaat tgtaggaaat cttacatttt tgcaataaca    480
aacattaatg aaagcaaaac attataaaag taattttaat tcaccacata cttatcaatt    540
tcttgatgct tccaaatgac atctaccaga tatggttttg tggacatctt tttctgttta    600
cataa                                                                605
```

<210> SEQ ID NO 208
<211> LENGTH: 655
<212> TYPE: DNA
<213> ORGANISM: Homo sapiens

<400> SEQUENCE: 208

```
ggcgttgttc tggattcccg tcgtaactta aagggaaact tcacaatgt ccggagccct     60 tgatgtcctg caaatgaagg aggaggatgt ccttaagttc cttgcagcag gaacccactt    120
aggtggcacc aatcttgact tccagatgga acagtacatc tataaaagga aaagtgatgg    180
catctatatc ataaatctca agaggacctg ggagaagctt ctgctggcag ctcgtgcaat    240
tgttgccatt gaaaaccctg ctgatgtcag tgttatatcc tccaggaata ctggccagag    300
ggctgtgctg aagtttgctg ctgccactgg agccactcca attgctggcc gcttcactcc    360
tggaaccttc actaaccaga tccaggcagc cttcgggag ccacggcttc ttgtggttac     420
tgaccccagg gctgaccacc agcctctcac ggaggcatct tatgttaacc tacctaccat    480
tgcgctgtgt aacacagatt ctcctctgcg ctatgtggac attgccatcc catgcaacaa    540
caagggagct cactcagtgg gtttgatgtg gtggatgctg gctcgggaag ttctgcgcat    600
gcgtggcacc atttcccgtg aacacccatg ggaggtcatg cctgatctgt acttc         655
```

<210> SEQ ID NO 209
<211> LENGTH: 621
<212> TYPE: DNA
<213> ORGANISM: Homo sapiens

<400> SEQUENCE: 209

```
catttagaac atggttatca tccaagacta ctctaccctg caacattgaa ctcccaagag     60
caaatccaca ttcctcttga gttctgcagc ttctgtgtaa atagggcagc tgtcgtctat    120
gccgtagaat cacatgatct gaggaccatt catggaagct gctaaatagc ctagtctggg    180
gagtcttcca taaagttttg catggagcaa acaaacagga ttaaactagg tttggttcct    240
tcagccctct aaaagcatag ggcttagcct gcaggcttcc ttgggctttc tctgtgtgtg    300
tagttttgta aacactatag catctgttaa gatccagtgt ccatggaaac cttcccacat    360
gccgtgactc tggactatat cagttttttgg aaagcagggt tcctctgcct gctaacaagc    420
ccacgtggac cagtctgaat gtctttcctt tacacctatg tttttaaata gtcaaacttc    480
aagaaacaat ctaaacaagt ttctgttgca tatgtgtttg tgaacttgta tttgtattta    540
gtaggcttct atattgcatt taacttgttt ttgtaactcc tgattcttcc ttttcggata    600
ctattgatga ataaagaaat t                                              621
```

<210> SEQ ID NO 210
<211> LENGTH: 533
<212> TYPE: DNA
<213> ORGANISM: Homo sapiens
<220> FEATURE:
<221> NAME/KEY: unsure
<222> LOCATION: (20)
<223> OTHER INFORMATION: n=A,T,C or G
<221> NAME/KEY: unsure
<222> LOCATION: (21)
<223> OTHER INFORMATION: n=A,T,C or G
<221> NAME/KEY: unsure
<222> LOCATION: (61)
<223> OTHER INFORMATION: n=A,T,C or G

<400> SEQUENCE: 210

```
cgccttgggg agccggcggn ngagtccggg acgtggagac ccgggtccc ggcagccggg      60
nggcccgcgg gcccagggtg gggatgcacc gccgcgggt gggagctggc gccatcgcca     120
agaagaaact tgcagaggcc aagtataagg agcgagggac ggtcttggct gaggaccagc    180
tagcccagat gtcaaagcag ttggacatgt tcaagaccaa cctggaggaa tttgccagca    240
aacacaagca ggagatccgg aagaatcctg agttccgtgt gcagttccag gacatgtgtg    300
caaccattgg cgtggatccg ctggcctctg aaaaggatt ttggtctgag atgctgggcg     360
tgggggactt ctattacgaa ctaggtgtcc aaattatcga agtgtgcctg cgctgaagc     420
atcggaatgg aggtctgata actttggagg aactacatca acaggtgttg aagggaaggg    480
gcaagttcgc ccaggatgtc agtcaagatg acctgatcag agccatcaag aaa            533
```

<210> SEQ ID NO 211
<211> LENGTH: 451
<212> TYPE: DNA
<213> ORGANISM: Homo sapiens

<400> SEQUENCE: 211

```
ttagcttgag ccgagaacga ggcgagaaag ctggagaccg aggagaccgc ctagagcgga     60
gtgaacgggg aggggaccgt ggggaccggc ttgatcgtgc gcggacacct gctaccaagc    120
ggagcttcag caaggaagtg gaggagcgga gtagagaacg gccctcccag cctgaggggc    180
tgcgcaaggc agctagcctc acggaggatc gggaccgtgg gcgggatgcc gtgaagcgag    240
aagctgccct accccagtg agcccctga aggcggctct ctctgaggag gagttagaga       300
agaaatccaa ggctatcatt gaggaatatc tccatctcaa tgacatgaaa gaggcagtcc    360
agtgcgtgca ggagctggcc tcaccctcct tgctcttcat cttgtacgg catggtgtcg     420
agtctacgct ggagcgcagt gccattgctc g                                    451
```

<210> SEQ ID NO 212
<211> LENGTH: 471
<212> TYPE: DNA
<213> ORGANISM: Homo sapiens
<220> FEATURE:
<221> NAME/KEY: unsure
<222> LOCATION: (54)
<223> OTHER INFORMATION: n=A,T,C or G

<400> SEQUENCE: 212

```
gtgattattc ttgatcaggg agaagatcat ttagatttgt tttgcattcc ttanaatgga     60
gggcaacatt ccacagctgc cctggctgtg atgagtgtcc ttgcagggc cggagtagga    120
gcactggggt gggggcggaa ttggggttac tcgatgtaag ggattccttg ttgttgtgtt    180
gagatccagt gcagttgtga tttctgtgga tcccagcttg gttccaggaa ttttgtgtga    240
ttggcttaaa tccagttttc aatcttcgac agctgggctg gaacgtgaac tcagtagctg    300
aacctgtctg acccggtcac gttcttggat cctcagaact ctttgctctt gtcgggtgg     360
gggtgggaac tcacgtgggg agcggtggct gagaaaatgt aaggattctg gaatacatat    420
```
tccatgggac tttccttccc tctcctgctt cctcttttcc tgctccctaa c        471

<210> SEQ ID NO 213
<211> LENGTH: 511
<212> TYPE: DNA
<213> ORGANISM: Homo sapiens
<220> FEATURE:
<221> NAME/KEY: unsure
<222> LOCATION: (27)
<223> OTHER INFORMATION: n=A,T,C or G
<221> NAME/KEY: unsure
<222> LOCATION: (63)
<223> OTHER INFORMATION: n=A,T,C or G
<221> NAME/KEY: unsure
<222> LOCATION: (337)
<223> OTHER INFORMATION: n=A,T,C or G
<221> NAME/KEY: unsure
<222> LOCATION: (442)
<223> OTHER INFORMATION: n=A,T,C or G

<400> SEQUENCE: 213
ctaattagaa acttgctgta cttttttnttt tcttttaggg gtcaaggacc ctctttatag    60
ctnccatttg cctacaataa attattgcag cagtttgcaa tactaaaata tttttttatag   120 actttatatt tttccttttg ataaagggat gctgcatagt agagttggtg taattaaact    180
atctcagccg tttccctgct ttcccttctg ctccatatgc ctcattgtcc ttccagggag    240
ctcttttaat cttaaagttc tacatttcat gctcttagtc aaattctgtt acctttttaa    300
taactcttcc cactgcatat ttccatcttg aattggnggt tctaaattct gaaactgtag    360
ttgagataca gctatttaat atttctggga gatgtgcatc cctcttcttt gtggttgccc    420
aaggttgttt tgcgtaactg anactccttg atatgcttca gagaatttag gcaaacactg    480
gccatggccg tgggagtact gggagtaaaa t                                   511

<210> SEQ ID NO 214
<211> LENGTH: 521
<212> TYPE: DNA
<213> ORGANISM: Homo sapiens

<400> SEQUENCE: 214
agcattgcca ataatccct aattttccac taaaaatata atgaaatgat gttaagcttt     60
ttgaaaagtt taggttaaac ctactgttgt tagattaatg tatttgttgc ttcccttat    120 ctggaatgtg gcattagctt ttttattta accctcttta attcttattc aattccatga    180
cttaaggttg gagagctaaa cactgggatt tttggataac agactgacag ttttgcataa    240
ttataatcgg cattgtacat agaaaggata tggctacctt ttgttaaatc tgcactttct    300
aaatatcaaa aaagggaaat gaagtataaa tcaattttg tataatctgt ttgaaacatg    360
agttttattt gcttaatatt agggctttgc ccctttctg taagtctctt gggatcctgt    420
gtagaagctg ttctcattaa acaccaaaca gttaagtcca ttctctggta ctagctacaa    480
attcggtttc atattctact taacaattta aataaactga a                       521

<210> SEQ ID NO 215
<211> LENGTH: 381
<212> TYPE: DNA
<213> ORGANISM: Homo sapiens
<220> FEATURE:
<221> NAME/KEY: unsure
<222> LOCATION: (17)
<223> OTHER INFORMATION: n=A,T,C or G
<221> NAME/KEY: unsure
<222> LOCATION: (20)
<223> OTHER INFORMATION: n=A,T,C or G
<221> NAME/KEY: unsure
<222> LOCATION: (60)
<223> OTHER INFORMATION: n=A,T,C or G
<221> NAME/KEY: unsure
<222> LOCATION: (61)
<223> OTHER INFORMATION: n=A,T,C or G
<221> NAME/KEY: unsure
<222> LOCATION: (365)
<223> OTHER INFORMATION: n=A,T,C or G

<400> SEQUENCE: 215

| | | |
|---|---|---|
| gagcggagag cggaccngtn agagccctga gcagccccac cgccgccgcc ggcctagttn | 60 |
| ncatcacacc ccgggaggag ccgcagctgc cgcagccggc cccagtcacc atcaccgcaa | 120 |
| ccatgagcag cgaggccgag acccagcagc cgccgccgc ccccccgcc gccccgccc | 180 |
| tcagcgccgc cgacaccaag cccggcacta cgggcagcgg cgcagggagc ggtggcccgg | 240 |
| gcggcctcac atcggcggcg cctgccggcg gggacaagaa ggtcatcgca acgaaggttt | 300 |
| tgggaacagt aaaatggttc aatgtaagga acggatatgg tttcatcaac aggaatgaca | 360 |
| ccaangaaga tgtatttgta c | 381 |

<210> SEQ ID NO 216
<211> LENGTH: 425
<212> TYPE: DNA
<213> ORGANISM: Homo sapiens
<400> SEQUENCE: 216

| | | |
|---|---|---|
| ttactaacta ggtcattcaa ggaagtcaag ttaacttaaa catgtcacct aaatgcactt | 60 |
| gatggtgttg aaatgtccac cttcttaaat ttttaagatg aacttagttc taaagaagat | 120 |
| aacaggccaa tcctgaaggt actccctgtt tgctgcagaa tgtcagatat tttggatgtt | 180 |
| gcataagagt cctatttgcc ccagttaatt caacttttgt ctgcctgttt tgtggactgg | 240 |
| ctggctctgt tagaactctg tccaaaaagt gcatggaata taacttgtaa agcttcccac | 300 |
| aattgacaat atatatgcat gtgtttaaac caaatccaga aagcttaaac aatagagctg | 360 |
| cataatagta tttattaaag aatcacaact gtaaacatga gaataactta aggattctag | 420 |
| tttag | 425 |

<210> SEQ ID NO 217
<211> LENGTH: 181
<212> TYPE: DNA
<213> ORGANISM: Homo sapiens
<400> SEQUENCE: 217

| | | |
|---|---|---|
| gagaaaccaa atgataggtt gtagagcctg atgactccaa acaaagccat cacccgcatt | 60 |
| cttcctcctt cttctggtgc tacagctcca agggcccttc accttcatgt ctgaaatgga | 120 |
| actttggctt tttcagtgga agaatatgtt gaaggtttca ttttgttcta gaaaaaaaaa | 180 |
| a | 181 |

<210> SEQ ID NO 218
<211> LENGTH: 405
<212> TYPE: DNA
<213> ORGANISM: Homo sapiens
<400> SEQUENCE: 218

| | | |
|---|---|---|
| caggccttcc agttcactga caaacatggg gaagtgtgcc cagctggctg gaaacctggc | 60 |
| agtgatacca tcaagcctga tgtccaaaag agcaaagaat atttctccaa gcagaagtga | 120 |
| gcgctgggct gttttagtgc caggctgcgg tgggcagcca tgagaacaaa accttcttctg | 180 |
| tattttttt ttccattagt aaaacacaag acttcagatt cagccgaatt gtggtgtctt | 240 |

```
acaaggcagg cctttcctac aggggtgga gagaccagcc tttcttcctt tggtaggaat      300
ggcctgagtt ggcgttgtgg gcaggctact ggtttgtatg atgtattagt agagcaaccc      360
attaatcttt tgtagtttgt attaaacttg aactgagaaa aaaaa                      405

<210> SEQ ID NO 219
<211> LENGTH: 216
<212> TYPE: DNA
<213> ORGANISM: Homo sapiens
<220> FEATURE:
<221> NAME/KEY: unsure
<222> LOCATION: (207)
<223> OTHER INFORMATION: n=A,T,C or G
<221> NAME/KEY: unsure
<222> LOCATION: (210)
<223> OTHER INFORMATION: n=A,T,C or G

<400> SEQUENCE: 219
actccaagag ttagggcagc agagtggagc gatttagaaa gaacatttta aaacaatcag       60
ttaatttacc atgtaaaatt gctgtaaatg ataatgtgta cagattttct gttcaaatat      120
tcaattgtaa acttcttgtt aagactgtta cgtttctatt gcttttgtat gggatattgc      180
aaaaataaaa aggaaagaac cctcttnaan aaaaaa                                216

<210> SEQ ID NO 220
<211> LENGTH: 380
<212> TYPE: DNA
<213> ORGANISM: Homo sapiens

<400> SEQUENCE: 220
cttacaaatt gcccccatgt gtaggggaca cagaacccctt tgagaaaact tagattttttg     60 tctgtacaaa gtctttgcct ttttccttct tcattttttt ccagtacatt aaatttgtca      120
atttcatctt tgagggaaac tgattagatg ggttgtgttt gtgttctgat ggagaaaaca      180
gcaccccaag gactcagaag atgatttaaa cagttcagaa cagatgtgtg caatattggt      240
gcatgtaata atgttgagtg gcagtcaaaa gtcatgattt ttatcttagt tcttcattac      300
tgcattgaaa aggaaaacct gtctgagaaa atgcctgaca gtttaaattta aaactatggt      360 gtaagtcttt gacaaaaaaa                                                   380

<210> SEQ ID NO 221
<211> LENGTH: 398
<212> TYPE: DNA
<213> ORGANISM: Homo sapiens

<400> SEQUENCE: 221
ggttagtaag ctgtcgactt tgtaaaaaag ttaaaaatga aaaaaaagg aaaaatgaat        60 tgtatattta atgaatgaac atgtacaatt tgccactggg aggaggttcc ttttttgttgg    120 gtgagtctgc aagtgaattt cactgatgtt gatattcatt gtgtgtagtt ttatttcggt     180
cccagccccg tttccttta ttttggagct aatgccagct gcgtgtctag ttttgagtgc      240
agtaaaatag aatcagcaaa tcactcttat ttttcatcct tttccggtat tttttgggtt     300
gtttctgtgg gagcagtgta caccaactct tcctgtatat tgccttttg ctggaaaatg      360 ttgtatgttg aataaaattt tctataaaaa ttaaaaaa                              398

<210> SEQ ID NO 222
<211> LENGTH: 301
<212> TYPE: DNA
<213> ORGANISM: Homo sapiens
<220> FEATURE:
<221> NAME/KEY: unsure
<222> LOCATION: (49)
```

-continued

```
<223> OTHER INFORMATION: n=A,T,C or G
<221> NAME/KEY: unsure
<222> LOCATION: (64)
<223> OTHER INFORMATION: n=A,T,C or G

<400> SEQUENCE: 222
ttcgataatt gatctcatgg gctttccctg gaggaaaggt ttttttttgnt gtttattttt      60 taanaacttg aaacttgtaa actgagatgt ctgtagcttt tttgcccatc tgtagtgtat     120
gtgaagattt caaaacctga gagcactttt tctttgttta gaattatgag aaaggcacta     180
gatgacttta ggatttgcat ttttcccttt attgcctcat ttcttgtgac gccttgttgg     240
ggagggaaat ctgtttattt tttcctacaa ataaaaagct aagattctat atcgcaaaaa     300
a                                                                     301

<210> SEQ ID NO 223
<211> LENGTH: 200
<212> TYPE: DNA
<213> ORGANISM: Homo sapiens
<400> SEQUENCE: 223
gtaagtgctt aggaagaaac tttgcaaaca tttaatgagg atacactgtt cattttaaa       60 attccttcac actgtaattt aatgtgtttt atattctttt gtagtaaaac aacataactc     120
agatttctac aggagacagt ggttttattt ggattgtctt ctgtaatagg tttcaataaa     180
gctggatgaa cttaaaaaaa                                                 200

<210> SEQ ID NO 224
<211> LENGTH: 385
<212> TYPE: DNA
<213> ORGANISM: Homo sapiens
<400> SEQUENCE: 224
gaaaggtttg atccggactc aaagaaagca aaggagtgtg agccgccatc tgctggagca      60
gctgtaactg caagacctgg acaagagatt cgtcagcgaa ctgcagctca aagaaacctt    120
tctccaacac cagcaagccc taaccagggc cctcctccac aagttccagt atctcctgga    180
ccaccaaagg acagttctgc ccctggtgga cccccagaaa ggactgttac tccagcccta    240
tcatcaaatg tgttaccaag acatcttgga tcccctgcta cttcagtgcc tggaatgggt    300
aaacagagca cttaatgtta tttacagttt atattgtttt ctctggttac caataaaacg    360
ggccattttc aggtggtaaa aaaaa                                          385
```